United States Patent
Aicher et al.

(10) Patent No.: US 8,362,037 B2
(45) Date of Patent: *Jan. 29, 2013

(54) 2-AMINOPYRIDINE ANALOGS AS GLUCOKINASE ACTIVATORS

(75) Inventors: Thomas Daniel Aicher, Superior, CO (US); Steven Armen Boyd, Longmont, CO (US); Mark Joseph Chicarelli, Westminster, CO (US); Kevin Ronald Condroski, Broomfield, CO (US); Ronald Jay Hinklin, Longmont, CO (US); Ajay Singh, Aurora, CO (US)

(73) Assignee: Array BioPharma, Inc., Boulder, CO (US)

( * ) Notice: Subject to any disclaimer, the term of this patent is extended or adjusted under 35 U.S.C. 154(b) by 463 days.

This patent is subject to a terminal disclaimer.

(21) Appl. No.: 12/532,374

(22) PCT Filed: Mar. 19, 2008

(86) PCT No.: PCT/US2008/057543
§ 371 (c)(1),
(2), (4) Date: Sep. 21, 2009

(87) PCT Pub. No.: WO2008/118718
PCT Pub. Date: Oct. 2, 2008

(65) Prior Publication Data
US 2010/0105659 A1    Apr. 29, 2010

Related U.S. Application Data

(60) Provisional application No. 60/919,719, filed on Mar. 23, 2007, provisional application No. 60/974,260, filed on Sep. 21, 2007.

(51) Int. Cl.
*A61K 31/445* (2006.01)
*C07D 417/14* (2006.01)

(52) U.S. Cl. ........ 514/318; 514/326; 546/193; 546/207; 546/208; 546/210

(58) Field of Classification Search ................... 514/318, 514/326; 546/193, 207, 208, 209, 210
See application file for complete search history.

(56) References Cited

U.S. PATENT DOCUMENTS

| | | | |
|---|---|---|---|
| 5,260,311 A * | 11/1993 | Sauerberg et al. | 514/342 |
| 7,517,878 B2 | 4/2009 | Rudolph et al. | |
| 8,022,222 B2 * | 9/2011 | Aicher et al. | 546/270.7 |
| 8,022,223 B2 * | 9/2011 | Aicher et al. | 546/270.7 |
| 2006/0258701 A1 | 11/2006 | Mitsuya et al. | |
| 2008/0032996 A1 | 2/2008 | Mitsuya et al. | |
| 2009/0156603 A1 | 6/2009 | Aicher et al. | |
| 2010/0056530 A1 * | 3/2010 | Aicher et al. | 514/249 |
| 2011/0281874 A1 * | 11/2011 | Aicher et al. | 514/236.8 |

FOREIGN PATENT DOCUMENTS

WO   WO2007/117381    * 10/2007

OTHER PUBLICATIONS

Piotrowski et al. "Preparation of azabi . . . " CA122:265358 (1995).*
Office Action dated (mailed) Dec. 27, 2010 in U.S. Appl. No. 12/282,600.

* cited by examiner

*Primary Examiner* — Celia Chang
(74) *Attorney, Agent, or Firm* — Banner & Witcoff, Ltd.

(57) ABSTRACT

Provided are compounds that are useful in the treatment and/or prevention of diseases mediated by deficient levels of glucokinase activity, such as diabetes mellitus. Also provided are methods of treating or preventing diseases and disorders characterized by underactivity of glucokinase or which can be treated by activating glucokinase.

23 Claims, No Drawings

2-AMINOPYRIDINE ANALOGS AS GLUCOKINASE ACTIVATORS

The present invention relates to novel compounds, to pharmaceutical compositions comprising the compounds, to a process for making the compounds and to the use of the compounds in therapy. More particularly, it relates to certain glucokinase activators useful in the treatment of diseases and disorders that would benefit from activation of glucokinase.

Glucokinase (hexokinase IV or D) is a glycolytic enzyme that plays an important role in blood sugar regulation related to the glucose utilization and metabolism in the liver and pancreatic beta cells. Serving as a glucose sensor, glucokinase controls plasma glucose levels. Glucokinase plays a dual role in reducing plasma glucose levels: glucose-mediated activation of the enzyme in hepatocytes facilitates hepatic glucose update and glycogen synthesis, while that in pancreatic beta cells ultimately induces insulin secretion. Both of these effects in turn reduce plasma glucose levels.

Clinical evidence has shown that glucokinase variants with decreased and increased activities are associated with diabetes of the young type (MODY2) and persistent hyperinsulinemic hypoglycemia of infancy (PHHI), respectively. Also, non-insulin dependent diabetes mellitus (NIDDM) patients have been reported to have inappropriately low glucokinase activity. Furthermore, overexpression of glucokinase in dietary or genetic animal models of diabetes either prevents, ameliorates, or reverses the progress of pathological symptoms in the disease. For these reasons, compounds that activate glucokinase have been sought by the pharmaceutical industry.

It has now been found that aminothiazolyl and amino-1,2,4-thiadiazolyl substituted pyridine compounds having particularly desirable properties may be obtained by selecting an piperidin-4-yl group or a tetrahydropyridine group each having a particular substituent on the nitrogen atom of the group as the substituent at the 4 or 3 position of the thiazole or thiadiazole ring, respectively.

According to one aspect, the present invention provides a compound of general Formula I

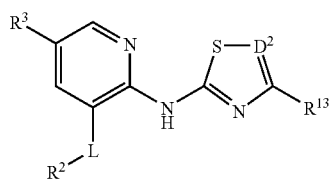

I or a salt thereof, wherein:
$R^{13}$ is a ring selected from the structures

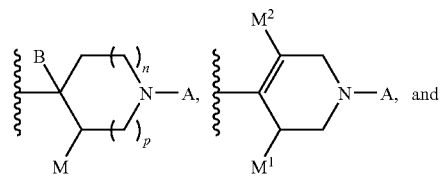

n and p are independently 1 or 2, wherein the sum of n and p is 2 or 3;
B is H, F, OH, or Me;
M and $M^1$ are independently H, F or Me;
$M^2$ is H or Me;
A is $C(=O)R^a$, $C(=O)OR^b$, $C(=O)NR^cR^d$, $SO_3H$, $SO_2NR^eR^f$, $SO_2(1\text{-}6C\text{ alkyl})$, (1-6C)fluoroalkyl, or (1-6C alkyl)OH;
$R^a$ is H, $CF_3$, (3-6C cycloalkyl), (1-6C alkyl), -(1-6C alkyl)OH, -(1-6C alkyl)-O-(1-6C alkyl), -(1-6C alkyl)$NH_2$, -(1-6C alkyl)NH(1-6C alkyl), or -(1-6C alkyl)N(1-6C alkyl)$_2$;
$R^b$ is (1-6C alkyl);
$R^c$ is H or (1-6C alkyl);
$R^d$ is H, (1-6C alkyl), or (1-6C alkyl)OH;
$R^e$ is H or (1-6C alkyl);
$R^f$ is H, (1-6C alkyl) or (1-6C alkyl)-N-(1-6C alkyl)$_2$;
L is O or S;
$D^2$ is N or CH;
$R^2$ is $Ar^1$, $hetAr^1$, $hetAr^c$, $hetAr^3$, cyclopentyl optionally substituted with OH, or N-alkyl-pyridinone-5-yl;
$Ar^1$ is aryl optionally substituted with one or more groups independently selected from $C_1$-$C_6$ alkyl, F, Br, Cl, $CF_3$, CN, $SO_2Me$, $C(=O)NH(1\text{-}3C\text{ alkyl})N(alkyl)_2$, $C(=O)NH(1\text{-}3C\text{ alkyl})hetCyc^1$, $OR^8$ and $C(=O)OR^8$;
$hetAr^1$ is a 5-6 membered heteroaryl group having 1-3 ring nitrogen atoms and optionally substituted with one or more groups independently selected from (1-6C alkyl), (1-6C alkyl)OH, Cl, and $CF_3$;
$hetAr^c$ is a partially unsaturated 5,5, 5,6 or 6,6 bicyclic ring system having 1-2 ring nitrogen atoms and optionally having a ring oxygen atom;
$hetAr^3$ is a 9-10 membered bicyclic heteroaryl ring having 1-3 ring nitrogen atoms;
$R^3$ is $SR^6$, Br, Cl, $CF_3$ or $OR^6$;
$R^6$ is aryl, $hetAr^a$ or $hetAr^b$, wherein said aryl, $hetAr^a$ and $hetAr^b$ are optionally substituted with one or more groups independently selected from (1-6C)alkyl, F, Br, Cl, $CF_3$, CN, $OR^8$, $C(=O)OR^8$, $C(=O)NH(1\text{-}3C\text{ alkyl})N(1\text{-}3C\text{alkyl})_2$ and $C(=O)NH(1\text{-}3C\text{ alkyl})hetCyc^2$,
or $R^6$ is polyhydroxy-(1-6C alkyl), (1-6C alkyl)OH, (1-6C alkyl)$R^9$, $CH(R^{11})$—$Ar^5$, $CH(R^{12})$-$hetAr^4$ or (5-6C)cycloalkyl substituted with 1-4 OH;
$R^{11}$ and $R^{12}$ are independently H, (1-6C)alkyl, (1-6C alkyl)OH, or $CF_3$;
$Ar^5$ is phenyl optionally substituted with one or more groups independently selected from F, Cl, Br, I and (1-6C alkyl);
$hetAr^4$ is a 5-6 membered heteroaryl having 1-2 ring nitrogen atoms;
each $R^8$ is independently H or $C_1$-$C_6$ alkyl;
$R^9$ is H, OMe, —$CO_2Me$, piperidin-4-yl, or N-acylpiperidin-4-yl;
$hetAr^a$ is a 5-6 membered heteroaryl ring having 1-4 nitrogen atoms or a 5-membered ring having 1-2 atoms independently selected from N and S;
$hetAr^b$ is a 9-10 membered bicyclic heteroaromatic ring having 2-6 atoms independently selected from N, S and O (provided the ring does not contain an O—O bond); and hetCyc¹ and hetCyc² are independently a 5-7 membered heterocyclic ring having 1-2 ring heteroatoms independently selected from N and O.

In certain embodiments of Formula I, A is C(=O)R$^a$, C(=O)OR$^b$, C(=O)NR$^c$R$^d$, SO$_3$H, SO$_2$NR$^e$R$^f$, SO$_2$(1-6C alkyl), or (1-6C alkyl)OH.

The compounds of Formula I include compounds wherein:
R$^{13}$ is a ring selected from the structures

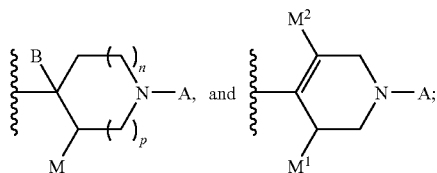

n and p are independently 1 or 2, wherein the sum of n and p is 2 or 3;
B is H, F, OH, or Me;
M and M¹ are independently H, F or Me;
M² is H or Me;
A is C(=O)R$^a$, C(=O)OR$^b$, C(=O)NR$^c$R$^d$, SO$_3$H, SO$_2$NR$^e$R$^f$, SO$_2$(1-6C alkyl), (1-6C)fluoroalkyl, or (1-6C alkyl)OH;
R$^a$ is H, CF$_3$, (3-6C cycloalkyl), (1-6C alkyl), -(1-6C alkyl)OH, -(1-6C alkyl)-O-(1-6C alkyl), -(1-6C alkyl)NH$_2$, -(1-6C alkyl)NH(1-6C alkyl), or -(1-6C alkyl)N(1-6C alkyl)$_2$;
R$^b$ is (1-6C alkyl);
R$^c$ is H or (1-6C alkyl);
R$^d$ is H, (1-6C alkyl), or (1-6C alkyl)OH;
R$^e$ is H or (1-6C alkyl);
R$^f$ is H, (1-6C alkyl) or (1-6C alkyl)-N-(1-6C alkyl)$_2$;
L is O or S;
D² is N or CH;
R² is Ar¹, hetAr¹, hetAr$^c$, hetAr³, cyclopentyl optionally substituted with OH, or N-alkyl-pyridinone-5-yl;
Ar¹ is phenyl or naphthyl optionally substituted with one or more groups independently selected from C$_1$-C$_6$ alkyl, OH, F, Br, CF$_3$, CN, SO$_2$Me, C(=O)NH(1-3C alkyl)N(alkyl)$_2$, and C(=O)NH(1-3C alkyl)hetCyc¹;
hetAr¹ is a 5-6 membered heteroaryl group having 1-3 ring nitrogen atoms and optionally substituted with one or more groups independently selected from (1-6C alkyl), (1-6C alkyl)OH, Cl, and CF$_3$;
hetAr$^c$ is a partially unsaturated 5,5, 5,6 or 6,6 bicyclic ring system having 1-2 ring nitrogen atoms and optionally having a ring oxygen atom;
hetAr³ is a 9-10 membered bicyclic heteroaryl ring having 1-3 ring nitrogen atoms;
R³ is SR$^6$, Br, Cl, CF$_3$ or OR$^6$;
R$^6$ is aryl, hetAr$^a$ or hetAr$^b$, wherein said aryl, hetAr$^a$ and hetAr$^b$ are optionally substituted with one or more groups independently selected from (1-6C)alkyl, F, Br, Cl, CF$_3$, CN, OR$^8$, C(=O)OR$^8$, C(=O)NH(1-3C alkyl)N(1-3Calkyl)$_2$ and C(=O)NH(1-3C alkyl)hetCyc²,
or R$^6$ is polyhydroxy-(1-6C alkyl), (1-6C alkyl)OH, (1-6C alkyl)R$^9$, CH(R$^{11}$)—Ar$^5$, CH(R$^{12}$)-hetAr$^4$ or (5-6C)cycloalkyl substituted with 1-4 OH;
R$^{11}$ and R$^{12}$ are independently H, (1-6C)alkyl, (1-6C alkyl)OH, or CF$_3$;
Ar$^5$ is phenyl optionally substituted with one or more groups independently selected from F, Cl, Br, I and (1-6C alkyl);
hetAr$^4$ is a 5-6 membered heteroaryl having 1-2 ring nitrogen atoms;

each R$^8$ is independently H or C$_1$-C$_6$ alkyl;
R$^9$ is H, OMe, —CO$_2$Me, piperidin-4-yl, or N-acylpiperidin-4-yl;
hetAr$^a$ is a 5-6 membered heteroaryl ring having 1-4 nitrogen atoms or a 5-membered ring having 1-2 atoms independently selected from N and S;
hetAr$^b$ is a 9-10 membered bicyclic heteroaromatic ring having 2-6 atoms independently selected from N, S and O (provided the ring does not contain an O—O bond); and
hetCyc¹ and hetCyc² is are independently a 5-7 membered heterocyclic ring having 1-2 ring heteroatoms independently selected from N and O.

The compounds of Formula I further include compounds wherein:
R$^{13}$ is

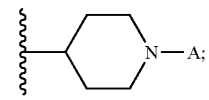

A is C(=O)(C$_1$-C$_6$ alkyl), C(=O)NH$_2$, (C=O)NH(C$_1$-C$_6$ alkyl), C(=O)N(C$_1$-C$_6$ alkyl)$_2$, C(=O)CH(C$_1$-C$_6$ alkyl)N(C$_1$-C$_6$ alkyl)$_2$, SO$_2$(C$_1$-C$_6$ alkyl), SO$_2$NH$_2$, SO$_2$NH(C$_1$-C$_6$ alkyl), S(C$_1$-C$_6$ alkyl)$_2$ or C(O)CH(CH$_3$)OH;
L is O;
D² is N or CH;
R² is aryl optionally substituted with one or more groups independently selected from C$_1$-C$_6$ alkyl, F, Br, and CF$_3$;
R³ is SR$^6$;
R$^6$ is aryl, hetAr$^a$ or hetAr$^b$, wherein R$^6$ is optionally substituted with one or more groups independently selected from C$_1$-C$_6$ alkyl, Br, Cl, CF$_3$, CN, OR$^8$, and C(=O)OR$^8$;
R$^8$ is C$_1$-C$_6$ alkyl;
hetAr$^a$ is a 5-6 membered heteroaryl ring having 1-4 nitrogen atoms; and
hetAr$^b$ is a 9-10 membered bicyclic heteroaromatic ring having 2-6 atoms independently selected from N, S and O (provided the ring does not contain an O—O bond).

The terms "(1-6C)alkyl" and "(1-3C)alkyl", as used herein refers to a saturated linear or branched-chain monovalent hydrocarbon radical of one to six carbon atoms or one to three carbon atoms, respectively, wherein the alkyl radical may be optionally substituted independently with one or more substituents described below. Examples include but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2 pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

In one embodiment, R$^{13}$ is a ring having the structure:

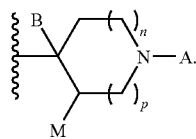

In one embodiment, $R^{13}$ is a ring having the structure:

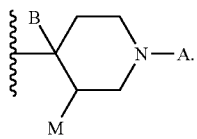

In one embodiment, $R^{13}$ is a ring having the structure:

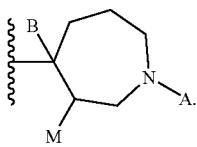

In one embodiment, $R^{13}$ is a ring having the structure:

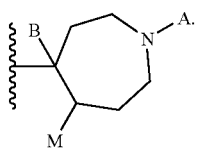

In one embodiment, $R^{13}$ is a ring having the structure:

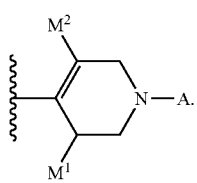

In one embodiment, $R^{13}$ is a ring having the structure:

Referring to the A group of Formula I, in certain embodiments A is $C(=O)R^a$.

In certain embodiments, A is $C(=O)R^a$ wherein $R^a$ is H, that is, A is $C(=O)H$.

In certain embodiments, A is $C(=O)R^a$ wherein $R^a$ is $CF_3$, that is, A is $C(=O)CF_3$.

In certain embodiments, A is $C(=O)R^a$ wherein $R^a$ is (1-6C)alkyl or (3-6C)cycloalkyl. In a particular embodiment, A is $C(=O)CH_3$, $C(=O)CH(CH_3)_2$, or $C(=O)$cyclopropyl.

In certain embodiments, A is $C(=O)R^a$ wherein $R^a$ is (1-6C alkyl)OH. Particular values for the A group include $C(=O)CH_2OH$ and $C(=O)CH(CH_3)OH$.

In certain embodiments, A is $C(=O)R^a$ wherein $R^a$ is (1-6C alkyl)-O-(1-6C alkyl). A particular value for A is $C(=O)CH_2OCH_3$.

In certain embodiments, A is $C(=O)R^a$ wherein $R^a$ is -(1-6C alkyl)$NH_2$, -(1-6C alkyl)NH(1-6C alkyl), or -(1-6C alkyl)N(1-6C alkyl)$_2$. Particular values for the A group include $C(=O)CH_2NMe_2$ and $C(=O)CH_2NH_2$.

In one embodiment, A is $C(=O)OR^b$. Particular values for the A group include $CO_2C(CH_3)_3$, $CO_2CH(CH_3)_2$ and $C(=O)CH_2CH_3$.

In certain embodiments, A is selected from $C(=O)H$, $C(=O)CF_3$, $C(=O)$-cyclopropyl, $C(=O)CH_3$, $C(=O)CH(CH_3)_2$, $C(=O)CH(CH_3)OH$, $C(=O)CH_2OCH_3$, $C(=O)CH_2NH_2$, and $C(=O)CH_2NMe_2$.

In certain embodiments, A is selected from $CO_2C(CH_3)_3$ and $CO_2CH(CH_3)_2$.

In one embodiment, A is $C(=O)NR^cR^d$. In one embodiment, $R^c$ is hydrogen. In another embodiment, $R^c$ is (1-6C alkyl), for example methyl or ethyl. In one embodiment, $R^d$ is H. In another embodiment, $R^d$ is (1-6C alkyl), for example methyl, ethyl or propyl. In another embodiment, $R^d$ is (1-6C alkyl)OH, for example $CH_2OH$ or $CH_2CH_2OH$. Particular values for the A group include $C(=O)NH_2$, $C(=O)NMe_2$ and $C(=O)NHCH_2CH_2OH$.

In certain embodiments, A is $C(=O)NH_2$.

In certain embodiments, A is $C(=O)NMe_2$ or $C(=O)NHCH_2CH_3$.

In one embodiment, A is $SO_3H$.

In one embodiment, A is $SO_2NR^eR^f$. In one embodiment, $R^e$ is hydrogen. In another embodiment, $R^e$ is (1-6C alkyl), for example methyl. In one embodiment, $R^f$ is H. In another embodiment, $R^f$ is (1-6C alkyl), for example methyl. In another embodiment, $R^f$ is (1-6C alkyl)N(1-6C alkyl)$_2$, for example (1-6C alkyl)NMe$_2$, for example $CH_2CH_2NMe_2$. Particular values for the A group include $SO_2NH_2$, $SO_2NMe_2$ and $SO_2NH(CH_2)_2N(CH_3)_2$. Another particular value for the A group is $SO_2NHCH_2CH_3$.

In one embodiment, A is $SO_2$(1-6C alkyl). A particular embodiment is $SO_2Me$.

In one embodiment, A is (1-6C)alkyl. Particular values for the A group include methyl and ethyl.

In one embodiment, A is (1-6C alkyl)OH. A particular value is $(CH_2)_2OH$.

In one embodiment, A is selected from $C(=O)(C_1-C_6$ alkyl), $C(=O)NH_2$, $C(=O)NMe_2$, $C(=O)CH_2NMe_2$, $SO_2Me$, $SO_2NH_2$, and $C(O)CH(CH_3)OH$.

In certain embodiments, A is $C(=O)(C_1-C_6$ alkyl). In a particular embodiment, A is $C(=O)CH_3$.

In certain embodiments, A is $C(=O)NH_2$.

In certain embodiments, A is $C(=O)NMe_2$.

In certain embodiments, A is $C(=O)CH_2NMe_2$.

In certain embodiments, A is $SO_2Me$.

In certain embodiments, A is $SO_2NH_2$.

In certain embodiments, A is $C(O)CH(CH_3)OH$.

Referring to the B group of Formula I, in one embodiment, B is hydrogen.

In another embodiment, B is methyl.

In another embodiment, B is F.

In another embodiment, B is OH.

Referring to the M group of Formula I, in one embodiment M is hydrogen.

In another embodiment, M is methyl.

In another embodiment, M is F.

Referring to the $M^1$ group of Formula I, in one embodiment $M^1$ is hydrogen.

In another embodiment, $M^1$ is methyl.

In another embodiment, $M^1$ is F.

Referring to the $M^2$ group of Formula I, in one embodiment $M^2$ is hydrogen.

In another embodiment, $M^2$ is methyl.

Particular mention is made of $R^{13}$ groups having the following structures:

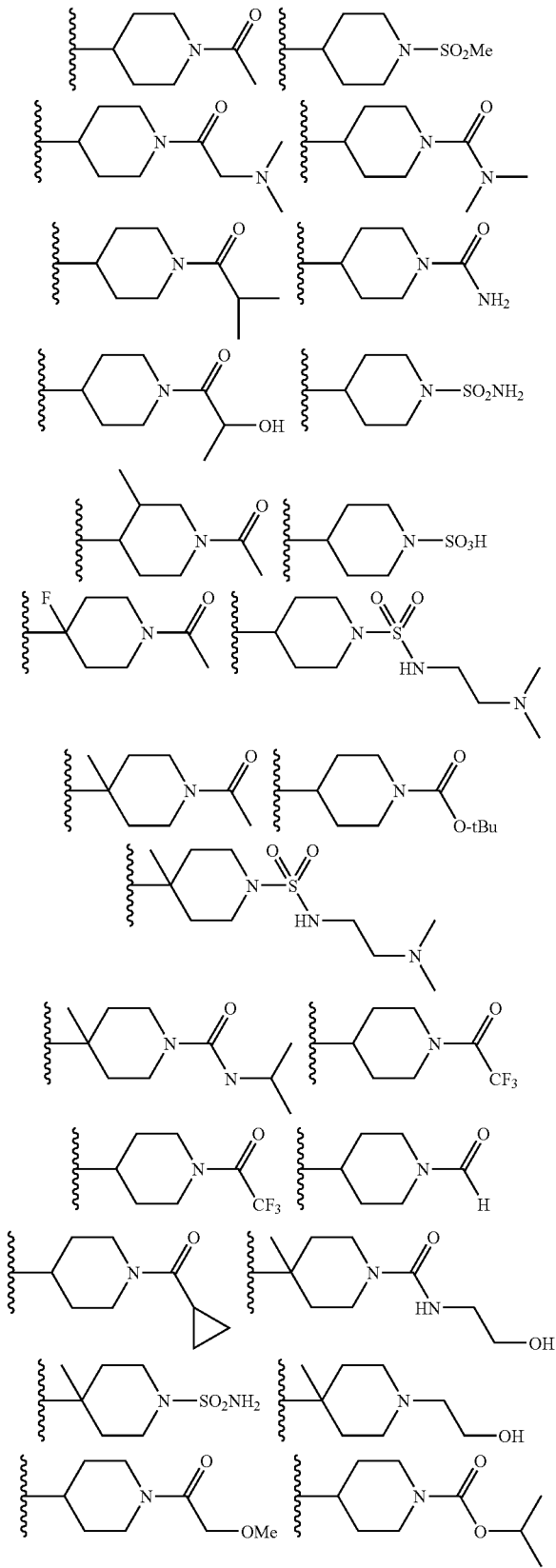

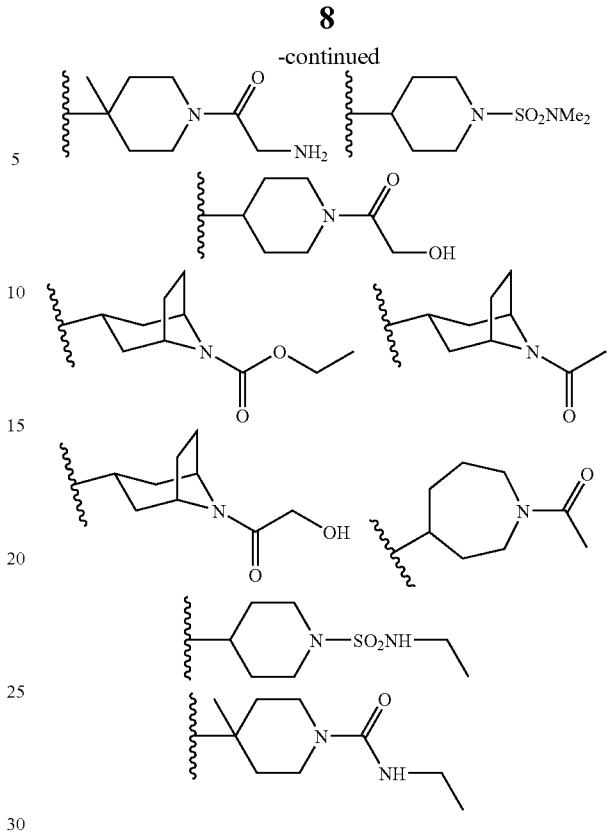

Referring to the $R^2$ group of Formula I, in one embodiment, $R^2$ is $Ar^1$, which is optionally substituted with one or more groups independently selected from $C_1$-$C_6$ alkyl, F, Br, Cl, $CF_3$, CN, $SO_2Me$, C(=O)NH(1-3C alkyl)N(alkyl)$_2$, C(=O)NH(1-3C alkyl)hetCyc$^1$, $OR^8$ and C(=O)$OR^8$.

In one embodiment, $R^2$ is aryl which is unsubstituted or substituted with one or more groups independently selected from $C_1$-$C_6$ alkyl, F, Br, $CF_3$, CN, $SO_2Me$, C(=O)NH(1-3C alkyl)N(alkyl)$_2$ and C(=O)NH(1-3C alkyl)hetCyc$^1$.

Examples of hetCyc$^1$ groups include 5-7 membered heterocyclic rings having 1-2 ring heteroatoms independently selected from N and O, such as pyrrolidinyl, piperidinyl, piperazinyl and morpholinyl rings.

In certain embodiments, $R^2$ is aryl optionally substituted with one or more groups independently selected from $C_1$-$C_6$ alkyl, Br, Cl, $CF_3$, CN, $OR^8$ and C(=O)$OR^8$.

In other embodiments, $R^2$ is aryl optionally substituted with one or more groups independently selected from $C_1$-$C_6$ alkyl, F, Br and $CF_3$.

In one embodiment, $R^2$ is phenyl which is unsubstituted or substituted with one or more groups independently selected from F, Br, Cl, Me, $CF_3$, CN, $SO_2Me$ and C(=O)NH(1-3C alkyl)N(Me)$_2$.

Additional values for $R^2$ include phenyl optionally substituted with one or two groups independently selected from F, Br and $CF_3$.

In certain embodiments, $R^2$ is naphthyl which is unsubstituted or substituted with one or more groups independently selected from F, Br, Cl, Me, $CF_3$, CN, $SO_2Me$, and C(=O)NH(1-3C alkyl)N(Me)$_2$.

Exemplary embodiments of R² include, but are not limited to, the structures:

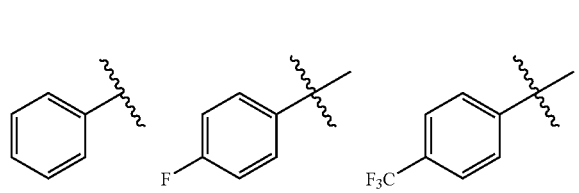

Additional examples of R² include the structures:

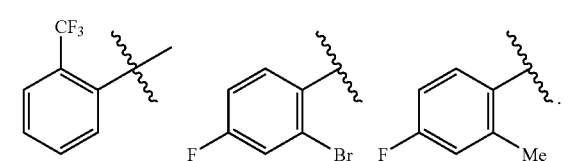

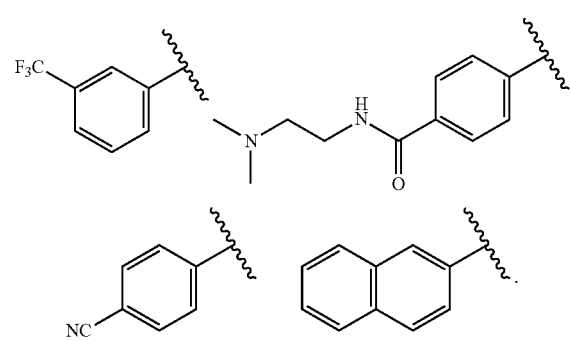

In one embodiment, R² is hetAr¹.

In one embodiment, hetAr¹ is unsubstituted. In another embodiment, hetAr¹ is substituted with one or more groups independently selected from (1-6C alkyl), (1-6C alkyl)OH, Cl, and CF₃.

In one embodiment, hetAr¹ is an optionally substituted 6-membered heteroaryl group having 1-2 ring nitrogen atoms. Examples of hetAr¹ include unsubstituted or substituted pyridyl, pyrazinyl and pyridazinyl groups. In certain embodiments, the 6-membered hetAr¹ is unsubstituted or substituted with one or more groups independently selected from methyl, ethyl, isopropyl, chloro, CF₃, CH₂OH, and CH₂CH₂OH. Examples include pyridyl, methylpyridyl, dimethylpyridyl, ethylpyridyl, isopropylpyridyl, chloropyridyl, trifluoromethylpyridyl, hydroxymethylpyridyl, hydroxyethylpyridyl, methylpyrazinyl and methylpyridazinyl.

Particular values for hetAr¹ include the structures:

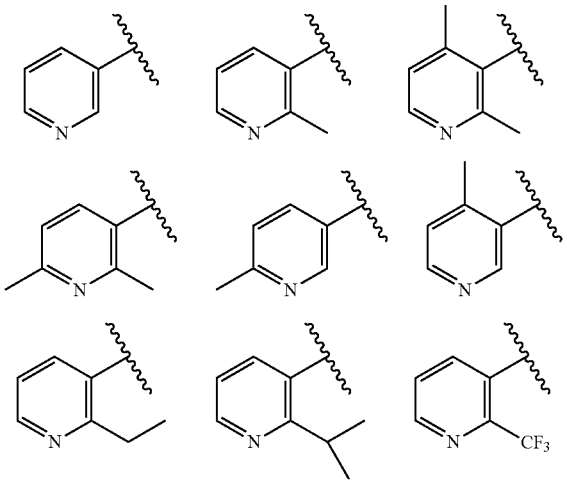

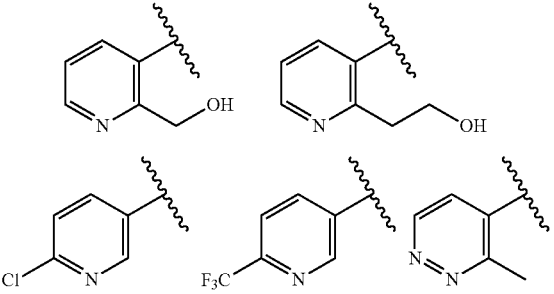

In another embodiment, hetAr¹ is an optionally substituted 5-membered heteroaryl group having 1-2 ring nitrogen atoms. An example is pyrazolyl which is unsubstituted or substituted with one or more (1-6C alkyl) groups, for example one or more methyl groups.

In another embodiment, hetAr¹ is an optionally substituted 5-membered heteroaryl group having 1-3 ring nitrogen atoms. Examples include pyrazolyl, imidazolyl and triazolyl groups. In certain embodiments, the 5-membered hetAr¹ is unsubstituted or substituted with one or more groups independently selected from (1-6C alkyl), CF₃, Cl, or (1-3C alkyl)OH, for example one or more groups independently selected from methyl, ethyl, isopropyl, CF₃, CH₂OH and CH₂CH₂OH.

Particular values for hetAr¹ include the structures:

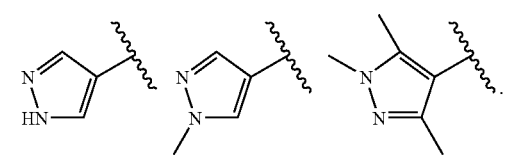

Additional values for hetAr¹ include the structures:

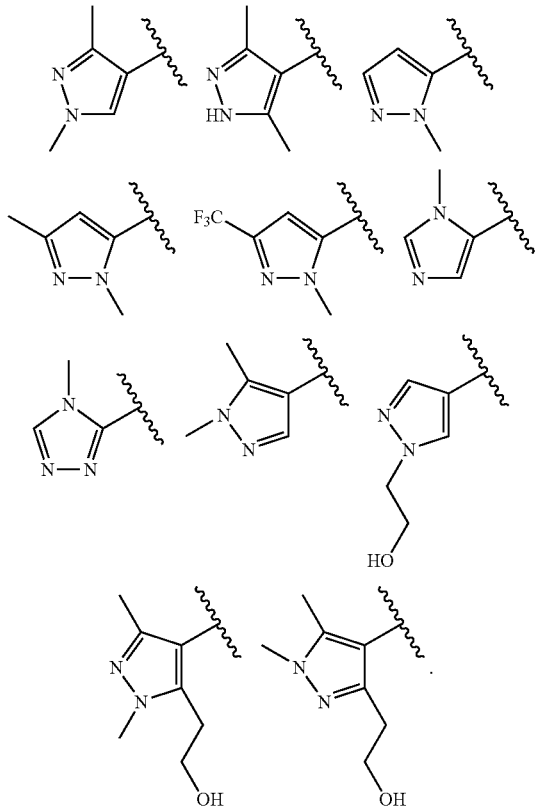

In certain embodiments, R² is hetAr^c wherein herAr^c is a partially unsaturated 5,5, 5,6 or 6,6 bicyclic ring system having 1-2 ring nitrogen atoms and optionally having a ring oxygen atom. Examples of such ring systems include 5,6,7,8-tetrahydroquinolinyl, 5,6,7,8-tetrahydroisoquinolinyl, 5,6,7,8-tetrahydroquinazolinyl, 6,7-dihydro-5H-cyclopenta[d]pyrimidinyl, 6,7-dihydro-5H-cyclopenta[b]pyridinyl, 6,7-dihydro-5H-cyclopenta[c]pyridinyl, 2,3-dihydrofuro[2,3-b]pyridinyl, 2,3-dihydrofuro[2,3-c]pyridinyl, 2,3-dihydrofuro[3,2-b]pyridinyl, 2,3-dihydrofuro[3,2-c]pyridinyl, 3,4-dihydro-2H-pyrano[2,3-b]pyridinyl, 3,4-dihydro-2H-pyrano[2,3-c]pyridinyl, 3,4-dihydro-2H-pyrano[3,2-c]pyridinyl, 3,4-dihydro-2H-pyrano[3,2-b]pyridinyl, 4,5,6,7-tetrahydro-1H-benzo[d]imidazolyl, and 1,4,5,6-tetrahydrocyclopenta[d]imidazolyl rings. Particular examples of hetAr^c include the structures:

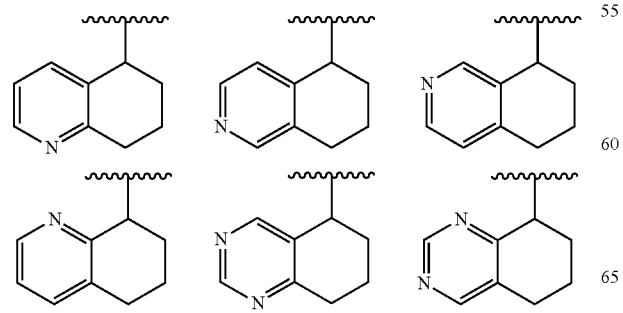

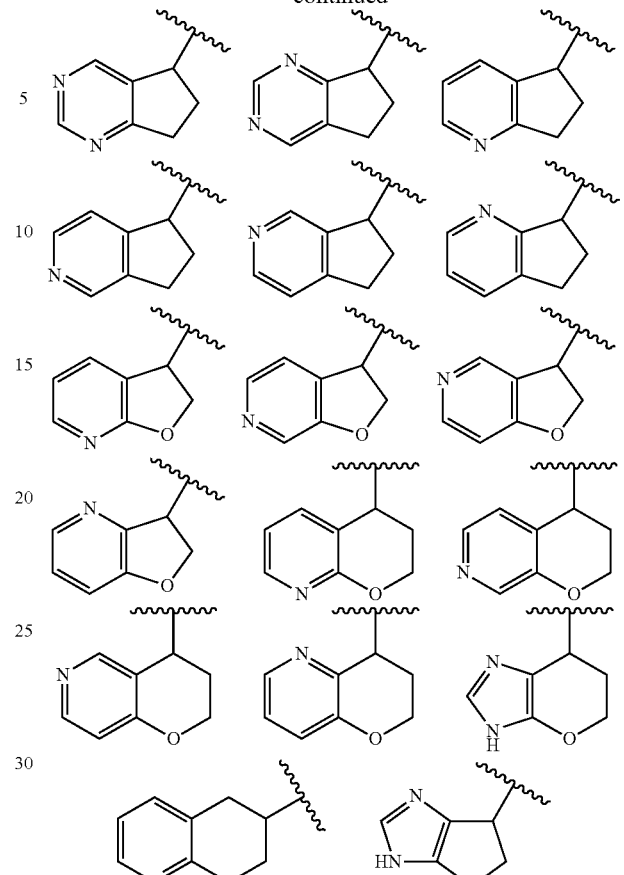

In certain embodiments, R² is hetAr³ wherein herAr³ is a 9-10 membered bicyclic heteroaryl ring having 1-3 ring nitrogen atoms. Examples of such ring systems include [1,2,4]triazolo[4,3-a]pyridinyl and [1,2,4]triazolo[1,5-a]pyridinyl rings. Particular values for hetAr³ include the structures:

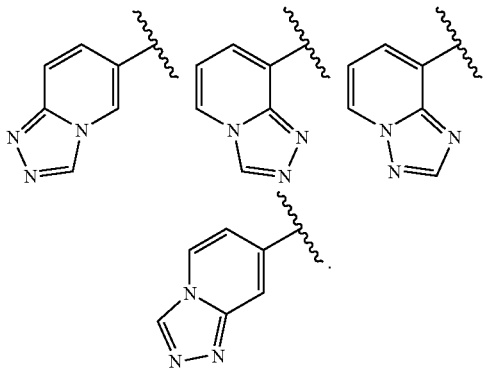

An additional value for hetAr³ is the structure:

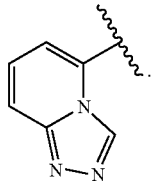 [SMILES: *c1cccc2nncn12]

In one embodiment, R² is cyclopentyl. In another embodiment, R² is cyclopentyl substituted with OH.

In one embodiment, R² is 1-methylpyridin-2(1H)-one-5-yl.

Referring to the R³ group of Formula I, in certain embodiments R³ is SR⁶ wherein R⁶ is aryl.

In certain embodiments, the aryl group represented by R⁶ is unsubstituted. In other embodiments, the aryl group is substituted with one or more groups independently selected from (1-6C)alkyl, F, Br, Cl, CF₃, CN, OR⁸, C(=O)OR⁸, C(=O)NH(1-3C alkyl)N(1-3Calkyl)₂ and C(=O)NH(1-3C alkyl)hetCyc². In certain embodiments the aryl group is substituted with one or two groups independently selected from F, Cl, (1-6C)alkyl, CN, CF₃, and —O(C₁-C₆ alkyl). Examples of hetCyc² groups include 5-7 membered heterocyclic rings having 1-2 ring heteroatoms independently selected from N and O, such as pyrrolidinyl, piperidinyl, piperazinyl and morpholinyl rings.

In other embodiments, the aryl group is substituted with one or two groups independently selected from CN, CF₃, and —O(C₁-C₆ alkyl).

In a particular embodiment, the aryl group is an optionally substituted phenyl.

Exemplary embodiments of R³ when represented by —S-aryl include phenylthio, (chlorophenyl)thio, (fluorophenyl)thio, (methylphenyl)thio, (trifluromethylphenyl)thio, (dimethylphenyl)thio, (cyanotrifluoromethylphenyl)thio, (cyanophenyl)thio, and (methoxyphenyl)thio.

Particular values of R³ when represented by S-aryl include the structures:

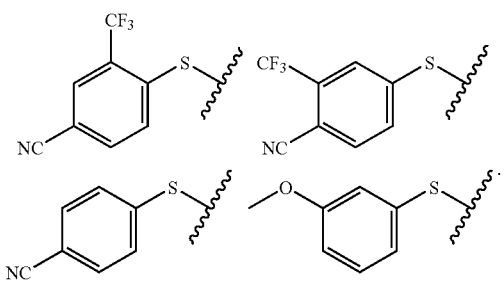

Additional values of R³ when represented by S-aryl include the structures:

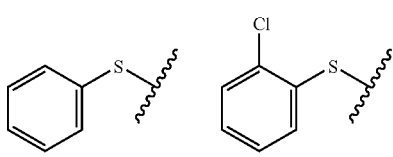

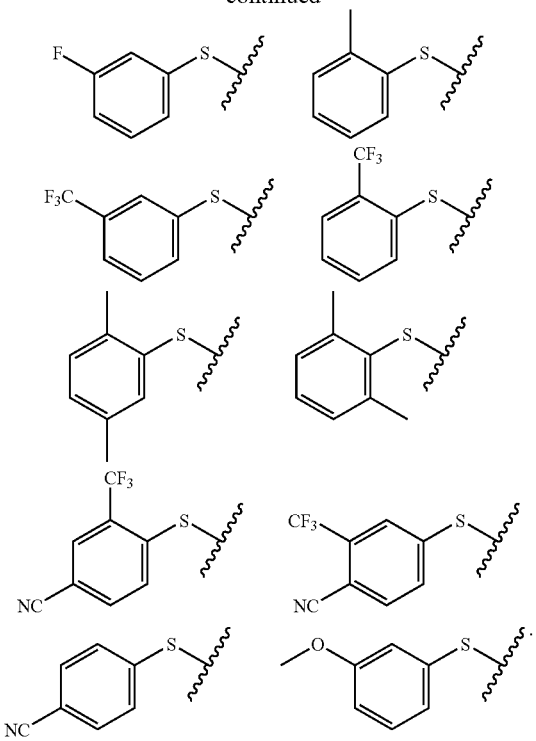

In another embodiment of Formula I, R³ is SR⁶ wherein. R⁶ is hetAr^a, and hetAr^a is an optionally substituted 5-6 membered heteroaryl ring having 1-4 nitrogen atoms or having 1-2 atoms independently selected from N and S.

In certain embodiments of Formula I, R³ is SR⁶ wherein R⁶ is hetAr^a, and hetAr^a is a 5-6 membered heteroaryl ring having 1-4 nitrogen atoms. In particular examples, hetAr^a is a 5-6 membered ring having 1-2 nitrogen atoms. Examples include pyridyl and pyrimidyl rings.

In other embodiments, hetAr^a is a 5-membered ring having from 1-3 ring nitrogen atoms. Examples include pyrrolyl, imidazolyl and triazolyl rings. In other embodiments, hetAr^a is a thiazolyl ring.

In certain embodiments, hetAr^a is unsubstituted. In other embodiments, hetAr^a is substituted with one or more groups independently selected from (1-6C)alkyl, F, Br, Cl, CF₃, CN, OR⁸, C(=O)OR⁸ and C(=O)NH(1-3C alkyl)N(1-3Calkyl)₂.

Particular examples of substituents for hetAr^a include methyl, Cl, CF₃, CN, OCH(Me)₂, OMe, CO₂H, CO₂Me, CO₂Et, and C(=O)NH(CH₂)₂NMe₂.

In other embodiments, hetAr^a is substituted with one or two groups independently selected from Cl, CN, —O(C₁-C₆ alkyl), C(=O)O(C₁-C₆ alkyl), and CF₃.

Particular values for R³ when represented by S-hetAr^a include the structures:

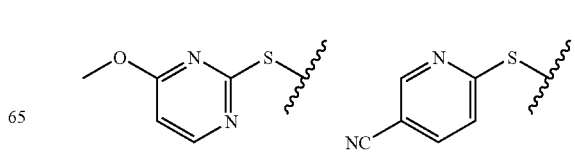

-continued

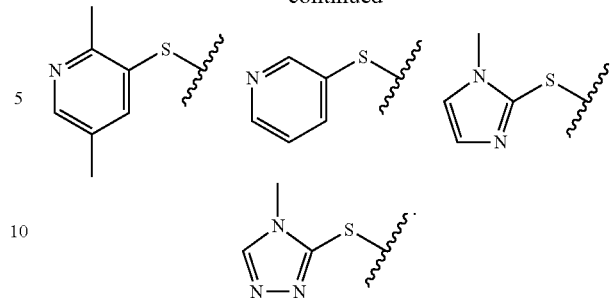

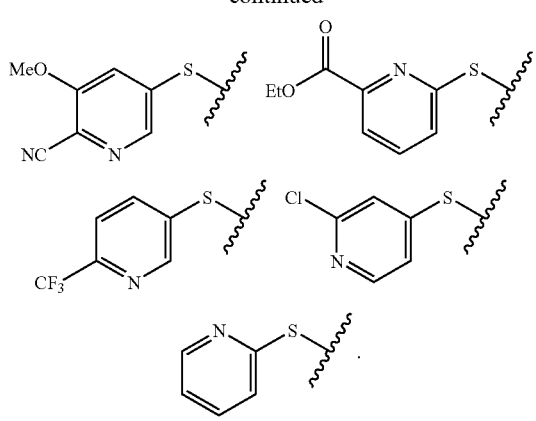

Additional values for R³ when represented by S-hetAr^a include the structures:

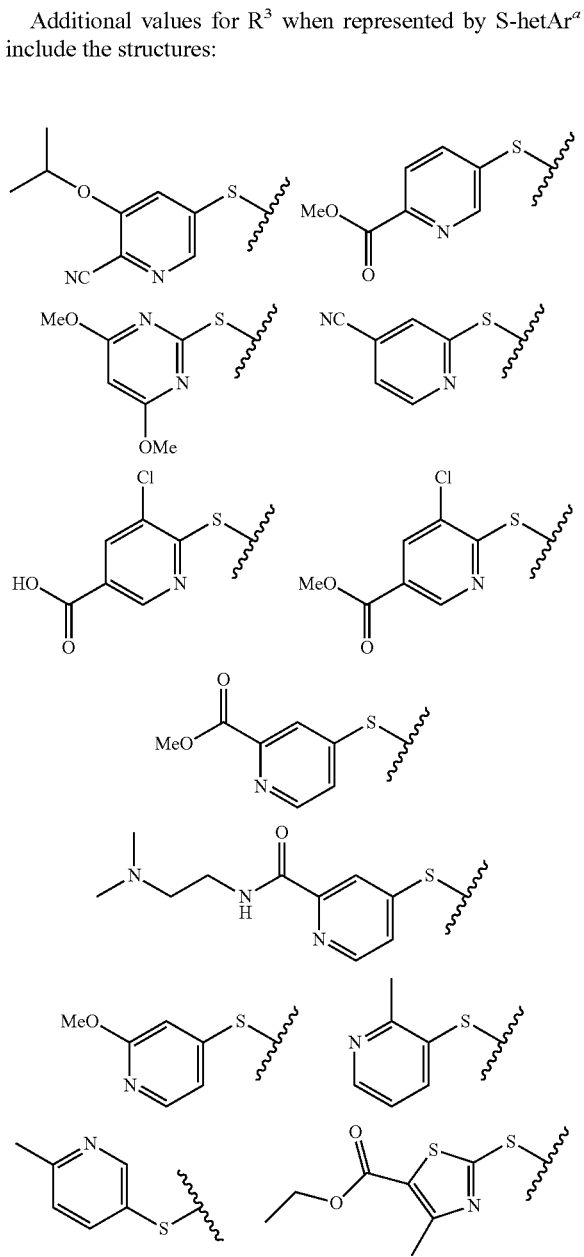

An additional value for R³ when represented by S-hetAr^a includes the structure:

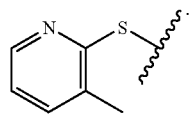

In certain embodiments of Formula I, R³ is SR⁶ wherein R⁶ is hetAr^b and hetAr^b is a 9-10 membered bicyclic heteroaromatic ring having 2-6 heteroatoms independently selected from N, S and O (provided the ring does not contain an O—O bond). In particular embodiments, hetAr^b is a 9-10 membered bicyclic heteroaromatic ring having 2-3 heteroatoms independently selected from N, S and O. Examples include 5,6 and 6,6 fused heteroaryl rings. Particular examples include thienopyridyl, thienopyrimidyl, isoxazolopyridyl and pyrazolopyrimidyl rings.

Additional examples of hetAr^b include imidazopyridine rings.

In certain embodiments, hetAr^b is unsubstituted. In certain embodiments, hetAr^b is substituted with one or more groups independently selected from (1-6C)alkyl, F, Br, Cl, CF₃, CN, OR⁸, C(=O)OR⁸ and C(=O)NH(1-3C alkyl)N(1-3Calkyl)₂. In particular embodiments, herAr^a is optionally substituted with one or two groups independently selected from Br, Cl, C₁-C₆ alkyl, and OR⁸. Particular substituents include Br, Cl, Me, and OMe.

In other embodiments, hetAr^b is substituted with one or two groups independently selected from Br, Cl and C₁-C₆ alkyl.

Particular values of R³ when represented by S-hetAr^b include the structures:

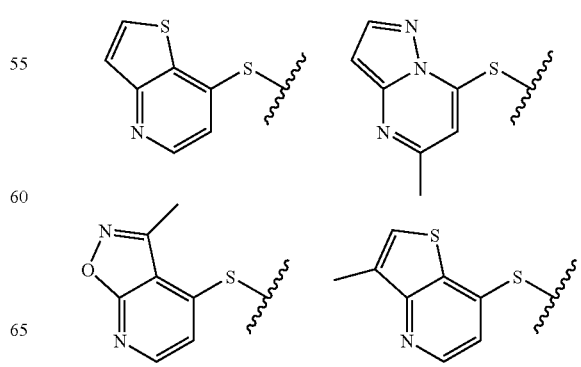

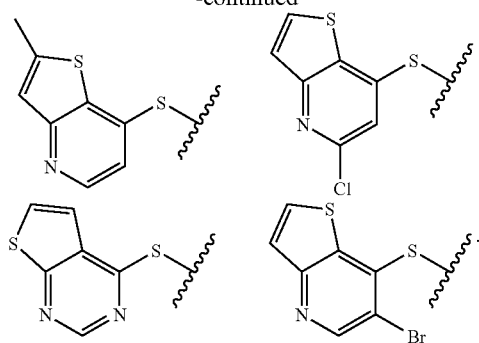

Additional values of R³ when represented by S-hetAr^b include the structures:

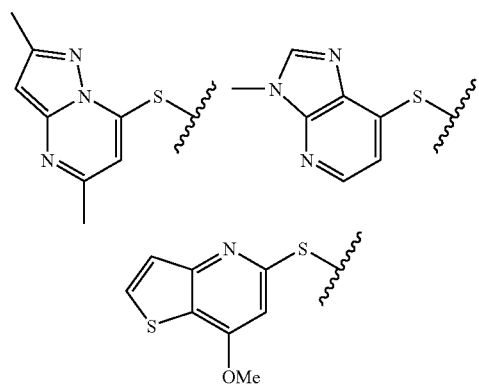

In certain embodiments, R³ is SR⁶ wherein R⁶ is (1-6C alkyl)OH or a polyhydroxy-substituted (1-6C alkyl). Examples of polyhydroxy-substituted alkyl groups include 1-6C alkyl groups substituted with 2 to 3 hydroxy groups. Particular values for R³ include groups having the structures:

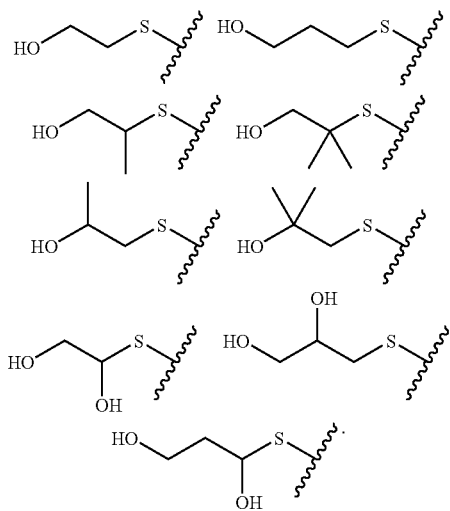

In certain embodiments, R³ is SR^b where R^b is (5-6C) cycloalkyl substituted with 1-4 OH groups, for example 1-2 OH groups.

In another embodiment of Formula I, R³ is SR⁶ wherein R⁶ is CH(R¹¹)—Ar⁵. In certain embodiments, R¹¹ is H. In certain embodiments, R¹¹ is (1-6C)alkyl, for example (1-3C alkyl), for example methyl. A particular value of R¹¹ is methyl. In certain embodiments, R¹¹ is (1-6C alkyl)OH. In certain embodiments, R¹¹ is CH₂OH. In certain embodiments, Ar⁵ is an unsubstituted phenyl. In other embodiments, Ar⁵ is phenyl which is substituted with one or more groups independently selected from F, Cl, Br, and (1-6C)alkyl. Particular values for R³ when represented by S—CH(R¹¹)—Ar⁵ include the structures:

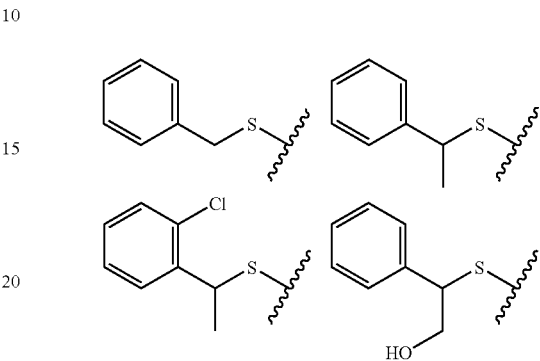

In another embodiment of Formula I, R³ is SR⁶ wherein R⁶ is CH(R¹²)-hetAr⁴. In certain embodiments, R¹² is H. In certain embodiments, R¹² is (1-6C)alkyl, for example (1-3C alkyl), for example methyl. A particular value of R¹² is methyl. In certain embodiments, R¹² is (1-6C alkyl)OH. In certain embodiments, R¹² is CH₂OH. In certain embodiments, hetAr⁴ is pyridyl. In other embodiments, hetAr⁴ is pyrimidyl. Particular values for R³ when represented by S—CH(R¹²)-hetAr⁴ include the structures:

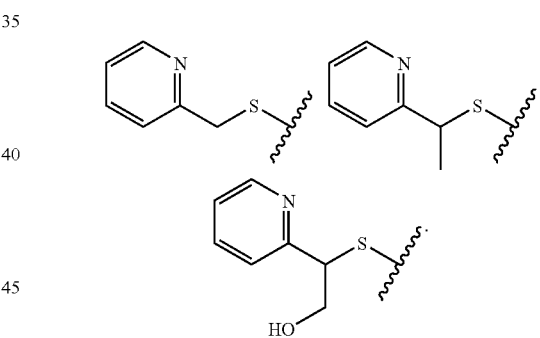

In certain embodiments, R³ is SR⁶ wherein R⁶ is (1-6C alkyl)R⁹. In other embodiments of Formula I, R³ is SR⁶ wherein R⁶ is (1-3C alkyl)R⁹. Particular examples include the structures:

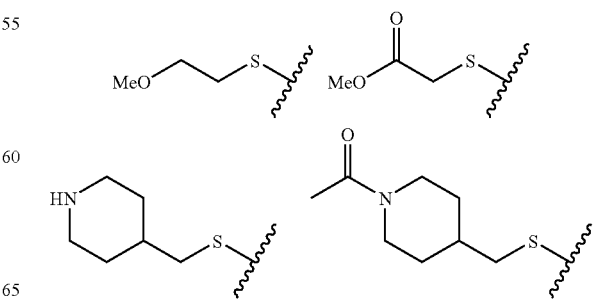

In certain embodiments, $R^3$ is $OR^6$.

In certain embodiments, $R^3$ is $OR^6$ where $R^6$ is aryl, hetAr$^a$ or hetAr$^b$, wherein said aryl, hetAr$^a$ and hetAr$^b$ are optionally substituted with one or more groups independently selected from (1-6C)alkyl, F, Br, Cl, CF$_3$, CN, OR$^8$, C(=O)OR$^8$, C(=O)NH(1-3C alkyl)N(1-3 Calkyl)$_2$ and C(=O)NH(1-3C alkyl)hetCyc$^2$.

In other embodiments of Formula I, $R^3$ is $OR^6$ and $R^6$ is aryl. In certain embodiments, the aryl group is an unsubstituted phenyl. In other embodiments, the aryl group is phenyl which is substituted with one or more groups independently selected from F, Cl, Br, I, (1-6C alkyl) and (1-6C alkyl)OH. In certain embodiments, the phenyl group is optionally substituted with Cl or CH$_2$OH. Particular values of $R^3$ when represented by $OR^6$ include the structures:

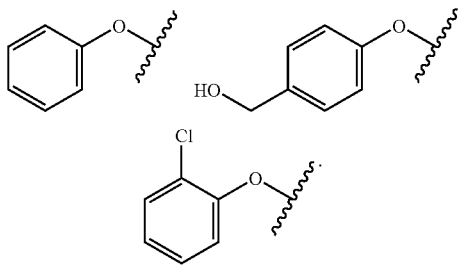

In other embodiments of Formula I, $R^3$ is $OR^6$ and $R^6$ is hetAr$^a$ or hetAr$^b$. In certain embodiments, hetAr$^a$ is a 6-membered heteroaryl having 1-2 ring nitrogens, for example pyridyl. In certain embodiments, the hetAr$^a$ is unsubstituted. In other embodiments, hetAr$^a$ is substituted with one or more groups independently selected from (1-6C)alkyl, for example one or more methyl groups. Particular values include the structures:

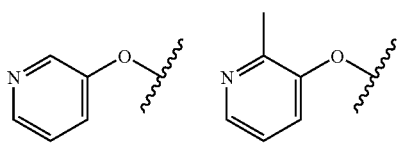

In certain embodiments, $R^3$ is $OR^6$ wherein $R^6$ is polyhydroxy-(1-6C alkyl), (1-6C alkyl)OH, (1-6C alkyl)R$^9$, CH(R$^{11}$)—Ar$^5$, CH(R$^{12}$)-hetAr$^4$ or (5-6C)cycloalkyl substituted with 1-4 OH, wherein said $R^9$, $R^{11}$, Ar$^5$, $R^{12}$ and hetAr$^4$ are as defined above.

In certain embodiments, $R^3$ is $OR^6$ wherein $R^6$ is (1-6C alkyl)R$^9$. In a particular embodiment, $R^6$ is OMe.

In embodiments of Formula I, $R^3$ is Br.

In certain embodiments of Formula I, $R^3$ is Cl.

In certain embodiments of Formula I, $R^3$ is CF$_3$.

In one embodiment of Formula I, L is O.

In one embodiment of Formula I, L is S.

In one embodiment of Formula I, $D^2$ is CH.

In one embodiment of Formula I, $D^2$ is N.

The compound of Formula I also include compound of Formula Id

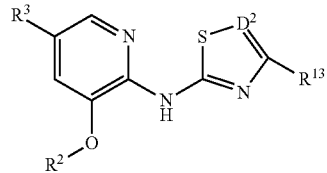

and salts thereof, wherein:
$R^{13}$ is

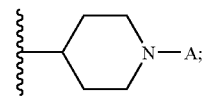

A is C(=O)(C$_1$-C$_6$ alkyl), C(=O)NH$_2$, C(=O)NMe$_2$, C(=O)CH$_2$NMe$_2$, SO$_2$Me, or SO$_2$NH$_2$;
$D^2$ is N or CH;
$R^2$ is phenyl optionally substituted with F; and
$R^3$ is selected from

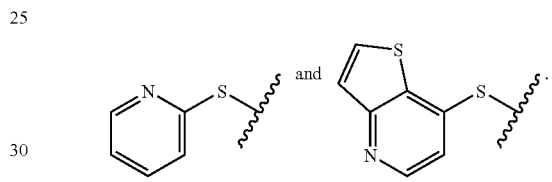

In certain embodiments, of Formula Id, A is C(=O)(C$_1$-C$_6$ alkyl).
In certain embodiments, of Formula Id, A is C(=O)NH$_2$.
In certain embodiments, of Formula Id, A is C(=O)NMe$_2$.
In certain embodiments, of Formula Id, A is C(=O)CH$_2$NMe$_2$.
In certain embodiments, of Formula Id, A is SO$_2$Me.
In certain embodiments, of Formula Id, A is SO$_2$NH$_2$.
In certain embodiments, of Formula Id, $D^2$ is N.
In certain embodiments, of Formula Id, $D^2$ is CH.
In certain embodiments, of Formula Id, $R^2$ is phenyl
In certain embodiments, of Formula Id, $R^2$ is fluorophenyl.
In certain embodiments, of Formula Id, $R^3$ is

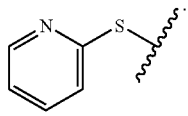 [SMILES: *Sc1ccccn1]

In certain embodiments, of Formula Id, $R^3$ is

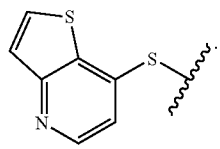

It has been found that compounds of Formula Id have improved pharmacokinetic properties, such as increased exposure (i.e., increased blood levels of the parent compound over time).

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

Compounds of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

For illustrative purposes, Schemes A-Q show general methods for preparing the compounds of the present invention as well as key intermediates. For a more detailed description of the individual reaction steps, see the Examples section below.

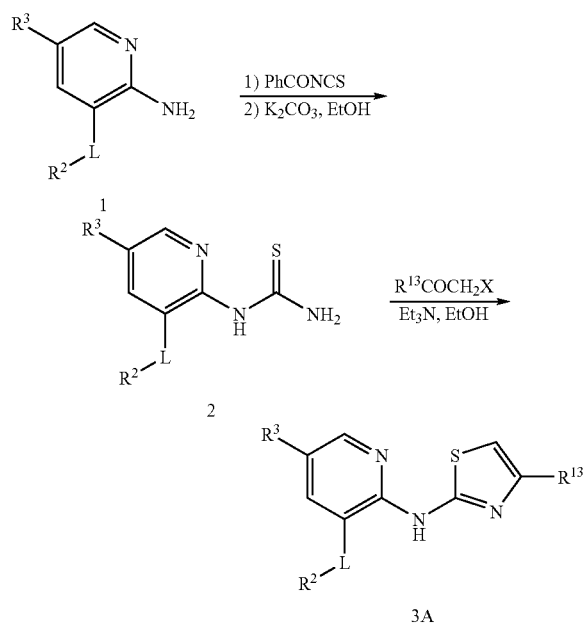

Scheme A shows a method of preparing compounds (3A) of Formula I. To prepare compound (3A), a 2-aminoheterocycle (1) is reacted with benzoylisothiocyanate to afford a benzoylthiourea intermediate, which is hydrolyzed to the thiourea (2) with a base such as, but not limited to, potassium carbonate in a suitable solvent such as, but not limited to, ethanol. Alternatively, the aminoheterocycle (1) can be treated with an inorganic or ammonium isothiocyanate, e.g., Meckler's procedure, in the presence of an acid to afford the thiourea (2) in one Step. Treatment of the thiourea (2) with an α-haloketone $R^{13}COCH_2X$, wherein X=OTs, Cl, Br, I, or $NR_3$ (wherein $R=C_1-C_6$ alkyl), in a suitable base such as triethylamine, Hunig's base, DBU, alkali carbonate, sodium hydroxide, etc. and a suitable solvent such as ethanol affords the thiazole (3A). If the desired α-halo ketone $R^{13}COCH_2X$ is not commercially available, it can be prepared by various methods known to those skilled in the art. Examples include, but are not limited to, bromination of commercially or readily synthesized methyl ketones (*Tetrahedron* (1970) 5611-5615; *Organic Synthesis* (1946) 13-15; *Tetrahedron* (1990) 2943-2964), diazomethane treatment of carbonyl chlorides, oxidation of 1-chloro-2-alkanols, bromination of silyl enol ethers, or halogenation of β-keto esters followed by decarboxylation.

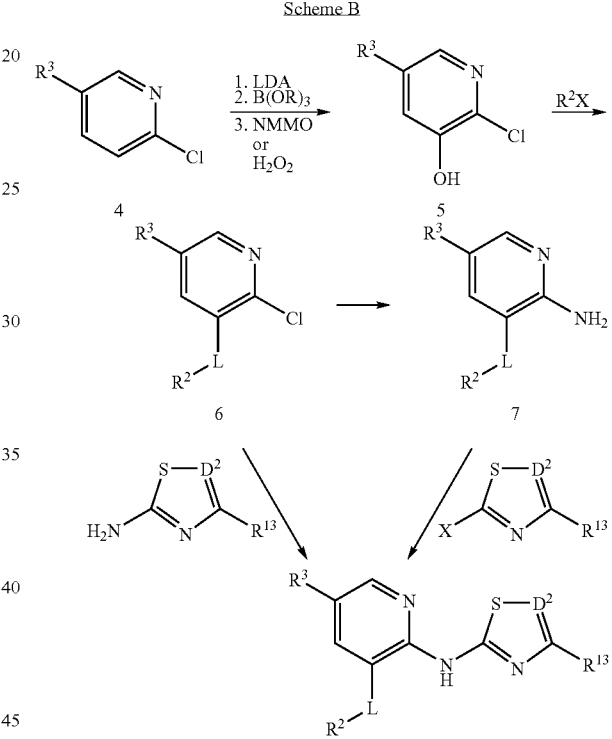

Scheme B shows an alternative method of preparing a compound of Formula I. According to Scheme B, hydroxylated heteroaryl halide (5) (if not commercially available) can be prepared from heteroaryl halide (4) by: 1) ortho metalation with LDA or another suitable base; 2) conversion of the anion to the boronate via reaction with $B(OR)_3$; and 3) oxidation of the boronate with a suitable oxidant such as N-methylmorpholine oxide or hydrogen peroxide. The ortho metalated species can also be quenched with $(TMSO)_2$ to obtain the hydroxylated material (5) directly upon acidic workup. The hydroxylated heteroaromatic compound (5) can be alkylated with $R^2X$ in the presence of a base such as, but not limited to, cesium carbonate or sodium hydride and in a suitable solvent such as, but not limited to, DMF to afford compound (6). Compound (6) can be converted to compound (7) by the method of Hartwig et al. (for an example of this transformation via analogy see: *Organic Letters* (2001) 2729-2732), or by treatment with a Pd catalyst and benzophenone imine, or by heating in the presence of ammonia (or $NH_2PG$ where PG is a protecting group).

Compound (7) can be converted to compound (3) of Formula I upon reaction with a halo-substituted thiazole or halo-substituted thiadiazole in the presence of a base catalyst or metal (e.g., copper or palladium) catalyst. Alternatively, compound (6) can be converted directly to a compound (3) of Formula I upon treatment with an amino-substituted thiazole or amino-substituted thiadiazole via base catalysis or via copper or palladium catalysis; i.e., the Buchwald reaction.

Scheme C

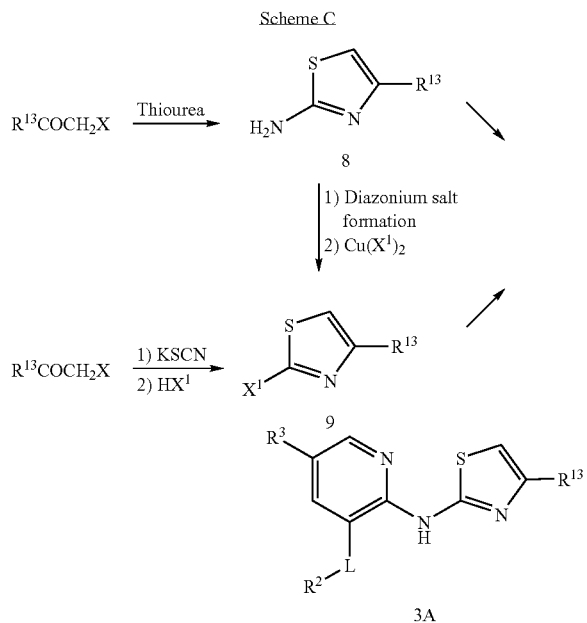

Scheme C shows a method of preparing 2-aminothiazole and 2-halothiazole intermediates (8) and (9), respectively, which are suitable for use in preparing compounds of Formula I as shown in Scheme B. According to Scheme C, α-haloketone $R^{13}COCH_2X$ can be treated with thiourea in the presence of a suitable base such as potassium carbonate or triethylamine in an appropriate solvent such as DMF or ethanol to afford aminothiazole (8). The aminothiazole (8) can be converted to a diazonium salt intermediate by numerous methods including, but not limited to, treatment with sodium nitrite in acid or isobutylnitrite. Treatment of the in situ diazonium salt with $Cu(X^1)_2$ ($X^1$=Cl or Br) or HBr affords the corresponding 2-halothiazole (9). Alternatively, using the Hantzsch synthetic method, the α-haloketone $R^{13}COCH_2X$ can be treated first with KSCN, then with FIX wherein X is Cl or Br, to provide the 2-halothiazole (9). The 2-halothiazole compounds (8) and (9) can be converted into compound (3A) by the methods shown in Scheme B.

Scheme D

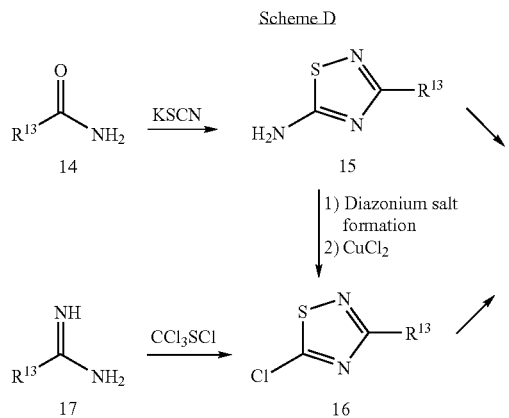

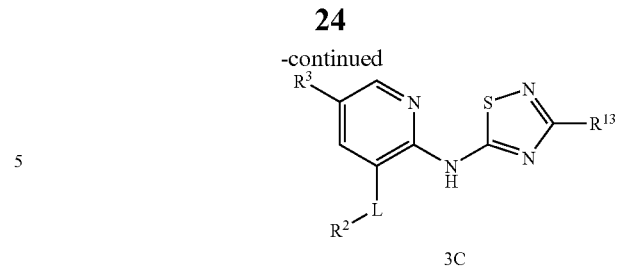

Scheme D shows a method of preparing 5-amino-1,2,4-thiadiazole and 5-chloro-1,2,4-thiadiazole intermediates (15) and (16), respectively, which are suitable for use in preparing compounds of Formula I as shown in Scheme B. According to Scheme D, primary amide (14) can be converted into 5-amino-1,2,4 thiadiazole (15) by heating with KSCN in an appropriate solvent such as methanol or ethanol (*Adv. Heterocycl. Chem.*, (1982) 32, 285). Formation of the diazonium salt of compound (15), followed by treatment of the in situ diazonium salt with $CuCl_2$ affords the corresponding 5-chloro-1,2,4-thiadiazole (16). The corresponding bromo derivative can also be synthesized through the use of $CuBr_2$. Alternatively, reaction of amidine (17) with perchloromethyl mercaptan affords 5-chloro-1,2,4-thiadiazole (16) (*Bioorg. Med. Chem.*, (2003) 11, 5529-5537). Intermediates (15) and (16) can be converted into compound (3C) of Formula I by the methods shown in Scheme B.

Scheme E

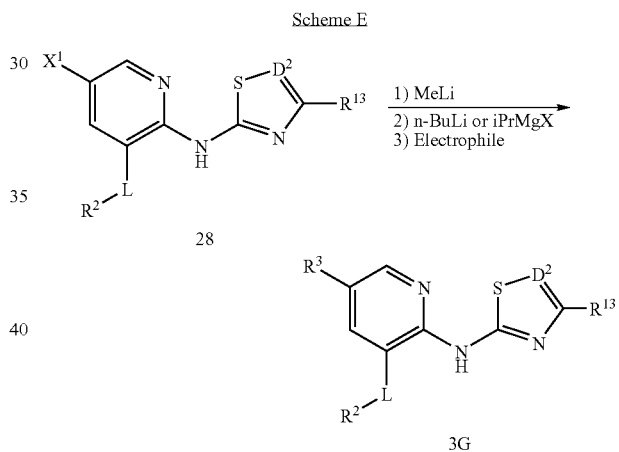

Scheme E shows an alternative method of preparing compound (3G) of Formula I. According to Scheme E, the halo-substituted heterocycle (28) (prepared by the method of Scheme A or B) wherein $X^1$ is Cl, Br or I, is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with an, electrophile to provide compound (3G).

Scheme F

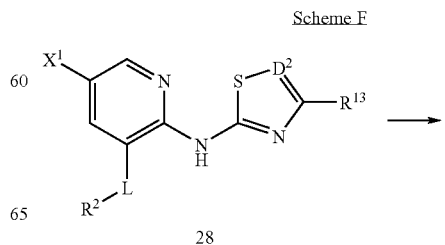

-continued

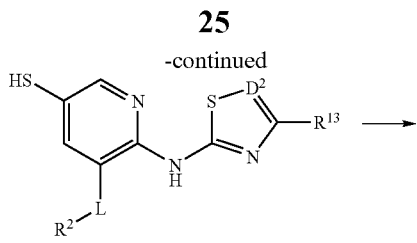

29

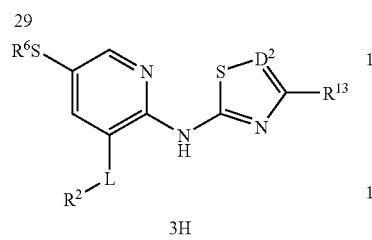

3H

Scheme F shows a method of preparing compounds (3H) of Formula I from a halo substituted heterocycle (28). According to Scheme F, the halo-substituted heterocycle (28), prepared by the method of Scheme A or B, can be converted to a thiol (29) via one of several procedures. According to one method, the halo-substituted heterocycle (28) is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with either elemental sulfur to form the corresponding mercapto-substituted compound (29). Alternatively, the halide (28) can be converted under Pd-mediated conditions to thiol (29) utilizing potassium triisopropylsilanethiolate (*Tetrahedron Letters* (1994) 3225-3226). The thiol can be reacted with a variety of electrophiles using standard reaction conditions to provide the corresponding ether (3H) of Formula I. Suitable electrophiles include, but are not limited to, activated heteroaryl halides such as, but not limited to, 2-fluorocyanobenzene, 4-fluorocyanobenzene, 2-fluoronitrobenzene, 4-fluoronitrobenzene, 2-chloro-4-nitropyridine, 2-halopyridine, 2-halopyrimidine, 4-halopyrimidine, aryl halides and heteroaryl halides.

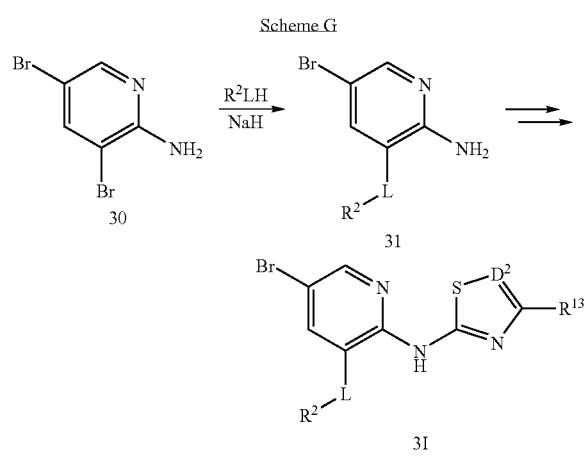

Scheme G shows a method of adding a linker L, wherein L is O, to a core heterocycle to provide a compound (3I) of Formula I wherein $R^3$ is Br. According to Scheme G, 2-amino-3,5-dibromopyrazine (30) is reacted with $R^2LH$, wherein L is O or S, in the presence of a suitable base such as $K_2CO_3$ or NaH in a suitable solvent such as DMF or ethanol to afford compound (31) regioselectively. Compound (31) can be converted to compound (3I) of Formula I by the method of Scheme A or B. Compound (3I) can be converted into additional 5-substituted compounds of Formula I by the methods shown in Scheme E or F.

Scheme H

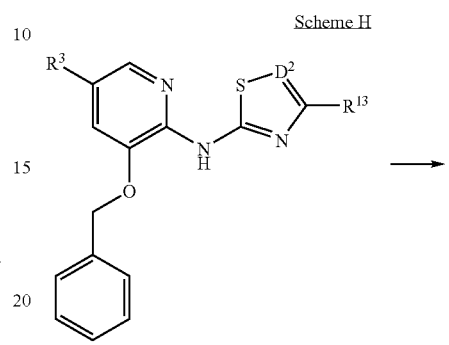

32

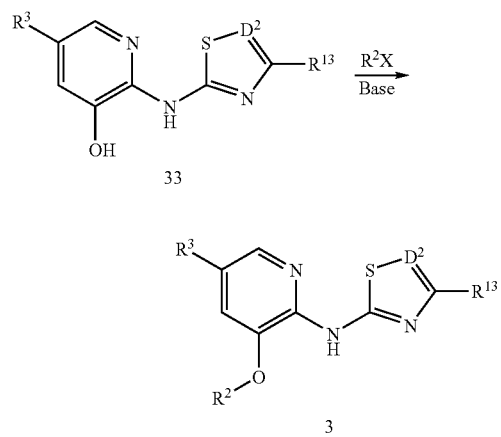

Scheme H shows an alternate method of adding the linker $OR^2$ to a core heterocycle to provide a compound (3) of Formula I. According to Scheme H, a benzyl ether (32), prepared by the method of Scheme A or B, can be converted to the hydroxyl substituted heterocycle (33), for example by hydrolysis with a strong acid (e.g., 6N HCl) or by hydrogenation (e.g., $H_2$ or ammonium formate in the presence of a metal catalyst). Alkylation of the hydroxylated heterocycle (33) with $R^2X$, wherein X=F, Cl, Br, I, or $NR_3$ (where R is $C_1$-$C_6$ alkyl) in the presence of a base such as, but not limited to, cesium carbonate, in a suitable solvent such as, but not limited to, DMF, or via copper or palladium catalysis (i.e., the Ullman reaction) affords compound (3) of Formula I.

Scheme I

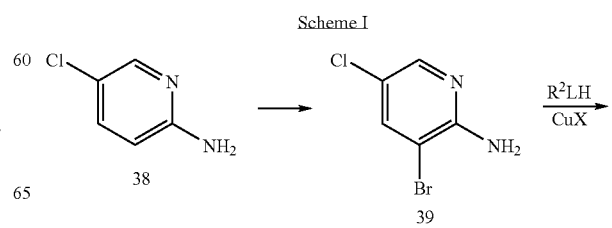

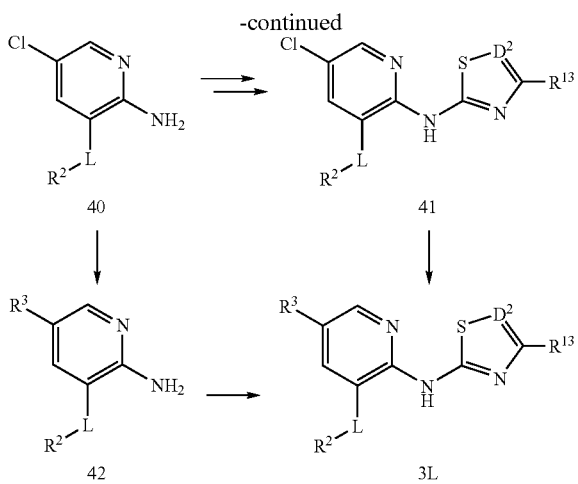

Scheme J shows an alternative method of preparing a compound (3L) of Formula I. According to Scheme J, reaction of compound (43) with R²LH (where L is O) in the presence of a suitable base such cesium carbonate or sodium hydride either with or without a metal catalyst (i.e.; Pd₂dba₃ or CuI) in DMSO or DMF affords compound (44) wherein L is O.

The 2-aminopyridine (44) is then regioselectively brominated with a suitable brominating agent such as NBS or bromine to provide compound (45). The brominated product (45) can be converted to compound (46) by the method of Scheme A or B. Compound (46) can be converted to 5-substituted compounds (3L) of Formula I by the method of Scheme E or F. Alternatively, the brominated 2-aminopyridine (45) can be converted to a 5-substituted compound (47) by the method of Scheme E or F, and then the thiazolyl or thiadiazolyl group can be added to compound (47) by the method of Scheme A or B to provide compound (3L).

Scheme I shows an alternative method of preparing a compound (3L) of Formula I. According to Scheme I, the 2-aminopyridine (38) is regioselectively brominated with a suitable brominating agent such as NBS or bromine to provide compound (39). The brominated compound can be converted to compound (40) upon reaction with R²LH (wherein L is O) in the presence of a suitable base such as cesium carbonate, sodium hydride or triethylamine in the presence of a metal catalyst (i.e.; CuI or Pd₂dba₃) in a suitable solvent such as DMSO or DMF. The chlorinated product (40) can be converted to compound (41) by the method of Scheme A or B. Compound (41) can be converted to a 5-substituted compound (3L) of Formula I by the method of Scheme E or F. Alternatively, the chlorinated 2-aminopyridine (40) can be converted to a 5-substituted compound (42) by the method of Scheme E or F, and then the thiazolyl or thiadiazolyl group can be added to compound (42) by the method of Scheme A or B to provide compound (3L).

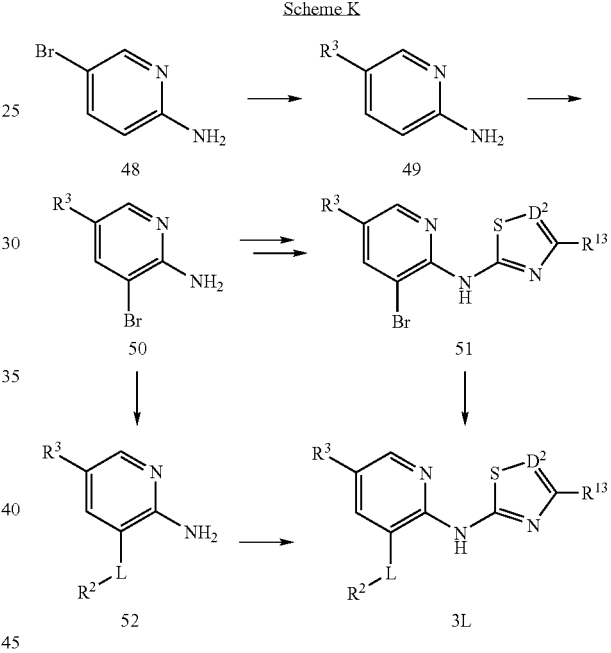

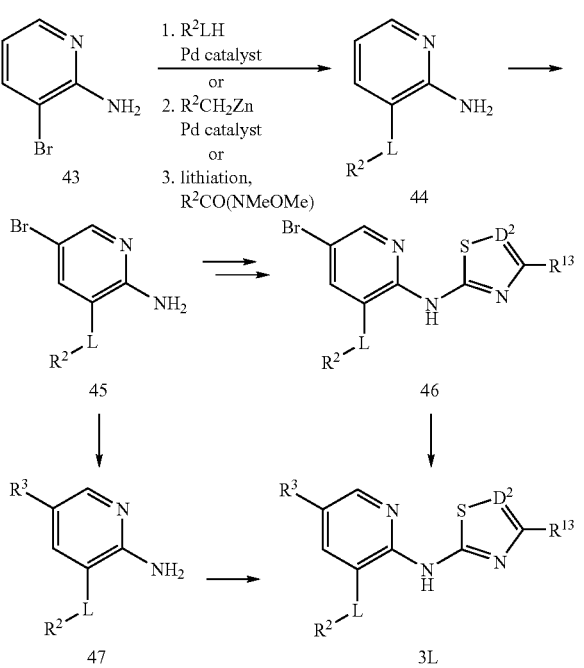

Scheme K shows an alternative method of preparing a compound (3L) of Formula I. According to Scheme K, reaction of compound (48) (which if not commercially available can be made from commercial aminopyridines via regioselective bromination) in the presence of a suitable base such cesium carbonate or sodium hydride and with or without a metal catalyst (e.g., Pd₂dba₃ or CuI) in DMSO or DMF affords compound (49) by a method such as: ipso replacement using R⁶SH; Buchwald thioether formation with R⁶SH, etc., according to procedures well known in the literature. The 2-aminopyridine (49) is then regioselectively brominated with a suitable brominating agent such as NBS or bromine to provide compound (50). The brominated product (50) can be converted to compound (51) by the method of Scheme A or B. Compound (51) can be converted to 5-substituted compounds (3L) of Formula I by Buchwald ether formation with R²OH. Alternatively, the brominated 2-aminopyridine (50) can first be converted to compound (52) by the Buchwald chemistry, and compound (52) can be converted to (3L) by the method of Scheme A or B.

Scheme L

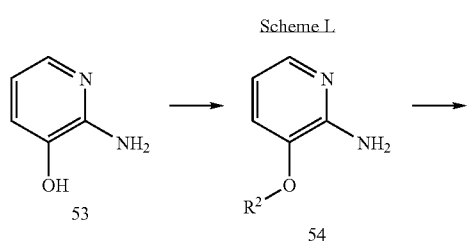

Scheme L shows an alternative method of preparing a compound (3L) of Formula I. Treatment of compound (53) with R2X in the presence of a suitable base such as cesium carbonate or sodium hydride, with or without a metal catalyst, affords compound 54. Subsequently, compound (54) can be regioselectively brominated to afford compound (55). This compound can be converted to compound (56) via the methods described in Schemes E or F. Compound (56) is then converted to compound (3L) via the procedures found in Schemes A or B. Alternatively, compound (55) can be converted to compound (57) via the procedures found in Schemes A or B, and then converted to compound (3L) via the procedures found in Schemes E or F.

Scheme M

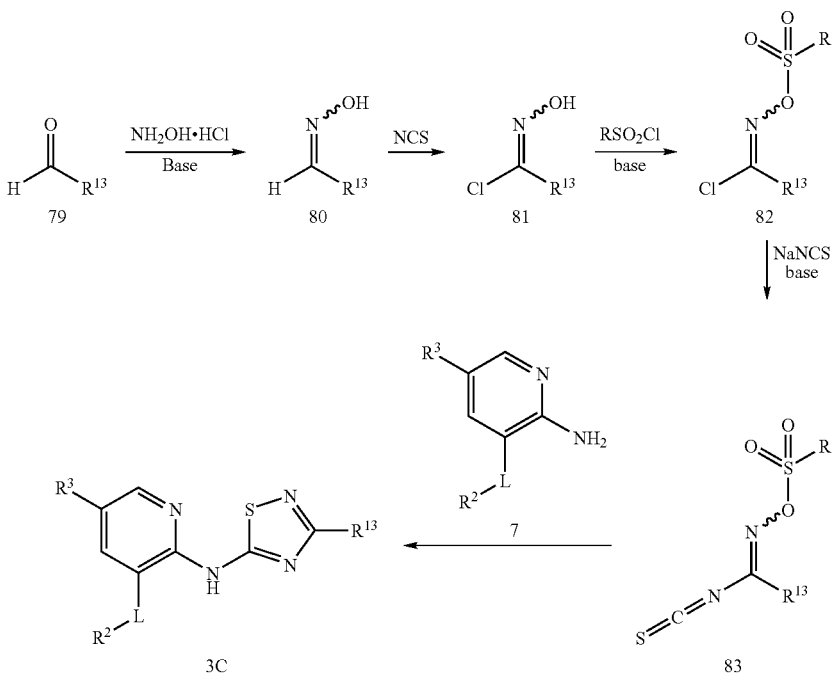

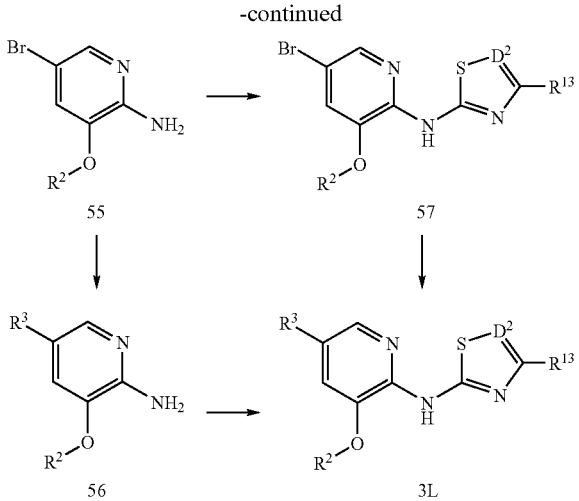

Scheme M shows an alternative method for producing compounds of the formula 3C wherein $D^2$ is N. Formation of oxime (80) from aldehyde (79) allows for the chlorination with N-chlorosuccinimide in a suitable solvent, such as DMF, to produce compound (81). Compound (81) is sulfonylated with a sulfonyl chloride having the formula R'SO$_2$Cl wherein R' is, $C_1$-$C_6$ alkyl (for example, methyl) or aryl optionally substituted with $C_1$-$C_6$ alkyl (for example, tolyl) in the presence of a base, such as but not limited to triethylamine, to afford compound (82) (See, for example, Gibbons, L. U.S. Pat. No. 3,983,246). Reaction of compound (82) with a thiocyanate salt, such as NaNCS, in a suitable solvent, such as acetonitrile, and in the presence of a base, such as but not limited to pyridine, affords the activated intermediate (83) (see, for example, Takeuchi, K., JP 2001081084). Intermediate (83) can be reacted in situ with an appropriate amino heterocycle (7) to afford compounds of the structure (3C) of Formula I.

Scheme N

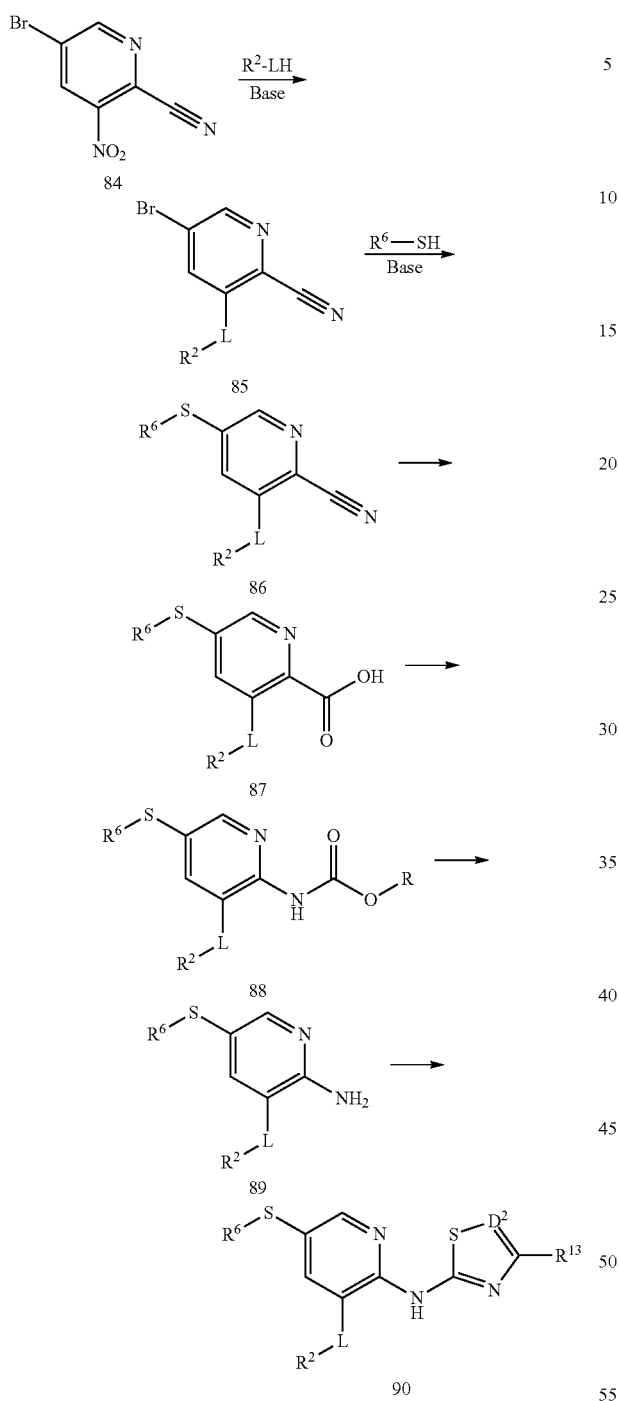

Scheme O the presence of an appropriate alcohol affords the carbamate (88). The carbamate can be removed using various conditions, depending on the alcohol used in the previous Step, to provide the 2-aminopyridine (89). Using procedures outlined in Schemes A or B, compounds (90) of the Formula I can be synthesized from compound (89).

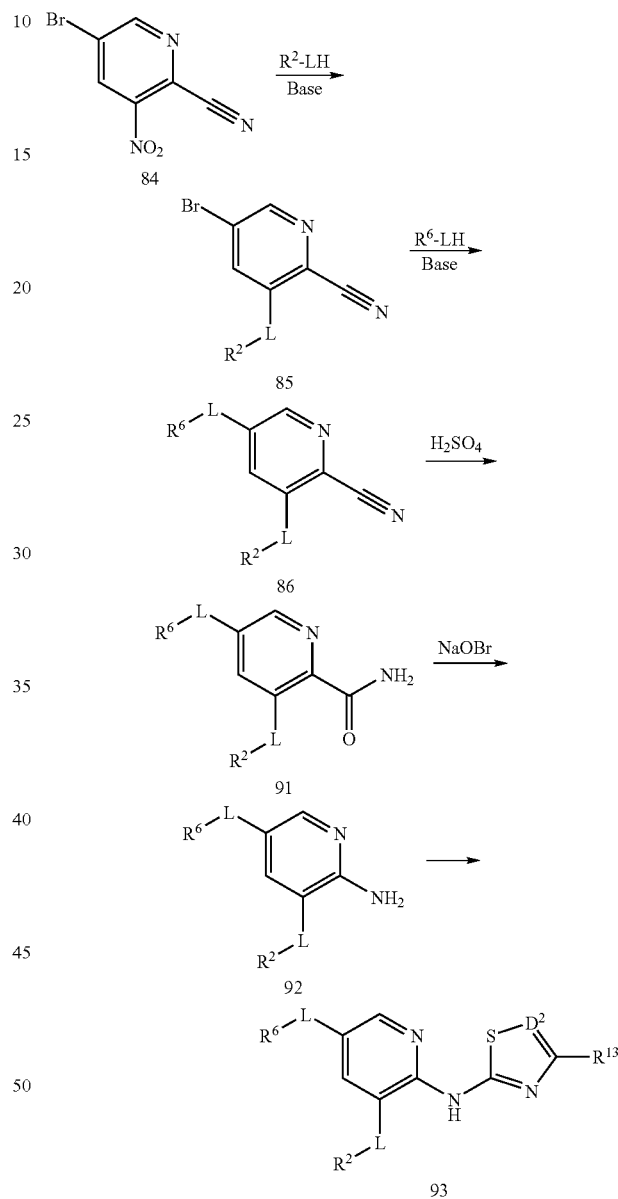

Scheme N shows an alternative method for the construction of compounds of Formula I. Starting from the commercially available 2-cyanopyridine (84), selective nucleophilic displacement can be achieved with compounds of the formula $R^2LH$ and an appropriate base, such as sodium hydride, in a suitable solvent, such as DMF to provide compound (85). Addition of a second nucleophile having the formula $R^6SH$, under similar conditions, affords the functionalized 2-cyanopyridine (86). Hydrolysis of the nitrile can occur under many conditions, with NaOH in aqueous ethanol being preferred, to afford the picolinate (87). Curtius rearrangement in Scheme O shows another alternative method for the construction of compounds of Formula I. Starting from the commercially available 5-bromo-3-nitropicolinonitrile (84), selective nucleophilic displacement can be achieved with compounds of the formula $R^2LH$ and an appropriate base, such as sodium hydride, in a suitable solvent, such as DMF to provide compound (85). Addition of a second nucleophile having the formula $R^6LH$, under similar conditions, affords the functionalized 2-cyanopyridine (86). Hydrolysis of the nitrile to the amide (91) can occur under standard conditions, such as with concentrated $H_2SO_4$. A Hofmann reaction to convert (91) to the aminopyridine (92) can occur under standard conditions, such as with NaOBr. Using procedures outlined in Schemes A, B or M, compounds (93) of the Formula I can be synthesized from compound (92).

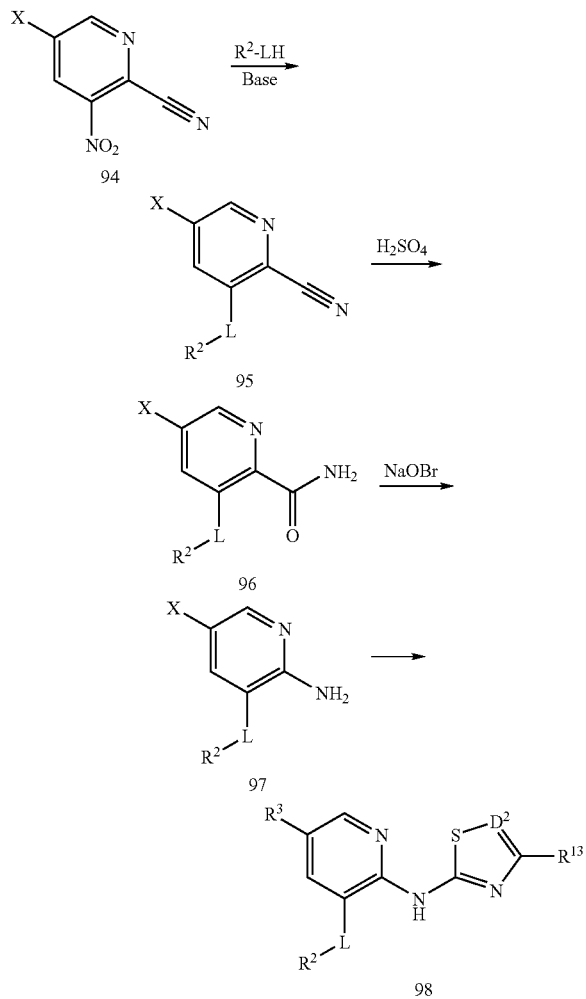

Scheme P shows an alternative method for the construction of compounds of Formula I. Starting from the commercially available substituted pyridine (94) in which X is Br or Cl, selective nucleophilic displacement can be achieved with compounds of the formula $R^2LH$ and an appropriate base, such as sodium hydride, in a suitable solvent, such as DMF to provide compound (95). Hydrolysis of the nitrile to the amide (96) can occur under standard conditions, such as with concentrated $H_2SO_4$. A Hofmann reaction to convert (96) to the aminopyridine (97) can occur under standard conditions, such as with NaOBr. Using procedures outlined in Schemes A, B, E, F or M, compounds (97) of the Formula I can be synthesized from compound (98).

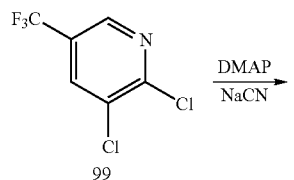

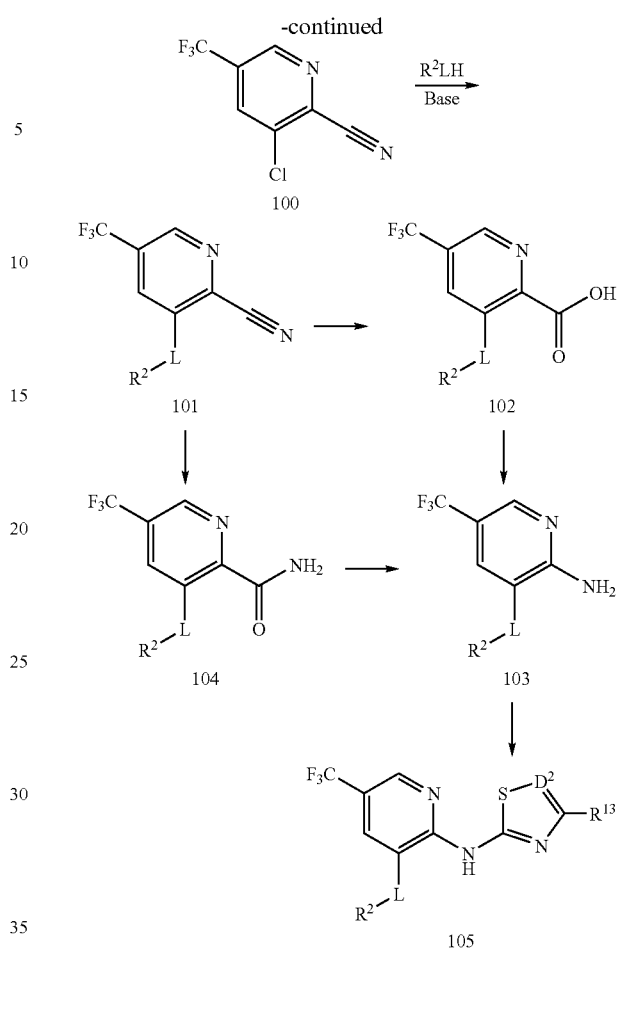

Scheme Q shows a method of synthesizing compounds of Formula I where $R^3$ is $CF_3$ (105). The 2,3-dichloro-5-(trifluoromethyl)pyridine (99) is reacted with DMAP, followed by a cyanide source, such as NaCN, to provide the cyanopyridine (100). Nucleophilic displacement of the chlorine with compounds of the formula $R^2LH$ and an appropriate base, such as sodium hydride, in a suitable solvent, such as DMF provides compound (101). Utilizing the routes in Schemes N or M the cyanopyridine (101) can be converted into the aminopyridine (103). Using procedures outlined in Schemes A, B, E, F or M, compounds (103) of the Formula I can be synthesized from compound (103).

Accordingly, another embodiment of the invention provides a method for preparing a compound of Formula I or a salt thereof, comprising:

(a) reacting a corresponding compound of the formula (II)

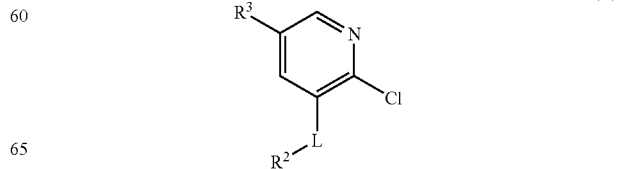

with a compound of the formula (III)

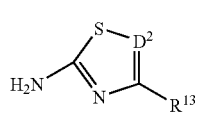

in the presence of a base catalyst or metal catalyst; or (b) reacting a corresponding compound of the formula (IV)

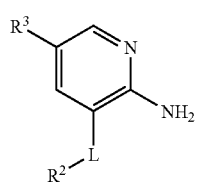

with a compound of the formula (V)

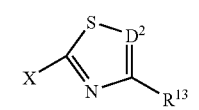

wherein X is a leaving atom or group in the presence of a base catalyst or metal catalyst; or (c) for a compound of Formula I wherein $D^2$ is CH, reacting a corresponding compound of the formula (VI)

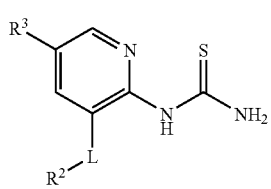

with a compound of the formula $R^{13}COCH_2X$, wherein X is a leaving group or atom in the presence of a base; or (d) for a compound of Formula I wherein $D^2$ is N, reacting a corresponding compound of the formula (VII)

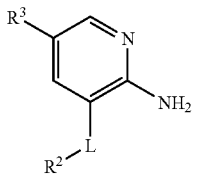

with a compound having the formula (VIII)

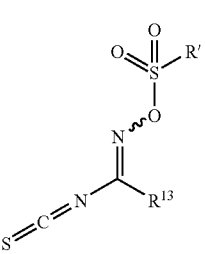

where R' is C1-C6 alkyl or aryl optionally substituted with C1-C6 alkyl, in the presence of a base; or (e) for compounds of Formula I where $R^3$ is $SR^6$, reacting a corresponding compound having the formula (IX)

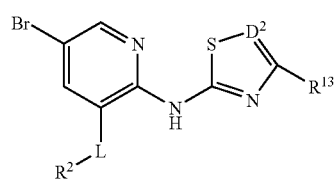

with a compound having the formula $R^6SH$ in the presence of a suitable base; or (f) reacting a corresponding compound having the formula (X)

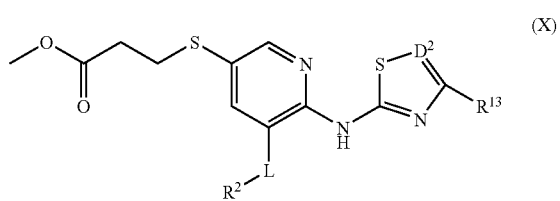

with a compound having the formula $R^6X$ wherein X is a leaving atom or group in the presence of a suitable base; or (g) reacting a corresponding compound having the formula (XI)

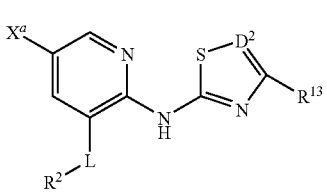

wherein $X^a$ is a leaving atom or group, with a compound having the formula $R^3$—$X^b$ wherein $X^b$ is a leaving atom or a leaving group, in the presence of a suitable base; or (h) reacting a corresponding compound having the formula (XII)

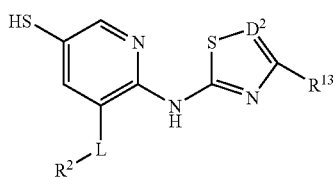

with a compound having the formula $R^6$—$X^c$ wherein $X^c$ is a leaving atom or group in the presence of a suitable base; or (i) reacting a corresponding compound having the formula (XIII)

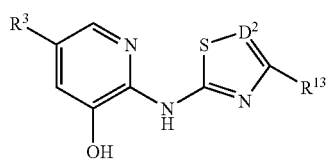

with a compound having the formula $R^2$—$X^d$, wherein $X^d$ is a leaving atom or group in the presence of a base or in the presence of a copper or palladium catalyst; or (j) reacting a corresponding compound having the formula (XIV)

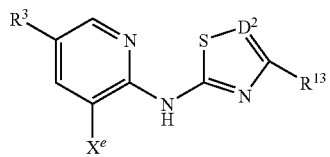

wherein $X^e$ is a leaving group or atom, with a compound having the formula $R^2LH$ wherein L is O or S, in the presence of a palladium catalyst and a suitable base; or (k) for a compound of Formula I wherein A is —C(═O)($C_1$-$C_6$ alkyl), reacting a corresponding compound having the formula (XV):

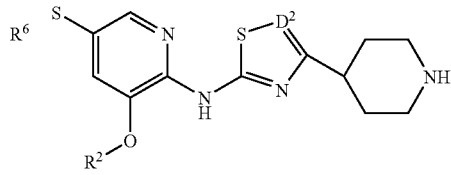

with a $C_1$-$C_6$ alkyl anhydride in the presence of a base; or (l) for a compound of Formula I wherein A is C(═O)$NH_2$, reacting a corresponding compound having Formula (XV) with potassium cyanate in the presence of a tertiary amine base; or (m) for a compound of Formula I wherein A is C(═O)$NMe_2$, reacting a corresponding compound having formula (XV) with dimethylcarbamic chloride in the presence of a tertiary amine base; or (n) for a compound of formula I wherein A is C(═O)$CH_2NMe_2$, reacting a compound having formula (XV) with 2-(dimethylamino)acetyl chloride hydrochloride in the presence of a tertiary amine base; or (o) for a compound of formula I wherein A is $SO_2Me$, reacting a compound having formula (XV) with methanesulfonyl chloride in the presence of a tertiary amine base; or (p) for a compound of formula I wherein A is $SO_2NH_2$, reacting a compound having formula (XV) with dimethylsulfamoyl chloride in the presence of a tertiary amine base;

(q) for a compound of Formula I wherein A is —C(═O)($C_1$-$C_6$ alkyl), reacting a corresponding compound having the formula (XVa) or (XVb)

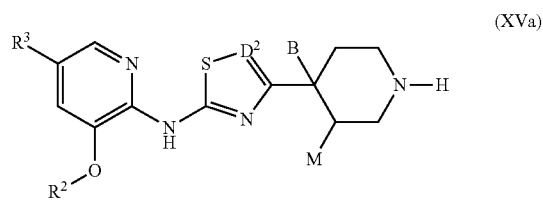

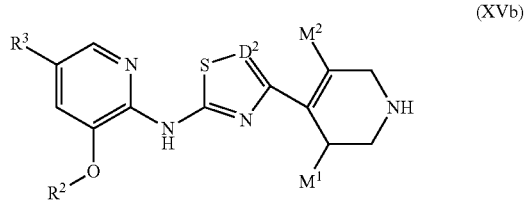

with a $C_1$-$C_6$ alkyl anhydride in the presence of a base; or (r) for a compound of Formula I wherein A is C(═O)$NH_2$, reacting a corresponding compound having Formula (XVa) or (XVb) with potassium cyanate in the presence of a tertiary amine base; or (s) for a compound of Formula I wherein A is C(═O)$NMe_2$, reacting a corresponding compound having formula (XVa) or (XVb) with dimethylcarbamic chloride in the presence of a tertiary amine base; or (t) for a compound of Formula I wherein A is C(═O)$CH_2NMe_2$, reacting a compound having formula (XVa) or (XVb) with 2-(dimethylamino)acetyl chloride hydrochloride in the presence of a tertiary amine base; or (u) for a compound of Formula I wherein A is $SO_2Me$, reacting a compound having formula (XVa) or (XVb) with methanesulfonyl chloride in the presence of a tertiary amine base; or (v) for a compound of Formula I wherein A is $SO_2NH_2$, reacting a compound having formula (XVa) or (XVb) with dimethylsulfamoyl chloride in the presence of a tertiary amine base;

(w) for a compound of Formula I wherein $R^3$ is $SR^6$ and $R^6$ is $CH_2C(CH_3)_2OH$, reacting a corresponding compound having the formula XVI

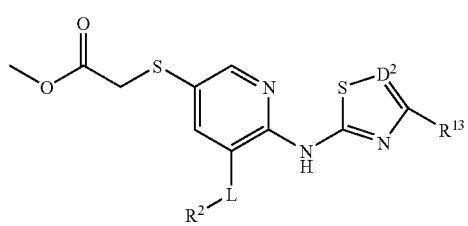

with a methyl magnesium halide; or (x) for a compound of Formula I wherein $R^3$ is $SR^6$ and $R^6$ is $CH_2CH_2OH$, reducing a corresponding compound having the formula XVI; or (y) for a compound having the Formula I wherein A is $C(=O)CH_2OH$, hydrolyzing a corresponding compound wherein A is $C(=O)CH_2OC(=O)$alkyl; or (z) for a compound having the Formula I wherein L is O, reacting a corresponding compound having the formula (XIII)

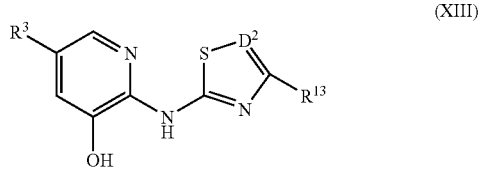

(XIII)

with a compound having the formula HO—$R^2$ wherein $R^2$ is as defined for Formula I, in the presence of a coupling reagent; and removing any protecting group or groups and, if desired, forming a salt.

Referring to method (b), X can be a leaving atom (for example, Cl, Br) or a leaving group (e.g., OTs or OTf).

Referring to method (c), X can be a leaving group (such as OTs or $NR_3$ wherein R is $C_1$-$C_6$ alkyl) or a leaving atom (for example Cl, Br, or I).

Referring to method (e), a suitable base may be, for example, an alkyl lithium base such as methyl lithium, butyl lithium, or a mixture thereof.

Referring to method (f), X can be a leaving atom such as a halogen (e.g., F, Cl or Br) or a leaving group such as a sulfonate (e.g., OMs or OTs). A suitable base may be, for example, an alkali metal alkoxide such as potassium t-butoxide.

Referring to method (g), $X^a$ may be a leaving atom such as a halogen, such as Br, Cl or I, and $X^b$ may be a leaving atom such as a halogen (e.g., F, Cl or Br) or a leaving group such as a sulfonate (e.g., OMs or OTs). A suitable base may be, for example, an alkyl lithium such as methyl lithium, butyl lithium, or a combination thereof.

Referring to method (h), $X^c$ may be a leaving atom such as a halogen (e.g., F, Cl or Br) or a leaving group such as a sulfonate (e.g., OMs or OTs).

Referring to method (i), $X^d$ may be a leaving group or atom e.g., a halogen such as Cl or Br; or a triflate or tosylate group. Suitable bases include alkali metal carbonates such as $CsCO_3$.

Referring to method (j), $X^e$ may be a leaving group such as a sulfonate (e.g., OMs or OTs), or a leaving atom such as a halogen (e.g., Br, I). Suitable palladium catalysts include $Pd(OAc)_2$ and a suitable ligand. Suitable bases include alkali metal carbonates, hydrides, or alkoxides, such as $K_2CO_3$, NaH, NaOt-Bu. Suitable solvents include toluene. The reaction is conveniently performed at temperatures ranging from ambient temperature to 100° C.

Referring to methods (k)-(v), suitable bases include a tertiary amine base, for example, pyridine or triethylamine.

Referring to method (w), suitable methyl magnesium halides include methyl magnesium bromide.

Referring to method (x), suitable reducing agents include lithium borohydride, lithium aluminum hydride, or a mixture thereof.

Referring to method (y), the ester is suitably hydrolyzed under basic conditions. Suitable bases include metal carbonates such as potassium carbonate.

Referring to method (z), the coupling reagent may be any suitable reagent(s) known to those skilled in the art, for example, diisopropyl azodicarboxylate (DIAD) or diethylazodicarboxylate (DEAD) in combination with $PPh_3$.

The compounds of Formulas (IX), (X), (XI), (XII), (XIII), (XIV), (XV), (XVa) and (XVb) are also believed to be novel and are provided as further aspects of this invention.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the present invention can be used as prophylactics or therapeutic agents for treating diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed below. Furthermore, the compounds of the present invention can be also used to prevent the progression of the borderline type, impaired glucose tolerance, IFG (impaired fasting glucose) or IFG (impaired fasting glycemia) to diabetes mellitus.

Compounds of this invention can further be used as prophylactics or therapeutic agents for treating hyperglycemia, hypertention, and cognitive impairment.

Accordingly, another aspect of the invention provides methods of treating or preventing diseases or conditions described herein by administering to a mammal, such as a human, a therapeutically effective amount of a compound of Formula I.

In particular, the invention provides a method of treating diseases or disorders mediated by deficient levels of glucokinase activity or which can be treated by activating glucokinase, comprising administering to said mammal a therapeutically effective amount of a compound of formula (I).

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "mammal" refers to a warm-blooded animal that has or is at risk of developing a disease described herein and includes, but is not limited to, guinea pigs, dogs, cats, rats, mice, hamsters, and primates, including humans.

In certain embodiments, the methods of this invention are useful for treating diabetes mellitus. Diabetes mellitus is a condition where the fasting plasma glucose level (glucose concentration in venous plasma) is greater than or equal to 126 mg/dL (tested on two occasions) and the 2-hour plasma glucose level of a 75 g oral glucose tolerance test (OGTT) is greater than or equal to 200 mg/dL. Additional classic symptoms include polydipsia, polyphagia and polyuria.

In certain embodiments, the methods of this invention are useful for treating the syndrome of impaired glucose tolerance (IGT). IGT is diagnosed by the presentation of a fasting plasma glucose level of less than 126 mg/dL and a 2-hour post-oral glucose challenge lever greater than 140 mg/dL.

The compounds of the present invention can be also used as prophylactics or therapeutic agents of diabetic complications such as, but not limited to, neuropathy, nephropathy, retinopathy, cataract, macroangiopathy, osteopenia, diabetic hyperosmolar coma), infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance, etc.

The compounds of the present invention can be also used as prophylactics or therapeutic agents in the treatment of diseases and disorders such as, but not limited to, obesity, metabolic syndrome (syndrome X), hyperinsulinemia, hyperinsulinemia-induced sensory disorder, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia), low HDL levels, high LDL levels, atherosclerosis and its sequelae, vascular restenosis, neurodegenerative disease, depression, CNS disorders, liver steatosis, osteoporosis, hypertension, renal diseases (e.g., diabetic nephropathy, glomerular nephritis, glomerulosclerosis, nephrotic syndrome, hypertensive nephrosclerosis, terminal renal disorder etc.), myocardiac infarction, angina pectoris, and cerebrovascular disease (e.g., cerebral infarction, cerebral apoplexy).

The compounds of the present invention can be also used as prophylactics or therapeutic agents in the treatment of diseases and disorders such as, but not limited to, osteoporosis, fatty liver, hypertension, insulin resistant syndrome, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, inflammatory colitis, ulcerative colitis), pancreatitis, visceral obesity syndrome, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), polycystic ovary syndrome, muscular dystrophy, tumor (e.g., leukemia, breast cancer, prostate cancer, skin cancer etc.), irritable bowel syndrome, acute or chronic diarrhea, spondylitis deformans, osteoarthritis, remission of swelling, neuralgia, pharyngolaryngitis, cystitis, SIDS, and the like.

The compounds of the present invention can be used in combination with one or more additional drugs, for example a compound that works by the same or a different mechanism of action, such as insulin preparations, agents for improving insulin resistance, alpha-glucosidase inhibitors, biguanides, insulin secretagogues, dipeptidylpeptidase IV (DPP IV) inhibitors, beta-3 agonists, amylin agonists, phosphotyrosine phosphatase inhibitors, gluconeogenesis inhibitors, sodium-glucose cotransporter inhibitors, known therapeutic agents for diabetic complications, antihyperlipidemic agents, hypotensive agents, antiobesity agents The compounds of the invention may be administered by any convenient route, e.g. into the gastrointestinal tract (e.g. rectally or orally), the nose, lungs, musculature or vasculature or transderrnally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

This invention also provides the use of a compound of Formula I in the treatment of diseases or disorders mediated by deficient levels of glucokinase activity or which can be treated by activating glucokinase.

An additional aspect of the invention is the use of a compound of Formula I in the preparation of a medicament for the treatment or prevention of diseases or disorders mediated by deficient levels of glucokinase activity or which can be treated by activating glucokinase.

EXAMPLES

Compounds of this invention include compounds of the Examples described below with the exception of compounds labeled as "representative examples". The representative examples were found to be weakly active in the assays described herein, and are provided to illustrate synthetic routes to compounds of the invention or to describe intermediates useful in the synthesis of compounds of this invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane ($CH_2Cl_2$, methylene chloride), toluene, and dioxane were purchased from Aldrich in Sure seal bottles and used as received.

The reactions set forth below were done generally under a positive pressure of nitrogen or argon or with a drying tube

Example 1

1-(4-(2-(5-bromo-3-phenoxypyridin-2-ylamino)thiazol-4-yl)piperidin-1-yl)ethanone hydrochloride

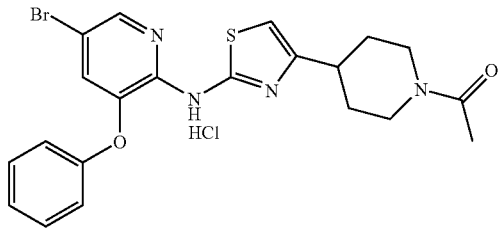 [SMILES: CC(=O)N1CCC(c2csc(Nc3ncc(Br)cc3Oc3ccccc3)n2)CC1 ; Cl]

Step A: An nitrogen-purged 22 L 5-necked flask was charged with DMF (9 L) followed by slow addition of 2-aminopyridin-3-ol (250.0 g, 2270 mmol) and stirred with mechanical overhead agitator at ambient temperature for 30 minutes to dissolve material. 60% Sodium hydride (87.17 g, 2180 mmol) was added in portions with vigorous stirring and a nitrogen sweep of the reaction vessel. The pot temperature rose from 16° C. to 25° C. during the NaH addition. After the addition was complete, the reaction was stirred at ambient temperature for 60 minutes to ensure all NaH was consumed. 2,4-Dibromo-1-fluorobenzene (225.3 mL, 1816 mmol) was added and heated to 110° C. under nitrogen for 24 hours. The reaction was cooled to 60° C. and transferred to a 20 L flask and the majority of the DMF removed. The resultant sludge was diluted with 1N NaOH (8 L) and EtOAc (8 L) and the mixture was passed through a plug of celite and washed with EtOAc. The layers were separated and the aqueous was extracted with EtOAc (4 L). The combined organic layers were washed with 1 N NaOH (4 L) and 50% saturated brine (4 L), water (2 L) and concentrated until solids started to form. Hexanes (4 L) were added slowly and the mixture was concentrated to around 2 L volume. Hexanes (4 L) were added and the mixture was stirred for 1 hour to allow to cool to ambient temperature. The resulting slurry was filtered, dried on the filter and then dried under high vacuum overnight to afford 3-(2,4-dibromophenoxy)pyridin-2-amine (277.3 g, 44.4% yield).

Step B: A 2 L Parr bottle was charged with sodium acetate (28.6 g, 349 mmol), 10% Pd(OH)$_2$/C (5.0 g, 7.12 mmol) and 3-(2,4-dibromophenoxy)pyridin-2-amine (60 g, 174 mmol) in 1 L EtOH and placed under 35 psi hydrogen for 18 hours. The reaction was filtered through a plug of celite and then concentrated. The residue was redissolved in CH$_2$Cl$_2$ and washed with aqueous sodium bicarbonate. The organic layer was dried over sodium sulfate, filtered and concentrated. The dark residue was dissolved in EtOAc and charcoal added. The mixture was stirred for 30 minutes then filtered though a plug of celite. The crude material was triturated with 4:1 (EtOAc and hexanes) to afford 3-phenoxypyridin-2-amine (23.2 g, 71.4% yield).

Step C: A 3 L flask was charged with 3-phenoxypyridin-2-amine (63.6 g, 342 mmol) and CHCl$_3$ (1500 mL). The reaction was cooled to 0° C. and bromine (21.0 mL, 410 mmol) was added dropwise. The reaction was stirred for 1 hour. Another 1 mL of bromine was added and the reaction was poured into saturated aqueous NaHCO$_3$ (1500 mL) and extracted with CH$_2$Cl$_2$. The organic layer was dried with sodium sulfate and 25 g charcoal. The mixture was filtered through Celite and concentrated in vacuo. The residue was dissolved in CH$_2$Cl$_2$ and passed through a plug of silica (1 L) eluting with 30% EtOAc/Hexanes to afford 5-bromo-3-phenoxypyridin-2-amine (64.02 g, 70.70% yield).

Step D: A 2 L flask was charged with 5-bromo-3-phenoxypyridin-2-amine (64.0 g, 241.4 mmol) and benzoyl isothiocyanate (35.82 mL, 265.6 mmol) in THF (600 mL) and stirred at ambient temperature overnight, then concentrated to about 50 mL. A mixture of Hexanes:EtOAc (9:1) (900 mL) was added with vigorous stirring. The resulting suspension was filtered and the solid was washed with hexanes then dried to afford 1-benzoyl-3-(5-bromo-3-phenoxypyridin-2-yl)thiourea (94.32 g, 91.2% yield) as a yellow solid.

Step E: A 2 L flask was charged with 1-benzoyl-3-(5-bromo-3-phenoxypyridin-2-yl)thiourea (94.3 g, 220 mmol) and THF (900 mL). 2M NaOH (330 mL, 660 mmol) was added and the reaction was heated at reflux overnight. The reaction was cooled to ambient temperature and 300 mL water was added slowly and then the THF was removed in vacuo to afford an aqueous slurry which was filtered, washed with water and dried to give 1-(5-bromo-3-phenoxypyridin-2-yl)thiourea (66.35 g, 93% yield) as a light tan solid.

Step F: A 25 mL flask was charged with 1-(5-bromo-3-phenoxypyridin-2-yl)thiourea (500 mg, 1.54 mmol), tert-butyl 4-(2-bromoacetyl)piperidine-1-carboxylate (661 mg, 2.16 mmol), triethylamine (0.376 mL, 2.70 mmol), and THF (10 mL). The reaction was heated to 60° C. for 3 hours. The reaction was cooled to ambient temperature and poured into water and extracted with EtOAc. The organic layer was dried with sodium sulfate, filtered and concentrated in vacuo. The residue was purified on silica (30% EtOAc in hexanes). The isolated material was dissolved in CH$_2$Cl$_2$:MeOH (1:1) and 4N HCl in dioxane added. The reaction was concentrated to afford 5-bromo-3-phenoxy-N-(4-(piperidin-4-yl)thiazol-2-yl)pyridin-2-amine dihydrochloride (650 mg, 83.6% yield) as a pale yellow solid.

Step G: A 20 mL vial was charged with 5-bromo-3-phenoxy-N-(4-(piperidin-4-yl)thiazol-2-yl)pyridin-2-amine dihydrochloride (80 mg, 0.159 mmol), triethylamine (0.088 mL, 0.64 mmol) and THF (2 mL). Acetic anhydride (0.015 mL, 0.16 mmol) was added and stirred at ambient temperature for 30 minutes. The reaction was poured into saturated aqueous NaHCO$_3$ and extract with EtOAc (2×20 mL). The organic layer was dried with sodium sulfate, filtered and concentrated in vacuo. The residue was purified on silica gel (5% methanol in EtOAc) to afford the title compound (47.6 mg, 58.8% yield) as a white solid after HCl salt formation. $^1$H NMR (d$_6$-DMSO) δ 11.00 (bs, 1H), 8.23 (d, 1H), 7.44 (m, 2H), 7.40 (d, 1H), 7.21 (t, 1H), 7.11 (d, 2H), 6.70 (s, 1H), 4.41 (d, 1H), 3.12 (m, 1H), 2.83 (tt, 1H), 2.62 (td, 1H), 2.50 (m, 1H), 2.00 (s, 3H), 1.93 (m, 2H), 1.55 (qd, 1H), 1.42 (qd, 1H). Mass spectrum (apci) m/z=475.2 (M+H—HCl).

Example 2

1-(4-(2-(5-bromo-3-(phenylthio)pyridin-2-ylamino)thiazol-4-yl)piperidin-1-yl)ethanone

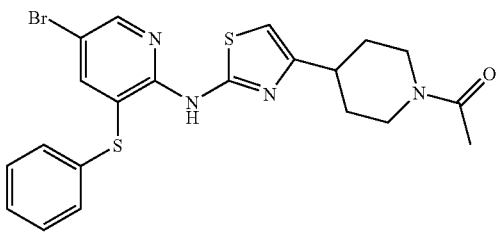 [SMILES: CC(=O)N1CCC(c2nsc(Nc3ncc(Br)cc3Oc3ccccc3)n2)CC1]

Step A: Preparation of 1-acetyl-N-methoxy-N-methylpiperidine-4-carboxamide. To a solution of 1-acetylpiperidine-4-carboxylic acid (58.50 g, 342 mmol) in dichloromethane (700 mL) was added di(1H-imidazol-1-yl)methanone (58.18 g, 359 mmol). After the addition the mixture was agitated for two hours and N-methoxymethanamine hydrochloride (35.00 g, 359 mmol) was added at once. The mixture was agitated overnight at ambient temperature and 4M HCl in dioxane (75 mL) was added slowly. The slurry was agitated for 30 minutes and then filtered. Filtrate was washed twice with sodium bicarbonate solution, dried and concentrated in vacuo to give the title compound (59.10 g, 80.72% yield).

Step B: Preparation of 1,1'-(piperidine-1,4-diyl)diethanone. In a 1000 mL flask, 1-acetyl-N-methoxy-N-methylpiperidine-4-carboxamide (59.10 g, 276 mmol) was dissolved in THF (800 mL) and cooled to 0° C. Methylmagnesium bromide (110.3 mL, 331 mmol) (3.0M in diethyl ether) was added slowly and the resulting white slurry was agitated for 1 hour. The reaction was quenched with 300 mL of 2M HCl and the solvent was evaporated. The resulting aqueous slurry was filtered and the solids were washed with water and small amount of ether to provide the title compound (38.4 g, 82.2% yield).

Step C: Preparation of 1-(1-acetylpiperidin-4-yl)-2-bromoethanone. In a 1000 mL flask, 1,1'-(piperidine-1,4-diyl)diethanone (38.0 g, 225 mmol) was dissolved in methanol (700 mL) and bromine (12.1 mL, 236 mmol) was added. After agitating for 3 hours the solvent was removed in vacuo. The resulting solid was washed with ethyl acetate, then distributed between ethyl acetate and sodium carbonate. The organic phase was separated, washed with brine, dried and evaporated to give the title compound.

Step D: Preparation of 2-nitro-3-(phenylthio)pyridine: 3-chloro-2-nitropyridine (30.6 g, 193 mmol) was dissolved in DMSO (200 mL). Benzenethiol (20.7 mL, 203 mmol) was added followed by cesium carbonate (69.3 g, 212 mmol) and stirred at ambient temperature for 1.5 hours. The solution was diluted with water (750 mL) and the resultant solids filtered. The crude material was recrystallized from EtOAc (400 ml) and with adding hexanes (1 L) to give an A-crop of 23.5 g. The filtrate was concentrated and recrystallized from EtOAc/hexanes to give 7.87 g. The solids were dried on high vacuum to provide the title compound (31.38 g, 69.8% yield).

Step E: Preparation of 5-bromo-3-(phenylthio)pyridin-2-amine: A 500 mL flask was charged with 2-nitro-3-(phenylthio)pyridine (16.3 g, 70.2 mmol) and AcOH (250 mL) and cooled in a water bath. Zinc (22.9 g, 351 mmol) was slowly added and stirred for 5 minutes. The reaction was filtered through celite and the cake washed with CH$_2$Cl$_2$. The CH$_2$Cl$_2$ was removed in vacuo and solution reacted with slow addition of bromine (3.6 mL, 70.2 mmol). After 10 minutes, the HOAc was removed in vacuo and partitioned between EtOAc and saturated aqueous sodium bicarbonate. The organic layer was dried with sodium sulfate, filtered and concentrated in vacuo. The residue was purified on silica gel (1.5 L SiO$_2$ and 30% EtOAc in hexanes) to afford the title compound (18.2 g, 92.21% yield).

Step F: Preparation of 1-benzoyl-3-(5-bromo-3-(phenylthio)pyridin-2-yl)thiourea: 5-Bromo-3-(phenylthio)pyridin-2-amine (17 g, 60.5 mmol), benzoyl isothiocyanate (9.79 mL, 72.6 mmol), and THF (300 mL) were stirred at 40° C. overnight. The THF was concentrated to ~1/2 volume and 9:1 hexanes:EtOAc (500 mL) added and precipitate filtered to afford the title compound (25.7 g, 95.7% yield).

Step G: Preparation of 1-(5-bromo-3-(phenylthio)pyridin-2-yl)thiourea: 1-Benzoyl-3-(5-bromo-3-(phenylthio)pyridin-2-yl)thiourea (25.7 g, 57.8 mmol) and MeOH (250 mL). Sodium hydroxide (38.6 mL, 116 mmol) was added and stirred at ambient temperature for 8 hours. The reaction was diluted with water (250 mL), filtered and washed with water. The precipitate was dried in vacuum oven to afford the title compound (19.0 g, 96.5% yield).

Step H: Preparation of 1-(4-(2-(5-bromo-3-(phenylthio)pyridin-2-ylamino)thiazol-4-yl)piperidin-1-yl)ethanone. Prepared according to Example 1, Step F, using 1-(1-acetylpiperidin-4-yl)-2-bromoethanone. $^1$H NMR (CDCl$_3$) δ 1.58-1.64 (in, 2H), 1.99-2.11 (m, 5H), 2.64-2.86 (m, 2H), 3.16 (t, 1H), 3.88 (d, 1H), 4.68 (d, 1H), 6.44 (s, 1H), 7.18-7.32 (m, 5H), 7.92 (s, 1H), 8.23 (s, 1H), 8.50 (s, 1H).

Example 3

1-(4-(2-(3-phenoxy-5-(thieno[3,2-b]pyridin-7-ylthio)pyridin-2-ylamino)thiazol-4-yl)piperidin-1-yl)ethanone dihydrochloride

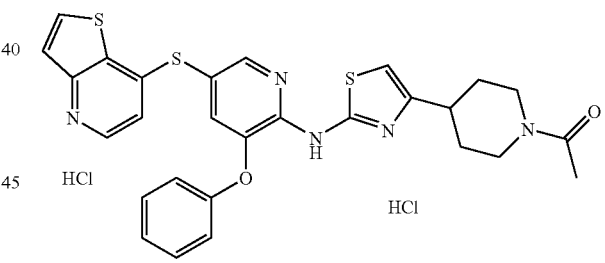

Step A: 1-(5-bromo-3-phenoxypyridin-2-yl)thiourea (Example 1, Step E; 30.0 g, 92.5 mmol) and 1-(1-acetylpiperidin-4-yl)-2-bromoethanone (Example 2, Step C, 32.1 g, 130 mmol) were suspended in ethanol (400 mL) and DIEA (48.3 mL, 278 mmol) was added. The resulting mixture was heated to 60° C. for 4 hours and then at ambient temperature overnight. The reaction was concentrated to dryness, dissolved in CH$_2$Cl$_2$ and washed with saturated aqueous sodium bicarbonate, water, dried over Na$_2$SO$_4$, filtered and concentrated. The resulting material was purified on silica eluting with 3% MeOH/EtOAc to give 1-(4-(2-(5-bromo-3-phenoxypyridin-2-ylamino)thiazol-4-yl)piperidin-1-yl)ethanone (41.6 g, 95.0% yield) as a tan solid.

Step B: A mixture of 1-(4-(2-(5-Bromo-3-phenoxypyridin-2-ylamino)thiazol-4-yl)piperidin-1-yl)ethanone (40.0 g, 84.5 mmol), 4,5-bis(diphenylphosphino)-9,9-dimethyl-9H-xanthene (2.44 g, 4.22 mmol), Pd$_2$dba$_3$ (1.93 g, 2.11 mmol), methyl 3-mercaptopropanoate (18.7 mL, 169 mmol), N-ethyl-N-isopropylpropan-2-amine (15.4 mL, 88.7 mmol), and dioxane (250 mL) was heated to 95° C. under nitrogen for 2 hours. The reaction was cooled to ambient temperature and the resultant solids were filtered through celite washing with $CH_2Cl_2$. The filtrate was concentrated to a yellow oil and purified on silica eluting with 3%-5% MeOH/EtOAc to afford methyl 3-(6-(4-(1-acetylpiperidin-4-yl)thiazol-2-ylamino)-5-phenoxypyridin-3-ylthio)propanoate as a yellow oil.

Step C: A mixture of methyl 3-(6-(4-(1-acetylpiperidin-4-yl)thiazol-2-ylamino)-5-phenoxypyridin-3-ylthio)propanoate (20.2 g, 39.3 mmol) and 7-chlorothieno[3,2-b]pyridine (7.34 g, 43.3 mmol) in DMSO (500 mL) was purged with nitrogen for 30 minutes and then KOtBu (13.9 g, 118.0 mmol) was added and the reaction was stirred at ambient temperature for 2 hrs. The mixture was poured into saturated aqueous $NH_4Cl$ (1 L) and extracted with EtOAc (1 L). The organics were washed with water (3×500 mL), dried over $Na_2SO_4$ and concentrated to a residue that was purified on silica eluting with 3-5% MeOH/EtOAc. The purified free base was dissolved in $CH_2Cl_2$ (300 mL) and 1N HCl in $Et_2O$ (300 mL) was added the slurry was concentrated to dryness to afford 1-(4-(2-(3-phenoxy-5-(thieno[3,2-b]pyridin-7-ylthio)pyridin-2-ylamino)thiazol-4-yl)piperidin-1-yl)ethanone dihydrochloride (19.5 g, 78%) as a yellow solid which was dried in a high vacuum oven at 45° C. overnight. $^1$H NMR ($d_6$-DMSO) δ 8.65 (d, 1H), 8.48 (d, 1H), 8.46 (d, 1H), 7.77 (d, 1H), 7.54 (d, 1H), 7.41 (m, 2H), 7.18 (m, 4H), 6.82 (s, 1H), 4.43 (m, 1H), 3.88 (m, 1H), 3.14 (m, 1H), 2.89 (m, 1H), 2.64 (m, 1H), 2.01 (s, 3H), 1.96 (m, 2H), 1.58 (m, 1H), 1.45 (m, 1H). Mass spectrum (apci) m/z=560.4 (M+H-2HCl).

Example 4

1-(4-(5-(5-bromo-3-phenoxypyridin-2-ylamino)-1,2,4-thiadiazol-3-yl)piperidin-1-yl)ethanone

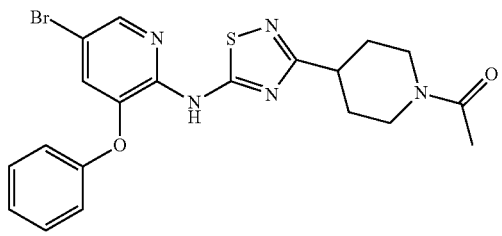

Step A: A solution of tert-butyl 4-formylpiperidine-1-carboxylate (50.0 g, 234 mmol) in MeOH (200 mL) and water (200 mL) was cooled in an ice-bath and then hydroxylamine hydrochloride (19.5 g, 272 mmol) and sodium carbonate (12.4 g, 117 mmol) were added. The resulting mixture was stirred at 13-15° C. overnight. The solution was concentrated in vacuo to an aqueous suspension, which was extracted with EtOAc. The organic extract was washed with 100 mL brine, dried ($MgSO_4$), filtered, concentrated to provide tert-butyl 4-((hydroxyimino)methyl)piperidine-1-carboxylate (53.1 g, 99.2% yield) as a white crystalline solid.

Step B: A 250 mL flask was charged with tert-butyl 4-((hydroxyimino)methyl)piperidine-1-carboxylate (2.0 g, 8.8 mmol) and DMF (100 mL). 1-chloropyrrolidine-2,5-dione (1.2 g, 8.8 mmol) was added and stirred at ambient temperature overnight. The reaction was poured into 1:1 brine:water and extracted with EtOAc. The organic layer was washed twice with water, dried over sodium sulfate, filtered and concentrated to afford tert-butyl 4-(chloro(hydroxyimino)methyl)piperidine-1-carboxylate (2.3 g, 100%).

Step C: A 500 mL flask was charged with tert-butyl 4-(chloro(hydroxyimino)methyl)piperidine-1-carboxylate (2.3 g, 8.7 mmol), methanesulfonyl chloride (0.68 mL, 8.7 mmol), and $Et_2O$ (200 mL). Triethylamine (1.2 mL, 8.7 mmol) was added slowly over ~1 minute and the reaction was stirred at ambient temperature for 10 minutes. The resultant precipitate was filtered and the filtrate concentrated and purified on silica (100% $CH_2Cl_2$) to afford tert-butyl 4-(chloro(methylsulfonyloxyimino)methyl)piperidine-1-carboxylate (1.6 g, 53.63% yield) as a c.c. oil.

Step D: A 20 mL vial was charged with tert-butyl 4-(chloro(methylsulfonyloxyimino)methyl)piperidine-1-carboxylate (193 mg, 0.566 mmol), pyridine (0.137 mL, 1.70 mmol), NaSCN (45.9 mg, 0.566 mmol), and $CH_3CN$ (4 mL). The reaction was heated to 40° C. for 40 minutes. 5-Bromo-3-phenoxypyridin-2-amine (100 mg, 0.377 mmol) was added and the reaction was stirred at 50° C. for two days. The reaction was poured into saturated aqueous $NaHCO_3$ and extracted with EtOAc (1×25 mL). The organic layer was dried with sodium sulfate, filtered and concentrated in vacuo. The residue was purified on silica gel (30% EtOAc in hexanes). The purified material was dissolved in 1:1 $CH_2Cl_2$/methanol and 4N HCl in dioxane added. After 30 minutes the reaction was concentrated and dried in vacuum oven to afford 5-bromo-3-phenoxy-N-(3-(piperidin-4-yl)-1,2,4-thiadiazol-5-yl)pyridin-2-amine dihydrochloride (150 mg, 78.7% yield) as a white solid.

Step E: Preparation of 1-(4-(5-(5-bromo-3-phenoxypyridin-2-ylamino)-1,2,4-thiadiazol-3-yl)piperidin-1-yl)ethanone: Prepared from 5-bromo-3-phenoxy-N-(3-(piperidin-4-yl)-1,2,4-thiadiazol-5-yl)pyridin-2-amine dihydrochloride according to Example 1, Step F. $^1$H NMR ($CDCl_3$) δ 9.01 (s, 1H), 8.21 (d, 1H), 7.46 (m, 2H), 7.30 (m, 1h), 7.19 (d, 1H), 7.09 (m, 2H), 4.57 (m, 1H), 3.89 (m, 1h), 3.22 (m, 1H), 3.07 (m, 1H), 2.83 (m, 1H), 2.11 (m, 5H), 1.95-1.75 (m, 2H). Mass spectrum (apci) m/z=476.2 (M+H).

Example 5

1-(4-(5-(3-phenoxy-5-(thieno[3,2-b]pyridin-7-ylthio)pyridin-2-ylamino)-1,2,4-thiadiazol-3-yl)piperidin-1-yl)ethanone dihydrochloride

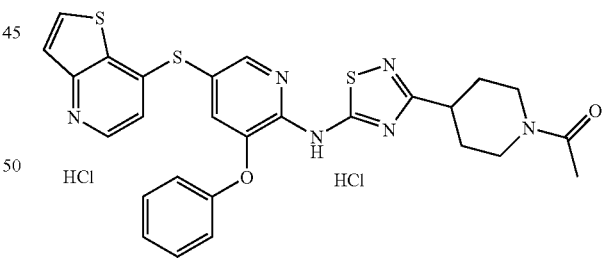

Step A: A 1 L flask was charged with tert-butyl 4-(5-(5-bromo-3-phenoxypyridin-2-ylamino)-1,2,4-thiadiazol-3-yl)piperidine-1-carboxylate (Example 4, Step D, 24.4 g, 45.8 mmol), N-ethyl-N-isopropylpropan-2-amine (16.0 mL, 91.7 mmol), 4,5-bis(diphenylphosphino)-9,9-dimethyl-9H-xanthene (1.33 g, 2.29 mmol), and dioxane (450 mL). Nitrogen was bubbled through the solution for 30 minutes. Methyl 3-mercaptopropanoate (5.46 mL, 50.4 mmol) and $Pd_2dba_3$ (1.05 g, 1.15 mmol) were added and the reaction was heated at 95° C. overnight. The reaction was cooled to ambient temperature and the resultant solids were filtered through celite. The filtrate was concentrated and purified on silica (30 to 40% EtOAc in hexanes) to afford tert-butyl 4-(5-(5-(3- methoxy-3-oxopropylthio)-3-phenoxypyridin-2-ylamino)-1,2,4-thiadiazol-3-yl)piperidine-1-carboxylate (18.1 g, 69.1% yield) as a white foam.

Step B: A 250 mL flask was charged with tert-butyl 4-(5-(5-(3-methoxy-3-oxopropylthio)-3-phenoxypyridin-2-ylamino)-1,2,4-thiadiazol-3-yl)piperidine-1-carboxylate (10 g, 17 mmol), 7-chlorothieno[3,2-b]pyridine (3.6 g, 21 mmol), and DMSO (125 mL). Nitrogen was bubbled vigorously through the solution for 10 minutes. Potassium 2-methylpropan-2-olate (5.9 g, 52 mmol) was added and the reaction was stirred at ambient temperature under nitrogen for 5 hours. The reaction was poured into saturated aqueous $NH_4Cl$ and extracted with EtOAc (1×500 mL). The organic layer was washed with water and brine, dried with sodium sulfate, filtered and concentrated in vacuo. The residue was purified on silica (50 to 75% EtOAc in hexanes) to afford tert-butyl 4-(5-(3-phenoxy-5-(thieno[3,2-b]pyridin-7-ylthio)pyridin-2-ylamino)-1,2,4-thiadiazol-3-yl)piperidine-1-carboxylate (10 g, 92% yield) as a white foam.

Step C: tert-butyl 4-(5-(3-phenoxy-5-(thieno[3,2-b]pyridin-7-ylthio)pyridin-2-ylamino)-1,2,4-thiadiazol-3-yl)piperidine-1-carboxylate (10 g, 16 mmol) was dissolved in 1:1 $CH_2Cl_2$:methanol and 4N HCl in dioxane was added (80 mL). The reaction was stirred for 1 hour and then concentrated in vacuo to afford 3-phenoxy-N-(3-(piperidin-4-yl)-1,2,4-thiadiazol-5-yl)-5-(thieno[3,2-b]pyridin-7-ylthio)pyridin-2-amine trihydrochloride (10 g, 100%).

Step D: A 250 mL flask was charged with 3-phenoxy-N-(3-(piperidin-4-yl)-1,2,4-thiadiazol-5-yl)-5-(thieno[3,2-b]pyridin-7-ylthio)pyridin-2-amine trihydrochloride (5.6 g, 8.92 mmol), triethylamine (9.94 mL, 71.3 mmol), and $CH_2Cl_2$ (100 mL). Acetic anhydride (1.26 mL, 13.4 mmol) was added and the reaction was stirred at ambient temperature for 10 minutes. The reaction was poured into saturated aqueous $NaHCO_3$ and extracted with $CH_2Cl_2$. The organic layer was dried with sodium sulfate, filtered and concentrated in vacuo. The residue was purified on silica (5 to 10% methanol in EtOAc) to afford 1-(4-(5-(3-phenoxy-5-(thieno[3,2-b]pyridin-7-ylthio)pyridin-2-ylamino)-1,2,4-thiadiazol-3-yl)piperidin-1-yl)ethanone dihydrochloride (4.16 g, 73.6% yield) as a yellow solid after HCl salt formation. $^1$H NMR ($d_6$-DMSO) δ 12.48 (bs, 1H), 8.56 (d, 1H), 8.53 (d, 1H), 8.28 (d, 1H), 7.65 (d, 1H), 7.57 (d, 1H), 7.40 (m, 2H), 7.18 (m, 1H), 7.14 (m, 2H), 7.07 (d, 1H), 4.32 (m, 1H), 3.20 (m, 1H), 3.07 (m, 1H), 2.77 (m, 1H), 2.01 (m, 5H), 1.73 (m, 1H), 1.59 (m, 1H). Mass spectrum (apci) m/z=561.3 (M+H-2HCl).

Example 6

1-(4-(5-(3-(4-fluorophenoxy)-5-(thieno[3,2-b]pyridin-7-ylthio)pyridin-2-ylamino)-1,2,4-thiadiazol-3-yl)piperidin-1-yl)ethanone dihydrochloride

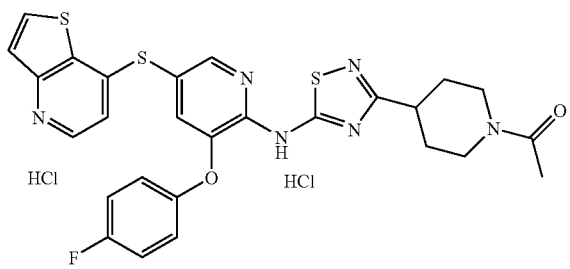 [SMILES: CC(=O)N1CCC(c2nsc(Nc3ncc(Sc4ccnc5ccsc45)cc3Oc3ccc(F)cc3)n2)CC1 ; Cl ; Cl]

Steps A-C: Preparation of 5-bromo-3-(4-fluorophenoxy)pyridin-2-amine: Prepared according to Example 1, steps A-C, using 1,4-dibromo-2,5-difluorobenzene.

Step D: Preparation of tert-butyl 4-(5-(5-bromo-3-(4-fluorophenoxy)pyridin-2-ylamino)-1,2,4-thiadiazol-3-yl)piperidine-1-carboxylate: Prepared according to Example 4, Step D.

Steps E and F: Preparation of tert-butyl 4-(5-(3-(4-fluorophenoxy)-5-(thieno[3,2-b]pyridin-7-ylthio)pyridin-2-ylamino)-1,2,4-thiadiazol-3-yl)piperidine-1-carboxylate: Prepared according to Example 3, steps B and C.

Step G: Preparation of N-(3-(4-fluorophenoxy)-5-(thieno[3,2-b]pyridin-7-ylthio)pyridin-2-yl)-3-(piperidin-4-yl)-1,2,4-thiadiazol-5-amine trihydrochloride: Prepared according to Example 5, Step C.

Step H: Preparation of 1-(4-(5-(3-(4-fluorophenoxy)-5-(thieno[3,2-b]pyridin-7-ylthio)pyridin-2-ylamino)-1,2,4-thiadiazol-3-yl)piperidin-1-yl)ethanone dihydrochloride: Prepared according to Example 1, Step G. $^1$H NMR ($d_6$-DMSO) δ 12.49 (bs, 1H), 8.57 (d, 1H), 8.52 (d, 1H), 8.32 (d, 1H), 7.67 (d, 1H), 7.58 (d, 1H), 7.21 (m, 4H), 7.08 (d, 1H), 4.32 (m, 1H), 3.85 (m, 1H), 3.20 (m, 1H), 3.07 (m, 1H), 2.77 (m, 1H), 2.01 (m, 5H), 1.74 (m, 1H), 1.59 (m, 1H). Mass spectrum (apci) m/z=579.2 (M+H-2HCl).

Example 7

1-(4-(2-(3-(4-fluorophenoxy)-5-(thieno[3,2-b]pyridin-7-ylthio)pyridin-2-ylamino)thiazol-4-yl)piperidin-1-yl)ethanone

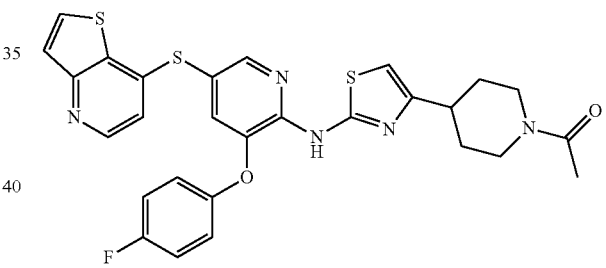

Steps A-C: Preparation of tert-butyl 4-(2-(5-bromo-3-(4-fluorophenoxy)pyridin-2-ylamino)thiazol-4-yl)piperidine-1-carboxylate: Prepared according to Example 1, steps D-F using 5-bromo-3-(4-fluorophenoxy)pyridin-2-amine (Example 6, Step C).

Steps D and E: Preparation of tert-butyl 4-(2-(3-(4-fluorophenoxy)-5-(thieno[3,2-b]pyridin-7-ylthio)pyridin-2-ylamino)thiazol-4-yl)piperidine-1-carboxylate: Prepared according to Example 3, steps B and C.

Step F: Preparation of N-(3-(4-fluorophenoxy)-5-(thieno[3,2-b]pyridin-7-ylthio)pyridin-2-yl)-4-(piperidin-4-yl)thiazol-2-amine trihydrochloride: Prepared according to Example 5, Step C.

Step G: Preparation of 1-(4-(2-(3-(4-fluorophenoxy)-5-(thieno[3,2-b]pyridin-7-ylthio)pyridin-2-ylamino)thiazol-4-yl)piperidin-1-yl)ethanone: Prepared according to Example 1, Step G: $^1$H NMR ($d_6$-DMSO) δ 11.21 (bs, 1H), 8.50 (d, 1H), 8.37 (d, 1H), 8.18 (d, 1H), 7.60 (d, 1H), 7.41 (d, 1H), 7.25-7.14 (m, 4H), 6.92 (d, 1H), 6.74 (s, 1H), 4.33 (d, 1H), 3.87 (d, 1H), 3.13 (t, 1H), 2.85 (m, 1H), 2.64 (t, 1H), 2.01 (s, 3H), 1.95 (m, 2H), 1.59 (m, 1H), 1.45 (m, 1H).

The following compounds were also prepared according to one or more of the procedures of Examples 1-7.

| Example | Structure | Name | Data |
|---|---|---|---|
| 8 | 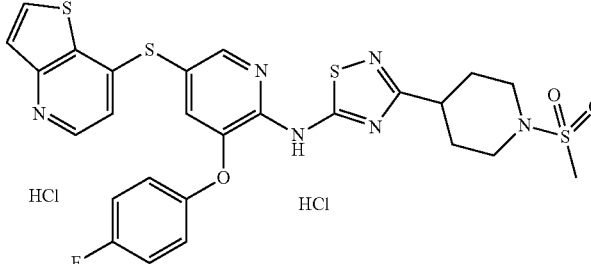 | N-(3-(4-fluorophenoxy)-5-(thieno[3,2-b]pyridin-7-ylthio)pyridin-2-yl)-3-(1-(methylsulfonyl)piperidin-4-yl)-1,2,4-thiadiazol-5-amine dihydrochloride | $^1$H NMR (d$_6$-DMSO) δ 12.53 (bs, 1H), 8.61 (d, 1H), 8.54 (d, 1H), 8.39 (d, 1H), 7.72 (d, 1H), 7.61 (d, 1H), 7.23 (m, 4H), (d, 1H), 3.60 (m, 2H), 2.92 (m, 2H), 2.88 (s, 3H), 2.14 (m, 2H), 1.82 (m, 2H). Mass spectrum (apci) m/z = 615.2 (M + H − 2HCl). |
| 9 | 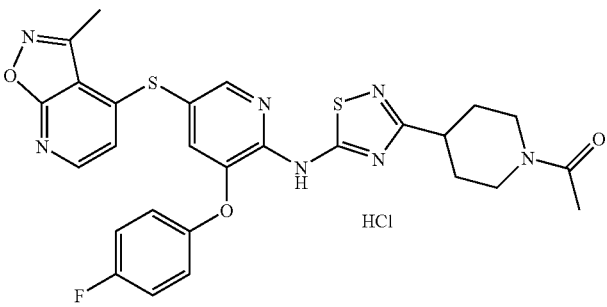 [SMILES: CC(=O)N1CCC(c2nsc(Nc3ncc(Sc4ccnc5onc(C)c45)cc3Oc3ccc(F)cc3)n2)CC1 ; Cl] | 1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone hydrochloride | $^1$H NMR (d$_6$-DMSO) δ 12.48 (bs, 1H), 8.49 (d, 1H), 8.32 (d, 1H), 7.54 (m, 1H), 7.25 (m, 4H), 6.75 (d, 1H), 4.32 (m, 1H), 3.85 (m, 1H), 3.20 (m, 1H), 3.07 (m, 1H), 2.77 (m, 1H), 2.69 (s, 3H), 2.02 (m, 5H), 1.74 (m, 1H), 1.60 (m, 1H). Mass spectrum (esi) m/z = 578.1 (M + H − HCl). |
| 10 | 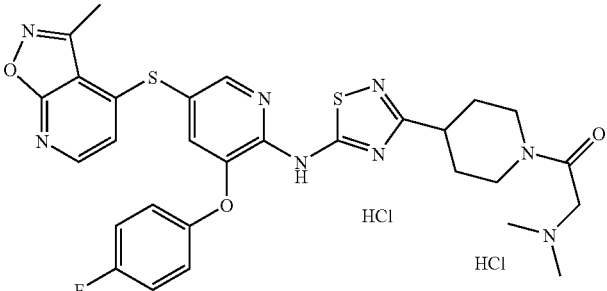 | 2-(dimethylamino)-1-(4-(5-(3-(4-fluorophenoxy)-5-(3-methylisoxazolo[5,4-b]pyridin-4-ylthio)pyridin-2-ylamino)-1,2,4-thiadiazol-3-ylpiperidin-1-yl)ethanone dihydrochloride | $^1$H NMR (d$_6$-DMSO) δ 12.48 (bs, 1H), 9.54 (bs, 1H), 8.49 (d, 1H), 8.32 (d, 1H), 7.55 (d, 1H), 7.25 (m, 4H), 6.74 (d, 1H), 4.32 (m, 3H), 3.65 (m, 1H), 3.20 (m, 2H), 2.96 (m, 1H), 2.82 (d, 6H), 2.70 (s, 3H), 2.09 (m, 2H), 1.82 (m, 1H), 1.65 (m, 1H). Mass spectrum (esi) m/z = 621.1(M + H − 2HCl) |
| 11 | 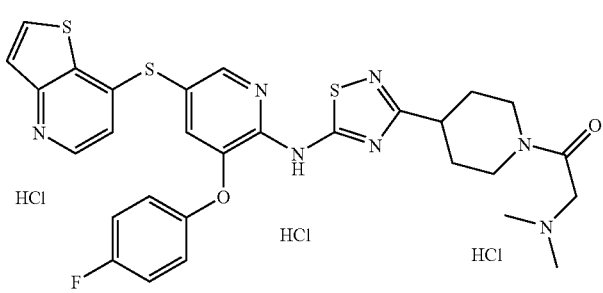 [SMILES: CN(C)CC(=O)N1CCC(c2nsc(Nc3ncc(Sc4ccnc5ccsc45)cc3Oc3ccc(F)cc3)n2)CC1 ; Cl ; Cl ; Cl] | 2-(dimethylamino)-1-(4-(5-(3-(4-fluorophenoxy)-5-(thieno[3,2-b]pyridin-7-ylthio)pyridin-2-ylamino)-1,2,4-thiadiazol-3-yl)ethanonetrihydrochloride | $^1$H NMR (d$_6$-DMSO) δ 12.49 (bs, 1H), 9.62 (bs, 1H), 8.58 (d, 1H), 8.52 (d, 1H), 8.33 (d, 1H), 7.69 (d, 1H), 7.59 (d, 1H), 7.23 (m, 4H), 7.08 (d, 1H), 4.41-4.22 (m, 3H), 3.66 (d, 1H), 3.28-3.11 (m, 2H), 3.01-2.89 (m, 2H), 2.82 (d, 6H), 2.09 (m, 2H), 1.82 (m, 1H), 1.65 (m, 1H). Mass spectrum (apci) m/z = 622.2 (M + H − 3HCl). |
| 12 | 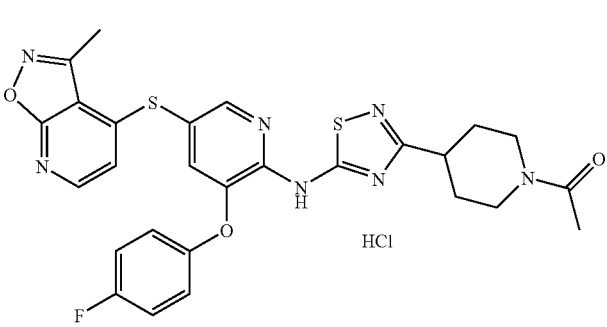 [SMILES: CC(=O)N1CCC(c2nsc(Nc3ncc(Sc4ccnc5onc(C)c45)cc3Oc3ccc(F)cc3)n2)CC1 ; Cl] | 1-(4-(5-(3-(4-fluorophenxoy)-5-(3-methylisoxazolo[5,4-b]pyridin-4-ylthio)pyridin-2-ylamino)-1,2,4-thiadiazol-3-yl)piperidin-1-yl)ethanone hydrochloride | $^1$H NMR (d$_6$-DMSO) δ 12.48 (bs, 1H), 8.49 (d, 1H), 8.32 (d, 1H), 7.54 (m, 1H), 7.25 (m, 4H), 6.75 (d, 1H), 4.33 (d, 1H), 3.85 (d, 1H), 3.20 (m, 1H), 3.07 (m, 1H), 2.77 (t, 1H), 2.69 (s, 3H), 2.02 (m, 5H), 1.74 (m, 1H), 1.60 (m, 1H). Mass spectrum (apci) m/z = 578.1 (M + H − HCl). |

| Example | Structure | Name | Data |
|---|---|---|---|
| 13 | 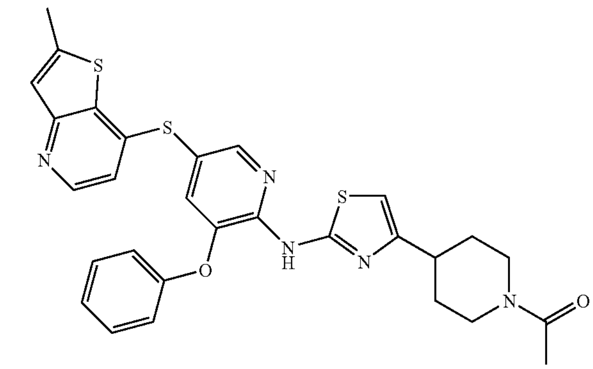 [SMILES: CC(=O)N1CCC(c2csc(Nc3ncc(Sc4ccnc5cc(C)sc45)cc3Oc3ccccc3)n2)CC1] | 1-(4-(2-(5-(2-Methylthieno[3,2-b]pyridin-7-ylthio)-3-phenoxypyridin-2-ylamino)thiazol-4-yl)piperidin-1-yl)ethanone | $^1$H (CDCl$_3$) δ 1.59-1.70 (m, 2H), 2.04-2.12 (m, 5H), 2.63 (d, J = 1.2 Hz, 3H), 2.70 (t, J = 11.5 Hz, 1H), 2.84-2.90 (m, 1H), 3.19 (t, J = 11.7 Hz, 1H), 3.91 (d, J = 13.9 Hz, 1H), 4.72 (d, J = 13.3 Hz, 1H), 6.51 (s, 1H), 6.66 (d, J = 5.3 Hz, 1H), 7.04 (s, 1H), 7.06 (d, J = 1.0 Hz, 1H), 7.17-7.23 (m, 3H), 7.39 (t, J = 7.9 Hz, 2H), 8.29 (d, J = 2.0 Hz, 1H), 8.37 (d, J = 5.1 Hz, 1H), 8.84 (brs, 1H). |
| 14 | 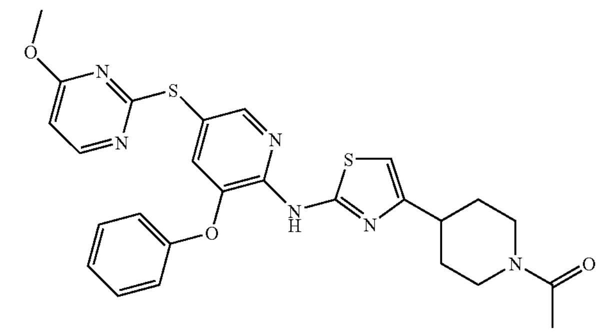 | 1-(4-(2-(5-(4-Methoxypyrimidin-2-ylthio)-3-phenoxypyridin-2-ylamino)thiazol-4-yl)piperidin-1-yl)ethanone | $^1$H NMR (CDCl$_3$) δ 1.59-1.70 (m, 2H), 2.03-2.12 (m, 5H), 2.69 (t, J = 11.6 Hz, 1H), 2.83-2.89 (m, 1H), 3.14-3.22 (m, 1H), 3.76 (s, 3H), 3.90 (d, J = 13.5 Hz, 1H), 4.71 (d, J = 13.2 Hz, 1H), 6.39 (d, J = 5.7 Hz, 1H), 6.48 (s, 1H), 7.08 (s, 1H), 7.10 (s, 1H), 7.20 (t, J = 7.4 Hz, 1H), 7.32 (d, J = 1.8 Hz, 1H), 7.39 (t, J = 8.0 Hz, 2H), 8.15 (d, J = 5.9 Hz, 1H), 8.27 (d, J = 1.8 Hz, 1H), 8.77 (br s, 1H). |
| 15 | 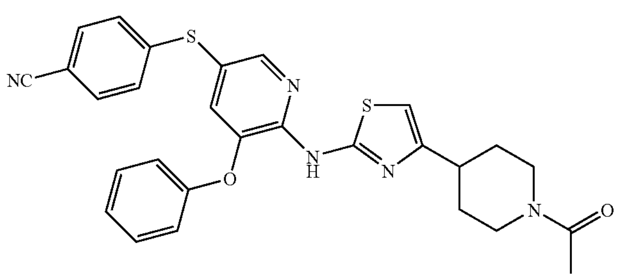 | 4-(6-(4-(1-Acetylpiperidin-4-yl)thiazol-2-ylamino)-5-phenoxypyridin-3-ylthio)benzonitrile | $^1$H NMR (CDCl$_3$) δ 1.59-1.71 (m, 2H), 1.96-2.12 (m, 5H), 2.70 (t, J = 11.5 Hz, 1H), 2.84-2.90 (m, 1H), 3.15-3.22 (m, 1H), 3.91 (d, J = 13.5 Hz, 1H), 4.72 (d, J = 13.3 Hz, 1H), 6.51 (s, 1H), 7.05 (s, 1H), 7.07 (s, 1H), 7.09 (s, 1H), 7.11 (s, 1H), 7.12 (d, J = 2.0 Hz, 1H), 7.22-7.26 (m, 1H), 7.41 (t, J = 8.1 Hz, 2H), 7.46 (s, 1H), 7.48 (s, 1H), 8.24 (d, J = 2.0 Hz, 1H), 8.83 (br s, 1H). |
| 16 | 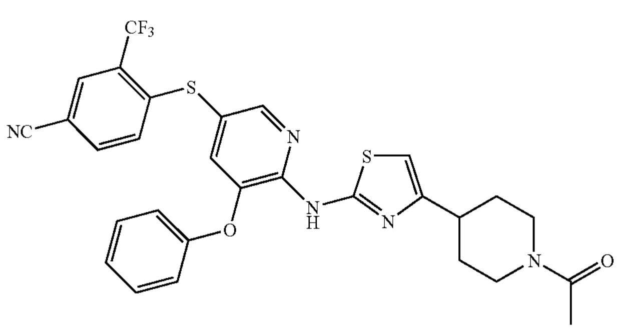 | 4-(6-(4-(1-Acetylpiperidin-4-yl)thiazol-2-ylamino)-5-phenoxypyridin-3-ylthio)-3-(trifluoromethyl)benzonitrile | $^1$H NMR (CDCl$_3$) δ 1.64-1.70 (m, 2H), 2.04-2.12 (m, 5H), 2.70 (t, J = 12.8 Hz, 1H), 2.88 (t, J = 11.5 Hz, 1H), 3.19 (t, J = 12.9 Hz, 1H), 3.91 (d, J = 13.7 Hz, 1H), 4.72 (d, J = 13.3 Hz, 1H), 6.53 (s, 1H), 6.97 (d, J = 8.4 Hz, 1H), 7.07 (d, J = 8.0 Hz, 2H), 7.10 (s, 1H), 7.11-7.26 (m, 1H), 7.42 (t, J = 7.9 Hz, 2H), 7.54 (d, J = 8.4 Hz, 1H), 7.87 (s, 1H), 8.25 (d, J = 1.8 Hz, 1H), 8.88 (br s, 1H). |

-continued

| Example | Structure | Name | Data |
|---|---|---|---|
| 17 | 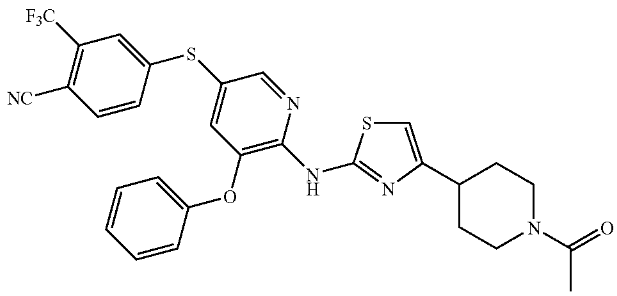 | 4-(6-(4-(1-Acetylpiperidin-4-yl)thiazol-2-ylamino)-5-phenoxypyridin-3-ylthio)-2-(trifluoromethyl)benzonitrile | $^1$H NMR (CDCl$_3$) δ 1.59-1.71 (m, 2H), 2.04-2.12 (m, 5H), 2.70 (t, J = 11.5 Hz, 1H), 2.85-2.90 (m, 1H), 3.15-3.22 (m, 1H), 3.91 (d, J = 13.7 Hz, 1H), 4.72 (d, J = 13.3 Hz, 1H), 6.53 (s, 1H), 7.06 (s, 1H), 7.07 (s, 1H), 7.10 (d, J = 1.8 Hz, 1H), 7.22-7.25 (m, 2H), 7.39 (s, 1H), 7.42 (t, J = 8.1 Hz, 2H), 7.63 (d, J = 8.2 Hz, 1H), 8.25 (d, J = 1.94 Hz, 1H), 8.87 (br s 1H). |
| 18 | 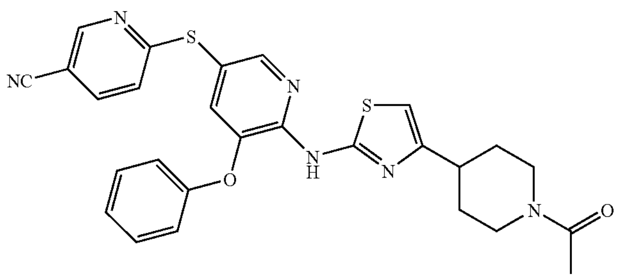 | 6-(6-(4-(1-Acetylipiperidin-4-yl)thiazol-2-ylamino)-5-phenoxypyridin-3-ylthio)nicotinonitrile | $^1$H NMR (CDCl$_3$) δ 1.62-1.71 (m, 2H), 2.04-2.12 (m, 5H), 2.70 (t, J = 11.5 Hz, 1H), 2.84-2.90 (m, 1H), 315-3.22 (m, 1H), 3.91 (d, J = 13.9 Hz, 1H), 4.72 (d, J = 13.5 Hz, 1H), 6.51 (s, 1H), 7.03 (d, J = 8.4 Hz, 1H), 7.09 (s, 1H), 7.11 (s, 1H), 7.18 (d, J = 2.0 Hz, 1H), 7.22-7.26 (m, 1H), 7.42 (t, J = 8.0 Hz, 2H), 7.66-7.69 (m, 1H), 8.25 (d, J = 1.8 Hz, 1H), 8.58 (d, J = 1.6 Hz, 1H), 8.84 (br s, 1H). |
| 19 | 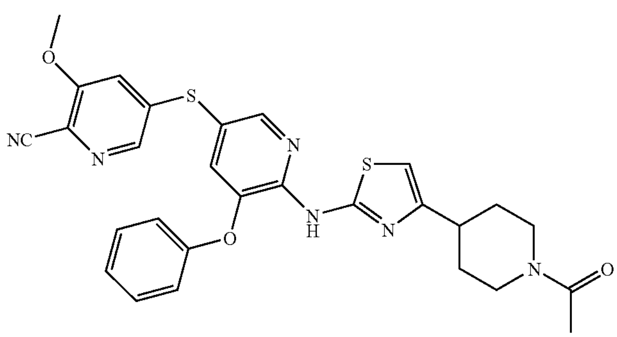 | 5-(6-(4-(1-Acetylpiperidin-4-yl)thiazol-2-ylamino)-5-phenoxypyridin-3-ylthio)nicotinonitrile | $^1$H NMR (CDCl$_3$) δ 1.59-1.71 (m, 2H), 2.03-2.12 (m, 5H), 2.70 (t, J = 11.5 Hz, 1H), 2.84-2.90 (m, 1H), 3.18 (t, J = 11.7 Hz, 1H), 3.86 (s, 3H), 3.91 (d, J = 13.7 Hz, 1H), 4.72 (d, J = 13.1 Hz, 1H), 6.52 (s, 1H), 6.96 (d, J = 1.8 Hz, 1H), 7.06 (s, 1H), 7.07 (s, 1H), 7.09 (d, J = 13.3 Hz, 1H), 7.11-7.26 (m, 1H), 7.43 (t, J = 8.0 Hz, 2H), 7.87 (d, J = 1.8 Hz, 1H), 8.26 (d, J = 1.8 Hz, 1H), 8.85 (br s, 1H). |
| 20 | 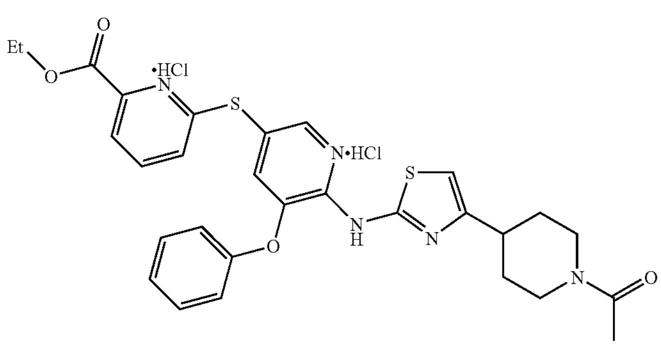 | Ethyl 6-(6-(4-(1-acetyl-piperidin-4-yl)thiazol-2-ylamino)-5-phenoxy-pyridin-3-ylthio)picolinate dihydrochloride | $^1$H NMR (d$_6$ DMSO) δ 1.28 (t, J = 7.0 Hz, 3H), 1.39-1.48 (m, 1H), 1.53-1.62 (m, 1H), 1.91-2.00 (m, 5H), 2.63 (t, J = 12.6 Hz, 1H), 2.84 (t, J = 11.4 Hz, 1H), 3.13 (t, J = 11.9 Hz, 1H), 3.87 (d, J = 13.7 Hz, 1H), 4.28-4.33 (m, 2H), 4.42 (d, J = 13.1 Hz, 1H), 6.73 (s, 1H), 7.10-7.21 (m, 3H), 7.29 (d, J = 7.8 Hz, 1H), 7.38 (t, J = 7.9 Hz, 2H), 7.42 (d, J = 1.8 Hz, 1H), 7.77 (d, J = 7.6 Hz, 1H), 7.83 (t, J = 7.7 Hz, 1H), 8.31 (d, J = 2.0 Hz, 1H), 11.13 (br s, 1H). |

| Example | Name | Data |
|---|---|---|
| 21 | 1-(4-(2-(3-Phenoxy-5-(6-(trifluoromethyl)pyridin-3-ylthio)pyridin-2-ylamino)thiazol-4-yl)piperidin-1-yl)ethanone | $^1$H NMR (d$_6$ DMSO) δ 1.43-1.58 (m, 2H), 1.91-2.00 (m, 5H), 2.63 (t, J = 13.2 Hz, 1H), 2.83 (br s, 1H), 3.13 (t, J = 11.9 Hz, 1H), 3.86 (d, J = 13.5 Hz, 1H), 4.42 (d, J = 13.7 Hz, 1H), 6.74 (s, 1H), 7.12-7.16 (m, 3H), 7.38-7.41 (m, 3H), 7.75-7.79 (m, 2H), 8.33 (s, 1H), 8.57 (s, 1H), 11.14 (s, 1H). |
| 22 | 1-(4-(2-(5-(6-Bromothieno[3,2-b]pyridin-7-ylthio)-3-phenoxypyridin-2-ylamino)thiazol-4-yl)piperidin-1-yl)ethanone | $^1$H NMR (d$_6$ DMSO) δ 142-1.46 (m, 1H), 1.55-1.58 (m, 1H), 1.93 (t, J = 16.7 Hz, 2H), 2.00 (s, 3H), 2.63 (t, J = 12.4 Hz, 1H), 2.83 (br s, 1H), 3.12 (t, J = 12.8 Hz, 1H), 3.86 (d, J = 13.1 Hz, 1H), 4.42 (d, J = 12.3 Hz, 1H), 6.74 (s, 1H), 7.01 (d, J = 7.2 Hz, 2H), 7.12-7.14 (m, 1H), 7.34 (t, J = 7.3 Hz, 2H), 7.41 (s, 1H), 7.50 (d, J = 5.5 Hz, 1H), 8.07 (d, J = 5.5 Hz, 1H), 8.39 (s, 1H), 8.73 (s, 1H), 11.23 (s, 1H). |
| 23 | 2-(dimethylamino)-1-(4-(2-(3-(4-fluoropheoxy)-5-(thieno[3,2-b]pyridin-7-ylthio)pyridin-2-ylamino)thiazol-4-yl)piperidin-1-yl)ethanonedihydrochloride | $^1$H NMR (d$_6$-DMSO) δ 9.60 (bs, 1H), 8.58 (d, 1H), 8.40 (d, 1H), 8.33 (d, 1H), 7.68 (d, 1H, 7.47 (d, 1H), 7.27-7.17 (m, 4H), 7.05 (d, 1H), 6.78 (s, 1H), 4.45-4.28 (m, 3H), 3.67 (d, 2H), 3.18 (t, 1H), 2.93 (m, 1H), 2.82 (s, 3H), 2.04 (d, 2H), 1.65 (m, 1H), 1.50 (m, 1H). |
| 24 | N-(3-(4-fluorophenoxy)-5-(thieno[3,2-b]pyridin-7-ylthio)pyridin-2-yl)-4-(1-(methylsulfonyl)piperidin-4-yl)thiazol-2-aminehydrochloride | $^1$H NMR (d$_6$-DMSO) δ 8.57 (d, 1H), 8.40 (d, 1H), 8.32 (d, 1H), 7.67 (d, 1H), 7.46 (d, 1H), 7.26-7.16 (m, 4H), 7.05 (d, 1H), 6.80 (s, 1H), 3.64 (d, 2H), 2.88 (s, 3H), 2.84 (t, 2H), 2.73 (m, 1H), 2.08 (d, 2H), 1.66 (m, 2H) |
| 25 | 1-(4-(2-(3-(4-fluorophenoxy)-5-(3-methyl-isoxazolo[5,4-b]pyridin-4-ylthio)pyridin-2-ylamino)thiazol-4-yl)piperidin-1-yl)ethanone hydrochloridce | $^1$H NMR (d$_6$-DMSO) δ 11.28 (bs, 1H), 8.35 (d, 1H), 8.32 (d, 1H), 7.41 (d, 1H), 7.27-7.19 (m, 4H), 6.76 (s, 1H), 6.72 (d, 1H), 4.43 (d, 1H), 3.87(d, 1H), 3.14 (t, 1H), 2.86 (m, 1H), 2.69 (s, 3H), 2.65 (m, 1H), 2.01 (s, 3H), 1.95 (m, 2H), 1.60 (m, 1H), 1.45 (m, 1H). |

| Example | Structure | Name | Data |
|---|---|---|---|
| 26 | 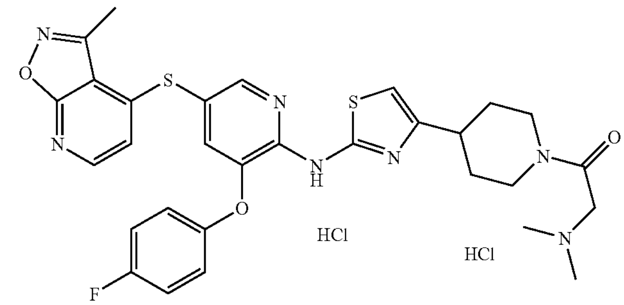 [SMILES: Cc1noc2nccc(Sc3cnc(Nc4nc(C5CCN(C(=O)CN(C)C)CC5)cs4)c(Oc4ccc(F)cc4)c3)c12 ; Cl ; Cl] | 2-(dimethylamino)-1-(4-(2-(3-(4-fluorophenoxy)-5-(3-methylisoxazolo[5,4-b]pyridin-4-ylthio)pyridin-2-ylamino)thiazol-4-yl)piperidin-1-yl)ethanonedihydrochloride | $^1$H NMR (d$_6$-DMSO) δ 11.23 (bs, 1H), 9.54 (bs, 1H), 8.36 (d, 1H), 8.32 (d, 1H), 7.42 (d, 1H), 7.28-7.19 (m, 4H), 6.78 (s, 1H), 6.71 (d, 1H), 4.42 (d, 1H), 4.30 (m, 2H), 3.66 (d, 1H), 3.19 (t, 1H), 2.91 (m, 2H), 2.81 (d, 6H), 2.69 (s, 3H), 2.04 (d, 2H), 1.65 (m, 1H), 1.51 (m, 1H) |
| 27 | 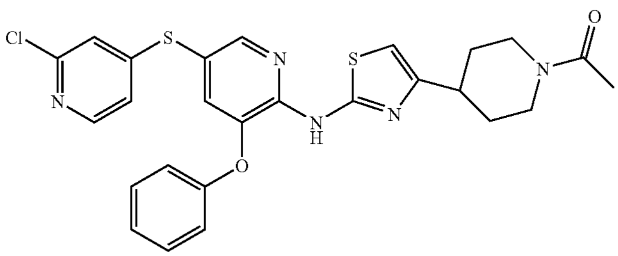 [SMILES: CC(=O)N1CCC(c2csc(Nc3ncc(Sc4ccnc(Cl)c4)cc3Oc3ccccc3)n2)CC1] | 1-(4-(2-(5-(2-chloro-pyridin-4-ylthio)-3-phenoxypyridin-2-ylamino)thiazol-4-yl)piperidin-1-yl)ethanone | $^1$H NMR (CDCl$_3$) δ 8.24 (s, 1H), 8.13 (d, 1H), 7.42 (t, 2H), 7.24 (t, 1H), 7.07-7.12 (m, 2H), 6.82-6.86 (m, 2H), 6.52 (s, 1H), 4.72 (m, 1H), 3.91 (m, 1H), 3.19 (m, 1H), 2.88 (m, 1H), 2.70 (m, 1H), 2.12 (m, 1H), 2.03-2.11 (m, 2H), 1.60-1.71 (m, 2H). |

Example 28

1-(4-(2-(5-(Thieno[3,2-b]pyridin-7-ylthio)-3-(4-(trifluoromethyl)phenoxy)pyridin-2-ylamino)thiazol-4-yl)piperidin-1-yl)ethanone

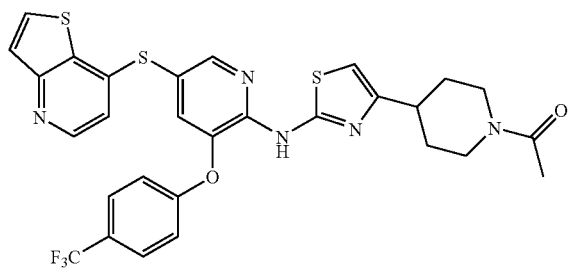 [SMILES: CC(=O)N1CCC(c2csc(Nc3ncc(Sc4ccnc5ccsc45)cc3Oc3ccc(C(F)(F)F)cc3)n2)CC1]

Steps A-C: Preparation of 5-bromo-3-(4-(trifluoromethyl)phenoxy)pyridin-2-amine: Prepared according to Example 1, steps A-C, using 2-bromo-1-fluoro-4-(trifluoromethyl)benzene.

Steps D and E: Preparation of 1-(5-bromo-3-(4-(trifluoromethyl)phenoxy)pyridin-2-yl)thiourea: Prepared according to Example 1, steps D and E.

Step F-H: Preparation of 1-(4-(2-(5-(Thieno[3,2-b]pyridin-7-ylthio)-3-(4-(trifluoromethyl)phenoxy)pyridin-2-ylamino)thiazol-4-yl)piperidin-1-yl)ethanone: Prepared according to Example 3. $^1$H NMR (d$_6$ DMSO) δ 1.23-1.47 (m, 1H), 1.52-1.60 (m, 1H), 1.93 (t, J=15.5 Hz, 2H), 2.00 (s, 3H), 2.62 (t, J=12.4 Hz, 1H), 2.83 (br s, 1H), 3.12 (t, J=12.1 Hz, 1H), 3.85 (d, J=13.1 Hz, 1H), 4.42 (d, J=13.3 Hz, 1E1), 6.76 (s, 1H), 6.95 (d, J=5.1 Hz, 1H), 7.23 (d, J=6.4 Hz, 2H), 7.59 (d, J=5.5 Hz, 1H), 7.72 (d, J=8.4 Hz, 2H), 7.79 (s, 1H), 8.16 (d, J=5.5 Hz, 1H), 8.48 (d, J=2.0 Hz, 1H), 8.51 (d, J=4.9 Hz, 1H), 11.44 (s, 1H).

Example 29

1-(4-(2-(5-(Thieno[3,2-b]pyridin-7-ylthio)-3-(2-(trifluoromethyl)phenoxy)pyridin-2-ylamino)thiazol-4-yl)piperidin-1-yl)ethanone

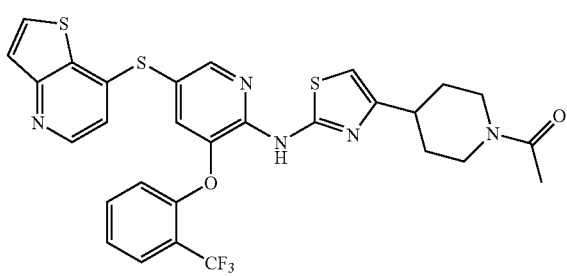 [SMILES: CC(=O)N1CCC(c2csc(Nc3ncc(Sc4ccnc5ccsc45)cc3Oc3ccccc3C(F)(F)F)n2)CC1]

Steps A-C: Preparation of 5-bromo-3-(2-(trifluoromethyl)phenoxy)pyridin-2-amine: Prepared according to Example 1, steps A-C, using 4-bromo-1-fluoro-2-(trifluoromethyl)benzene.

Steps D and E: Preparation of 1-(5-bromo-3-(2-(trifluoromethyl)phenoxy)pyridin-2-yl)thiourea: Prepared according to Example 1, steps D and E.

Step F-H: 1-(4-(2-(5-(Thieno[3,2-b]pyridin-7-ylthio)-3-(2-(trifluoromethyl)phenoxy)pyridin-2-ylamino)thiazol-4-yl)piperidin-1-yl)ethanone: Prepared according to Example 3. $^1$H NMR (d$_6$DMSO) δ 1.40-1.49 (m, 1H), 1.54-1.62 (m, 1H), 1.91-2.00 (m, 5H), 2.63 (t, J=12.3 Hz, 1H), 2.85 (br s, 1H), 3.13 (t, J=12.3 Hz, 1H), 3.87 (d, J=13.8 Hz, 1H), 4.43 (d, J=13.1 Hz, 1H), 6.76 (br s, 1H), 6.88 (d, J=5.1 Hz, 1H), 7.21 (br s, 1H), 7.32-7.36 (m, 2H), 7.58 (d, J=5.5 Hz, 1H), 7.65 (t, J=7.8 Hz, 1H), 7.77 (d, J=7.6 Hz, 1H); 8.16 (d, J=5.5 Hz, 1H), 8.42 (d, J=2.0 Hz, 1H), 8.48 (d, J=5.1 Hz, 1H), 11.35 (br s, 1H).

Example 30

1-(4-(5-(5-(Thieno[3,2-b]pyridin-7-ylthio)-3-(2-(trifluoromethyl)phenoxy)pyridin-2-ylamino)-1,2,4-thiadiazol-3-yl)piperidin-1-yl)ethanone

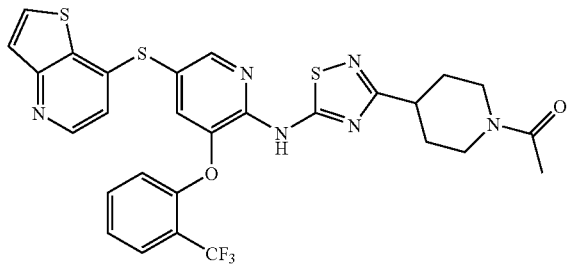 [SMILES: CC(=O)N1CCC(c2nsc(Nc3ncc(Sc4ccnc5ccsc45)cc3Oc3ccccc3C(F)(F)F)n2)CC1]

Step A: Preparation of tert-butyl 4-(5-(5-bromo-3-(2-(trifluoromethyl)phenoxy)pyridin-2-ylamino)-1,2,4-thiadiazol-3-yl)piperidine-1-carboxylate: Prepared according to Example 4, Step D, using 5-bromo-3-(2-(trifluoromethyl)phenoxy)pyridin-2-amine (Example 34, Steps A-C).

Step B: Preparation of tert-butyl 4-(5-(5-(3-methoxy-3-oxopropylthio)-3-(2-(trifluoromethyl)phenoxy)pyridin-2-ylamino)-1,2,4-thiadiazol-3-yl)piperidine-1-carboxylate: Prepared according to Example 3, Step. B.

Step C: Preparation of N-(3-(piperidin-4-yl)-1,2,4-thiadiazol-5-yl)-5-(thieno[3,2-b]pyridin-7-ylthio)-3-(2-(trifluoromethyl)phenoxy)pyridin-2-amine trihydrochloride: Prepared according to Example 3; Step C.

Step D: Preparation of 1-(4-(5-(5-(Thieno[3,2-b]pyridin-7-ylthio)-3-(2-(trifluoromethyl)phenoxy)pyridin-2-ylamino)-1,2,4-thiadiazol-3-yl)piperidin-1-yl)ethanone: Prepared according to Example 1, Step G. $^1$H NMR (d$_6$ DMSO) δ 1.55-1.65 (m, 1H), 1.69-1.79 (m, 1H), 1.97-2.05 (m, 5H), 2.77 (t, J=11.3 Hz, 1H), 3.05-3.10 (m, 1H), 3.20 (t, J=11.5 Hz, 1H), 3.85 (d, J=13.5 Hz, 1H), 4.33 (d, J=13.1 Hz, 1H), 6.91 (d, J=5.1 Hz, 1H), 7.25 (d, J=8.0 Hz, 1H), 7.36 (t, J=7.7 Hz, 1H), 7.48 (d, J=1.8 Hz, 1H), 7.58 (d, J=5.5 Hz, 1H), 7.65 (t, J=7.8 Hz, 1H), 7.78 (d, J=7.8 Hz, 1H), 8.15 (d, J=5.5 Hz, 1H), 8.48 (d, J=5.1 Hz, 1H), 8.54 (d, J=1.8 Hz, 1H), 12.62 (s, 1H).

Example 31

1-(4-(2-(5-(3-methylthieno[3,2-b]pyridin-7-ylthio)-3-phenoxypyridin-2-ylamino)thiazol-4-yl)piperidin-1-yl)ethanone

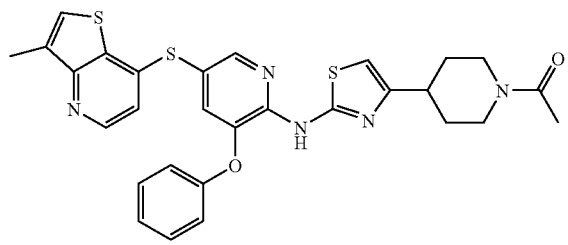 [SMILES: CC(=O)N1CCC(c2csc(Nc3ncc(Sc4ccnc5c(C)csc45)cc3Oc3ccccc3)n2)CC1]

Step A: Preparation of 3-amino-4-methylthiophene-2-carboxylic acid: Methyl 3-amino-4-methylthiophene-2-carboxylate (4.67 g, 27.3 mmol) and NaOH (2N in H$_2$O, 68 mL, 136 mmol) were stirred at 100° C. for 1 hour. The solution was cooled to 0° C. and acidified to pH=5 with addition of concentrated HCl solution to form a precipitate. The solution was filtered and the solid was dried under vacuum to give the title compound (2.8 g, 65%).

Step B: Preparation of 4-methylthiophen-3-amine: 3-amino-4-methylthiophene-2-carboxylic acid (5.64 g, 36 mmol) in HCl (6N in H$_2$O, 30 mL, 179 mmol) was stirred at 50° C. overnight, then cooled to ambient temperature and neutralized by the addition of solid NaHCO$_3$. The solution was extracted with dichloromethane (2 times), dried over Na$_2$SO$_4$, filtered and concentrated to yield the title compound (3.8 g, 94% yield).

Step C: Preparation of 2,2-dimethyl-5-((4-methylthiophen-3-ylamino)methylene)-1,3-dioxane-4,6-dione: A stirred solution of 2,2-dimethyl-1,3-dioxane-4,6-dione (4.85 g, 34 mmol) in trimethoxymethane (37 mL, 337 mmol) was heated to 90° C. under nitrogen. After 2 hours, a solution was 4-methylthiophen-3-amine (3.81 g, 34 mmol) was added (as a solution in trimethoxymethane (37 mL, 337 mmol). The reaction stirred at 90° C. for 6 hours and then was allowed to cool to ambient temperature and concentrated. The material was placed in the refrigerator where it solidified after two days to obtain the title compound (9 g, quantitative).

Step D: Preparation of 3-methylthieno[3,2-b]pyridin-7-ol: A solution of Dowtherm A (7 mL) was heated in oil bath at 235° C. under nitrogen. 2,2-Dimethyl-5-((4-methylthiophen-3-ylamino)methylene)-1,3-dioxane-4,6-dione (5.0 g, 19 mmol) was added in portions over a 20 minutes period. After the last portion was added, the solution stirred at 235° C. for another 5 minutes. The solution was removed from the oil bath and allowed to cool to ambient temperature. Upon cooling, the product precipitated out of solution. Diethyl ether was added and the solid was filtered and dried to give the title compound (3.2 g) with residual amounts of Dowtherm A remaining.

Step E: Preparation of 7-chloro-3-methylthieno[3,2-b]pyridine: Phosphorous oxychloride (2.2 mL, 24 mmol) in 1,2-dichloroethane (12 mL) was charged with 3-methylthieno[3,2-b]pyridin-7-ol (2.0 g, 12 mmol). The reaction stirred overnight at reflux under nitrogen. The mixture was the cooled and concentrated. Saturated NaHCO$_3$ solution was carefully added to neutralize the residue. The biphasic mixture was extracted with dichloromethane, dried, and concentrated. Flash chromatography (15% EtOAc/hexanes) of the crude material gave the title compound (1.23 g, 55%).

Step F: Preparation of 1-(4-(2-(5-(3-methylthieno[3,2-b]pyridin-7-ylthio)-3-phenoxypyridin-2-ylamino)thiazol-4-yl)piperidin-1-yl)ethanone: 7-chloro-3-methylthieno[3,2-b]pyridine (0.072 g, 0.39 mmol) and methyl 3-(6-(4-(1-acetylpiperidin-4-yl)thiazol-2-ylamino)-5-phenoxypyridin-3-ylthio)propanoate (Example 3, Step B, 0.20 g, 0.39 mmol) were dissolved in DMSO (3 mL). The solution was degassed for 15 minutes under nitrogen. KOtBu (0.13 g, 1.2 mmol) was added and the reaction stirred at ambient temperature for two hours. The solution was quenched with water, extracted with dichloromethane, dried, and concentrated. Flash chromatography of the crude material gave the title compound (0.100 g, 44% yield). $^1$H NMR (400 MHz, CDCl$_3$) δ 1.60-1.72 (m, 2H), 2.03-2.09 (m, 2H), 2.11 (s, 3H), 2.51 (s, 3H), 2.66-2.73 (m, 1H), 2.83-2.90 (m, 1H), 3.15-3.22 (m, 1H), 3.88-3.94 (m, 1H), 4.70-4.73 (m, 1H), 6.51 (s, 1H), 6.75 (d, 1H), 7.05 (d, 2H), 7.17-7.25 (m, 2H), 7.36-7.40 (m, 3H), 8.30 (d, 1H), 8.48 (d, 1H), 8.84 (bs, 1H).

Example 32

1-(4-(2-(5-(5-chlorothieno[3,2-b]pyridin-7-ylthio)-3-phenoxypyridin-2-ylamino)thiazol-4-yl)piperidin-1-yl)ethanone

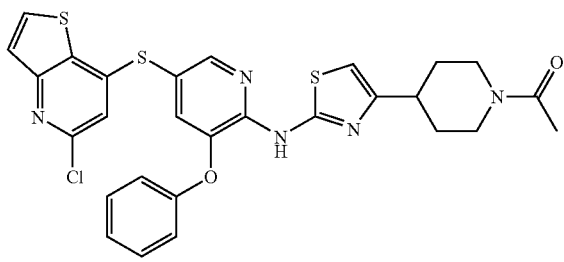 [SMILES: CC(=O)N1CCC(c2csc(Nc3ncc(Sc4cc(Cl)nc5ccsc45)cc3Oc3ccccc3)n2)CC1]

Steps A and B: Preparation of Thiophen-3-amine: Prepared according to Example 31, Steps A and B, using methyl 3-aminothiophene-2-carboxylate as the starting material.

Step C: Preparation of 5,7-dichlorothieno[3,2-b]pyridine: Malonic acid (2.66 g, 25.5 mmol) and thiophen-3-amine (2.53 g, 25.5 mmol) were suspended in phosphorous oxychloride (50 mL). The solution was refluxed overnight under nitrogen. The solution was cooled, quenched with ice water, neutralized with solid NaHCO$_3$, extracted with CH$_2$Cl$_2$, dried, and concentrated. Flash chromatography (10% EtOAc/hexanes) gave the title compound as a yellow solid.

Step D and E: Preparation of 1-(4-(2-(5-(5-chlorothieno[3,2-b]pyridin-7-ylthio)-3-phenoxypyridin-2-ylamino)thiazol-4-yl)piperidin-1-yl)ethanone: Prepared according to Example 34, Steps E and F. $^1$H NMR (400 MHz, CDCl$_3$) δ1.60-1.73 (m, 2H), 2.05-2.10 (m, 2H), 2.12 (s, 3H), 2.66 (t, 1H), 2.85-2.91 (m, 1H), 3.17 (t, 1H), 3.91 (d, 1H), 4.71 (d, 1H), 6.53 (s, 1H), 6.67 (s, 1H), 7.08 (d, 2H), 7.17 (s, 1H), 7.22-7.26 (m, 1H), 7.41 (t, 2H), 7.47 (d, 1H), 7.76 (d, 1H), 8.32 (s, 1H), 8.96 (s, 1H).

Example 33

1-(4-(2-(3-phenoxy-5-(thieno[2,3-d]pyrimidin-4-ylthio)pyridin-2-ylamino)thiazol-4-yl)piperidin-1-yl)ethanone

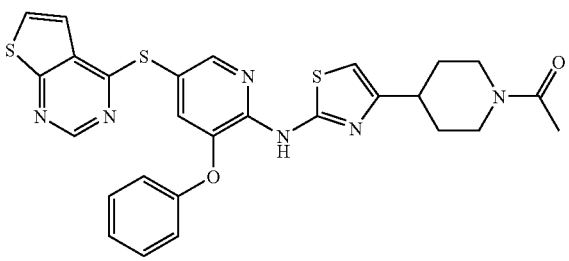 [SMILES: CC(=O)N1CCC(c2csc(Nc3ncc(Sc4ncnc5sccc45)cc3Oc3ccccc3)n2)CC1]

Step A: Thieno[2,3-d]pyrimidin-4(3H)-one: Methyl 2-aminothiophene-3-carboxylate (10 g, 64 mmol) was charged with formamide (50 mL). The reaction was heated at 190° C. under nitrogen for 3 hours, then cooled to ambient temperature. The resulting slurry was poured into 125 mL of water and extracted with chloroform:isopropyl alcohol mixture (2 times). The solution was concentrated and triturated to afford the title compound (2.25 g, 23%).

Step B: 4-Chlorothieno[2,3-d]pyrimidine: Thieno[2,3-d]pyrimidin-4(3H)-one (1.2 g, 7.9 mmol) was diluted in 1,2-dichloroethane (10 mL). Phosphorous oxychloride (1.4 mL, 15.7 mmol) was added. The reaction was stirred at 90° C. for 16 hours. An additional equivalent of phosphorous oxychloride (0.7 mL, 7.9 mmol) was added and the solution continued stirring for 4 hours. The solution was cooled, concentrated, and neutralized with saturated NaHCO$_3$ solution. The material was extracted with a chloroform:isopropyl alcohol mixture and the organic layer was separated and concentrated. Flash chromatography gave the title compound (0.39 g, 29%).

Step C: 1-(4-(2-(3-Phenoxy-5-(thieno[2,3-d]pyrimidin-4-ylthio)pyridin-2-ylamino)thiazol-4-yl)piperidin-1-yl)ethanone: 4-chlorothieno[2,3-d]pyrimidine (0.050 g, 0.29 mmol) and methyl 3-(6-(4-(1-acetylpiperidin-4-yl)thiazol-2-ylamino)-5-phenoxypyridin-3-ylthio)propanoate (Example 3, Step B, 0.15 g, 0.29 mmol) were dissolved in DMSO (3 mL). The solution was degassed for 15 minutes. KOtBu (0.098 g, 0.88 mmol) was added and the reaction stirred at ambient temperature for two hours. The solution was quenched with water, extracted with dichloromethane, dried, and concentrated. Flash chromatography of the crude material gave the title compound (0.075, 46%). $^1$H NMR (400 MHz, CDCl$_3$) δ 1.60-1.72 (m, 2H), 2.08-2.15 (m, 2H), 2.11 (m, 3H), 2.65-2.75 (m, 1H), 2.82-2.93 (m, 1H), 3.15-3.24 (m, 1H), 3.91 (d, 1H), 4.72 (d, 1H), 6.49 (s, 1H), 7.15 (d, 2H), 7.19 (t, 1H), 7.27-7.29 (m, 1H), 7.36-7.42 (m, 3H), 7.53 (d, 1H), 8.27 (d, 1H), 8.68 (s, 1H), 8.81 (s, 1H),

Example 34

1-(4-(5-(3-phenoxy-5-(pyridin-2-ylthio)pyridin-2-ylamino)-1,2,4-thiadiazol-3-yl)piperidin-1-yl)ethanone

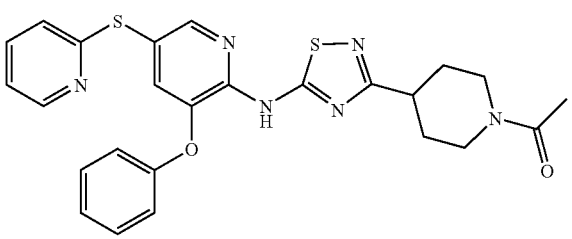 [SMILES: CC(=O)N1CCC(c2nsc(Nc3ncc(Sc4ccccn4)cc3Oc3ccccc3)n2)CC1]

Step A: A nitrogen purged flask was charged with 5-bromo-3-phenoxypyridin-2-amine (5.00 g, 18.9 mmol) and THF (80 mL) and cooled to –78° C. Methyllithium (14.1 mL, 22.6 mmol) was added and stirred for 5 minutes. Butyllithium (9.05 mL, 22.6 mmol) was added and the reaction was stirred for 10 minutes at –78° C. (solids precipitated). 2-(2-(Pyridin-3-yl)disulfanyl)pyridine (10.4 g, 47.2 mmol) was added and the reaction was warmed to ambient temperature and stirred for 18 hours. The reaction was poured into saturated aqueous NH$_4$Cl and extracted with EtOAc, dried over sodium sulfate, filtered and concentrated. The residue was dissolved in methanol and NaBH$_4$ (excess) was added and stirred for 10 minutes. The reaction was poured into saturated aqueous NH$_4$Cl and extracted with EtOAc (2×75 mL). The organic layer was dried with sodium sulfate, filtered and concentrated in vacuo. The residue was purified on silica (100% EtOAc to 1% methanol in EtOAc) to afford crude product. The material was dissolved in 2% MeOH in CH$_2$Cl$_2$ and washed with 1N NaOH. The organic layer was separated, dried, filtered, and concentrated to give 3-phenoxy-5-(pyridin-2-ylthio)pyridin-2-amine (10.4 g, 47.2 mmol).

Step B: A 20 mL vial was charged with pyridine (0.493 mL, 6.09 mmol), NaNCS (0.165 g, 2.03 mmol), tert-butyl 4-(chloro(methylsulfonyloxyimino)methyl(piperidine-1-carboxylate (0.692 g, 2.03 mmol) and CH₃CN (4 mL). The reaction was heated to 40° C. for 40 minutes. 3-Phenoxy-5-(pyridin-2-ylthio)pyridin-2-amine (0.400 g, 1.35 mmol) was added and stirred at 50° C. over the weekend. The reaction was poured into saturated aqueous NaHCO₃ and extracted with EtOAc (1×25 mL). The organic layer was dried with sodium sulfate, filtered and concentrated in vacuo. The residue was purified on silica (20-25% EtOAc in hexanes) to provide tert-butyl 4-(5-(3-phenoxy-5-(pyridin-2-ylthio)pyridin-2-ylamino)-1,2,4-thiadiazol-3-yl)piperidine-1-carboxylate (0.598 g, 78.5% yield).

Step C: Tert-butyl 4-(5-(3-phenoxy-5-(pyridin-2-ylthio)pyridin-2-ylamino)-1,2,4-thiadiazol-3-yl)piperidine-1-carboxylate (0.587 g, 1.04 mmol) was dissolved in 1:1 CH₂Cl₂/ acyl chloride, sulfamoyl chloride or sulfonyl chloride and a suitable base, such as a tertiary amine base (for example, triethylamine or pyridine).

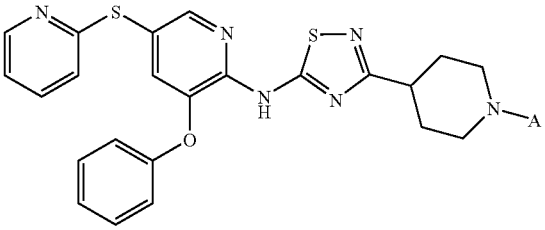

| Example | A | Name | NMR Data |
|---|---|---|---|
| 35 | ![A35] | 2-(dimethylamino)-1-(4-(5-(3-phenxoy-5-(pyridin-2-ylthio)pyridin-2-ylamino)-1,2,4-thiadiazol-3-yl)piperidin-1-yl)ethanonedihydrochloride | ¹H NMR (d₆-DMSO) δ 12.34 (s, 1H), 9.54 (bs, 1H), 8.39 (d, 1H), 8.37 (m, 1H), 7.67 (dt, 1H), 7.48 (d, 1H), 7.43 (t, 2H), 7.21-7.11 (m, 5H), 4.32 (m, 3H), 3.65 (d, 1H), 3.23 (m, 1H), 3.14 (m, 1H), 2.96 (t, 1H), 2.81 (d, 6H), 2.08 (d, 2H), 1.85-1.60 (m, 2H). |
| 36 | ![A36] | N,N-dimethyl-4-(5-(3-phenoxy-5-(pyridin-2-ylthio)pyridin-2-ylamino)-1,2,4-thiadiazol-3-yl)piperidine-1-carboxamide dihydrochloride | ¹H NMR (d₆-DMSO) δ 12.34 (s, 1H), 8.39 (d, 1H), 8.37 (m, 1H), 7.66 (dt, 1H), 7.47 (d, 1H), 7.42 (t, 2H), 7.21-7.11 (m, 5H), 3.58 (d, 2H), 2.96 (m, 1H), 2.84 (t, 2H), 2.73 (s, 6H), 1.96 (m, 2H), 1.74 (m, 2H). |
| 37 | ![A37] | 2-methyl-1-(4-(5-(3-phenoxy-5-(pyridin-2-ylthio)pyridin-2-ylamino)-1,2,4-thiadiazol-3-yl)piperidin-1-yl)propan-1-one dihydrochloride | ¹H NMR (d₆-DMSO) δ 12.34 (s, 1H), 8.39 (d, 1H), 8.37 (m, 1H), 7.66 (dt, 1H), 7.47 (d, 1H), 7.42 (t, 2H), 7.21-7.11 (m, 5H), 4.37 (d, 1H), 3.98 (d, 1H), 3.20 (t, 1H), 3.07 (m, 1H), 2.89 (m, 1H), 2.75 (t, 1H), 2.02 (m, 2H), 1.70 (m, 1H), 1.57 (m, 1H), 1.00 (d, 6H). |
| 38 | ![A38] | 3-(1-(methylsulfonyl)piperidin-4-yl)-N-(3-phenoxy-5-(pyridin-2-ylthio)pyridin-2-yl)-1,2,4-thiadiazol-5-aminedihydrochloride | ¹H NMR (d₆-DMSO) δ 12.36 (s, 1H), 8.40 (d, 1H), 8.37 (m, 1H), 7.67 (dt, 1H), 7.48 (d, 1H), 7.43 (t, 2H), 7.21-7.11 (m, 5H), 3.59 (d, 2H), 2.95-2.86 (m, 6H), 2.14 (d, 2H), 1.81 (m, 2H). | methanol and 4N HCl in dioxane was added and stirred at ambient temperature for 1 hour. The reaction was concentrated and dried in vacuum oven. The HCl salt was partitioned between 5% MeOH in CH₂Cl₂ and saturated aqueous sodium bicarbonate. The organic layer was separated, dried over sodium sulfate, filtered and concentrated to give N-(3-phenoxy-5-(pyridin-2-ylthio)pyridin-2-yl)-3-(piperidin-4-yl)-1,2,4-thiadiazol-5-amine (0.473 g, 98.0% yield).

Step D: 3-Phenoxy-N-(3-(piperidin-4-yl)-1,2,4-thiadiazol-5-yl)-5-(pyridin-2-ylthio)pyridin-2-amine (0.075 g, 0.16 mmol), TEA (0.090 mL, 0.65 mmol), and acetic anhydride (0.017 g, 0.16 mmol) were added to THF and stirred for 3 hours. Water was added and the reaction was extracted with CH₂Cl₂. The organic layer was dried, filtered, and concentrated. The residue was purified by silica gel (5% MeOH in CH₂Cl₂) to provide the title compound (0.044 g, 54% yield).
¹H NMR (d₆-DMSO) δ 12.34 (s, 1H), 8.38 (m, 2H), 7.67 (dt, 1H), 7.48 (d, 1H), 7.42 (t, 2H), 7.21-7.11 (m, 5H), 4.32 (d, 1H), 3.84 (d, 1H), 3.19 (m, 1H), 3.05 (m, 1H), 2.76 (t, 1H), 2.01 (m, 5H), 1.74 (m, 1H), 1.59 (m, 1H).

The following compounds were made according to Example 34, Step D, using the appropriate acid anhydride, Example 39

4-(5-(3-phenoxy-5-(pyridin-2-ylthio)pyridin-2-ylamino)-1,2,4-thiadiazol-3-yl)piperidine-1-carboxamide dihydrochloride

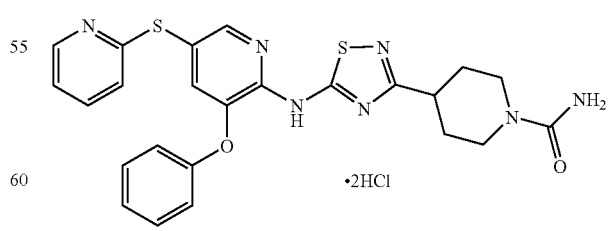

To a solution of N-(3-phenoxy-5-(pyridin-2-ylthio)pyridin-2-yl)-3-(piperidin-4-yl)-1,2,4-thiadiazol-5-amine (Example 34, Step C, 0.055 g, 0.119 mmol) in CH₂Cl₂ (4 mL) was added pyridine (0.0940 g, 1.19 mmol), acetic acid (0.0714 g, 1.19 mmol), TEA (0.033 mL, 0.238 mmol), and potassium cyanate (0.0193 g, 0.238 mmol). The reaction was stirred for 18 hours. Water was added and the reaction was extracted with $CH_2Cl_2$. The organic layer was dried, filtered, and concentrated. The residue was purified by silica gel (1-4% MeOH in $CH_2Cl_2$) to give the title compound (0.0333 g, 48.4% yield) after HCl salt formation. $^1$H NMR ($d_6$-DMSO) δ 12.33 (s, 1H), 8.39 (d, 1H), 8.37 (m, 1H), 7.67 (dt, 1H), 7.47 (d, 1H), 7.42 (t, 2H), 7.21-7.11 (m, 5H), 3.94 (d, 2H), 2.97 (m, 1H), 2.83 (t, 2H), 1.19 (m, 2H), 1.64 (m, 2H).

Example 40

(R)-2-hydroxy-1-(4-(5-(3-phenoxy-5-(pyridin-2-ylthio)pyridin-2-ylamino)-1,2,4-thiadiazol-3-yl)piperidin-1-yl)propan-1-one

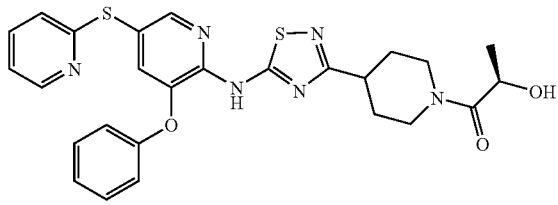 [SMILES: C[C@@H](O)C(=O)N1CCC(c2nsc(Nc3ncc(Sc4ccccn4)cc3Oc3ccccc3)n2)CC1]

N-(3-phenoxy-5-(pyridin-2-ylthio)pyridin-2-yl)-3-(piperidin-4-yl)-1,2,4-thiadiazol-5-amine (Example 34, Step C, 0.075 g, 0.16 mmol), (S)-2-hydroxypropanoic acid (0.018 g, 0.19 mmol), N1-((ethylimino)methylene)-N3,N3-dimethylpropane-1,3-diamine hydrochloride (0.047 g, 0.24 mmol), and N,N-dimethylpyridin-4-amine (0.002 g, 0.016 mmol) were dissolved in $CH_2Cl_2$ (5 mL). Triethylamine (0.033 g, 0.32 mmol) was added and the solution was stirred at ambient temperature for 3 hours. Water was added and extracted with $CH_2Cl_2$, dried, filtered, and concentrated. The residue was purified by silica gel (1-2% MeOH in $CH_2Cl_2$) to give (R)-2-hydroxy-1-(4-(5-(3-phenoxy-5-(pyridin-2-ylthio)pyridin-2-ylamino)-1,2,4-thiadiazol-3-yl)piperidin-1-yl)propan-1-one (0.023 g, 27% yield). $^1$H NMR ($d_6$-DMSO) δ 12.34 (s, 1H), 8.39 (d, 1H), 8.37 (m, 1H), 7.66 (dt, 1H), 7.47 (d, 1H), 7.42 (t, 2H), 7.21-7.11 (m, 5H), 4.82 (t, 1H), 4.45 (m, 1H), 4.34 (m, 1H), 4.01 (m, 1H), 3.25-3.04 (m, 2H), 2.84 (m, 1H), 2.02 (d, 2H), 1.81-1.55 (m, 2H), 1.18 (d, 3H).

Example 41

(S)-2-hydroxy-1-(4-(5-(3-phenoxy-5-(pyridin-2-ylthio)pyridin-2-ylamino)-1,2,4-thiadiazol-3-yl)piperidin-1-yl)propan-1-one

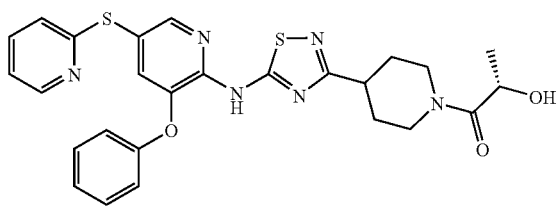 [SMILES: C[C@H](O)C(=O)N1CCC(c2nsc(Nc3ncc(Sc4ccccn4)cc3Oc3ccccc3)n2)CC1]

Prepared according to Example 40. $^1$H NMR ($d_6$-DMSO) δ 12.34 (s, 1H), 8.39 (d, 1H), 8.37 (m, 1H), 7.66 (dt, 1H), 7.47 (d, 1H), 7.42 (t, 2H), 7.21-7.11 (m, 5H), 4.82 (t, 1H), 4.45 (m, 1H), 4.34 (m, 1H), 4.01 (m, 1H), 3.25-3.04 (m, 2H), 2.84 (m, 1H), 2.02 (d, 2H), 1.81-1.55 (m, 2H), 1.18 (d, 3H).

Example 42

4-(5-(3-Phenoxy-5-(pyridin-2-ylthio)pyridin-2-ylamino)-1,2,4-thiadiazol-3-yl)piperidine-1-sulfonamide bis(2,2,2-trifluoroacetate)

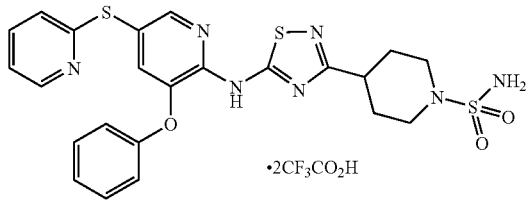 [SMILES: NS(=O)(=O)N1CCC(c2nsc(Nc3ncc(Sc4ccccn4)cc3Oc3ccccc3)n2)CC1 ; "·2CF3CO2H"]

N-(3-phenoxy-5-(pyridin-2-ylthio)pyridin-2-yl)-3-(piperidin-4-yl)-1,2,4-thiadiazol-5-amine (Example 34, Step C, 7.2 g, 14.01 mmol) and sulfamide (1.414 g, 14.71 mmol) were dissolved in dioxane (15 mL) and heated to reflux overnight. The reaction was cooled and water was added and extracted with $CH_2Cl_2$. The organic layer was dried over sodium sulfate, filtered and concentrated. The residue was purified by silica gel (1:1EtOAc in $CH_2Cl_2$). The purified material was dissolved in $CH_2Cl_2$ and 2M HCl in ether was added. The solution was concentrated and dried in a vacuum oven to afford 4-(5-(3-phenoxy-5-(pyridin-2-ylthio)pyridin-2-ylamino)-1,2,4-thiadiazol-3-yl)piperidine-1-sulfonamide hydrochloride (3.145 g, 38.8% yield). $^1$H NMR ($d_6$-DMSO) δ 12.35 (s, 1H), 8.39 (d, 1H), 8.37 (m, 1H), 7.67 (dt, 1H), 7.48 (d, 1H), 7.42 (t, 2H), 7.21-7.11 (m, 5H), 6.73 (bs, 2H), 3.47 (d, 2H), 2.87 (m, 1H), 2.71 (t, 2H), 2.11 (d, 2H), 1.85 (m, 2H).

Example 43

1-(4-(2-(3-phenoxy-5-(pyridin-2-ylthio)pyridin-2-ylamino)thiazol-4-yl)piperidin-1-yl)ethanone dihydrochloride

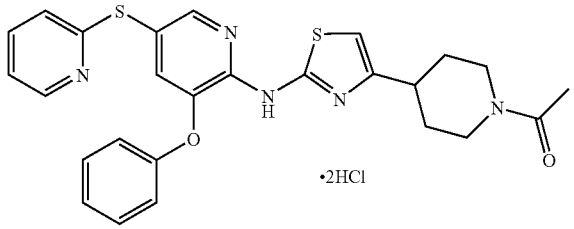 [SMILES: CC(=O)N1CCC(c2csc(Nc3ncc(Sc4ccccn4)cc3Oc3ccccc3)n2)CC1 ; "·2HCl"]

Step A: A 125 mL flask was charged with 3-phenoxy-5-(pyridin-2-ylthio)pyridin-2-amine (Example 34, Step A, 1.15 g, 3.89 mmol) and benzoyl isothiocyanate (0.699 g, 4.28 mmol) in THF (50 mL) and stirred at ambient temperature for 18 hours. The THF was removed in vacuo and the residue was dissolved in $CH_2Cl_2$ (10 mL) and added dropwise to 100 mL of 9:1 hexanes:EtOAc. The solvent was decanted and the residue was dried to provide 1-benzoyl-3-(3-phenoxy-5-(pyridin-2-ylthio)pyridin-2-yl)thiourea (1.57 g, 88.2% yield) as a yellow solid.

Step B: A mixture of 1-benzoyl-3-(3-phenoxy-5-(pyridin-2-ylthio)pyridin-2-yl)thiourea (2.10 g, 4.58 mmol) and K₂CO₃ (3.16 g, 22.9 mmol) was refluxed in EtOH (50 mL) for 18 hours. The reaction was cooled to ambient temperature, filtered and concentrated. The residue was purified by silica gel to provide 1-(3-phenoxy-5-(pyridin-2-ylthio)pyridin-2-yl)thiourea (0.484 g, 29.8% yield).

Step C: A mixture of 1-(3-phenoxy-5-(pyridin-2-ylthio)pyridin-2-yl)thiourea (0.075 g, 0.21 mmol), triethylamine (0.073 mL, 0.53 mmol), and 1-(1-acetylpiperidin-4-yl)-2-bromoethanone (0.087 g, 0.26 mmol) was refluxed in Ethanol (10 mL) for 3 hours. The reaction was concentrated and the residue was purified by silica gel (1% MeOH in CH₂Cl₂) to provide 1-(4-(2-(3-phenoxy-5-(pyridin-2-ylthio)pyridin-2-ylamino)thiazol-4-yl)piperidin-1-yl)ethanone dihydrochloride (0.093 g, 76.2% yield) after HCl salt formation. ¹H NMR (d₆-DMSO) δ 8.38 (m, 1H), 8.29 (d, 1H), 7.67 (dt, 1H), 7.45-7.37 (m, 3H), 7.21-7.08 (m, 5H), 6.78 (s, 1H), 4.32 (d, 1H), 3.87 (d, 1H), 3.13 (t, 1H), 2.87 (m, 1H), 2.64 (t, 1H), 2.01 (s, 3H), 1.95 (m, 2H), 1.63-1.39 (m, 2H).

Example 44

1-(3-methyl-4-(2-(3-phenoxy-5-(pyridin-2-ylthio)pyridin-2-ylamino)thiazol-4-yl)piperidin-1-yl)ethanone dihydrochloride

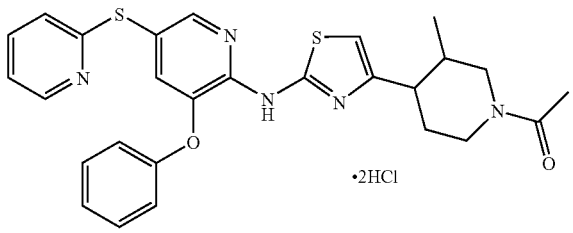 [SMILES: CC(=O)N1CCC(c2csc(Nc3ncc(Sc4ccccn4)cc3Oc3ccccc3)n2)C(C)C1 ; "·2HCl"]

Step A: Preparation of tert-butyl 4-(methoxy(methyl)carbamoyl)-3-methylpiperidine-1-carboxylate: To a solution of 1-(tert-butoxycarbonyl)-3-methylpiperidine-4-carboxylic acid (3.00 g, 12.3 mmol) in CH₂Cl₂ (200 mL) was added di(1H-imidazol-1-yl)methanone (2.19 g, 13.6 mmol) portionwise. After the bubbling ceased (~60 minutes), N-methoxymethanamine hydrochloride (1.32 g, 13.6 mmol) was added in one portion. The mixture was stirred overnight at ambient temperature, then washed with water, 1N HCl, and saturated sodium bicarbonate. The organic layer was dried, filtered, and concentrated to give the desired product (2.29 g, 64.8% yield) as a colorless oil.

Step B: Preparation of tert-butyl 4-acetyl-3-methylpiperidine-1-carboxylate: 3.0 M methylmagnesium chloride in THF (4.50 mL, 13.5 mmol) was added dropwise to a solution of tert-butyl 4-(methoxy(methyl)carbamoyl)-3-methylpiperidine-1-carboxylate (3.10 g, 10.8 mmol) in THF (50 mL) at 0° C. The reaction was warmed to ambient temperature and stirred for 90 minutes. The reaction was partitioned between ether and 2N HCl, washed the organic layer twice with water, brine, dried, and concentrated to afford the title compound (2.32 g, 84.3% yield) as clear oil.

Step C: Preparation of tert-butyl 4-(2-bromoacetyl)-3-methylpiperidine-1-carboxylate: To a cooled (−78° C.) solution of LDA (5.69 mL, 11.4 mmol) in THF (100 mL) was added dropwise over 40 minutes a solution of tert-butyl 4-acetyl-3-methylpiperidine-1-carboxylate (2.29 g, 9.48 mmol) in THF (40 mL). After an additional 25 minutes, chlorotrimethylsilane (2.41 mL, 18.9 mmol) was added, dropwise over 20 minutes. After stirring for 1 hour the reaction was poured into 600 mL saturated sodium bicarbonate and extracted with ether (2×400 mL). The combined ether layers were washed with brine, dried, filtered, and concentrated. The crude material was dissolved in 500 mL THF, cooled to 0° C., and treated with sodium bicarbonate (1.20 g, 14.2 mmol), followed by NBS (1.69 g, 9.48 mmol). The reaction was warmed to ambient temperature while stirring for 90 minutes, then poured into 400 mL of saturated sodium bicarbonate solution and extracted with Et₂O. The combined organic layers were washed with saturated NaHCO₃, brine, dried, and concentrated to give the title compound (3.35 g, 110% yield).

Step D: Preparation of tert-butyl 3-methyl-4-(2-(3-phenoxy-5-(pyridin-2-ylthio)pyridin-2-ylamino)thiazol-4-yl)piperidine-1-carboxylate: Prepared according to Example 1, Step F affords the title compound (0.302 g, 68.6% yield).

Step E: Preparation of N-(4-(3-methylpiperidin-4-yl)thiazol-2-yl)-3-phenoxy-5-(pyridin-2-ylthio)pyridin-2-amine: A 25 mL flask was charged with tert-butyl 3-methyl-4-(2-(3-phenoxy-5-(pyridin-2-ylthio)pyridin-2-ylamino)thiazol-4-yl)piperidine-1-carboxylate (0.296 g, 0.514 mmol), CH₂Cl₂ (3 mL) and MeOH (3 mL). 4N HCl in dioxane (6 mL) was added and the reaction was stirred for 1 hour and then concentrated. The crude material was dissolved in CH₂Cl₂ and washed with saturated aqueous sodium bicarbonate. The organic layer was dried over sodium sulfate, filtered and concentrated to afford N-(4-(3-methylpiperidin-4-yl)thiazol-2-yl)-3-phenoxy-5-(pyridin-2-ylthio)pyridin-2-amine (0.202 g, 82% yield)

Step F: Preparation of 1-(3-methyl-4-(2-(3-phenoxy-5-(pyridin-2-ylthio)pyridin-2-ylamino)thiazol-4-yl)piperidin-1-yl)ethanone dihydrochloride: Prepared according to Example 1, Step G, to provide the title compound (0.0553 g, 51.4% yield) as a 1:1 mixture of diastereomers. ¹H NMR (d₆-DMSO) δ 8.37 (d, 1H), 8.29 (s, 1H), 7.67 (dt, 1H), 7.43 (t, 2H), 7.37 (d, 1H), 7.17 (m, 4H), 7.10 (d, 1H), 6.73 (d, 1H), 4.50 (d, 0.5H), 4.27 (d, 0.5H), 3.94 (d, 0.5H), 3.74 (d, 0.5H), 3.33 (d, 0.5H), 3.15 (t, 0.5H), 3.04 (m, 1H), 2.87 (d, 0.5), 2.67 (m, 0.5H), 2.32 (m, 1H), 2.05 (s, 1.5H), 1.98 (s, 1.5H), 1.89-1.69 (m, 2H), 0.64 (d, 1.5H), 0.56 (d, 1.5H).

Example 45

1-(4-(2-(3-(2-bromo-4-fluorophenoxy)-5-(3-methoxyphenylthio)pyridin-2-ylamino)thiazol-4-yl)piperidin-1-yl)ethanone hydrochloride

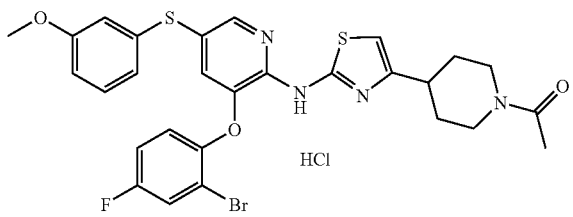 [SMILES: COc1cccc(Sc2cnc(Nc3nc(C4CCN(C(C)=O)CC4)cs3)c(Oc3ccc(F)cc3Br)c2)c1 ; Cl]

Step A: A 1 L flask was charged with 2-bromo-4-fluorophenol (20.5 g, 107 mmol) and DMF (500 mL). The reaction was cooled to 0° C. and NaH (2.84 g, 118 mmol) was added slowly and stirred for 15 minutes. 5-Bromo-3-nitropicolinonitrile (24.5 g, 107 mmol) was added and reaction stirred at 0° C. for 20 minutes. Saturated NH₄Cl (300 mL) was added and poured into 1L water and stirred. The resultant solids were filtered and dried in a vacuum oven overnight to afford 5-bromo-3-(2-bromo-4-fluorophenoxy)picolinonitrile (38.3 g, 95.8% yield).

Step B: A 500 mL flask was charged with 5-bromo-3-(2-bromo-4-fluorophenoxy)picolinonitrile (10 g, 26.9 mmol), 3-methoxybenzenethiol (3.34 mL, 26.9 mmol), and DMF (250 mL). The reaction was cooled to 0° C. and NaH (0.710 g, 29.6 mmol) was added slowly. The reaction stirred for 30 minutes at 0° C. The reaction was poured into saturated aqueous sodium bicarbonate and extracted with EtOAc. The organic layer was dried with sodium sulfate, filtered and concentrated in vacuo to afford 3-(2-bromo-4-fluorophenoxy)-5-(3-methoxyphenylthio)picolinonitrile (12.0 g, 104% yield) as an amber oil.

Step C: A 500 mL flask was charged with 3-(2-bromo-4-fluorophenoxy)-5-(3-methoxyphenylthio)picolinonitrile (10.0 g, 23.2 mmol) and EtOH (200 mL). Potassium hydroxide (46.4 mL, 116 mmol) was added and reaction heated to reflux overnight. The reaction was cooled to ambient temperature concentrated to half volume, poured into dilute HCl and extracted with EtOAc (2×300 mL). The organic layer was dried with sodium sulfate, filtered and concentrated in vacuo to afford 3-(2-bromo-4-fluorophenoxy)-5-(3-methoxyphenylthio)picolinic acid (10.8 g, 103% yield).

Step D: A 500 mL flask was charged with 3-(2-bromo-4-fluorophenoxy)-5-(3-methoxyphenylthio)picolinic acid (10.0 g, 22.2 mmol), 2-methylpropan-2-ol (11.6 mL, 133 mmol), triethylamine (4.0 mL, 28.9 mmol), and Toluene (200 mL). The reaction was heated to 100° C. and DPPA (4.8 mL, 22.2 mmol) was added dropwise. The reaction was stirred for 10 minutes, then cooled to ambient temperature, poured into dilute NaOH and extracted with EtOAc. The organic layer was dried with sodium sulfate, filtered and concentrated in vacuo. The residue was purified on silica (10 to 20% EtOAc in hexanes) to afford tert-butyl 3-(2-bromo-4-fluorophenoxy)-5-(3-methoxyphenylthio)pyridin-2-ylcarbamate (8.4 g, 72.5% yield).

Step E: A 250 mL flask was charged with tert-butyl 3-(2-bromo-4-fluorophenoxy)-5-(3-methoxyphenylthio)pyridin-2-ylcarbamate (9.1 g, 17 mmol) and 1:1 mixture of CH$_2$Cl$_2$ and MeOH (100 mL). 4N HCl in dioxane was added (50 mL) and the reaction was stirred at ambient temperature overnight. The solvent was removed and dried on high vacuum to afford 3-(2-bromo-4-fluorophenoxy)-5-(3-methoxyphenylthio)pyridin-2-amine (8.0 g, 109% yield) as a yellow solid.

Step F: A 250 mL flask was charged with 3-(2-bromo-4-fluorophenoxy)-5-(3-methoxyphenylthio)pyridin-2-amine (7.4 g, 17.6 mmol), benzoyl isothiocyanate (3.08 mL, 22.8 mmol), and THF (125 mL). The reaction was stirred at ambient temperature overnight. Hexanes (700 mL) added and the reaction was stirred at ambient temperature for 1 hour. The solution was decanted to afford 5.6 g of material as a yellow foam. The mother liquor was concentrated and suspended in 9:1 Hexanes:EtOAc (200 mL) to afford another 4.7 g of product after filtration. Total yield of 1-benzoyl-3-(3-(2-bromo-4-fluorophenoxy)-5-(3-methoxyphenylthio)pyridin-2-yl)thiourea (10.3 g, 100%).

Step G: A 250 mL flask was charged with 1-benzoyl-3-(3-(2-bromo-4-fluorophenoxy)-5-(3-methoxyphenylthio)pyridin-2-yl)thiourea (10.3 g, 17.6 mmol) and EtOH (125 mL). Sodium hydroxide (11.7 mL, 35.2 mmol) was added and the reaction was heated to 50° C. overnight. The reaction was cooled to ambient temperature and poured into 750 mL water and stirred vigorously for 1 hour. The resultant solids were filtered to afford 1-(3-(2-bromo-4-fluorophenoxy)-5-(3-methoxyphenylthio)pyridin-2-yl)thiourea (6.5 g, 76.8% yield) as a pale yellow solid.

Step H: A 50 mL flask was charged with 1-(3-(2-bromo-4-fluorophenoxy)-5-(3-methoxyphenylthio)pyridin-2-yl)thiourea (1.5 g, 3.12 mmol), triethylamine (0.740 mL, 5.31 mmol), tert-butyl 4-(2-bromoacetyl)piperidine-1-carboxylate (1.15 g, 3.75 mmol), and EtOH (25 mL). The reaction was heated to 70° C. for 2 hours. The reaction was partitioned between EtOAc and water. The organic layer was dried with sodium sulfate, filtered and concentrated. The residue was purified on silica (10% EtOAc in hexanes) to afford tert-butyl 4-(2-(3-(2-bromo-4-fluorophenoxy)-5-(3-methoxyphenylthio)pyridin-2-ylamino)thiazol-4-yl)piperidine-1-carboxylate (1.76 g, 82.0% yield).

Step I: A 20 mL vial was charged with tert-butyl. 4-(2-(3-(2-bromo-4-fluorophenoxy)-5-(3-methoxyphenylthio)pyridin-2-ylamino)thiazol-4-yl)piperidine-1-carboxylate (100 mg, 0.145 mmol) and CH$_2$Cl$_2$ (2 mL). TFA (2 mL) was added and stirred at ambient temperature for 5 minutes. The reaction was poured into water and diluted with CH$_2$Cl$_2$. Solid Na$_2$CO$_3$ added slowly to neutralize the TFA. The reaction was extracted and dried to afford 3-(2-bromo-4-fluorophenoxy)-5-(3-methoxyphenylthio)-N-(4-(piperidin-4-yl)thiazol-2-yl)pyridin-2-amine (88 mg, 103% yield) as a yellow solid.

Step J: Prepared according to Example 1, Step G using 3-(2-bromo-4-fluorophenoxy)-5-(3-methoxyphenylthio)-N-(4-(piperidin-4-yl)thiazol-2-yl)pyridin-2-amine. $^1$H NMR (d$_6$-DMSO) δ 11.20 (bs, 1H), 8.17 (d, 1H), 7.74 (m, 1H), 7.31 (m, 2H), 7.21 (t, 1H), 6.93 (d, 1H), 6.78 (m, 1H), 6.74 (s, 1H), 6.71 (m, 2H), 4.43 (d, 1H), 3.87 (d, 1H), 3.69 (s, 3H), 3.14 (m, 1H), 2.86 (m, 1H), 2.64 (m, 1H), 2.01 (s, 3H), 1.95 (m, 2H), 1.58 (m, 1H), 1.45 (m, 1H). Mass spectrum (apci) m/z=631.4 (M+H—HCl).

Example 46

1-(4-(2-(3-(2-bromo-4-fluorophenoxy)-5-(3-methoxyphenylthio)pyridin-2-ylamino)thiazol-4-yl)piperidin-1-yl)-2-(dimethylamino)ethanone dihydro chloride

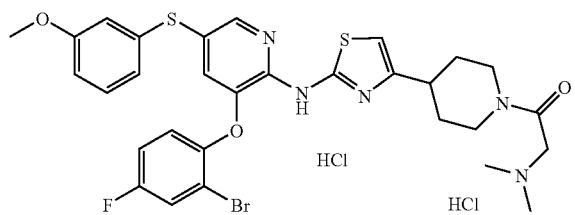 [SMILES: COc1cccc(Sc2cnc(Nc3nc(C4CCN(C(=O)CN(C)C)CC4)cs3)c(Oc3ccc(F)cc3Br)c2)c1 ; Cl ; Cl]

Prepared according to Example 1, Step G from 3-(2-bromo-4-fluorophenoxy)-5-(3-methoxyphenylthio)-N-(4-(piperidin-4-yl)thiazol-2-yl)pyridin-2-amine (Example 50, Step I). $^1$H NMR (d$_6$-DMSO) δ 11.15 (bs, 1H), 9.60 (bs, 1H), 8.17 (d, 1H), 7.75 (m, 1H), 7.32 (m, 2H), 7.21 (t, 1H), 6.94 (d, 1H), 6.79 (m, 1H), 6.75 (s, 1H), 6.71 (m, 2H), 4.42 (d, 1H), 4.31 (qd, 2H), 3.69 (s, 3H), 3.19 (t, 1H), 2.93 (m, 1H), 2.82 (m, 6H), 2.04 (d, 2H), 1.64 (m, 1H), 1.52 (m, 1H). Mass spectrum (apci) m/z=674.3 (M+H-2HCl).

Example 47

1-(4-(2-(3-(4-fluoro-2-methylphenoxy)-5-(3-methoxyphenylthio)pyridin-2-ylamino)thiazol-4-yl)piperidin-1-yl)ethanone hydrochloride

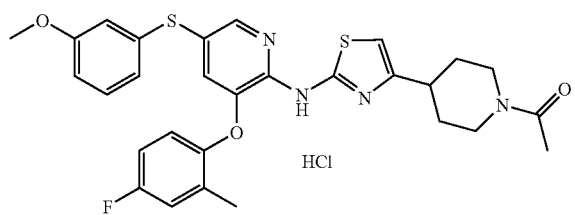 [SMILES: COc1cccc(Sc2cnc(Nc3nc(C4CCN(C(C)=O)CC4)cs3)c(Oc3ccc(F)cc3C)c2)c1 ; Cl]

Step A: Preparation of 4-(2-(3-(4-fluoro-2-methylphenoxy)-5-(3-methoxyphenylthio)pyridin-2-ylamino)thiazol-4-yl)piperidine-1-carboxylate trifluoroacetate: A 10 mL flask was charged with tert-butyl 4-(2-(3-(2-bromo-4-fluorophenoxy)-5-(3-methoxyphenylthio)pyridin-2-ylamino)thiazol-4-yl)piperidine-1-carboxylate (Example 50, Step H, 200 mg, 0.29 mmol) and THF (3 mL). The reaction was cooled to −78° C. and methyllithium (0.22 mL, 0.35 mmol) was added and stirred for 5 minutes. Butyllithium (0.140 mL, 0.35 mmol) was added and the reaction was stirred for 5 minutes. Iodomethane (0.0273 mL, 0.436 mmol) was added and the reaction was stirred for 5 minutes and then poured into saturated aqueous NH$_4$Cl and extracted with EtOAc (1×20 mL). The organic layer was dried with sodium sulfate, filtered and concentrated in vacuo to afford a mixture of products. The residue was purified on a reverse phase column (35 to 100% ACN in water with 0.1% TFA) to afford the title compound (70 mg, 33% yield).

Step B: Preparation of N-(3-(4-fluoro-2-methylphenoxy)-5-(3-methoxyphenylthio)pyridin-2-yl)-4-(piperidin-4-yl)thiazol-2-amine ditrifluoroacetate: A 10 mL flask was charged with tert-butyl 4-(2-(3-(4-fluoro-2-methylphenoxy)-5-(3-methoxyphenylthio)pyridin-2-ylamino)thiazol-4-yl)piperidine-1-carboxylate trifluoroacetate (70 mg, 0.097 mmol) and CH$_2$Cl$_2$ (2 mL). TFA (2 mL) was added and the reaction was stirred at ambient temperature for 30 minutes. The solvent was removed and residue was dried on high vacuum overnight. The crude material was taken on to the next reaction without further purification.

Step C: Preparation of 1-(4-(2-(3-(4-fluoro-2-methylphenoxy)-5-(3-methoxyphenylthio)pyridin-2-ylamino)thiazol-4-yl)piperidin-1-yl)ethanone hydrochloride: A 20 mL vial was charged with 3-(4-fluoro-2-methylphenoxy)-5-(3-methoxyphenylthio)-N-(4-(piperidin-4-yl)thiazol-2-yl)pyridin-2-amine ditrifluoroacetate (70 mg, 0.098 mmol) and CH$_2$Cl$_2$ (2 mL). Triethylamine (0.109 mL, 0.78 mmol) was added followed by acetic anhydride (0.012 mL, 0.12 mmol) and the reaction was stirred for 5 minutes. The reaction was poured into saturated aqueous NaHCO$_3$ and extracted with CH$_2$Cl$_2$. The organic layer was dried with sodium sulfate, filtered and concentrated in vacuo. The residue was purified on silica gel (20 to 40% EtOAc in hexanes) to afford the title compound (44.8 mg, 76.3% yield) after HCl salt formation. $^1$H NMR (d$_6$-DMSO) δ 11.20 (bs, 1H), 8.14 (d, 1H), 7.22 (m, 2H), 7.04 (m, 2H), 6.88 (d, 1H), 6.77 (m, 2H), 6.71 (m, 2H), 4.43 (d, 1H), 3.88 (d, 1H), 3.69 (s, 3H), 3.14 (t, 1H), 2.87 (m, 1H), 2.65 (m, 1H), 2.19 (s, 3H), 2.01 (s, 3H), 1.95 (m, 2H), 1.58 (m, 1H); 1.45 (m, 1H). Mass spectrum (apci) m/z=565.3 (M+H—HCl).

Example 48

1-(4-(2-(3-(4-fluorophenoxy)-5-(3-methoxyphenylthio)pyridin-2-ylamino)thiazol-4-yl)piperidin-1-yl)ethanone hydrochloride

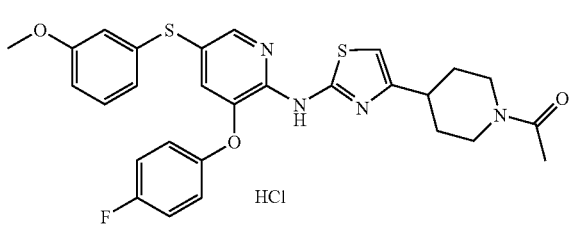 [SMILES: COc1cccc(Sc2cnc(Nc3nc(C4CCN(C(C)=O)CC4)cs3)c(Oc3ccc(F)cc3)c2)c1 ; Cl]

Step A: Preparation of 3-(4-fluorophenoxy)-5-(3-methoxyphenylthio)-N-(4-(piperidin-4-yl)thiazol-2-yl)pyridin-2-amine ditrifluoroacetate: A 10 mL flask was charged with tert-butyl 4-(2-(3-(4-fluorophenoxy)-5-(3-methoxyphenylthio)pyridin-2-ylamino)thiazol-4-yl)piperidine-1-carboxylate (byproduct of the reaction in Example 47 Step A; 68 mg, 0.11 mmol) and CH$_2$Cl$_2$ (2 mL). TFA (2 mL) was added and stirred at ambient temperature for 30 minutes. The reaction was concentrated and taken on to next reaction without further purification.

Step B: Preparation of 1-(4-(2-(3-(4-fluorophenoxy)-5-(3-methoxyphenylthio)pyridin-2-ylamino)thiazol-4-yl)piperidin-1-yl)ethanone hydrochloride: Prepared according to Example 1, Step G. $^1$H NMR (d$_6$-DMSO) δ 11.10 (bs, 1H), 8.19 (m, 1H), 7.22 (m, 4H), 7.15 (m, 2H), 6.79 (m, 1H), 6.74 (m, 3H), 4.42 (d, 1H), 3.87 (d, 1H), 3.70 (s, 3H), 3.13 (t, 1H), 2.85 (t, 1H), 2.63 (t, 1H), 2.01 (d, 3H), 1.94 (m, 2H), 1.57 (m, 1H), 1.44 (m, 1H). Mass spectrum (esi) m/z=551.0 (M+H—HCl).

Example 49

4-(2-(3-(4-fluorophenoxy)-5-(thieno[3,2-b]pyridin-7-ylthio)pyridin-2-ylamino)thiazol-4-yl)piperidine-1-sulfonamide 2,2,2-trifluoroacetate

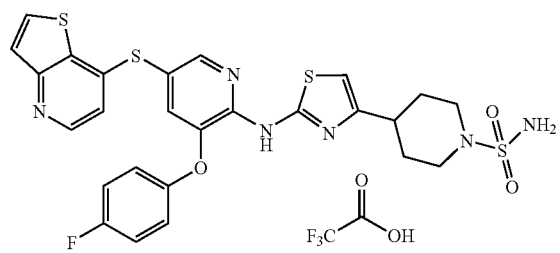

Prepared according to Example 41 from 3-(4-fluorophenoxy)-N-(4-(piperidin-4-yl)thiazol-2-yl)-5-(thieno[3,2-b]pyridin-7-ylthio)pyridin-2-amine (Example 8, Step F). $^1$H NMR (d$_6$-DMSO) δ 11.22 (s, 1H), 8.49 (d, 1H), 8.37 (d, 1H), 8.16 (d, 1H), 7.59 (d, 1H), 7.41 (d, 1H), 7.26-7.14 (m, 4H), 6.90 (d, 1H), 6.78 (s, 1H), 6.73 (s, 2H), 3.53 (d, 2H), 2.65 (m, 3H), 2.05 (m, 2H), 1.69 (m, 2H).

Example 50

4-(2-(3-(4-fluorophenoxy)-5-(thieno[3,2-b]pyridin-7-ylthio)pyridin-2-ylamino)thiazol-4-yl)piperidine-1-carboxamide hydrochloride

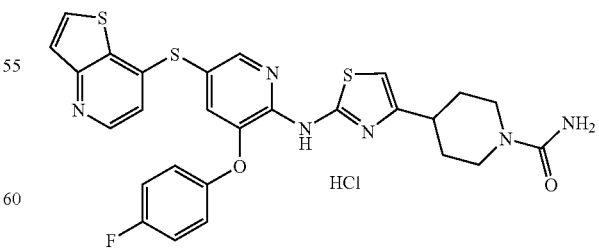

Prepared according to Example 39 from 3-(4-fluorophenoxy)-N-(4-(piperidin-4-yl)thiazol-2-yl)-5-(thieno[3,2-b]pyridin-7-ylthio)pyridin-2-amine (Example 8, Step F). $^1$H NMR (d$_6$-DMSO) δ 8.62 (d, 1H), 8.43 (m, 2H), 7.73 (d, 1H), 7.50 (d, 1H), 7.27-7.18 (m, 4H), 7.14 (d, 1H), 6.79 (s, 1H), 4.01 (d, 2H), 2.78 (m, 3H), 1.88 (d, 2H), 1.50 (m, 2H).

Example 51

1-(4-(5-(5-bromo-3-(2-methylpyridin-3-yloxy)pyridin-2-ylamino)-1,2,4-thiadiazol-3-yl)piperidin-1-yl)ethanone

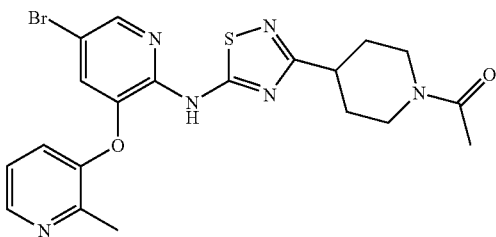 [SMILES: CC(=O)N1CCC(c2nsc(Nc3ncc(Br)cc3Oc3cccnc3C)n2)CC1]

Steps A-C: Preparation of 1-acetyl-N-(methylsulfonyloxy)piperidine-4-carbimidoyl chloride: Prepared according to Example 4, steps A-C, using 1-acetylpiperidine-4-carbaldehyde.

Step D: A flask was charged with 2-methylpyridin-3-ol (3.0 g, 27.5 mmol) and DMF (100 mL). Sodium hydride (0.760 g, 30.2 mmol) was added and stirred for 5 minutes. 5-Bromo-3-nitropicolinonitrile (6.26 g, 27.5 mmol) was added and stirred for 10 minutes. The reaction was poured into a flask containing 300 mL saturated NH$_4$Cl and 300 mL water with vigorous stirring. The solids were filtered and dried under high vacuum to afford 5-bromo-3-(2-methylpyridin-3-yloxy)picolinonitrile (7.78 g, 97.6% yield) as light tan solid.

Step E: A flask was charged with 5-bromo-3-(2-methylpyridin-3-yloxy)picolinonitrile (60 g, 207 mmol) and sulfuric acid (203 g, 2068 mmol). The reaction was stirred at ambient temperature overnight. Water (500 mL) was added carefully and neutralized using 50% sodium hydroxide to pH 5.0. The mixture was extracted with dichloromethane and ethyl acetate, dried and concentrated to afford 5-bromo-3-(2-methylpyridin-3-yloxy)picolinamide (63.0 g, 204 mmol, 98.9% yield) as yellow solid.

Step F: A flask was charged with 2M sodium hydroxide (256 mL, 511 mmol) and cooled to 0° C. Bromine (7.85 mL, 153 mmol) was added and stirred for 15 minutes. 5-bromo-3-(2-methylpyridin-3-yloxy)picolinamide (31.5 g, 102 mmol) in dioxane (650 mL) was added and stirred at ambient temperature overnight. The aqueous layer was extracted with ethyl acetate and DCM. The organic layers were washed with water, brine, dried, concentrated and purified over silica gel (25-50-75-100% ethyl acetate in hexanes) to afford 5-bromo-3-(2-methylpyridin-3-yloxy)pyridin-2-amine (12 g, 41.9% yield) as a yellow solid.

Step G: 1-acetyl-N-(methylsulfonyloxy)piperidine-4-carbimidoyl chloride (2.27 g, 8.03 mmol), pyridine (1.95 mL, 24.1 mmol) and sodium thiocyanate (0.651 g, 8.03 mmol) were dissolved in acetonitrile (45 mL). The solution was heated to 40° C. for 40 minutes. 5-bromo-3-(2-methylpyridin-3-yloxy)pyridin-2-amine (1.50 g, 5.35 mmol) was added and the reaction was heated at 60° C. overnight. The solution was cooled to 0° C., filtered and the solid was dried to give 1-(4-(5-(5-bromo-3-(2-methylpyridin-3-yloxy)pyridin-2-ylamino)-1,2,4-thiadiazol-3-yl)piperidin-1-yl)ethanone (2.63 g, 5.37 mmol, 100% yield) as a white solid. $^1$H NMR (CDCl$_3$) δ 1.78-1.97 (m, 2H), 2.01-2.20 (m, 2H), 2.12 (s, 3H), 2.51 (s, 3H), 2.86 (t, 1H), 3.05-3.11 (m, 1H), 3.24 (t, 1H), 3.90 (d, 1H), 4.57 (d, 1H), 6.97 (d, 1H), 7.24-7.37 (m, 2H), 8.23 (d, 1H), 8.50 (d, 1H), 9.10 (bs, 1H).

Example 52

1-(4-(5-(5-(2,6-dimethylphenylthio)-3-(2-methylpyridin-3-yloxy)pyridin-2-ylamino)-1,2,4-thiadiazol-3-yl)piperidin-1-yl)ethanone

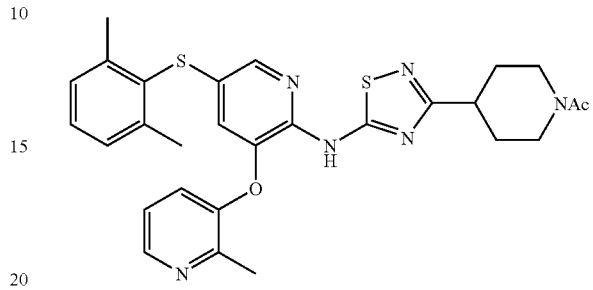

1-(4-(5-(5-bromo-3-(2-methylpyridin-3-yloxy)pyridin-2-ylamino)-1,2,4-thiadiazol-3-yl)piperidin-1-yl)ethanone (0.10 g, 0.20 mmol), xantphos (0.059 g, 0.10 mmol), K$_3$PO$_4$ (0.11 g, 0.53 mmol), and Pd$_2$dba$_3$ (0.047 g, 0.051 mmol) were diluted in degassed toluene (2 mL). 2,6-dimethylbenzenethiol (0.041 mL, 0.31 mmol) was added and the reaction stirred at 110° C. overnight. The solution was cooled and flash chromatographed (10% MeOH/EtOAc) to give 1-(4-(5-(5-(2,6-dimethylphenylthio)-3-(2-methylpyridin-3-yloxy)pyridin-2-ylamino)-1,2,4-thiadiazol-3-yl)piperidin-1-yl)ethanone (0.051 g, 46% yield) as a tan solid. $^1$H NMR (CDCl$_3$) δ 1.77-1.94 (m, 4H), 2.10 (s, 3H), 2.38 (s, 6H), 2.43 (s, 3H), 2.80 (t, 1H), 3.04 (t, 1H), 3.20 (t, 1H), 3.88 (s, 1H), 4.53 (d, 1H), 6.53 (s, 1H), 7.13-7.23 (m, 5H), 7.64 (s, 1H), 8.42 (s, 1H), 9.02 (bs, 1H).

Example 53

1-(4-(2-(3-phenoxy-5-(trifluoromethyl)pyridin-2-ylamino)thiazol-4-yl)piperidin-1-yl)ethanone

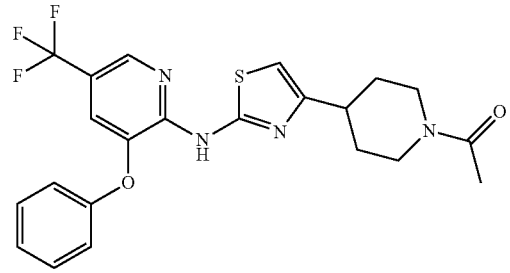 [SMILES: CC(=O)N1CCC(c2csc(Nc3ncc(C(F)(F)F)cc3Oc3ccccc3)n2)CC1]

Step A: 2,3-dichloro-5-(tifluoromethyl)pyridine (5.65 mL, 40.5 mmol) was combined with 4-(dimethylamino)pyridine (5.20 g, 42.6 mmol) and propionitrile (65 mL), heated to reflux and agitated overnight. The mixture was cooled to ambient temperature and solution of sodium cyanide (3.00 g, 61.2 mmol) in water (11 mL) was added. After stirring for 5 hours, the reaction was diluted with water (25 mL) and organic phase was separated, washed with water and 2M HCl, dried and evaporated to give the product, 3-chloro-5-(trifluoromethyl)picolinonitrile (6.33 g, 75.7% yield) as red liquid.

Step B: 3-Chloro-5-(trifluoromethyl)picolinonitrile (0.220 g, 1.07 mmol) was combined with sodium phenoxide trihydrate (0.272 g, 1.60 mmol) and DMF (5 mL). The resulting mixture was heated to 80° C. and agitated for one hour. The mixture was then cooled, diluted with ether and washed with 1M NaOH, water (3×), brine, dried and evaporated to give crude 3-phenoxy-5-(trifluoromethyl)picolinonitrile (0.190 g, 67.5% yield) as red oil.

Step C: 3-Phenoxy-5-(trifluoromethyl)picolinonitrile (0.190 g, 0.719 mmol) was combined with 2 ml of sulfuric acid and agitated for 3 hours. Ice was added to the mixture, and the solution was basified with ammonium hydroxide solution. The resulting slurry was filtered and solids washed with water and dried in the air to afford 3-phenoxy-5-(trifluoromethyl)picolinamide (0.171 g, 84.3% yield) as a white solid.

Step D: 3M Potassium hydroxide (57.4 mL, 172 mmol) was cooled to 0° C. and bromine (3.31 mL, 64.6 mmol) was added. The mixture was agitated at 0° C. for 15 minutes and added to a solution of 3-phenoxy-5-(trifluoromethyl)picolinamide (12.1 g, 43.1 mmol) in dioxane (100 ml). The mixture was agitated for 3 hours, quenched with solution of sodium sulfite and dioxane was evaporated in vacuo. The residual slurry was filtered and washed with water to give 3-phenoxypyridin-2-amine (8.91 g, 81.6% yield) as yellow solid.

Step E: 3-Phenoxy-5-(trifluoromethyl)pyridin-2-amine (0.472 g, 1.86 mmol) was combined with benzoyl isothiocyanate (0.376 mL, 2.79 mmol) and THF (5 mL). The mixture was heated to 55° C. and agitated overnight. The solvent was evaporated and the residue purified by column chromatography on silica gel, eluted with 10% ethyl acetate/hexane to afford 1-benzoyl-3-(3-phenoxy-5-(trifluoromethyl)pyridin-2-yl)thiourea (0.460 g, 59.4% yield) as white solid.

Step F: 1-Benzoyl-3-(3-phenoxy-5-(trifluoromethyl)pyridin-2-yl)thiourea (0.230 g, 0.551 mmol) was dissolved in methanol (7 mL) and a 1M solution of sodium hydroxide (3.00 mL, 3.00 mmol) was added. The resulting mixture was heated to 50° C. and agitated for one hour. Methanol was then evaporated and the resulting slurry was filtered and solids were washed with water and dried to give 1-(3-phenoxy-5-(trifluoromethyl)pyridin-2-yl)thiourea (0.147 g, 85.2% yield) as white solid.

Step G: 1-(3-phenoxy-5-(trifluoromethyl)pyridin-2-yl)thiourea (0.076 g, 0.243 mmol) was suspended in ethanol (3 mL) and diisopropylethylamine (0.127 mL, 0.728 mmol) was added, followed by 1-(1-acetylpiperidin-4-yl)-2-bromoethanone hydrobromide (0.120 g, 0.364 mmol). The mixture was heated to 60° C. and agitated for 3 hours, then diluted with ethyl acetate, washed with sodium bicarbonate, brine, dried and evaporated. The crude product was purified on silica gel (30% ethyl acetate/hexanes) to afford 1-(4-(2-(3-phenoxy-5-(trifluoromethyl)pyridin-2-ylamino)thiazol-4-yl)piperidin-1-yl)ethanone (0.065 g, 57.9% yield) as white solid. $^1H$ NMR ($d_6$-DMSO) δ 1.45-1.61 (m, 2H), 1.93-2.04 (m, 2H), 2.51-3.18 (m, 3H), 3.90 (d, 1H), 4.44 (d, 1H), 6.97 (s, 1H), 7.20-7.50 (m, 6H), 8.59 (s, 1H).

Example 54

1-(4-(2-(5-bromo-3-(cyclopentyloxy)pyridin-2-ylamino)thiazol-4-yl)piperidin-1-yl)ethanone

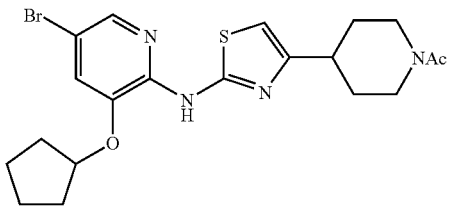

Step A: 2-nitropyridin-3-ol (5.0 g, 35.7 mmol), cyclopentanol (3.2 mL, 35.7 mmol), and triphenylphosphine (11.2 g, 42.8 mmol) were dissolved in THF (50 mL) under a nitrogen atmosphere. Diisopropyl azodicarboxylaate (8.4 mL, 42.8 mmol) was added in one portion. The mixture stirred at ambient temperature for 3 hours. The material was concentrated and flash chromatographed to give a mixture of 3-(cyclopentyloxy)-2-nitropyridine (10.9 g) and diisopropyldihydrazide. The mixture was used directly in the next Step.

Step B: 3-(cyclopentyloxy)-2-nitropyridine (8.2 g, 39.3 mmol) in acetic acid (90 mL) was cooled in a water bath. Zn dust (10 microns) (12.9 g, 197 mmol) was slowly added in portions over 15 minutes and the reaction stirred for an additional 30 minutes. The solution was filtered over celite and the solids were rinsed with DCM. The filtrate was concentrated to about 90 mL of acetic acid. To this solution was added bromine (2.0 mL, 39.3 mmol) in dropwise manner. After 15 minutes, the material was concentrated and neutralized with saturated $NaHCO_3$ solution. The material was extracted with dichloromethane and the organic layer was dried, and concentrated. Flash chromatography gave 5-bromo-3-(cyclopentyloxy)pyridin-2-amine (5.26 g, 52% yield) as a yellow solid.

Step C: Preparation of 1-benzoyl-3-(5-bromo-3-(cyclopentyloxy)pyridin-2-yl)thiourea: Prepared according to the procedure found in Example 1, Step D.

Step D: Preparation of 1-(5-bromo-3-(cyclopentyloxy)pyridin-2-yl)thiourea: Prepared according to the procedure found in Example 1, Step E.

Step E: Preparation of 1-(4-(2-(5-bromo-3-(cyclopentyloxy)pyridin-2-ylamino)thiazol-4-yl)piperidin-1-yl)ethanone: Prepared according to Example 1, Step F, using 1-(1-acetylpiperidin-4-yl)-2-bromoethanone hydrobromide. $^1H$ NMR ($CDCl_3$) δ 1.60-1.74 (m, 4H), 1.80-2.14 (m 8H) 2.10 (s, 3H), 2.70 (t, 1H), 2.81-2.88 (m, 1H), 3.18 (t, 1H), 3.91 (d, 1H), 4.72 (d, 1H), 4.80-4.83 (m, 1H), 6.41 (s, 1H), 7.12 (d, 1H), 7.95 (d, 1H), 8.42 (bs, 1H).

Example 55

5-(2-(3-(1-acetylpiperidin-4-yl)-1,2,4-thiadiazol-5-ylamino)-5-bromopyridin-3-yloxy)-1-methylpyridin-2(1H)-one

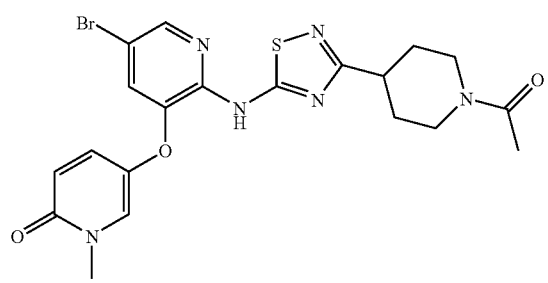 [SMILES: CC(=O)N1CCC(c2nsc(Nc3ncc(Br)cc3Oc3ccc(=O)n(C)c3)n2)CC1]

Step A: To a solution of pyridine-2,5-diol (1.0 g, 9.0 mmol) in dimethylformamide (150 mL) at 0° C. was added sodium hydride (60% dispersion in mineral oil, 0.30 g, 9.0 mmol) in portions, and the reaction stirred at 0° C. for 1 hour. To this reaction was added 5-bromo-3-nitropicolinonitrile (2.05 g, 9.00 mmol) and the reaction stirred overnight at ambient temperature. Sodium hydride (60% dispersion in mineral oil, 0.30 g, 9.0 mmol) was added to the reaction mixture in portions, followed by methyl iodide (2.56 g, 18.00 mmol), and the reaction was stirred at ambient temperature for 3 hours. The reaction was poured into water and the aqueous layer extracted with ethyl acetate. The organics were washed with 1N HCl, 1M NaOH, water, brine, dried over magnesium sulfate and concentrated in vacuo. The material purified over silica gel (2% ethyl acetate/dichloromethane) to afford 5-bromo-3-(1-methyl-6-oxo-1,6-dihydropyridin-3-yloxy)picolinonitrile (1.5 g, 54%).

Steps B and C: Preparation of 5-(2-amino-5-bromopyridin-3-yloxy)-1-methylpyridin-2(1H)-one: Prepared according to Example 51, steps E and F.

Step D: Prepared according to Example 4, Step D, to afford the title compound. ¹H NMR (d₆-DMSO) δ 12.13 (s, 1H), 8.27 (s, 1H), 7.85 (d, 1H), 7.56 (d, 1H), 7.47 (dd, 1H), 7.47 (dd, 1H), 6.46 (d, 1H), 4.32 (m, 1H), 3.84 (m, 1H), 3.42 (s, 3H), 3.23-3.16 (m, 1H), 3.09-3.01 (m, 1H), 2.79-2.72 (m, 1H), 2.06-1.93 (m, 4H), 1.72 (m, 1H), 1.58 (m, 1H).

Example 56 tert-Butyl 4-(5-(5-chloro-3-(4-cyanophenoxy)pyridin-2-ylamino)-1,2,4-thiadiazol-3-yl)piperidine-1-carboxylate

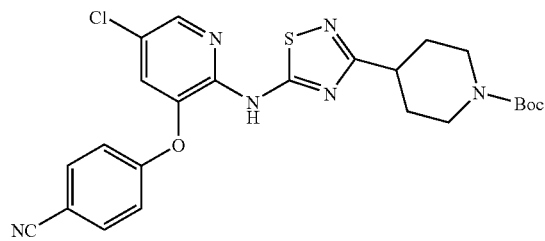

Step A: Preparation of 4-(2-aminopyridin-3-yloxy)benzonitrile: Prepared according to Example 1, Step A.

Step B: To a solution of 4-(2-aminopyridin-3-yloxy)benzonitrile (5.6 g, 26.5 mmol) in DMF (100 mL) was added N-chlorosuccinimide (4.25 g, 31.8 mmol) and stirred at 80° C. for 14 h. The reaction mixture was cooled to ambient temperature and poured into water (100 mL). The aqueous suspension was extracted with EtOAc and the combined organic layers were washed with water. The organic phase was dried (MgSO₄), filtered, and concentrated in vacuo. The residue was purified on silica gel (20% EtOAc/hexanes) and triturated with methanol to afford 4-(2-amino-5-chloropyridin-3-yloxy)benzonitrile (2.75 g, 42.2% yield) as a bright yellow solid.

Step C: Prepared from 4-(2-amino-5-chloropyridin-3-yloxy)benzonitrile according to the procedure in Example 4, Step D, to afford the title compound. ¹H NMR (d₆-DMSO) δ 12.31 (bs, 1H), 8.43 (dd, 1H), 7.90 (dd, 1H), 7.87 (d, 2H), 7.21 (d, 2H), 3.94 (m, 2H), 3.00-2.80 (m, 3H), 1.93 (m, 2H), 1.59 (m, 2H), 1.39 (s, 9H).

Example 57

4-(5-(3-phenoxy-5-(pyridin-2-ylthio)pyridin-2-ylamino)-1,2,4-thiadiazol-3-yl)piperidine-1-sulfonic acid citrate salt

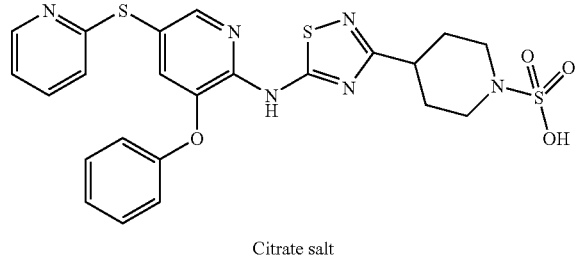 [SMILES: O=S(=O)(O)N1CCC(c2nsc(Nc3ncc(Sc4ccccn4)cc3Oc3ccccc3)n2)CC1]

Citrate salt

3-Phenoxy-N-(3-(piperidin-4-yl)-1,2,4-thiadiazol-5-yl)-5-(pyridin-2-ylthio)pyridin-2-amine (0.150 g, 0.324 mmol) and triethylamine (0.0328 g, 0.324 mmol) were dissolved in dichloromethane (3 mL) and cooled to 0° C. To this solution was added sulfurochloridic acid (0.0378 g, 0.324 mmol) dropwise, and the reaction was stirred overnight at ambient temperature. Saturated ammonium chloride was added and the reaction mixture was extracted with 10% methanol in dichloromethane. This generated an emulsion that would not separate. Brine was added and emulsion did not clear up. Saturated citric acid was added and it eliminated the emulsion. Layers were separated, dried, filtered and concentrated to provide 4-(5-(3-phenoxy-5-(pyridin-2-ylthio)pyridin-2-ylamino)-1,2,4-thiadiazol-3-yl)piperidine-1-sulfonic acid citrate salt (0.243 g, 102% yield). ¹H NMR (d₆-DMSO) δ 8.39 (d, 1H), 8.37 (m, 1H), 7.66 (dt, 1H), 7.47 (d, 1H), 7.42 (t, 2H), 7.11-7.20 (m, 5H), 3.41 (m, 2H), 2.74-2.59 (m, 5H), 2.46 (m, 2H), 1.96 (d, 2H), 1.74 (t, 2H).

Example 58

4(2-(3-phenoxy-5-(pyridin-2-ylthio)pyridin-2-ylamino)thiazol-4-yl)piperidine-1-sulfonamide hydrochloride

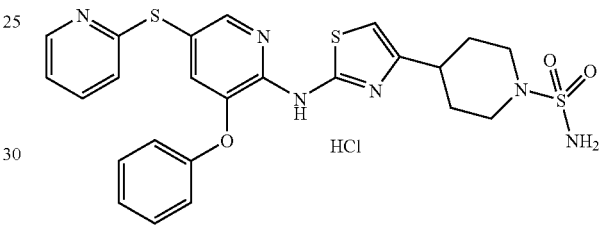

Step A: Preparation of N-(tert-butoxycarbonyl)-N-[4-(dimethylazaniumylidene)-1,4-dihydropyridin-1-ylsulfonyl]azanide: Chlorosulfonyl isocyanate (15.0 g, 106 mmol) was added dropwise to a cooled solution of 2-methylpropan-2-ol (7.85 g, 106 mmol) in dichloromethane (200 mL). N,N-dimethylpyridin-4-amine (25.9 g, 212 mmol) was added and the reaction was stirred at ambient temperature for 1 hour. The reaction mixture was washed several times with water, dried, filtered and concentrated. The resulting colorless powder was crystallized from acetonitrile to provide N-(tert-butoxycarbonyl)-N-[4-(dimethylazaniumylidene)-1,4-dihydropyridin-1-ylsulfonyl]azanide (18.14 g, 60.2 mmol, 56.8% yield).

Step B: tert-butyl 4-(2-(3-phenoxy-5-(pyridin-2-ylthio)pyridin-2-ylamino)thiazol-4-yl)piperidin-1-ylsulfonylcarbamate: 3-Phenoxy-N-(4-(piperidin-4-yl)thiazol-2-yl)-5-(pyridin-2-ylthio)pyridin-2-amine (0.075 g, 0.162 mmol) and N-(tert-butoxycarbonyl)-N-[4-(dimethylazaniumylidene)-1,4-dihydropyridin-1-ylsulfonyl]azanide (0.0490 g, 0.162 mmol) were dissolved in dichloromethane (2 mL) and stirred at ambient temperature for 18 hours. Water was added and the reaction mixture was extracted with dichloromethane. The organic layer was dried, filtered and concentrated. The crude material was purified by silica gel chromatography (25-50% ethyl acetate in hexanes) provided tert-butyl 4(2-(3-phenoxy-5-(pyridin-2-ylthio)pyridin-2-ylamino)thiazol-4-yl)piperidin-1-ylsulfonylcarbamate (0.0785 g, 75.4% yield).

Step C: 4-(2-(3-phenoxy-5-(pyridin-2-ylthio)pyridin-2-ylamino)thiazol-4-yl)piperidine-1-sulfonamide hydrochloride: Followed method of Example 1, Step G: ¹H NMR (d₆-DMSO) δ 8.37 (d, 1H), 8.29 (d, 1H), 7.67 (dt, 1H), 7.42 (t, 2H), 7.38 (d, 1H), 7.38 (d, 1H), 7.21-7.08 (m, 5H), 6.79 (s, 1H), 3.69 (m, 1H), 3.55-3.45 (m, 3H), 2.71-2.59 (m, 3H), 2.06 (d, 2H), 1.68 (m, 2H).

Example 59

N-(2-(dimethylamino)ethyl)-4-(2-(3-phenoxy-5-(thieno[3,2-b]pyridin-7-ylthio)pyridin-2-ylamino)thiazol-4-yl)piperidine-1-sulfonamide tri-trifluoroacetic acid salt

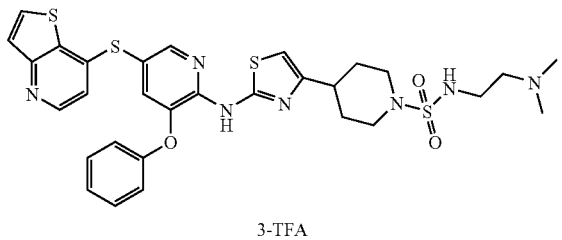 [SMILES: CN(C)CCNS(=O)(=O)N1CCC(c2csc(Nc3ncc(Sc4ccnc5ccsc45)cc3Oc3ccccc3)n2)CC1]

3-TFA

Step A: A solution of 2-chloroethanol (2.00 g, 24.84 mmol) in dichloromethane (15 mL) was added to a solution of chlorosulfonyl isocyanate (3.52 g, 24.8 mmol) in dichloromethane (15 mL) This mixture was slowly added to a 0° C. solution of N1,N1-dimethylethane-1,2-diamine (2.19 g, 24.8 mmol) and triethylamine (3.81 mL, 27.3 mmol). The reaction was stirred for 45 minutes, diluted with dichloromethane, washed with saturated ammonium chloride, concentrated and purified by silica gel chromatography. The isolated material was dissolved in methylene chloride and triethylamine (3.81 mL, 27.3 mmol) and stirred for 5 hours. The reaction mixture was washed with water and the organic layer was concentrated to give crude N-(2-(dimethylamino)ethyl)-2-oxooxazolidine-3-sulfonamide (3.96 g, 67.24% yield).

Step B: To a refluxing solution of N-(2-(dimethylamino)ethyl)-2-oxooxazolidine-3-sulfonamide (0.030 g, 0.11 mmol) and triethylamine (0.015 mL, 0.10 mmol) was added 3-phenoxy-N-(4-(piperidin-4-yl)thiazol-2-yl)-5-(thieno[3,2-b]pyridin-7-ylthio)pyridin-2-amine (0.054 g, 0.10 mmol) and the reaction was stirred for 2 hours. The reaction was cooled, filtered and dried. The crude material was purified by reverse phase chromatography with 0.1% TFA buffer to provide N-(2-(dimethylamino)ethyl)-4-(2-(3-phenoxy-5-(thieno[3,2-b]pyridin-7-ylthio)pyridin-2-ylamino)thiazol-4-yl)piperidine-1-sulfonamide tri-trifluoroacetic acid salt (0.041 g, 0.041 mmol, 36.9% yield) $^1$H NMR (d$_6$-DMSO) δ 8.50 (m, 2H), 8.16 (d, 1H), 7.59 (d, 1H), 7.39 (m, 2H), 7.13 (m, 4H), 6.95 (d, 1H), 3.55 (m, 2H), 2.96 (m, 3H), 2.83 (t, 2H), 2.34 (t, 2H), 2.15 (s, 6H), 2.07 (m, 2H), 1.80 (m, 2H).

Example 60

1-(4-methyl-4-(2-(3-phenoxy-5-(thieno[3,2-b]pyridin-7-ylthio)pyridin-2-ylamino)thiazol-4-yl)piperidin-1-yl)ethanone dihydrochloride

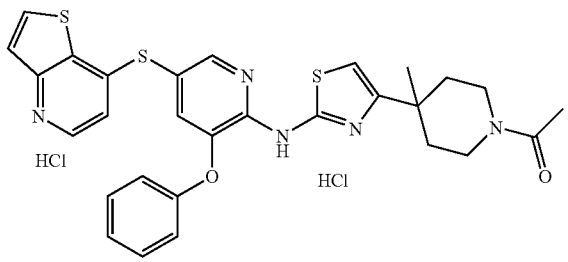 [SMILES: CC(=O)N1CCC(C)(c2csc(Nc3ncc(Sc4ccnc5ccsc45)cc3Oc3ccccc3)n2)CC1 ; Cl ; Cl]

Step A: Preparation of tert-butyl 4-(2-chloroacetyl)-4-methylpiperidine-1-carboxylate: Lithium diisopropylamide (30.9 mL, 46.4 mmol) was added dropwise to a solution containing ethyl N-Boc-4-methylpiperidine-4-carboxylate (2.52 g, 9.28 mmol), and chloroiodomethane (6.55 g, 37.1 mmol) in THF (100 mL) at −78° C. over 30 minutes. After addition, the reaction was stirred for 10 minutes, and then a solution of acetic acid (5 mL) in THF (45 mL) was added while keeping reaction mixture below −65° C. The reaction was stirred for an additional 10 minutes and partitioned between ethyl acetate and brine, washed with saturated bicarbonate, concentrated and purified by silica gel (10%-20% ethyl acetate in hexanes) to afford tert-butyl 4-(2-chloroacetyl)-4-methylpiperidine-1-carboxylate (1.15 g, 44.92% yield).

Steps B and C: Preparation of 1-(4-methyl-4-(2-(3-phenoxy-5-(thieno[3,2-b]pyridin-7-ylthio)pyridin-2-ylamino)thiazol-4-yl)piperidin-1-yl)ethanone dihydrochloride: Prepared according to Example 1, Steps F and G: $^1$H NMR (d$_6$-DMSO) δ 8.61 (d, 1H), 8.43 (d, 1H), 8.39 (d, 1H), 7.71 (d, 1H), 7.48 (d, 1H), 7.41 (m, 2H), 7.21-7.11 (m, 4H), 6.87 (s, 1H), 3.60 (m, 1H), 3.50 (m, 1H), 3.32 (m, 2H), 2.10 (m, 2H), 1.98 (s, 3H), 1.59 (m, 1H), 1.49 (m, 1H), 1.27 (s, 3H).

Example 61

4-(2-(3-(4-fluorophenoxy)-5-(pyridin-2-ylthio)pyridin-2-ylamino)thiazol-4-yl)-N-(2-hydroxyethyl)-4-methylpiperidine-1-carboxamide 2,2,2-trifluoroacetate

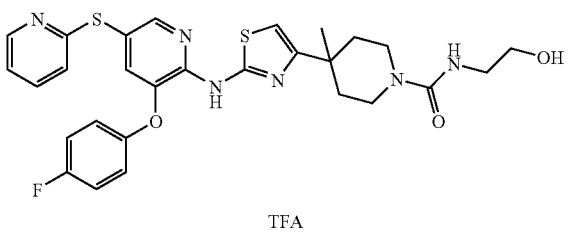 [SMILES: CC1(c2csc(Nc3ncc(Sc4ccccn4)cc3Oc3ccc(F)cc3)n2)CCN(C(=O)NCCO)CC1]

TFA

N-(3-(4-fluorophenoxy)-5-(pyridin-2-ylthio)pyridin-2-yl)-4-(4-methylpiperidin-4-yl)thiazol-2-amine (0.050 g, 0.10 mmol) and anhydrous K$_2$CO$_3$ (0.070 g, 0.51 mmol) were suspended in DMF (2 mL) and cooled to −78° C. Triphosgene (0.012 g, 0.041 mmol) was added as a solution in DCM (1 mL) and the reaction was warmed to 0° C. and stirred for 3 minutes. The reaction was cooled to −78° C. and 2-aminoethanol (0.025 g, 0.41 mmol) was added. The solution was stirred at ambient temperature for 2 hours. Water was added and the reaction mixture was extracted with ether and then washed with water. The crude product was purified by two reverse phase columns (with 0.1% TFA buffer) to give 4-(2-(3-(4-fluorophenoxy)-5-(pyridin-2-ylthio)pyridin-2-ylamino)thiazol-4-yl)-N-(2-hydroxyethyl)-4-methylpiperidine-1-carboxamide 2,2,2-trifluoroacetate (6.0 mg, 0.008 mmol, 8.5% yield). $^1$H NMR (d$_6$-DMSO) γ 11.02 (bs, 1H), 8.37 (m, 1H), 8.25 (d, 1H), 7.65 (dt, 1H), 7.33 (s, 1H), 7.28-7.17 (m, 4H), 7.14 (dd, 1H), 7.07 (d, 1H), 6.79 (s, 1H), 6.40 (bs, 1H), 3.38 (m, 4H), 3.21 (m, 2H), 3.07 (m, 2H), 2.06 (m, 2H), 1.48 (m, 2H), 1.23 (s, 3H).

Example 62

1-(4-fluoro-4-(2-(3-phenoxy-5-(thieno[3,2-b]pyridin-7-ylthio)pyridin-2-ylamino)thiazol-4-yl)piperidin-1-yl)ethanone dihydrochloride

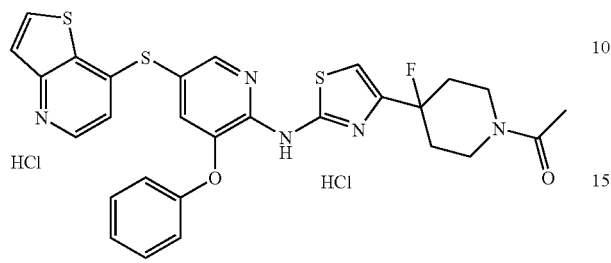

Step A: Preparation of tert-butyl 4-(2-chloroacetyl)-4-fluoropiperidine-1-carboxylate: Prepared according to the method of Example 60, Step A, using lithium diisopropylamide (12.8 mL, 19.1 mmol), 1-tert-butyl 4-methyl 4-fluoropiperidine-1,4-dicarboxylate (1.0 g, 3.83 mmol) and chloroiodomethane (2.70 g, 15.3 mmol). Obtained 0.837 g (78.2% yield) of the desired compound.

Steps B and C: Preparation of 1-(4-fluoro-4-(2-(3-phenoxy-5-(thieno[3,2-b]pyridin-7-ylthio)pyridin-2-ylamino)thiazol-4-yl)piperidin-1-yl)ethanone dihydrochloride: Prepared according to Example 1, Steps F and G. $^1$H NMR (d$_6$-DMSO) δ 8.60 (d, 1H), 8.43 (s, 1H), 8.38 (d, 1H), 7.71 (d, 1H), 7.48 (s, 1H), 7.41 (m, 2H), 7.20-7.10 (m, 4H), 7.05 (d, 1H), 6.54 (s, 1H), 4.13 (d, 1H), 3.62 (m, 2H), 2.57-2.44 (m, 3H), 2.04 (m, 3H).

Example 63

1-(4-methyl-4-(5-(3-(2-methylpyridin-3-yloxy)-5-(pyridin-2-ylthio)pyridin-2-ylamino)-1,2,4-thiadiazol-3-yl)piperidin-1-yl)ethanone dihydrochloride

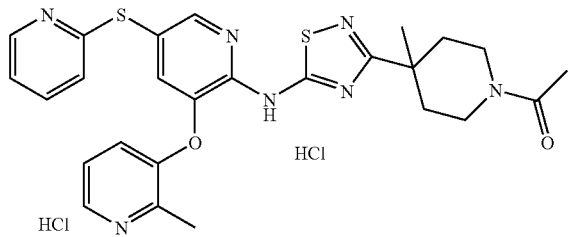 [SMILES: CC(=O)N1CCC(C)(c2nsc(Nc3ncc(Sc4ccccn4)cc3Oc3cccnc3C)n2)CC1 ; Cl ; Cl]

Step A: Preparation of tert-butyl 4-formyl-4-methylpiperidine-1-carboxylate: Tert-butyl 4-formylpiperidine-1-carboxylate (35.0 g, 164.1 mmol) was dissolved in dichloromethane (200 mL) and cooled to 0° C. Potassium tert-butoxide (23.9 g, 213 mmol) was added followed by addition of iodomethane (69.9 g, 492 mmol). The reaction was stirred at 0° C. for 30 minutes, and then warmed to ambient temperature and stirred for 1.5 hr. The reaction mixture was poured into brine (400 mL) and the organic layer was separated, dried, and filtered, and concentrated and purified by silica gel to provide tert-butyl 4-formyl-4-methylpiperidine-1-carboxylate (16.36 g, 72.0 mmol, 43.8% yield).

Steps B-D: Preparation of tert-butyl 4-(chloro(methylsulfonyloxyimino)methyl)-4-methylpiperidine-1-carboxylate: Prepared according to Example 4, Steps A-C Steps E and F: Preparation of 1-(4-methyl-4-(5-(3-(2-methylpyridin-3-yloxy)-5-(pyridin-2-ylthio)pyridin-2-ylamino)-1,2,4-thiadiazol-3-yl)piperidin-1-yl)ethanone dihydrochloride: Prepared according to Example 4, Step D, followed by the procedure of Example 1, Step F. $^1$H NMR (d$_6$-DMSO) δ 12.42 (s, 1H), 8.43 (d, 1H), 8.36 (d, 1H), 8.27 (d, 1H), 7.66 (dt, 1H), 7.52 (m, 1H), 7.33 (d, 1H), 7.27 (m, 1H), 7.14 (m, 2H), 3.90 (m, 1H), 3.61 (m, 1H), 3.20 (m, 1H), 2.93 (m, 1H), 2.54 (s, 3H), 2.40-2.25 (m, 2H), 2.18 (s, 3H), 1.61 (m, 1H), 1.49 (s, 1H), 1.28 (s, 3H).

Example 64

1-(4-(5-(3-(2-chlorophenylthio)-5-(4-(hydroxymethyl)phenoxy)pyridin-2-ylamino)-1,2,4-thiadiazol-3-yl)piperidin-1-yl)ethanone

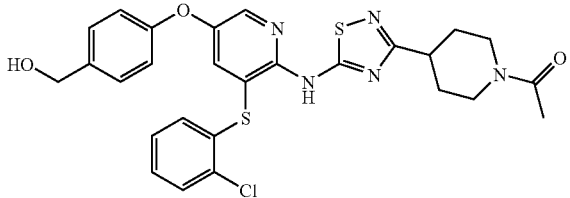 [SMILES: CC(=O)N1CCC(c2nsc(Nc3ncc(Oc4ccc(CO)cc4)cc3Sc3ccccc3Cl)n2)CC1]

Steps A-F: Preparation of tert-butyl 4-(5-(5-(4-bromophenoxy)-3-(2-chlorophenylthio)pyridin-2-ylamino)-1,2,4-thiadiazol-3-yl)piperidine-1-carboxylate: Prepared according to Example 45, steps A-E, followed by Example 4, Step D.

Step G: tert-Butyl 4-(5-(5-(4-bromophenoxy)-3-(2-chlorophenylthio)pyridin-2-ylamino)-1,2,4-thiadiazol-3-yl)piperidine-1-carboxylate (500 mg, 0.741 mmol) was dissolved in THF (7 mL) and cooled to −78° C. Methyllithium (556 μL, 0.889 mmol) was added and the reaction was stirred for 5 minutes. Butyllithium (356 μL, 0.889 mmol) was added and the reaction was stirred for 5 minutes. N,N-dimethylformamide (115 μL, 1.48 mmol) was added and the reaction was slowly warmed to ambient temperature. The reaction was poured into NH$_4$Cl, extracted with EtOAc, concentrated and purified on silica gel (5 to 10% EtOAc in hexanes) to afford tert-butyl 4-(5-(3-(2-chlorophenylthio)-5-(4-formylphenoxy)pyridin-2-ylamino)-1,2,4-thiadiazol-3-yl)piperidine-1-carboxylate (183 mg, 0.293 mmol, 39.6% yield) as a white solid.

Step H: Tert-butyl 4-(5-(3-(2-chlorophenylthio)-5-(4-formylphenoxy)pyridin-2-ylamino)-1,2,4-thiadiazol-3-yl)piperidine-1-carboxylate (183 mg, 0.293 mmol) was dissolved in methylene chloride (1 mL) and TFA (1 mL) was added. After stirring for 30 minutes, the reaction was poured into saturated aqueous sodium bicarbonate. The mixture was extracted with methylene chloride and concentrated to afford 4-(5-(2-chlorophenylthio)-6-(3-(piperidin-4-yl)-1,2,4-thiadiazol-5-ylamino)pyridin-3-yloxy)benzaldehyde (154 mg, 0.294 mmol).

Step I: 4-(5-(2-chlorophenylthio)-6-(3-(piperidin-4-yl)-1,2,4-thiadiazol-5-ylamino)pyridin-3-yloxy)benzaldehyde (154 mg, 0.294 mmol) was dissolved in methylene chloride (3 mL) and triethylamine (81.9 μL, 0.588 mmol) and acetic anhydride (33.3 μL, 0.353 mmol) were added. After stirring for 20 minutes, the reaction was poured into saturated aqueous sodium bicarbonate and extracted with methylene chloride. The organic layer was concentrated to afford 4-(6-(3-(1-acetylpiperidin-4-yl)-1,2,4-thiadiazol-5-ylamino)-5-(2-chlorophenylthio)pyridin-3-yloxy)benzaldehyde (161 mg, 0.284 mmol, 96.8% yield).

Step J: 4-(6-(3-(1-Acetylpiperidin-4-yl)-1,2,4-thiadiazol-5-ylamino)-5-(2-chlorophenylthio)pyridin-3-yloxy)benzaldehyde (30 mg, 0.0530 mmol) was dissolved in 1:1 EtOAc:methanol (2 mL) and NaBH$_4$ (10.0 mg, 0.265 mmol) was added. After stirring 30 minutes the reaction was poured into aqueous NH$_4$Cl, extracted with EtOAc and purified on silica gel (0 to 10% methanol in EtOAc) to afford 1-(4-(5-(3-(2-chlorophenylthio)-5-(4-(hydroxymethyl)phenoxy)pyridin-2-ylamino)-1,2,4-thiadiazol-3-yl)piperidin-1-yl)ethanone (19.9 mg, 0.0350 mmol, 66.1% yield) as a white solid. $^1$H NMR (CDCl$_3$) δ 9.23 (s, 1H), 8.30 (d, 1H), 7.64 (d, 1H), 7.43 (m, 1H), 7.38 (d, 2H), 7.16 (m, 2H), 7.01 (d, 2H), 6.76 (dd, 1H), 4.69 (d, 2H), 4.57 (d, 1H), 3.88 (d, 1H), 3.20 (t, 1H), 3.03 (m, 1H), 2.80 (t, 1H), 2.11 (s, 3H), 2.07 (m, 2H), 1.92-1.71 (m, 3H).

Example 65

1-(4-(2-(5-(3-hydroxypropylthio)-3-phenoxypyridin-2-ylamino)thiazol-4-yl)piperidin-1-yl)ethanone

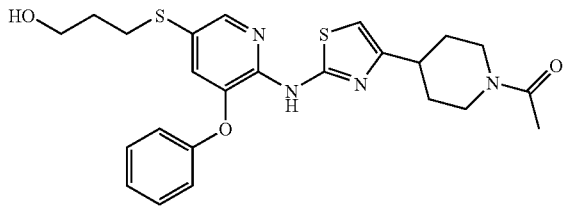 [SMILES: CC(=O)N1CCC(c2csc(Nc3ncc(SCCCO)cc3Oc3ccccc3)n2)CC1]

A solution of methyl 3-(6-(4-(1-acetylpiperidin-4-yl)thiazol-2-ylamino)-5-phenoxypyridin-3-ylthio)propanoate (100 mg, 0.195 mmol) in THF (10 mL) at 0° C. was treated dropwise with LiAlH$_4$ (1M in THF, 195 μL, 0.195 mmol). Once the addition was completed the ice bath was removed and the mixture was stirred at ambient temperature for 30 minutes. The mixture was cooled to 0° C. and quenched with successive addition of water (0.2 mL), 2N NaOH (0.6 mL), and water (0.2 mL). The mixture was stirred at ambient temperature for 30 minutes and the resulting solids were removed by filtration, washing with additional THF. The filtrate was concentrated in vacuo and the residue was purified by reverse phase C-18 chromatography using a gradient of 20%-90% CH$_3$CN/water to provide the title compound (20 mg, 0.0413 mmol, 21.2% yield) as a white solid. $^1$H NMR (DMSO-d$_6$) δ 10.77 (brs, 1H), 8.11 (s, 1H), 7.42 (m, 2H), 7.86 (s, 1H), 7.18 (m, 1H), 7.06 (d, 2H), 6.66 (s, 1H), 4.49 (t, 1H), 4.42 (d, 1H), 3.85 (d, 1H), 3.44 (q, 2H), 3.12 (t, 1H), 2.88 (t, 2H), 2.80 (m, 1H), 2.62 (t, 1H), 2.00 (s, 3H), 1.92 (t, 2H), 1.66-1.59 (m, 2H), 1.57-1.41 (m, 2H).

Example 66

1-(4-(5-(5-(2-hydroxyethylthio)-3-(2-methylpyridin-3-yloxy)pyridin-2-ylamino)-1,2,4-thiadiazol-3-yl)-4-methylpiperidin-1-yl)ethanone

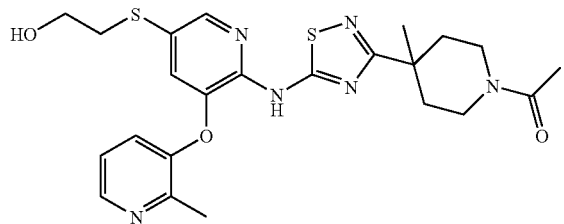 [SMILES: CC(=O)N1CCC(C)(c2nsc(Nc3ncc(SCCO)cc3Oc3cccnc3C)n2)CC1]

Step A: Methyl 3-(6-(3-(1-acetyl-4-methylpiperidin-4-yl)-1,2,4-thiadiazol-5-ylamino)-5-(2-methylpyridin-3-yloxy)pyridin-3-ylthio)propanoate (125 mg, 0.230 mmol) was dissolved in THF (10 mL) and potassium tert-butoxide (64.6 mg, 0.576 mmol) was added. The reaction was stirred for 30 seconds and 2-bromoethyl acetate (38.5 mg, 0.230 mmol) was added. The reaction was stirred for 3 hours. Water was added and the reaction was extracted with dichloromethane. The organic layer was concentrated, and the crude material was purified by silica gel chromatography (5-7% methanol in dichloromethane) to give 2-(6-(3-(1-acetyl-4-methylpiperidin-4-yl)-1,2,4-thiadiazol-5-ylamino)-5-(2-methylpyridin-3-yloxy)pyridin-3-ylthio)ethyl acetate (89 mg, 0.164 mmol, 71.2% yield).

Step B: A mixture of 2-(6-(3-(1-acetyl-4-methylpiperidin-4-yl)-1,2,4-thiadiazol-5-ylamino)-5-(2-methylpyridin-3-yloxy)pyridin-3-ylthio)ethyl acetate (89 mg, 0.164 mmol) and potassium carbonate (113 mg, 0.820 mmol) in ethanol (25 mL) was heated at reflux for 2 hr. The reaction was filtered and concentrated, and the residue was purified by reverse phase with 0.1% TFA buffer. The purified fractions were poured into saturated sodium bicarbonate and extracted with methylene chloride to afford 1-(4-(5-(5-(2-hydroxyethylthio)-3-(2-methylpyridin-3-yloxy)pyridin-2-ylamino)-1,2,4-thiadiazol-3-yl)-4-methylpiperidin-1-yl)ethanone (36.8 mg, 0.0735 mmol, 44.8% yield). $^1$H NMR (d$_6$-DMSO) δ 12.18 (s, 1H), 8.28 (d, 1H), 8.26 (dd, 1H), 7.44 (d, 1H), 7.25-7.15 (m, 2H), (4.89 (m, 1H), 3.89 (m, 1H), 3.60 (m, 1H), 3.52 (m, 2H), 3.18 (t, 1H), 3.00-2.88 (m, 3H), 2.53 (m, 3H), 2.31 (m, 2H), 1.97 (s, 3H), 1.62-1.40 (m, 2H), 1.26 (s, 3H).

Example 67

4-(6-(4-(1-acetylpiperidin-4-yl)thiazol-2-ylamino)-5-phenoxypyridin-3-ylthio)-N-(2-(dimethylamino)ethyl)picolinamide

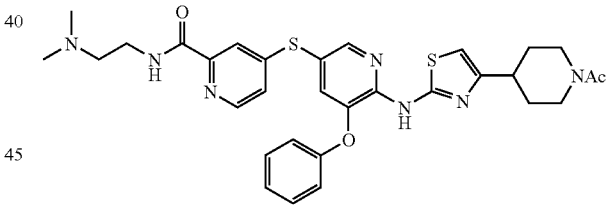

Step A: 4-Chloropicolinic acid (0.50 g, 3.2 mmol), 1-(3-dimethylaminopropyl)-3-ethylcarbodiimide hydrochloride (0.67 g, 3.5 mmol) and 1-hydroxybenzotriazole hydrate (0.53 g, 3.5 mmol) were dissolved in DMF (6 mL). N1,N1-dimethylethane-1,2-diamine (0.381 mL, 3.49 mmol) and DIEA (0.62 mL, 3.5 mmol) were added, and the reaction was stirred at 33° C. overnight. The solution was cooled, diluted with water and extracted with methylene chloride. The organic layer was dried and concentrated to give the crude 4-chloro-N-(2-(dimethylamino)ethyl)picolinamide (0.79 g).

Step B: Preparation of 4-(6-(4-(1-acetylpiperidin-4-yl)thiazol-2-ylamino)-5-phenoxypyridin-3-ylthio)-N-(2-(dimethylamino)ethyl)picolinamide: Prepared from methyl 3-(6-(4-(1-acetylpiperidin-4-yl)thiazol-2-ylamino)-5-phenoxypyridin-3-ylthio)propanoate and 4-chloro-N-(2-(dimethylamino)ethyl)picolinamide as described in Example 3, Step C. $^1$H NMR (CDCl$_3$) δ 1.62-1.70 (m, 2H), 2.07-2.12 (m, 2H), 2.11 (s, 3H), 2.28 (s, 6H), 2.51 (t, 2H), 2.71 (t, 1H), 2.88 (tt, 1H), 3.19 (t, 1H), 3.52 (dd, 2H), 3.90 (d, 1H), 4.71 (d, 1H), 6.51 (s, 1H), 7.00 (dd, 1H), 7.09-7.15 (m, 3H), 7.21 (t, 1H), 7.40 (t, 2H), 7.80 (d, 1H), 8.22 (bs, 1H), 8.24 (d, 1H), 8.28 (d, 1H), 8.84 (bs, 1H).

Example 68

4-(2-(3-(1-acetylpiperidin-4-yl)-1,2,4-thiadiazol-5-ylamino)-5-phenoxypyridin-3-ylthio)-N-(2-(dimethylamino)ethyl)benzamide

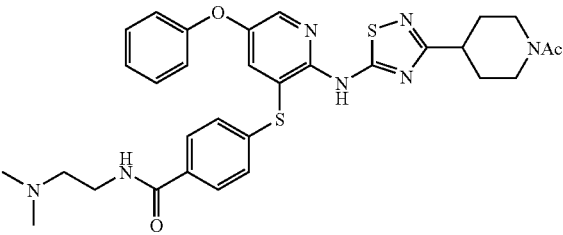

Steps A-E: Preparation of methyl 4-(2-(3-(1-acetylpiperidin-4-yl)-1,2,4-thiadiazol-5-ylamino)-5-phenoxypyridin-3-ylthio)benzoate: Prepared according to the procedures in Example 45, steps A and B, followed by the procedures of Example 51, steps E-G.

Step F: Methyl 4-(2-(3-(1-acetylpiperidin-4-yl)-1,2,4-thiadiazol-5-ylamino)-5-phenoxypyridin-3-ylthio)benzoate (0.15 g, 0.26 mmol) in EtOH was treated with NaOH (0.56 mL, 0.56 mmol). The solution was stirred at 60° C. for 1 hour. The solution was concentrated to give sodium (3-(1-acetylpiperidin-4-yl)-1,2,4-thiadiazol-5-yl)(3-(4-carboxylatophenylthio)-5-phenoxypyridin-2-yl)amide as a solid. To this salt was added 1-(3-dimethylaminopropyl)-3-ethylcarbodiimide hydrochloride (0.066 g, 0.35 mmol), 1-hydroxybenzotriazole hydrate (0.053 g, 0.35 mmol) in DMF (2 mL). N1,N1-dimethylethane-1,2-diamine (0.038 mL, 0.35 mmol) and DIEA (0.060 mL, 0.35 mmol) were added. The reaction stirred at 50° C. for 3 hours. The solution was then diluted with water, extracted with dichloromethane and concentrated. The crude material was purified via reverse phase HPLC to afford 4-(2-(3-(1-acetylpiperidin-4-yl)-1,2,4-thiadiazol-5-ylamino)-5-phenoxypyridin-3-ylthio)-N-(2-(dimethylamino)ethyl)benzamide (0.064 g, 36% yield). $^1$H NMR (CDCl$_3$) δ 1.76-1.88 (m, 2H), 2.04-2.12 (m 2H), 2.10 (s, 3H), 2.25 (s, 6H), 2.50 (t, 2H), 2.82 (t, 1H), 3.00-3.06 (m, 1H), 3.20 (t, 1H), 3.48 (dd, 2H), 3.87 (d, 1H), 4.54 (d, 1H), 6.80 (bs, 1H), 7.02 (d, 1H), 7.14-7.19 (m, 3H), 7.38 (t, 2H), 7.67 (d, 1H), 7.71 (d, 2H), 8.30 (d, 1H), 9.20 (bs, 1H).

Example 69

1-(4-(2-(5-(7-methoxythieno[3,2-b]pyridin-5-ylthio)-3-phenoxypyridin-2-ylamino)thiazol-4-yl)piperidin-1-yl)ethanone

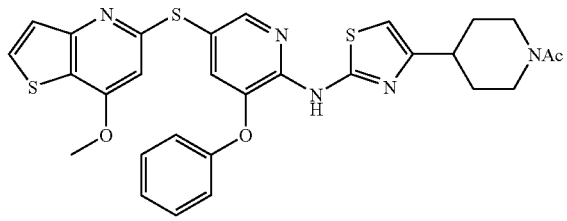

1-(4-(2-(5-(5-Chlorothieno[3,2-b]pyridin-7-ylthio)-3-phenoxypyridin-2-ylamino)thiazol-4-yl)piperidin-1-yl)ethanone (Example 32, 0.10 g, 0.17 mmol) was added to DMF (2 mL), and NaOMe (0.11 mL, 0.50 mmol) (25% in methanol) was added. The reaction stirred at ambient temperature for 1 hour and at 75° C. for 1 hour. The solution was then quenched with water, extracted with dichloromethane, dried, and concentrated. Purification via reverse phase HPLC gave 1-(4-(2-(5-(7-methoxythieno[3,2-b]pyridin-5-ylthio)-3-phenoxypyridin-2-ylamino)thiazol-4-yl)piperidin-1-yl)ethanone (0.004 g, 0.007 mmol, 4% yield) as a white solid. $^1$H NMR (CDCl$_3$) δ 1.60-1.67 (m, 2H), 2.03-2.09 (m, 2H), 2.11 (s, 3H), 2.67 (t, 1H), 2.86 (tt, 1H), 3.18 (t, 1H), 3.89 (d, 1H), 4.72 (d, 1H), 3.90 (s, 3H), 6.43 (s, 1H), 6.48 (s, 1H), 7.09 (d, 2H), 7.18 (t, 1H), 7.32-7.38 (m, 4H), 7.63 (d, 1H), 8.31 (d, 1H), 8.78 (s, 1H).

The following compounds were also prepared according to one or more of the procedures in Examples 1-69.

| Ex. # | Structure | Name | Data |
|---|---|---|---|
| 70 | 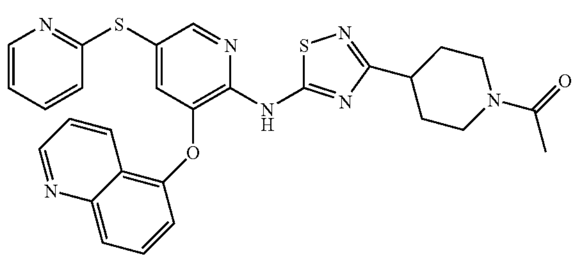 [SMILES: CC(=O)N1CCC(c2nsc(Nc3ncc(Sc4ccccn4)cc3Oc3cccc4ncccc34)n2)CC1] | 1-(4-(5-(5-(pyridin-2-ylthio)-3-(quinolin-5-yloxy)pyridin-2-ylamino)-1,2,4-thiadiazol-3-yl)piperidin-1-yl)ethanone | $^1$H NMR (d$_6$-DMSO) δ 12.56 (s, 1H), 8.98 (dd, 1H), 8.68 (m, 1H), 8.47 (d, 1H), 8.34 (m, 1H), 7.81 (d, 1H), 7.69 (d, 1H), 7.60-7.67 (m, 3H), 7.14 (m, 2H), 7.05 (d, 1H), 4.30 (d, 1H), 3.81 (d, 1H), 3.17 (t, 1H), 3.03 (m, 1H), 2.74 (t, 1H), 1.99 (s, 3H), 1.96 (m, 2H), 1.71 (m, 1H), 1.56 (m, 1H) |

| Ex. # | Structure | Name | Data |
|---|---|---|---|
| 71 | 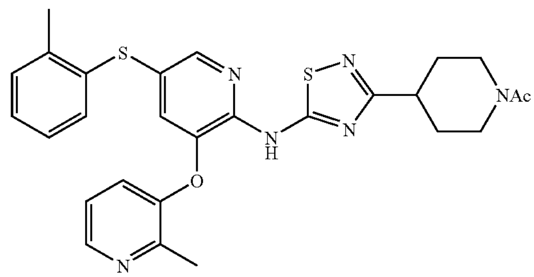 | 1-(4-(5-(3-(2-methyl-pyridin-3-yloxy)-5-(o-tolylthio)pyridin-2-ylamino)-1,2,4-thiadiazol-3-yl)piperidin-1-yl)ethanone | ¹H NMR (CDCl₃) δ 1.78-2.11 (m, 2H), 2.04-2.16 (m, 2H), 2.11 (s, 3H), 2.35 (s, 3H), 2.45 (s, 3H), 2.83 (t, 1H), 3.03-3.10 (m, 1H), 3.22 (t, 1H), 3.90 (d, 1H), 4.58 (d, 1H), 6.78 (d, 1H), 7.10-7.26 (m, 6H), 8.04 (d, 1H), 8.42 (d, 1H), 9.00 (d, 1H). |
| 72 | 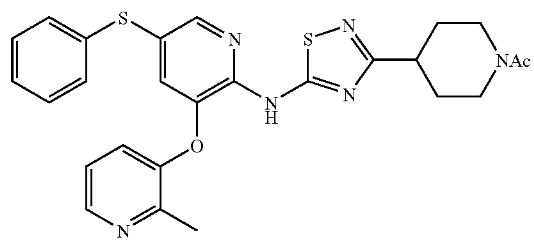 | 1-(4-(5-(3-(2-methyl-pyridin-3-yloxy)-5-(phenylthio)pyridin-2-ylamino)-1,2,4-thiadiazol-3-yl)piperidin-1-yl)ethanone | ¹H NMR (CDCl₃) δ 1.79-1.92 (m, 2H), 2.08-2.16 (m, 2H), 2.04 (s, 3H), 2.46 (d, 3H), 2.83 (t, 1H), 3.05-3.11 (m, 1H), 3.23 (t, 1H), 3.90 (d, 1H), 4.58 (d, 1H), 6.88 (d, 1H), 7.19-7.30 (m, 7H), 8.19 (s, 1H), 8.43 (d, 1H), 9.03 (s, 1H). |
| 73 | 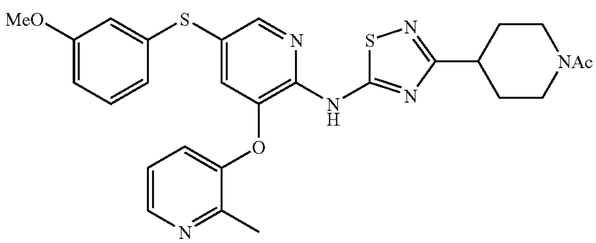 | 1-(4-(5-(5-(3-methoxy-phenylthio)-3-(2-methylpyridin-3-yloxy)pyridin-2-ylamino)-1,2,4-thiadiazol-3-yl)piperidin-1-yl)ethanone | ¹H NMR (CDCl₃) δ 1.76-1.95 (m, 2H), 2.07-2.15 (m, 2H), 2.11 (s, 3H), 2.47 (s, 3H), 2.83 (t, 1H), 3.05-3.11 (m, 1H), 3.24 (t, 1H), 3.75 (s, 3H), 3.88 (d, 1H), 4.57 (d, 1H), 6.75-6.79 (m, 2H), 6.91 (d, 1H), 7.16-7.25 (m, 4H), 8.21 (d, 1H), 8.43 (d, 1H), 9.10 (s, 1H). |
| 74 | 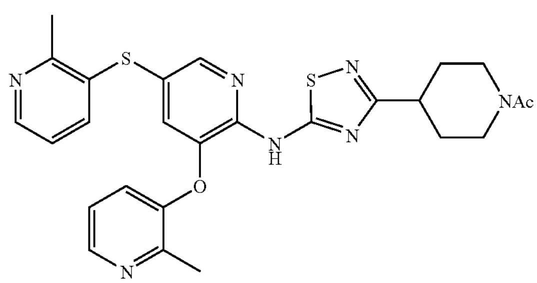 | 1-(4-(5-(3-(2-methyl-pyridin-3-yloxy)-5-(2-methylpyridin-3-ylthio)pyridin-2-ylamino)-1,2,4-thiadiazol-3-yl)piperidin-1-yl)ethanone | ¹H NMR (CDCl₃) δ 1.78-1.95 (m, 2H), 2.07-2.15 (m, 2H), 2.11 (s, 3H), 2.49 (s, 3H), 2.59 (s, 3H), 2.83 (t, 1H), 3.05-3.13 (m, 1H), 3.23 (t, 1H), 3.90 (d, 1H), 4.57 (d, 1H), 6.85 (d, 1H), 7.02 (dd, 1H), 7.20 (d, 1H), 7.22 (d, 1H), 7.27 (d, 1H), 8.15 (d, 1H), 8.35 (d, 1H), 8.45 (d, 1H), 9.13 (bs, 1H). |
| 75 | 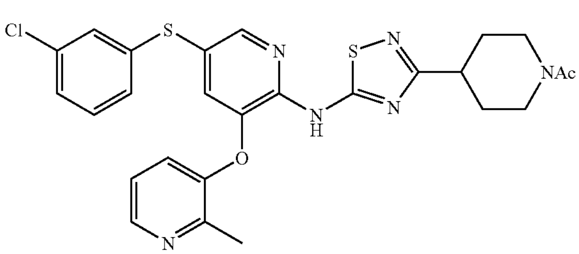 | 1-(4-(5-(5-(3-chloro-phenylthio)-3-(2-methyl-pyridin-3-yloxy)pyridin-2-ylamino)-1,2,4-thiadiazol-3-yl)piperidin-1-yl)ethanone | ¹H NMR (DMSO-d6) δ 1.56-1.76 (m, 2H), 1.95-2.04 (m, 2H), 2.00 (s, 3H), 2.50 (s, 3H), 2.75 (t, 1H), 3.02-3.07 (m, 1H), 3.19 (t, 1H), 3.84 (d, 1H), 4.31 (d, 1H), 7.20-7.32 (m, 6H), 7.42 (s, 1H), 8.25 (d, 1H), 8.38 (d, 1H), 12.4 (s, 1H). |

| Ex. # | Structure | Name | Data |
|---|---|---|---|
| 76 | 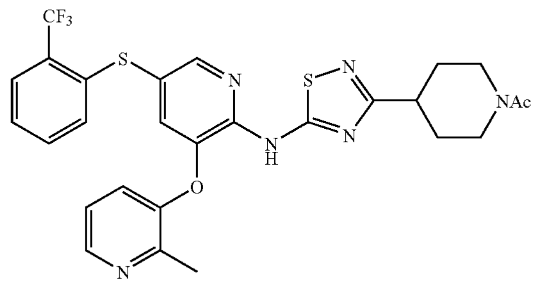 | 1-(4-(5-(3-(2-methyl-pyridin-3-yloxy)-5-(2-(trifluoromethyl)phenylthio)pyridin-2-ylamino)-1,2,4-thiadiazol-3-yl)piperidin-1-yl)ethanone | $^1$H NMR (CDCl$_3$) δ 1.79-1.91 (m, 2H), 2.04-2.16 (m, 2H), 2.11 (s, 3H), 2.46 (s, 3H), 2.83 (t, 1H), 3.04-3.11 (m, 1H), 3.22 (t, 1H), 3.88 (d, 1H), 4.57 (d, 1H), 6.90 (s, 1H), 7.13-7.40 (m, 5H), 7.67 (d, 1H), 8.22 (s, 1H), 8.44 (d, 1H), 9.16 (bs, 1H). |
| 77 | 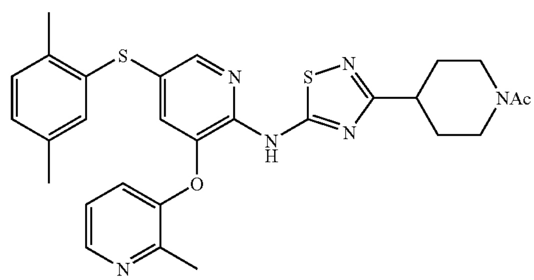 | 1-(4-(5-(5-(2,5-dimethylphenylthio)-3-(2-methylpyridin-3-yloxy)pyridin-2-ylamino)-1,2,4-thiadiazol-3-yl)piperidin-1-yl)ethanone | $^1$H NMR (CDCl$_3$) δ 1.68-1.93 (m, 2H), 2.05-2.17 (m, 2H), 2.11 (s, 3H), 2.23 (s, 3H), 2.29 (s, 3H), 2.45 (s, 3H), 2.85 (t, 1H), 3.03-3.11 (m, 1H), 3.22 (t, 1H), 3.88 (d, 1H), 4.57 (d, 1H), 6.73 (d, 1H), 6.95 (s, 1H), 7.00 (d, 1H), 7.09 (d, 1H), 7.17-7.26 (m, 2H), 8.01 (d, 1H), 8.43 (dd, 1H), 9.00 (s, 1H). |
| 78 | 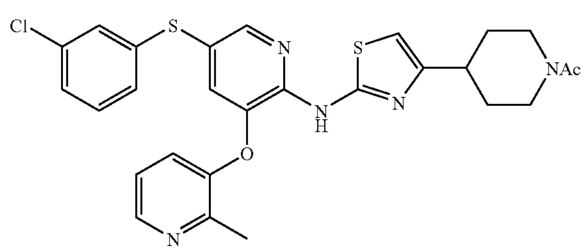 | 1-(4-(2-(5-(3-chlorophenylthio)-3-(2-methylpyridin-3-yloxy)pyridin-2-ylamino)thiazol-4-yl)piperidin-1-yl)ethanone | $^1$H NMR (DMSO-d6) δ 1.42-1.59 (m, 2H), 1.89-2.01 (m, 2H), 2.00 (s, 3H), 2.50 (s, 3H), 2.63 (t, 1H), 2.83 (t, 1H), 3.12 (t, 1H), 3.85 (d, 1H), 4.42 (d, 1H), 6.73 (bs, 1H), 7.12-7.34 (m, 7H), 8.24 (d, 1H), 8.27 (d, 1H), 11.29 (s, 1H). |
| 79 | 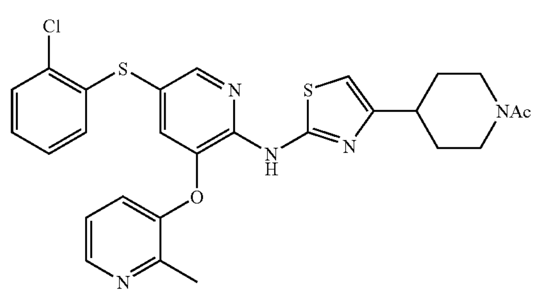 | 1-(4-(2-(5-(2-chlorophenylthio)-3-(2-methylpyridin-3-yloxy)pyridin-2-ylamino)thiazol-4-yl)piperidin-1-yl)ethanone | $^1$H NMR (DMSO-d6) δ 1.42-1.59 (m, 2H), 1.90-2.10 (m, 2H), 2.00 (s, 3H), 2.50 (s, 3H), 2.66 (t, 1H), 2.84 (t, 1H), 3.13 (t, 1H), 3.85 (d, 1H), 4.42 (d, 1H), 6.72 (s, 1H), 6.89 (d, 1H), 7.18-7.29 (m, 5H), 7.47 (d, 1H), 8.23 (d, 1H), 8.26 (d, 1H), 11.32 (s, 1H). |
| 80 | 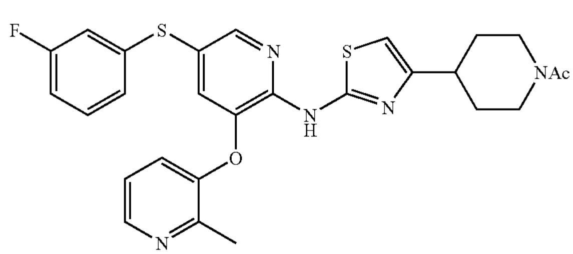 | 1-(4-(2-(5-(3-fluorophenylthio)-3-(2-methylpyridin-3-yloxy)pyridin-2-ylamino)thiazol-4-yl)piperidin-1-yl)ethanone | $^1$H NMR (DMSO-d6) δ 1.42-1.59 (m, 2H), 1.90-2.00 (m, 2H), 2.00 (s, 3H), 2.50 (s, 3H), 2.62 (t, 1H), 2.83 (t, 1H), 3.12 (t, 1H), 3.85 (d, 1H), 4.42 (d, 1H), 6.72 (s, 1H), 7.00-7.04 (m, 3H), 7.18-7.36 (m, 4H), 8.24 (d, 1H), 8.26 (d, 1H), 11.28 (s, 1H). |

-continued

| Ex. # | Structure | Name | Data |
|---|---|---|---|
| 81 | 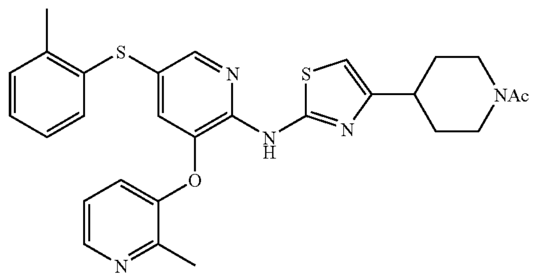 | 1-(4-(2-(3-(2-methylpyridin-3-yloxy)-5-(o-tolythio)pyridin-2-ylamino)thiazol-4-yl)piperidin-1-yl)ethanone | ¹H NMR (CDCl₃) δ 1.56-1.72 (m, 2H), 2.01-2.11 (m, 2H), 2.11 (s, 3H), 2.34 (s, 3H), 2.44 (s, 3H), 2.66 (t, 1H), 2.85 (td, 1H), 3.18 (t, 1H), 3.90 (d, 1H), 4.71 (d, 1H), 6.48 (s, 1H), 6.77 (d, 1H), 7.00-7.21 (m, 6H), 8.05 (d, 1H), 8.40 (d, 1H), 8.70 (bs, 1H). |
| 82 | 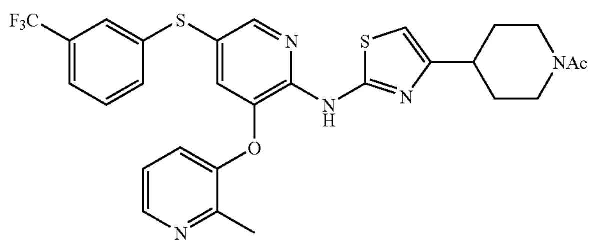 | 1-(4-(2-(3-(2-methylpyridin-3-yloxy)-5-(3-(trifluoromethyl)phenylthio)pyridin-2-ylamino)thiazol-4-yl)piperidin-1-yl)ethanone | ¹H NMR (CDCl₃) δ 1.60-1.71 (m, 2H), 2.03-2.15 (m, 2H), 2.13 (s, 3H), 2.48 (s, 3H), 2.70 (t, 1H), 2.82-2.92 (m, 1H), 3.20 (t, 1H), 3.90 (d, 1H), 4.72 (d, 1H), 6.52 (s, 1H), 6.86 (d, 1H), 7.16-7.41 (m, 6H), 8.23 (d, 1H), 8.42 (d, 1H), 8.76 (s, 1H). |
| 83 | 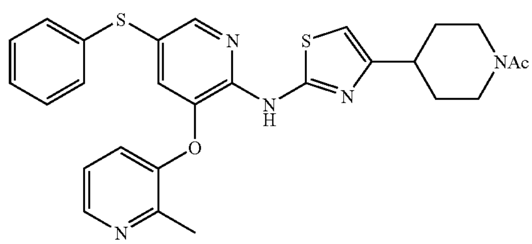 | 1-(4-(2-(3-(2-methylpyridin-3-yloxy)-5-(phenylthiopyridin-2-ylamino)thiazol-4-yl)piperidin-1-yl)ethanone | ¹H NMR (CDCl₃) δ 1.61-1.69 (m, 2H), 2.06-2.11 (m, 2H), 2.11 (s, 3H), 2.46 (s, 3H), 2.69 (t, 1H), 2.85 (t, 1H), 3.21 (t, 1H), 3.90 (d, 1H), 4.71 (d, 1H), 6.48 (s, 1H), 6.85 (s, 1H), 7.15-7.26 (m, 7H), 8.17 (s, 1H), 8.40 (d, 1H), 8.69 (bs, 1H). |
| 84 | 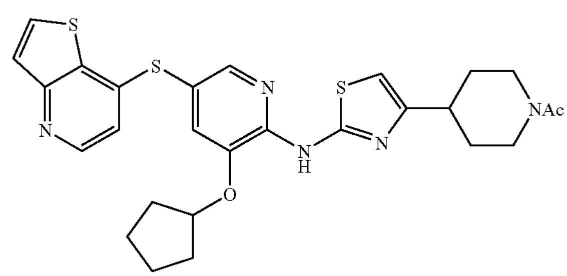 | 1-(4-(2-(3-(cyclopentyloxy)-5-(thieno[3,2-b-9pyridin-7-ylthio)pyridin-2-ylamino)thiazol-4-yl)piperidin-1-yl)ethanone | ¹H NMR (CDCl₃) δ 1.60-1.83 (m, 4H), 1.78-2.00 (m, 6H), 2.05-2.15 (m, 2H), 2.12 (s, 3H), 2.70 (t, 1H), 2.84-2.92 (m, 1H), 3.20 (t, 1H), 3.90 (d, 1H), 4.71 (d, 1H), 4.79-4.82 (m, 1H), 6.47 (s, 1H), 6.75 (d, 1H), 7.15 (d, 1H), 7.56 (d, 1H), 7.75 (d, 1H), 8.17 (d, 1H), 8.46 (d, 1H), 8.62 (s, 1H). |
| 85 | 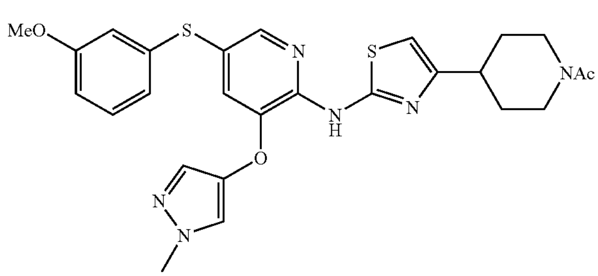 | 1-(4-(2-(5-(3-methoxyphenylthio)-3-(1-methyl-1H-pyrazol-4-yloxy)pyridin-2-ylamino)thiazol-4-yl)piperidin-1-yl)ethanone | ¹H NMR (CDCl₃) δ 1.60-1.78 (m, 2H), 2.00-2.17 (m, 2H), 2.17 (s, 3H), 2.70 (t, 1H), 2.87 (t, 1H), 3.20 (t, 1H), 3.87 (s, 3H), 3.91 (s, 3H), 3.92 (d, 1H), 4.70 (d, 1H), 6.47 (s, 1H), 6.67-6.74 (m, 3H), 7.14-7.21 (m, 2H), 7.28 (s, 1H), 7.32 (s, 1H), 8.13 (d, 1H), 8.70 (s, 1H). |

| Ex. # | Structure | Name | Data |
|---|---|---|---|
| 86 | 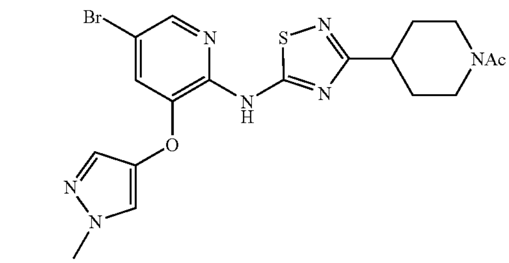 | 1-(4-(5-(5-bromo-3-(1-methyl-1H-pyrazol-4-yloxy)pyridin-2-ylamino)-1,2,4-thiadiazol-3-yl)piperidin-1-yl)ethanone | ¹H NMR (CDCl₃) δ 1.78-2.14 (m, 2H), 2.07-2.15 (m, 2H), 2.14 (s, 3H), 2.84 (t, 1H), 3.02-3.12 (m, 1H), 3.25 (t, 1H), 3.89 (d, 1H), 3.95 (s, 3H), 4.58 (d, 1H), 7.28 (d, 1H), 7.37 (s, 1H), 7.40 (s, 1H), 8.16 (d, 1H), 9.10 (s, 1H). |
| 87 (representative example) | 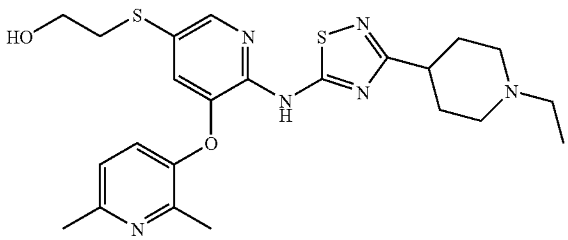 [SMILES: CCN1CCC(c2nsc(Nc3ncc(SCCO)cc3Oc3ccc(C)nc3C)n2)CC1] | 1-(5-(2,6-dimethylpyridin-3-yloxy)-6-(3-(1-ethyl-piperidin-4-yl)1,2,4-yl)-1,2,4-thiadiazol-5-ylamino)pyridin-3-ylthio)ethanol | ¹H NMR (CDCl₃) δ 1.38 (m, 3H), 2.36 (m, 2H), 2.41 (m, 2H), 2.67 (m, 1H), 2.73 (s, 3H), 2.77 (s, 3H), 3.00 (m, 3H), 3.13 (m, 3H), 3.53 (d, 1H), 3.81 (m, 3H), 7.39 (m, 1H), 7.45 (m, 1H), 7.64 (m, 1H), 8.32 (m, 1H). |
| 88 | 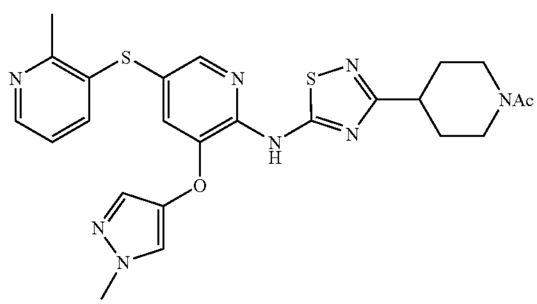 | 1-(4-(5-(3-(1-methyl-1H-pyrazol-4-yloxy)-5-(2-methyl-pyridin-3-ylthio)pyridin-2-ylamino)-1,2,4-thiadiazol-3-yl)piperidin-1-yl)ethanone | ¹H NMR (CDCl₃) δ 1.77-1.93 (m, 2H), 2.07-2.15 (m, 2H), 2.15 (s, 3H), 2.61 (s, 3H), 2.86 (t, 1H), 3.04-3.11 (m, 1H), 3.23 (t, 1H), 3.89 (d, 1H), 3.91 (s, 3H), 4.59 (d, 1H), 7.03 (dd, 1H), 7.19 (d, 1H), 7.23-7.26 (m, 1H), 7.32 (s, 1H), 7.34 (s, 1H), 8.10 (d, 1H), 8.34 (d, 1H), 9.07 (s, 1H) |
| 89 | 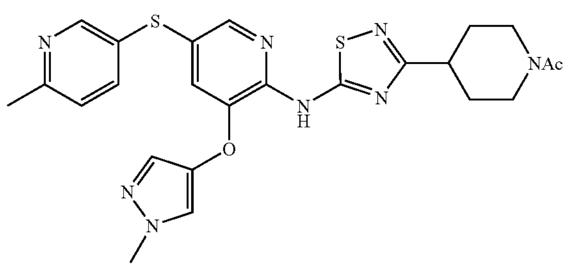 | 1-(4-(5-(3-(1-methyl-1H-pyrazol-4-ylxoy)-5-(6-methyl-pyridin-3-ylthio)pyridin-2-ylamino)-1,2,4-thiadiazol-3-yl)piperidin-1-yl)ethanone | ¹H NMR (CDCl₃) δ 1.78-1.91 (m, 2H), 2.06-2.16 (m, 2H), 2.11 (s, 3H), 2.53 (s, 3H), 2.83 (t, 1H), 3.03-3.11 (m, 1H), 3.24 (t, 1H), 3.87 (bs, 1H), 3.92 (s, 3H), 4.57 (d, 1H), 7.09 (d, 1H), 7.22 (s, 1H), 7.32 (s, 1H), 7.34 (s, 1H), 7.49 (d, 1H), 8.11 (s, 1H), 8.42 (s, 1H), 9.06 (bs, 1H). |
| 90 | 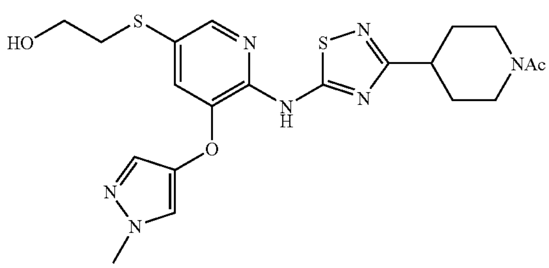 | 1-(4-(5-(5-(2-hydroxyethylthio)-3-(1-methyl-1H-pyrazol-4-yloxy)pyridin-2-ylamino)-1,2,4-thiadiazol-3-yl)piperidin-1-yl)ethanone | ¹H NMR (CDCl₃) δ 1.83-1.92 (m, 2H), 2.04-2.16 (m, 2H), 2.11 (s, 3H), 2.79-2.87 (m, 1H), 3.00 (t, 2H), 3.07 (tt, 1H), 3.22 (td, 1H), 3.70-3.74 (m, 2H), 3.87-3.91 (m, 1H), 3.94 (s, 3H), 4.55-4.59 (m, 1H), 7.28 (d, 1H), 7.35 (s, 1H), 7.38 (s, 1H), 8.17 (d, 1H), 9.05 (bs, 1H). |

| Ex. # | Structure | Name | Data |
|---|---|---|---|
| 91 | 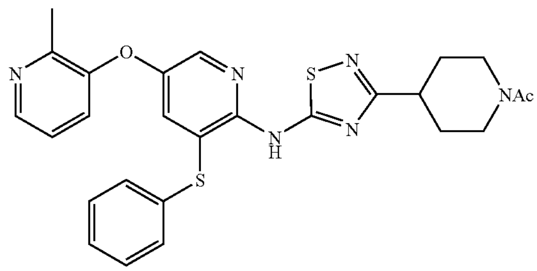 | 1-(4-(5-(5-(2-methylpyridin-3-yloxy)-3-(phenylthio)pyridin-2-ylamino)-1,2,4-thiadiazol-3-yl)piperidin-1-yl)ethanone | $^1$H NMR (CDCl$_3$) δ 1.75-1.98 (m, 2H), 2.03-2.16 (m, 2H), 2.17 (s, 3H), 2.57 (s, 3H), 2.80 (t, 1H), 3.00-3.09 (m, 1H), 3.20 (t, 1H), 3.85 (d, 1H), 4.60 (d, 1H), 7.17 (d, 1H), 7.22 (d, 1H), 7.23-7.38 (m, 5H), 7.57 (d, 1H), 8.19 (d, 1H), 8.38 (d, 1H), 9.23 (bs, 1H). |
| 92 | 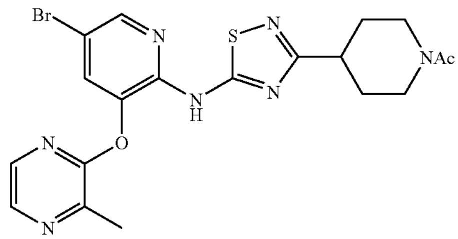 | 1-(4-(5-(5-bromo-3-(3-methylpyrazin-2-yloxy)pyridin-2-ylamino)-1,2,4-thiadiazol-3-yl)piperidin-1-yl)ethanone | $^1$H NMR (CDCl$_3$) δ 1.72-1.92 (s, 2H), 2.03-2.10 (m, 2H), 2.09 (s, 3H), 2.72 (s, 3H), 2.78 (t, 1H), 3.01-3.07 (m, 1H), 3.20 (t, 1H), 3.87 (d, 1H), 4.55 (d, 1H), 7.67 (d, 1H), 7.94 (d, 1H), 8.31 (d, 1H), 8.38 (d, 1H), 8.78 (s, 1H). |
| 93 | 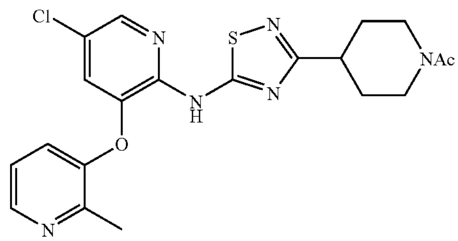 | 1-(4-(5-(5-chloro-3-(2-methylpyridin-3-yloxy)pyridin-2-ylamino)-1,2,4-thiadiazol-3-yl)piperidin-1-yl)ethanone | $^1$H NMR (CDCl$_3$) δ 1.70-1.92 (m, 2H), 2.08-2.15 (m, 2H), 2.10 (s, 3H), 2.50 (s, 3H), 2.86 (t, 1H), 3.04-3.12 (m, 1H), 3.23 (t, 1H), 3.90 (d, 1H), 4.57 (d, 1H), 6.85 (d, 1H), 7.24-7.34 (m, 2H), 8.14 (d, 1H), 8.49 (dd, 1H), 9.05 (s, 1H). |
| 94 | 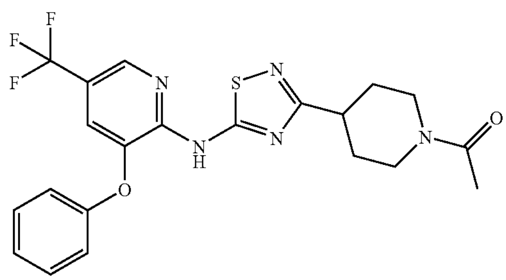 [SMILES: CC(=O)N1CCC(c2nsc(Nc3ncc(C(F)(F)F)cc3Oc3ccccc3)n2)CC1] | 1-(4-(5-(3-phenoxy-5-(trifluoromethyl)pyridin-2-ylamino)-1,2,4-thiadiazol-3-yl)piperidin-1-yl)ethanone | $^1$H NMR (d$_6$-DMSO) δ 1.72-1.94 (m, 2H), 2.04-2.15 (m, 2H), 2.80-3.26 (m, 3H), 3.90 (d, 1H), 4.57 (d, 1H), 7.10-7.51 (m, 6H), 8.48 (s, 1H), 9.33 (s, 1H). |
| 95 | 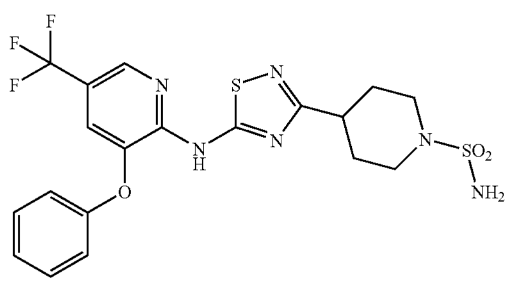 [SMILES: NS(=O)(=O)N1CCC(c2nsc(Nc3ncc(C(F)(F)F)cc3Oc3ccccc3)n2)CC1] | 4-(5-(3-phenoxy-5-(trifluoromethyl)pyridin-2-ylamino)-1,2,4-thiadiazol-3-yl)piperidine-1-sulfonamide | $^1$H NMR (d$_6$-DMSO) δ 1.83-2.13 (m, 2H), 2.68-2.90 (m, 3H), 3.45-3.70 (m, 4H), 6.74 (bs, 2H), 7.14-7.59 (m, 6H), 8.65 (s, 1H). |
| 96 | 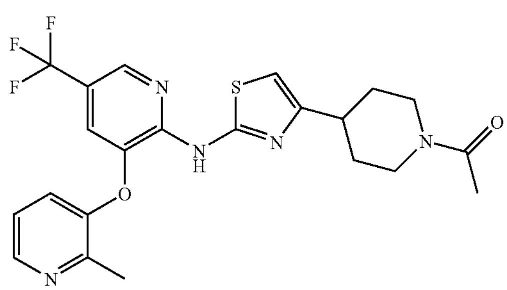 [SMILES: CC(=O)N1CCC(c2csc(Nc3ncc(C(F)(F)F)cc3Oc3cccnc3C)n2)CC1] | 1-(4-(2-(3-(2-methylpyridin-3-yloxy)-5-(trifluoromethyl)pyridin-2-ylamino)thiazol-4-yl)piperidin-1-yl)ethanone | $^1$H NMR (CDCl$_3$) δ 1.62-1.70 (m, 2H), 2.03-2.12 (m, 5H), 2.50 (s, 3H), 2.66-3.22 (m, 3H), 3.92 (d, 1H), 4.70 (d, 1H), 6.54 (s, 1H), 6.90 (s, 1H), 7.24-7.33 (m, 2H), 8.38 (s, 1H), 8.49 (s, 1H), 8.90 (bs, 1H). |

| Ex. # | Structure | Name | Data |
|---|---|---|---|
| 97 | 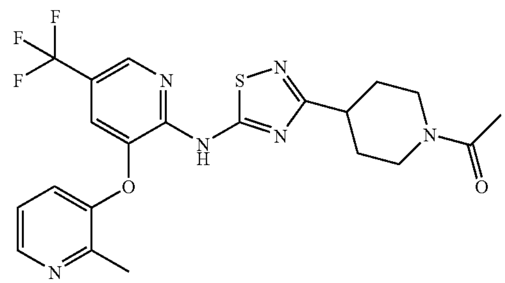 [SMILES: CC(=O)N1CCC(c2nsc(Nc3ncc(C(F)(F)F)cc3Oc3cccnc3C)n2)CC1] | 1-(4-(5-(3-(2-methylpyridin-3-yloxy)-5-(trifluoromethyl)pyridin-2-ylamino)-1,2,4-thiadiazol-3-yl)piperidin-1-yl)ethanone | $^1$H NMR (d$_6$-DMSO) δ 1.52-1.78 (m, 2H), 1.96-2.03 (m, 5H), 2.70-3.13 (m, 6H), 3.82 (d, 1H), 4.35 (d, 1H), 7.65-7.82 (m, 2H), 8.06 (s, 1H), 8.50 (d, 1H), 8.79 (s, 1H). |
| 98 | 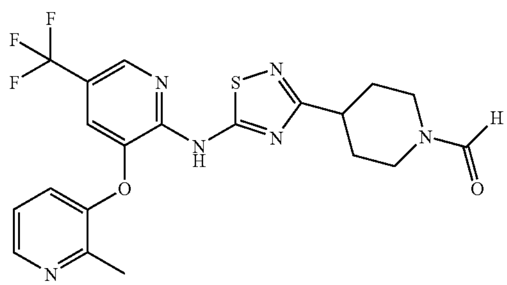 [SMILES: Cc1ncccc1Oc1cc(C(F)(F)F)cnc1Nc1nc(C2CCN(C=O)CC2)ns1] | 4-(5-(3-(2-methylpyridin-3-yloxy)-5-(trifluoromethyl)pyridin-2-ylamino)-1,2,4-thiadiazol-3-yl)piperidin-1-carbaldehyde | $^1$H NMR (d$_6$-DMSO) δ 1.51-1.75 (m, 2H), 1.99-2.05 (m, 2H), 2.75-3.21 (m, 6H), 3.72 (d, 1H), 4.15 (d, 1H), 7.65-7.82 (m, 2H), 8.01 (s, 1H), 8.07 (s, 1H), 8.50 (d, 1H), 8.80 (s, 1H). |
| 99 | 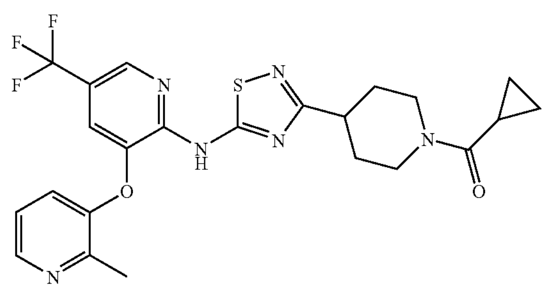 [SMILES: Cc1ncccc1Oc1cc(C(F)(F)F)cnc1Nc1nc(C2CCN(C(=O)C3CC3)CC2)ns1] | cyclopropyl(4-(5-(3-(2-methylpyridin-3-yloxy)-5-(trifluoromethyl)pyridin-2-ylamino)-1,2,4-thiadiazol-3-yl)piperidin-1-yl)methanone | $^1$H NMR (d$_6$-DMSO) δ 1.58-1.68 (m, 1H), 2.01-2.09 (m, 1H), 2.51-3.25 (m, 12H), 6.84 (s, 1H), 7.75-7.92 (m, 2H), 8.06 (s, 1H), 8.52 (d, 1H), 8.67 (s, 1H). |
| 100 | 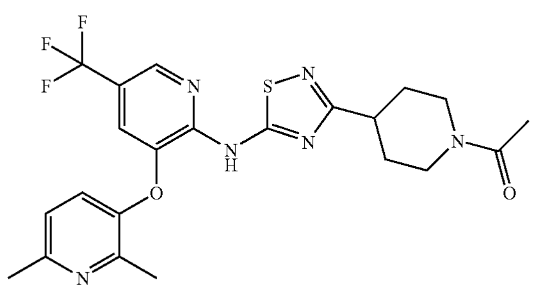 [SMILES: CC(=O)N1CCC(c2nsc(Nc3ncc(C(F)(F)F)cc3Oc3ccc(C)nc3C)n2)CC1] | 1-(4-(5-(3-(2,6-dimethylpyridin-3-yloxy)-5-(trifluoromethyl)pyridin-2-ylamino)-1,2,4-thiadiazol-3-yl)piperidin-1-yl)ethanone | $^1$H NMR (CDCl$_3$) δ 1.72-1.96 (m, 2H), 2.06-2.19 (m, 5H), 2.41 (s, 3H), 2.60 (s, 3H), 2.79-3.25 (m, 3H), 3.90 (d, 1H), 4.59 (d, 1H), 6.96 (s, 1H), 7.11-7.25 (m, 2H), 8.44 (s, 1H), 9.60 (bs, 1H). |
| 101 | 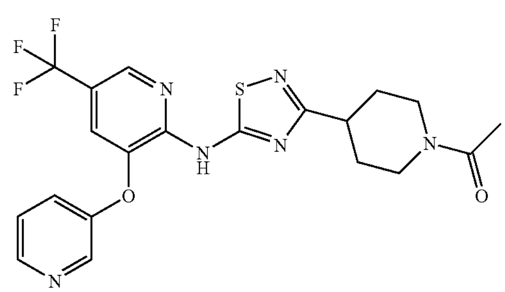 [SMILES: CC(=O)N1CCC(c2nsc(Nc3ncc(C(F)(F)F)cc3Oc3cccnc3)n2)CC1] | 1-(4-(5-(3-(pyridin-3-yloxy)-5-(trifluoromethyl)pyridin-2-ylamino)-1,2,4-thiadiazol-3-yl)piperidin-1-yl)ethanone | $^1$H NMR (d$_6$-DMSO) δ 1.52-1.78 (m, 2H), 1.93-2.03 (m, 5H), 2.70-3.23 (m, 3H), 3.82 (d, 1H), 4.33 (d, 1H), 7.86-8.06 (m, 2H), 8.18 (s, 1H), 8.62 (d, 1H), 8.80 (m, 2H). |

| Ex. # | Structure | Name | Data |
|---|---|---|---|
| 102 | 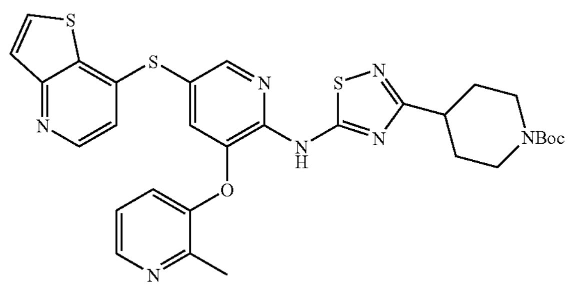 [SMILES: Cc1ncccc1Oc1cc(Sc2ccnc3ccsc23)cnc1Nc1nc(C2CCN(C(=O)OC(C)(C)C)CC2)ns1] | Tert-butyl 4-(5-(3-)2-methylpyridin-3-yloxy)-5-(thieno[3,2-b]pyridin-7-ylthio)pyridin-2-ylamino)1,2,4-thiadiazol-3-yl)piperidine-1-carboxylate | $^1$NMR (CDCl$_3$) δ 9.18 (bs, 1H), 8.48 (d, 1H), 8.44 (dd, 1H), 8.39 (d, 1H), 7.73 (d, 1H), 7.53 (d, 1H), 7.27 (m, 1H), 7.19 (dd, 1H), 6.99 (d, 1H), 6.76 (d, 1H), 4.16 (bm, 2H), 3.01 (m, 1H), 2.91 (t, 2H), 2.47 (s, 3H), 2.05 (m, 2H), 1.83 (m, 2H), 1.47 (s, 9H). |
| 103 | 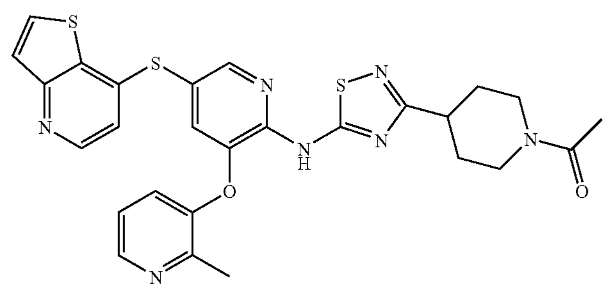 [SMILES: CC(=O)N1CCC(c2nsc(Nc3ncc(Sc4ccnc5ccsc45)cc3Oc3cccnc3C)n2)CC1] | 1-(4-(5-(3-(2-methyl-pyridin-3-yloxy)-5-(thieno[3,2-b]pyridin-7-ylthio)pyridin-2-ylamino)-1,2,4-thiadiazol-3-yl)piperidin-1-yl)ethanone | $^1$NMR (CDCl$_3$) δ 9.20 (bs, 1H), 8.49 (d, 1H), 8.44 (dd, 1H), 8.39 (d, 1H), 7.75 (d, 1H), 7.58 (d, 1H), 7.28 (m, 1H), 7.19 (dd, 1H), 7.00 (d, 1H), 6.77 (d, 1H), 4.59 (m, 1H), 3.91 (m, 1H), 3.23 (m, 1H), 3.10 (m, 1H), 2.84 (m, 1H), 2.47 (s, 3H), 2.14 (m, 1H), 2.17 (s, 3H), 2.09 (m, 1H), 1.87 (m, 2H). |
| 104 | 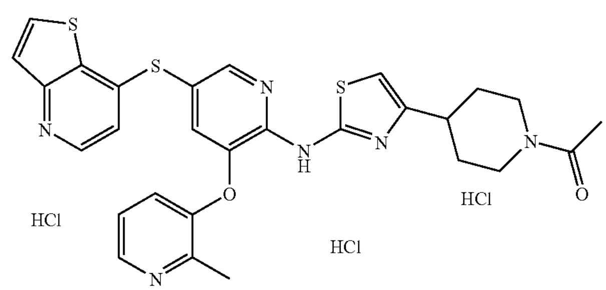 [SMILES: CC(=O)N1CCC(c2csc(Nc3ncc(Sc4ccnc5ccsc45)cc3Oc3cccnc3C)n2)CC1 ; Cl ; Cl ; Cl] | 1-(4-(2-(3-(2-methyl-pyridin-3-yloxy)-5-(thieno[3,2-b]pyridin-7-ylthio)pyridin-2-ylamino)thiazol-4-yl)piperidin-1-yl)ethanone trihydrochloride | $^1$H NMR (DMSO-d$_6$) δ 8.49 (d, 1H), 8.43 (d, 1H), 8.28 (m, 1H), 8.17 (d, 1H), 7.59 (d, 1H), 7.51 (m, 1H), 6.94 (d, 1H), 6.76 (m, 1H), 4.42 (m, 1H), 3.86 (m, 1H), 3.12 (m, 1H), 2.83 (m, 1H), 2.63 (m, 1H), 2.53 (s, 3H), 2.00 (s, 3H), 1.94 (m, 2H), 1.50 (m, 2H). |
| 105 | 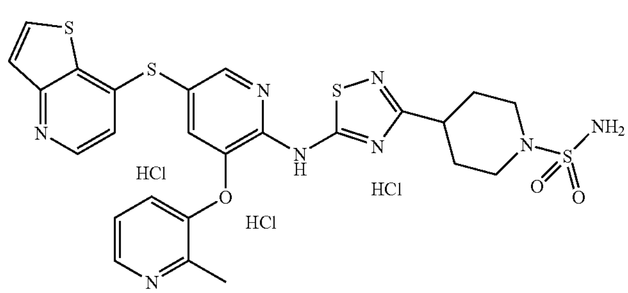 [SMILES: Cc1ncccc1Oc1cc(Sc2ccnc3ccsc23)cnc1Nc1nc(C2CCN(S(N)(=O)=O)CC2)ns1 ; Cl ; Cl ; Cl] | 4-(5-(3-(2-methyl-pyridin-3-yloxy)-5-(thieno[3,2-b]pyridin-7-ylthio)pyridin-2-ylamino)1,2,4-thiadiazol-3-yl)piperidine-1-sulfonamide trihydrochloride | $^1$H NMR (DMSO-d$_6$) δ 8.65 (d, 1H), 8.57 (d, 1H), 8.42 (d, 1H), 8.29 (d, 1H), 7.90 (m, 1H), 7.78 (m, 1H), 7.66 (d, 1H), 7.57 (m, 1H), 7.11 (d, 1H), 6.73 (bs, 2H), 3.47 (m, 2H), 2.87 (m, 1H), 2.71 (m, 2H), 2.50 (s, 3H, under DMSO), 2.10 (m, 2H), 1.83 (m, 2H). |
| 106 | 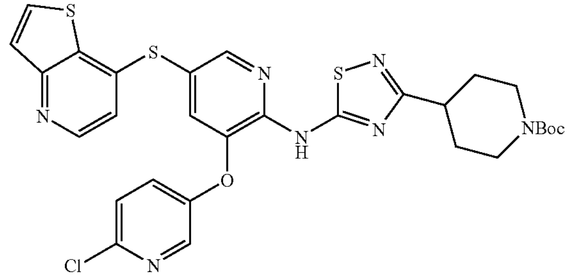 [SMILES: CC(C)(C)OC(=O)N1CCC(c2nsc(Nc3ncc(Sc4ccnc5ccsc45)cc3Oc3ccc(Cl)nc3)n2)CC1] | Tert-butyl 4-(5-(3-(6-chloropyridin-3-yloxy)-5-(thieno[3,2-b]pyridin-7-ylthio)pyridin-2-ylamino)-1,2,4-thiadiazol-3-yl)piperidine-1-carboxylate | $^1$H NMR (CDCl$_3$) δ 9.10 (s, 1H), 8.51 (d, 1H), 8.44 (d, 1H), 8.26 (t, 1H), 7.75 (d, 1H), 7.57 (d, 1H), 7.38 (s, 1H), 7.37 (s, 1H), 7.27 (m, 1H), 6.82 (d, 1H), 4.15 (m, 2H), 3.00 (s, 1H), 2.91 (m, 2H), 2.04 (m, 2H), 1.81 (m, 2H), 1.46 (s, 9H). |

| Ex. # | Structure | Name | Data |
|---|---|---|---|
| 107 | 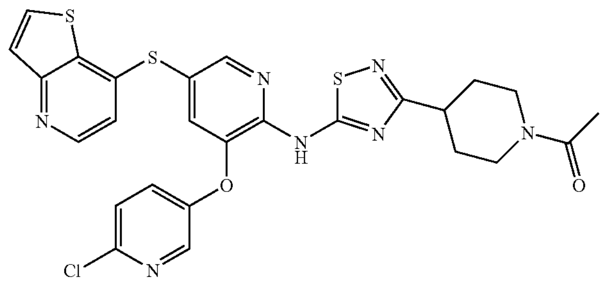 [SMILES: CC(=O)N1CCC(c2nsc(Nc3ncc(Sc4ccnc5ccsc45)cc3Oc3ccc(Cl)nc3)n2)CC1] | 1-(4-(5-(3-(6-chloro-pyridin-3-yloxy)-5-(thieno[3,2-b]pyridin-7-ylthio)pyridin-2-ylamino)1,2,4-thiadiazol-3-yl)piperidin-1-yl)ethanone | $^1$H NMR (CDCl$_3$) δ 9.21 (bs, 1H), 8.51 (d, 1H), 8.44 (d, 1H), 8.25 (t, 1H), 7.76 (d, 1H), 7.56 (d, 1H), 7.38 (s, 1H), 7.37 (s, 1H), 7.27 (m, 1H), 6.82 (d, 1H), 4.57 (m, 1H), 3.89 (m, 1H), 3.23 (m, 1H), 3.09 (m, 1H), 2.83 (m, 1H), 2.11 (s, 3H), 2.09 (m, 2H), 1.85 (m, 2H). |
| 108 | 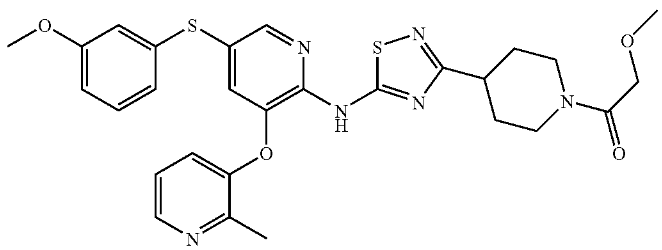 | 2-methoxy-1-(4-(5-(3-methoxy-phenylthio)-3-(2-methylpyridin-3-yloxy)pyridin-2-ylamino)-1,2,4-thiadiazol-3-yl)piperidin-1-yl)ethanone | $^1$H NMR (CDCl$_3$) δ 9.13 (bs, 1H), 8.37 (dd, 1H), 8.15 (d, 1H), 7.20 (dd, 1H), 7.13 (m, 2H), 6.86 (d, 1H), 6.68-6.73 (m, 3H), 4.48 (m, 1H), 4.07 (d, 2H), 3.89 (m, 1H), 3.70 (s, 3H), 3.38 (s, 3H), 3.13 (t, 1H), 3.03 (m, 1H), 2.82 (t, 1H), 2.41 (s, 3H), 2.06 (m, 2H), 1.81 (m, 2H). |
| 109 | 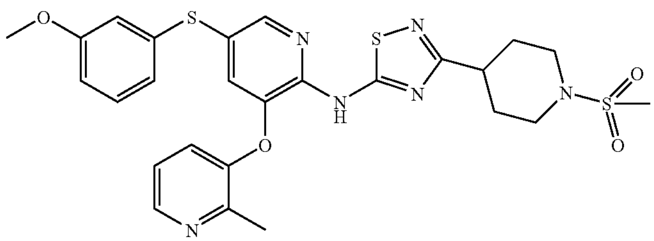 | N-(5-(3-methoxy-phenylthio)-3-(2-methylpyridin-3-yloxy)pyridin-2-yl)-3-(1-(methylsulfonyl)piperidin-4-yl)-1,2,4-thiadiazol-5-amine | $^1$H NMR (CDCl$_3$) δ 9.05 (s, 1H), 8.43 (dd, 1H), 8.20 (d, 1H), 7.27 (dd, 1H), 7.20 (m, 1H), 7.17 (m, 1H), 6.91 (d, 1H), 6.73-6.79 (m, 3H)+nl, 3.80 (m, 2H), 3.75 (s, 3H), 2.88-3.01 (m, 3H), 2.80 (s, 3H), 2.47 (s, 3H), 2.20 (m, 2H), 2.04 (m, 2H). |
| 110 | 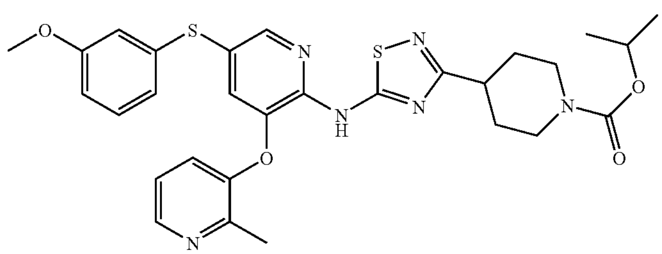 [SMILES: COc1cccc(Sc2cnc(Nc3nc(C4CCN(C(=O)OC(C)C)CC4)ns3)c(Oc3cccnc3C)c2)c1] | Isopropyl 4-(5-(5-(3-methoxyphenylthio)-3-(2-methylpyridin-3-yloxy)pyridin-2-ylamino)-1,2,4-thiadiazol-3-yl)piperidine-1-carboxylate | $^1$H NMR (CDCl$_3$) δ 9.04 (s, 1H), 8.38 (dd, 1H), 8.16 (d, 1H), 7.20 (dd, 1H), 7.14 (m, 2H), 6.86 (d, 1H), 6.69-6.74 (m, 3H), 4.88 (m, 1H), 4.15 (m, 2H), 3.70 (s, 3H), 2.85-3.00 (m, 3H), 2.42 (s, 3H), 2.01 (m, 2H), 1.78 (m, 2H), 1.20 (d, 6H). |
| 111 | 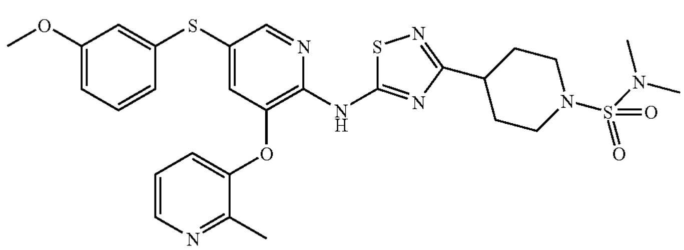 | 4-(5-(5-(3-methoxy-phenylthio)-3-(2-methylpyridin-3-yloxy)pyridin-2-ylamino)-1,2,4-thiadiazol-3-yl)-N,N-dimethylpiperidine-1-sulfonamide | $^1$H NMR (CDCl$_3$) δ 9.04 (s, 1H), 8.43 (dd, 1H), 8.20 (d, 1H), 7.25 (m, 1H), 7.18 (m, 2H), 6.91 (d, 1H), 6.73-6.79 (m, 3H), 3.75 (s, 3H), 3.74 (m, 2H), 2.92-3.02 (m, 3H), 2.83 (s, 6H), 2.47 (s, 3H), 2.16 (m, 2H), 1.97 (m, 2H). |
| 112 | 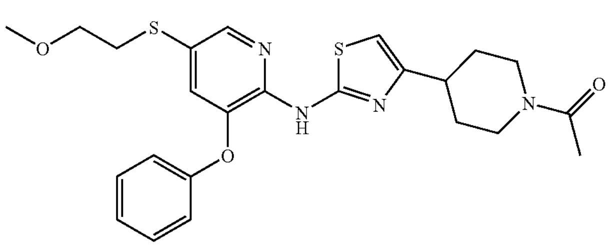 [SMILES: COCCSc1cnc(Nc2nc(C3CCN(C(C)=O)CC3)cs2)c(Oc2ccccc2)c1] | 1-(4-(2-(5-(2-methoxyethylthio)-3-phenoxypyridin-2-ylamino)thiazol-4-yl)piperidin-1-yl)ethanone | $^1$H NMR (dmso-d$_6$) δ 1.61 (m, 2H), 2.02 (m, 2H), 2.07 (s, 3H), 2.68 (t, 1H), 2.84 (m, 1H), 2.93 (t, 2H), 3.14 (t, 1H), 3.26 (s, 3H), 3.49 (t, 2H), 3.88 (d, 1H), 4.63 (d, 1H), 6.45 (s, 1H), 7.0 (s, 1H), 7.03 (s, 1H), 7.15 (s, 1H), 7.18 (m, 1H), 7.38 (m, 2H), 8.16 (s, 1H), 8.80 (s, 1H). |

-continued

| Ex. # | Structure | Name | Data |
|---|---|---|---|
| 113 | 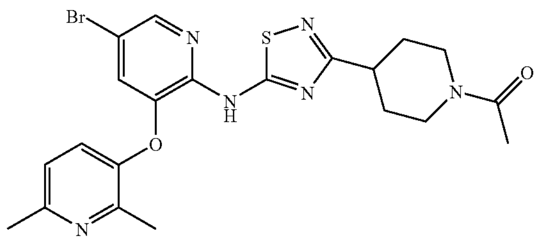 [SMILES: CC(=O)N1CCC(c2nsc(Nc3ncc(Br)cc3Oc3ccc(C)nc3C)n2)CC1] | 1-(4-(5-(5-bromo-3-(2,6-dimethylpyridin-3-yloxy)pyridin-2-ylamino)-1,2,3-thiadiazol-3-yl)piperidin-1-yl)ethanone | $^1$H NMR (DMSO-d$_6$) δ 1.58 (m, 2H), 1.72 (m, 2H), 2.00 (s, 3H), 2.55 (s, 3H), 2.55 (s, 3H), 2.74 (t, 1H), 3.06 (m, 1H), 3.19 (t, 1H), 3.82 (d, 1H), 4.32 (d, 1H), 7.40 (d, 1H), 7.64 (m, 2H), 8.42 (d, 1H), 12.28 (bs, 1H). |
| 114 | 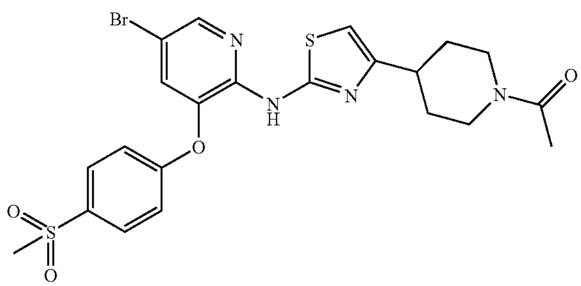 [SMILES: CC(=O)N1CCC(c2csc(Nc3ncc(Br)cc3Oc3ccc(S(C)(=O)=O)cc3)n2)CC1] | 1-(4-(2-(5-bromo-3-(4-(methylsulfonyl)phenoxy)pyridin-2-ylamino)thiazol-4-yl)piperidin-1-yl)ethanone | $^1$H NMR (DMSO-d$_6$) δ 11.20 (brs, 1H), 8.34 (s, 1H), 7.92 (d, 2H), 7.83 (s, 1H), 7.21 (m, 2H), 6.69 (s, 1H), 4.40 (d, 1H), 3.85 (d, 1H), 3.20 (s, 3H), 3.10 (m, 1H), 2.79 (m, 1H), 2.60 (m, 1H), 1.99 (s, 3H), 1.90 (m, 2H), 1.55-1.42 (m, 2H). |
| 115 | 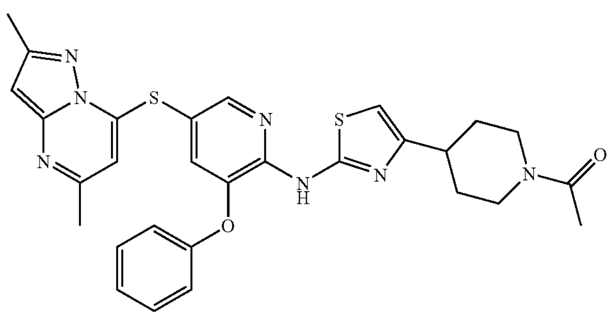 [SMILES: CC(=O)N1CCC(c2csc(Nc3ncc(Sc4cc(C)nc5cc(C)nn45)cc3Oc3ccccc3)n2)CC1] | 1-(4-(2-(5-(2,5-Dimethylpyrazolo[1,5-a]pyrimidin-7-ylthio)-3-phenoxypyridin-2-ylamino)thiazol-4-yl)piperidin-1-yl)ethanone | $^1$H NMR (DMSO-d$_6$) δ 1.41-1.49 (m, 1H), 1.54-1.62 (m, 1H), 1.91-2.00 (m, 5H), 2.38 (s, 3H), 2.42 (s, 3H), 2.64 (t, 1H), 2.85 (br s, 1H), 3.14 (t, 1H), 3.87 (d, 1H), 4.42 (d, 1H), 6.17 (s, 1H), 6.36 (s, 1H), 6.76 (br s, 1H), 7.15-7.43 (m, 3H), 7.41 (t, 2H), 7.41 (s, 1H), 8.40 (s, 1H), 11.29 (br s, 1H). |
| 116 | 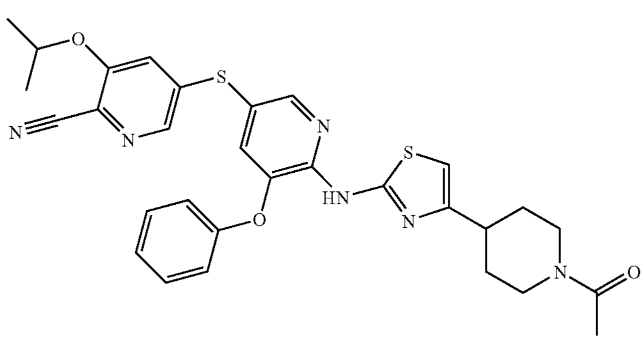 [SMILES: CC(=O)N1CCC(c2csc(Nc3ncc(Sc4cnc(C#N)c(OC(C)C)c4)cc3Oc3ccccc3)n2)CC1] | 5-(6-(4-(1-Acetylpiperidin-4-yl)thiazol-2-ylamino)-5-phenoxypyridin-3-ylthio)-3-isopropoxypicolinonitrile | $^1$H NMR (DMSO-d$_6$) δ 1.25 (d, 6H), 1.40-1.48 (m, 1H), 1.52-1.60 (m, 1H), 1.90-2.00 (m, 5H), 2.63 (t, 1H), 2.83 (t, 1H), 3.13 (t, 1H), 3.85-3.89 (m, 1H), 42 (d, 1H), 4.74-4.80 (m, 1H), 6.73 (br s, 1H), 7.10 (d, 2H), 7.17 (t, 1H), 7.40 (t, 2H), 7.44 (d, 1H), 7.49 (s, 1H), 7.96 (d, 1H), 8.33 (d, 1H), 11.16 (s, 1H). |
| 117 | 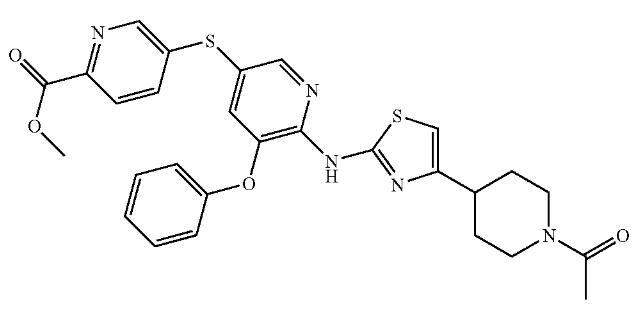 [SMILES: COC(=O)c1ccc(Sc2cnc(Nc3nc(C4CCN(C(C)=O)CC4)cs3)c(Oc3ccccc3)c2)cn1] | Methyl 5-(6-(4-(1-aceteylpiperidin-4-yl)thiazol-2-ylamino)-5-phenoxypyridin-3-ylthio)picolinate | $^1$H NMR (DMSO-d$_6$) δ 1.42-1.48 (m, 1H), 1.53-1.60 (m, 1H), 1.90-2.00 (m, 5H), 2.63 (t, 1H), 2.83 (br s, 1H), 3.13 (t, 1H), 3.85-3.88 (m, 4H), 4.42 (d, 1H), 6.74 (br s, 1H), 7.11 (d, 2H), 7.16 (t, 1H), 7.38-7.42 (m, 3H), 7.62-7.65 (m, 1H), 7.93 (d, 1H), 8.32 (d, 1H), 8.50 (d, 1H), 11.14 (s, 1H). |

| Ex. # | Structure | Name | Data |
|---|---|---|---|
| 118 | 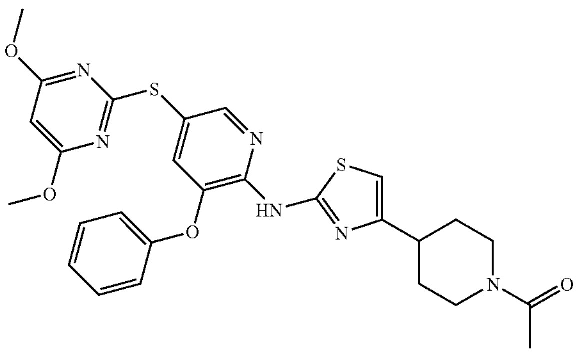 [SMILES: COc1cc(OC)nc(Sc2cnc(Nc3nc(C4CCN(C(C)=O)CC4)cs3)c(Oc3ccccc3)c2)n1] | 1-(4-(2-(5-(4,6-Dimethoxypyrimidin-2-ylthio-3-phenoxy-pyridin-2-ylamino)thiazol-4-yl)piperidin-1-yl)ethanone | $^1$H NMR (DMSO-d$_6$) δ 1.40-1.48 (m, 1H), 1.52-1.61 (m, 1H), 1.94 (t, 2H), 2.00 (s, 3H), 2.63 (t, 1H), 2.82 (br s, 1H), 3.12 (t, 1H), 3.70 (s, 6H), 3.86 (d, 1H), 4.42 (d, 1H), 5.96 (s, 1H), 6.71 (br s, 1H), 7.08 (d, 2H), 7.17 (t, 1H), 7.40 (t, 2H), 7.48 (s, 1H), 8.27 (s, 1H), 11.06 (s, 1H). |
| 119 | 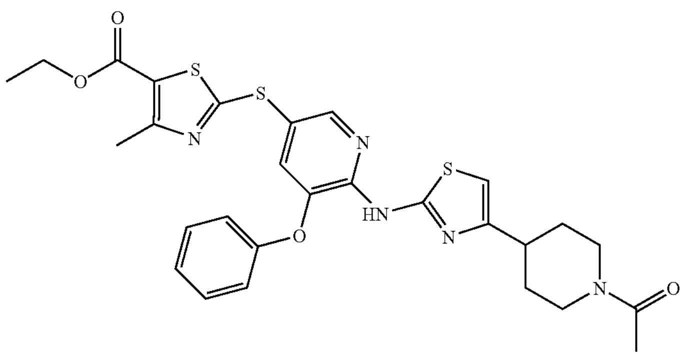 [SMILES: CCOC(=O)c1sc(Sc2cnc(Nc3nc(C4CCN(C(C)=O)CC4)cs3)c(Oc3ccccc3)c2)nc1C] | Ethyl 2-(6-(4-(1-acetylpiperidin-4-yl)thiazol-2-ylamino)-5-phenoxypyridin-3-ylthio)-4-methyl-thiazole-5-carboxylate | $^1$H NMR (DMSO-d$_6$) δ 1.22 (t, 3H), 1.43-1.49 (m, 1H), 1.53-1.61 (m, 1H), 1.90-2.00 (m, 5H), 2.55 (s, 3H), 2.63 (t, 1H), 2.84 (br s, 1H), 3.13 (t, 1H), 3.86 (d, 1H), .18-4.23 (m, 2H), 4.42 (d, 1H), 6.76 (br s, 1H), 7.11 (d, 2H), 7.19 (t, 1H), 7.41 (t, , 2H), 7.59 (s, 1H), 8.43 (d, 1H), 11.32 (br s, 1H). |
| 120 | 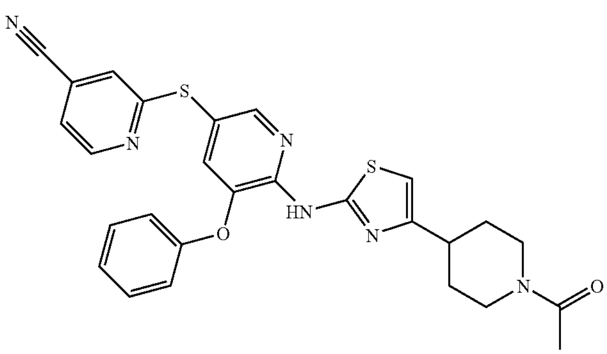 [SMILES: CC(=O)N1CCC(c2csc(Nc3ncc(Sc4cc(C#N)ccn4)cc3Oc3ccccc3)n2)CC1] | 2-(6-(4-(1-Acetylpiperidin-4-yl)thiazol-2-ylamino)-5-phenoxypyridin-3-ylthio)isonicotinonitrile | $^1$H NMR (DMSO-d$_6$) δ 1.42-1.49 (m, 1H), 1.53-1.62 (m, 1H), 1.91-2.00 (m, 5H), 2.63 (t, 1H), 2.83 (t, 1H), 3.13 (t, 1H), 3.86 (d, 1H), 4.42 (d, 1H), 6.73 (br s, 1H), 7.14-7.18 (m, 3H), 7.39-7.43 (m, 3H), 7.57-7.59 (m, 1H), 7.65 (s, 1H), 8.29 (d, 1H), 8.60 (d, 1H), 11.11 (s, 1H). |
| 121 | 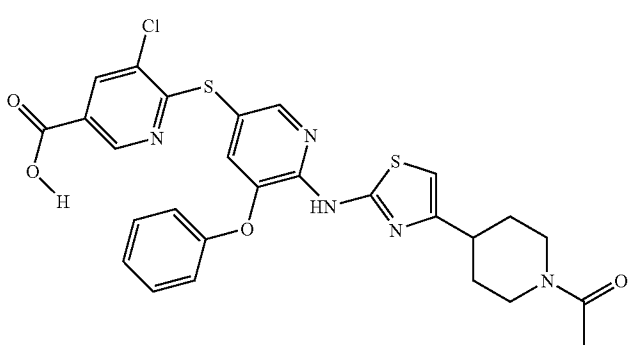 [SMILES: CC(=O)N1CCC(c2csc(Nc3ncc(Sc4ncc(C(=O)O)cc4Cl)cc3Oc3ccccc3)n2)CC1] | 6-(6-(4-(1-Acetylpiperidin-4-yl)thiazol-2-ylamino)-5-phenoxypyridin-3-ylthio)-5-chloronicotinic acid | $^1$H NMR (DMSO-d$_6$) δ 1.46 (br s, 1H), 1.59 (br s, 1H), 1.95-2.01 (m, 5H), 2.60-2.63 (m, 1H), 2.84 (br s, 1H), 3.13 (br s, 1H), 3.32 (br s, 1H), 3.86 (d, 1H), 4.42 (d, 1H), 6.72 (s, 1H), 7.13 (br s, 3H), 7.41 (br s, 3H), 8.19 (s, 1H), 8.25 (s, 1H), 8.71 (s, 1H), 11.14 (br s, 1H). |

| Ex. # | Structure | Name | Data |
|---|---|---|---|
| 122 | 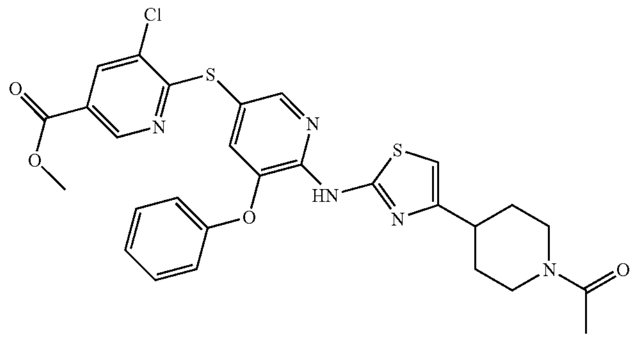 | Methyl 6-(6-(4-(1-acetylpiperidin-4-yl)thiazol-2-ylamino)-5-phenoxypyridin-3-ylthio)-5-chloronicotinate | ¹H NMR (DMSO-d₆) δ 1.40-1.61 (m, 2H), 1.91-2.01 (m, 5H), 2.63 (t, 1H), 2.81-2.83 (m, 1H), 3.13 (t, 1H), 3.86 (s, 4H), 4.42 (d, 1H), 6.73 (br s, 1H), 7.11-7.18 (m, 3H), 7.39-7.43 (m, 3H), 8.24-8.25 (m, 2H), 8.74 (d, 1H), 11.11 (s, 1H). |
| 123 | 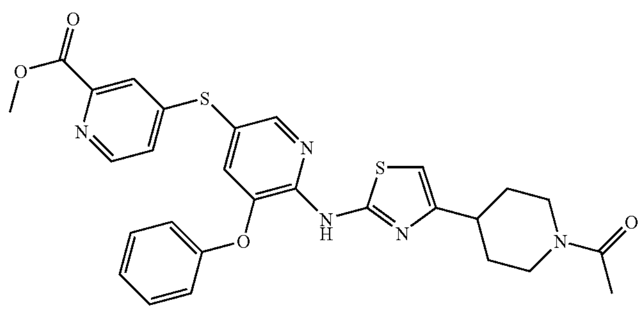 [SMILES: COC(=O)c1cc(Sc2cnc(Nc3nc(C4CCN(C(C)=O)CC4)cs3)c(Oc3ccccc3)c2)ccn1] | Methyl 4-(6-(4-(1-acetylpiperidin-4-yl)thiazol-2-ylamino)-5-phenoxypyridin-3-ylthio)picolinate | ¹H NMR (DMSO-d₆) δ 1.41-1.50 (m, 1H), 1.53-1.62 (m, 1H), 1.91-2.01 (m, 5H), 2.64 (t, 1H), 2.84 (br s, 1H), 3.13 (t, 1H), 3.85-3.88 (m, 4H), 4.42 (d, 1H), 6.76 (br s, 1H), 7.11-7.18 (m, 3H), 7.32-7.34 (m, 1H), 7.38-7.40 (m, 2H), 7.42-7.43 (m, 1H), 7.62 (s, 1H), 8.34 (d, 1H), 8.48 (d, , 1H), 11.23 (s, 1H). |
| 124 | 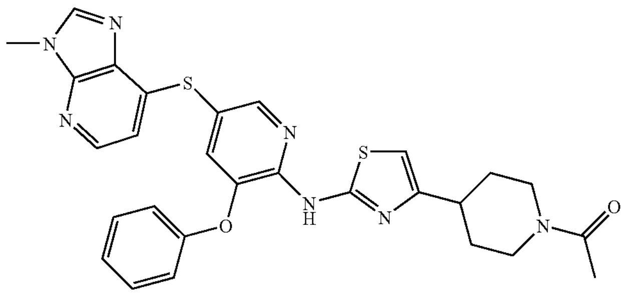 [SMILES: CC(=O)N1CCC(c2csc(Nc3ncc(Sc4ccnc5c4ncn5C)cc3Oc3ccccc3)n2)CC1] | 1-(4-(2-(5-(3-Methyl-3H-imidazo[4,5-b]pyridin-7-ylthio)-3-phenoxy-pyridin-2-ylamino)thiazol-4-yl)piperidin-1-yl)ethanone | ¹H NMR (DMSO-d₆) δ 1.41-1.49 (m, 1H), 1.54-1.62 (m, 1H), 1.91-2.01 (m, 5H), 2.64 (t, 1H), 2.81-2.84 (m, 1H), 3.13 (t, 1H), 3.82 (s, 3H), 3.87 (d, 1H), 4.42 (d, 1H), 6.61 (d, 1H), 6.74 (br s, 1H), 7.13-7.18 (m, 3H), 7.36 (d, 1H), 7.40 (t, 2H), 8.14 (d, 1H), 8.33 (d, 1H), 8.39 (s, 1H), 11.14 (s, 1H). |
| 125 | 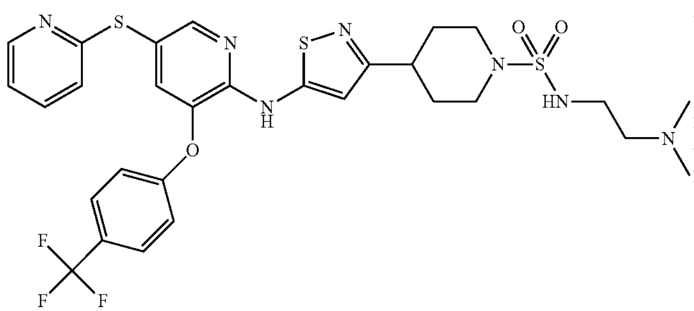 [SMILES: CN(C)CCNS(=O)(=O)N1CCC(c2cc(Nc3ncc(Sc4ccccn4)cc3Oc3ccc(C(F)(F)F)cc3)sn2)CC1] | N-(2-(Dimethylamino)ethyl)-4-(5-(5-(pyridin-2-ylthio)-3-(4-(trifluoromethyl)phenoxy)pyridin-2-ylamino)-1,2,4-thiadiazol-3-yl)piperidine-1-sulfonamide | ¹H NMR (DMSO-d₆) δ 1.75-1.83 (m, 2H), 2.07 (d, 2H), 2.37 (br s, 6H), 2.62-2.67 (m, 2H), 2.84 (t, 2H), 2.90-2.96 (m, 1H), 3.05 (d, 2H), 3.55 (d, 2H), 7.16-1.19 (m, 2H), 7.25 (s, 1H), 7.27 (s, 2H), 7.66-7.70 (m, 1H), 7.76 (d, 2H), 7.84 (d, 1H), 8.40 (d, 1H), 8.49 (d, 1H), 12.44 (br s, 1H). |
| 126 | 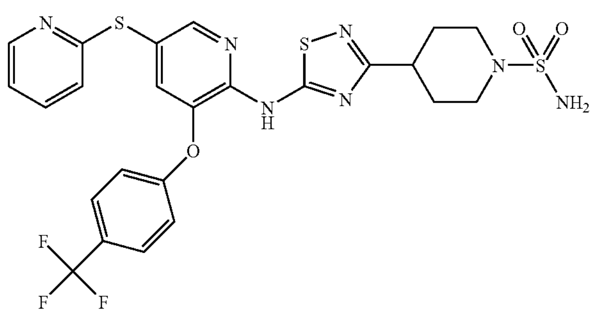 [SMILES: NS(=O)(=O)N1CCC(c2nsc(Nc3ncc(Sc4ccccn4)cc3Oc3ccc(C(F)(F)F)cc3)n2)CC1] | 4-(5-(5-(Pyridin-2-ylthio)-3-(4-(trifluoromethyl)phenoxy)pyridin-2-ylamino)-1,2,4-thiadiazol-3-yl)piperidine-1-sulfonamide | ¹H NMR (DMSO-d₆) δ 1.79-1.87 (m, 2H), 2.09 (d, 2H), 2.70 (t, 2H), 2.86 (t, 1H), 3.46 (d, 2H), 6.73 (s, 2H), 7.16-7.19 (m, 2H), 7.26 (d, 2H), 7.66-7.70 (m, 1H), 7.75 (s, 1H), 7.77 (s, 1H), 7.84 (d, 1H), 8.39 (d, 1H), 8.50 (d, 1H), 12.46 (s, 1H). |

| Ex. # | Structure | Name | Data |
|---|---|---|---|
| 127 | 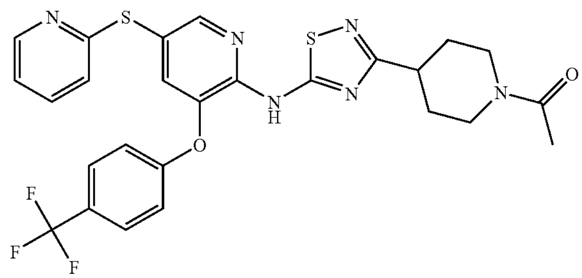 [SMILES: CC(=O)N1CCC(c2nsc(Nc3ncc(Sc4ccccn4)cc3Oc3ccc(C(F)(F)F)cc3)n2)CC1] | 1-(4-(5-(5-(Pyridin-2-ylthio)-3-(4-(trifluoromethyl)phenoxy)pyridin-2-ylamino)-1,2,4-thiadiazol-3-yl)piperidin-1-yl)ethanone | $^1$H NMR (DMSO-$d_6$) δ 1.52-1.63 (m, 1H), 1.67-1.84 (m, 1H), 1.95-2.03 (m, 5H), 2.75 (t, 1H), 3.02-3.07 (m, 1H), 3.18 (t, 1H), 3.83 (d, 1H), 4.31 (d, 1H), 7.15-7.18 (m, 2H), 7.26 (d, 2H), 7.66-7.70 (m, 1H), 7.76 (d, 2H), 7.84 (d, 1H), 8.40 (d, 1H), 8.49 (d, 1H), 12.44 (s, 1H). |
| 128 | 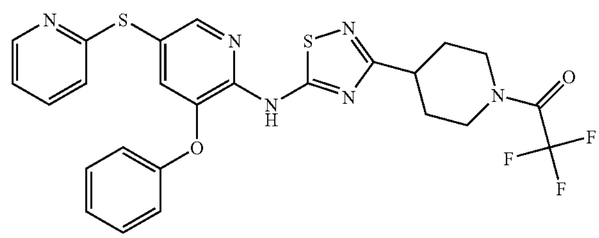 [SMILES: O=C(N1CCC(c2nsc(Nc3ncc(Sc4ccccn4)cc3Oc3ccccc3)n2)CC1)C(F)(F)F] | 2,2,2-Trifluoro-1-(4-(5-(3-phenoxy-5-(pyridin-2-ylthio)pyridin-2-ylamino)-1,2,4-thiadiazol-3-yl)piperidin-1-yl)ethanone | $^1$H NMR (DMSO-$d_6$) δ 1.68-1.84 (m 2H), 2.15 (t, 2H), 3.13-3.22 (m, 2H), 3.45 (t, 1H), 3.91 (d, 1H), 4.46 (d, 1H), 7.12-7.20 (m, 5H), 7.42 (t, 2H), 7.48 (d, 1H), 7.64-7.68 (m, 1H), 8.37 (d, 1H), 8.39 (d, , 1H), 12.36 (s, 1H). |
| 129 | 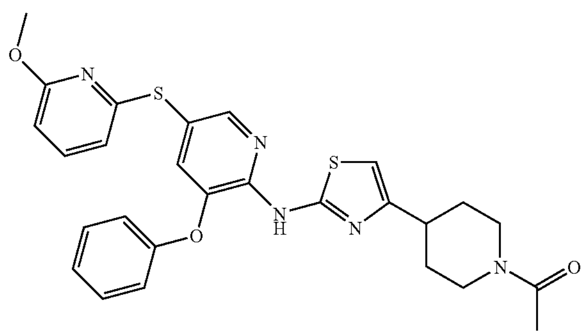 [SMILES: COc1cccc(Sc2cnc(Nc3nc(C4CCN(C(C)=O)CC4)cs3)c(Oc3ccccc3)c2)n1] | 1-(4-(2-(5-(6-Methoxypyridin-2-ylthio)-3-phenoxy-pyridin-2-ylamino)thiazol-4-yl)piperidin-1-yl)ethanone | $^1$H NMR (DMSO-$d_6$) δ 1.38-1.49 (m, 1H), 1.52-1.61 (m, 1H), 1.94 (t, 2H), 2.00 (s, 3H), 2.63 (t,, 1H), 2.83 (t, 1H), 3.13 (t, 1H), 3.65 (s, 3H), 3.86 (d, 1H), 4.42 (d, 1H), 6.54 (d, 1H), 6.64 (d, 1H), 6.72 (br s, 1H), 7.11 (d, 2H), 7.18 (t, 1H), 7.38-7.43 (m, 3H), 7.56 (t, 1H), 8.27 (d, 1H), 11.06 (s, 1H). |
| 130 | 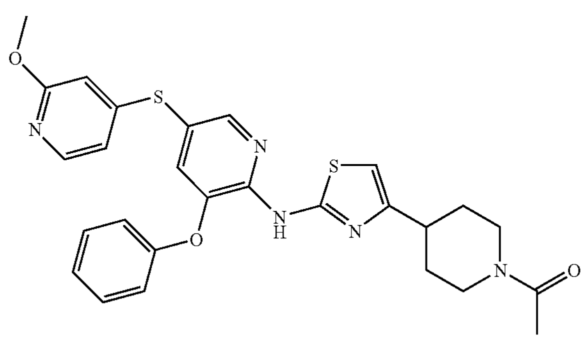 [SMILES: COc1cc(Sc2cnc(Nc3nc(C4CCN(C(C)=O)CC4)cs3)c(Oc3ccccc3)c2)ccn1] | 1-(4-(2-(5-(2-Methoxypyridin-4-ylthio)-3-phenoxy-pyridin-2-ylamino)thiazol-4-yl)piperidin-1-yl)ethanone | $^1$H NMR (DMSO-$d_6$) δ 1.40-1.48 (m, 1H), 1.56-1.61 (m, 1H), 1.91-2.00 (m, 5H), 2.64 (t, 1H), 2.81-2.84 (m, 1H), 3.13 (t, 1H), 3.79 (s, 3H), 3.86 (d, 1H), 4.42 (d, 1H), 6.37 (s, 1H), 6.67-6.69 (m, 1H), 6.74 (s, 1H), 7.12 (d, 2H), 7.18 (t, 1H), 7.32 (d, 1H), 7.41 (t, 2H), 7.98 (d, 1H), 8.28 (d, 1H), 11.16 (s, 1H). |
| 131 | 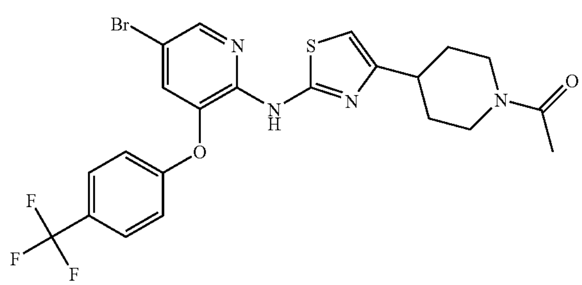 [SMILES: CC(=O)N1CCC(c2csc(Nc3ncc(Br)cc3Oc3ccc(C(F)(F)F)cc3)n2)CC1] | 1-(4-(2-(5-Bromo-3-(4-(trifluoromethyl)phenoxy)pyridin-2-ylamino)thiazol-4-yl)piperidin-1-yl)ethanone | $^1$H NMR (DMSO-$d_6$) δ 1.37-1.47 (m, 1H), 1.50-1.59 (m, 1H), 1.91 (t, 2H), 1.99 (s, 3H), 2.61 (t, 1H), 2.79 (t, 1H), 3.11 (t, 1H), 3.84 (d, 1H), 4.41 (d, 1H), 6.67 (s, 1H), 7.19 (d, 2H), 7.75 (d, 2H), 7.79 (d, 1H), 8.33 (d, 1H), 11.15 (s, 1H). |

| Ex. # | Structure | Name | Data |
|---|---|---|---|
| 132 | 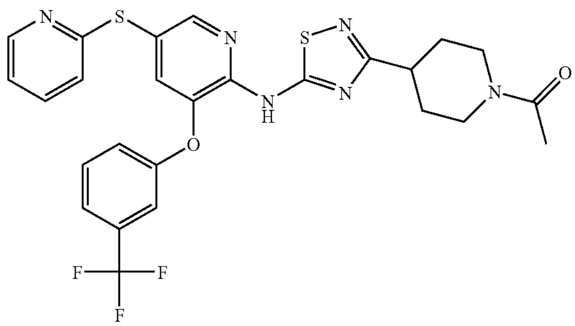 [SMILES: CC(=O)N1CCC(c2nsc(Nc3ncc(Sc4ccccn4)cc3Oc3cccc(C(F)(F)F)c3)n2)CC1] | 1-(4-(5-(5-(Pyridin-2-ylthio)-3-(3-(trifluoromethyl)phenoxy)pyridin-2-ylamino)-1,2,4-thiadiazol-3-yl)piperidin-1-yl)ethanone | $^1$H NMR (DMSO-d$_6$) δ 1.54-1.63 (m, 1H), 1.68-1.85 (m, 1H), 1.96-2.03 (m, 5H), 2.76 (t, 1H), 3.02-3.08 (m, 1H), 3.19 (t, 1H), 3.83 (d, 1H), 4.31 (d, 1H), 7.15-7.18 (m, 2H), 7.37 (d, 1H), 7.49-7.52 (m, 2H), 7.61 (d, 1H), 7.63-7.68 (m, 1H), 7.78 (d, 1H), 8.36-8.37 (m, 1H), 8.47 (d, 1H), 12.41 (s, 1H). |
| 133 | 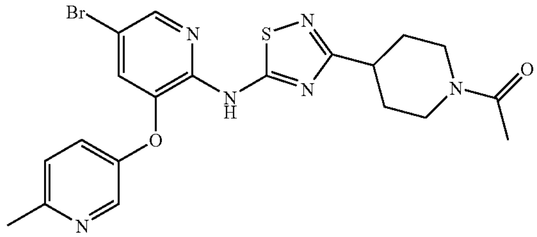 [SMILES: CC(=O)N1CCC(c2nsc(Nc3ncc(Br)cc3Oc3ccc(C)nc3)n2)CC1] | 1-(4-(5-(5-Bromo-3-(6-methylpyridin-3-yloxy)pyridin-2-ylamino)-1,2,4-thiadiazol-3-yl)piperidin-1-yl)ethanone | $^1$H NMR (DMSO-d$_6$) δ 1.53-1.62 (m, 1H), 1.68-1.77 (m, 1H), 1.95-2.01 (m, 5H), 2.48 (s, 3H), 2.75 (t, 1H), 3.00-3.08 (m, 1H), 3.18 (t, 1H), 3.84 (d, 1H), 4.31 (d, 1H), 7.30 (d, 1H), 7.43-7.46 (m, 1H), 7.63 (d, 1H), 8.34 (d, 1H), 8.38 (d, 1H), 12.45 (s, 1H). |
| 134 | 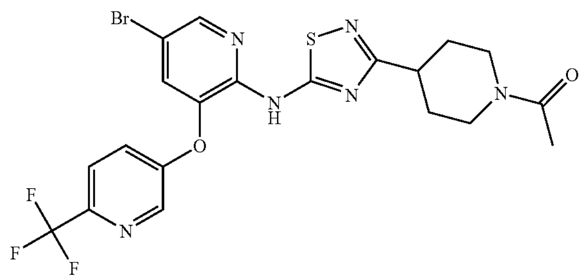 [SMILES: CC(=O)N1CCC(c2nsc(Nc3ncc(Br)cc3Oc3ccc(C(F)(F)F)nc3)n2)CC1] | 1-(4-(5-(5-Bromo-3-(6-(trifluoromethyl)pyridin-3-yloxy)pyridin-2-ylamino)-1,2,4-thiadiazol-3-yl)piperidin-1-yl)ethanone | $^1$H NMR (DMSO-d$_6$) δ 1.51-1.60 (m, 1H), 1.66-1.75 (m, 1H), 1.93-2.00 (m, 5H), 2.74 (t, 1H), 3.00-3.05 (m, 1H), 3.17 (t, 1H), 3.82 (d, 1H), 4.30 (d, 1H), 7.60 (d, 1H), 7.88 (d, 1H), 8.12 (d, 1H), 8.52 (d, 1H), 8.62 (d, 1H), 12.34 (s, 1H). |
| 135 | 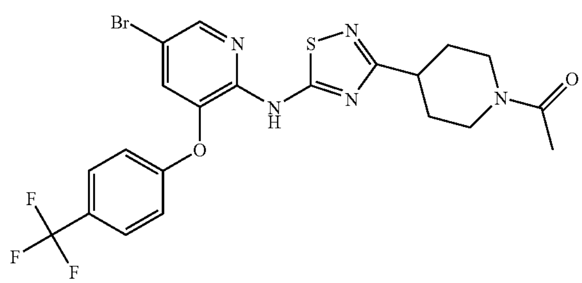 [SMILES: CC(=O)N1CCC(c2nsc(Nc3ncc(Br)cc3Oc3ccc(C(F)(F)F)cc3)n2)CC1] | 1-(4-(5-(5-Bromo-3-(4-(trifluoromethyl)phenoxy)pyridin-2-ylamino)-1,2,4-thiadiazol-3-yl)piperidin-1-yl)ethanone | $^1$H NMR (DMSO-d$_6$) δ 1.51-1.61 (m, 1H), 1.65-1.75 (m, 1H), 1.93-2.00 (m, 5H), 2.74 (t, 1H), 3.00-3.05 (m, 1H), 3.17 (t, 1H), 3.83 (d, 1H), 4.31 (d, 1H), 7.23 (d, 2H), 7.76 (d, 2H), 7.94 (d, 1H), 8.48 (d, 1H), 12.31 (s, 1H). |
| 136 | 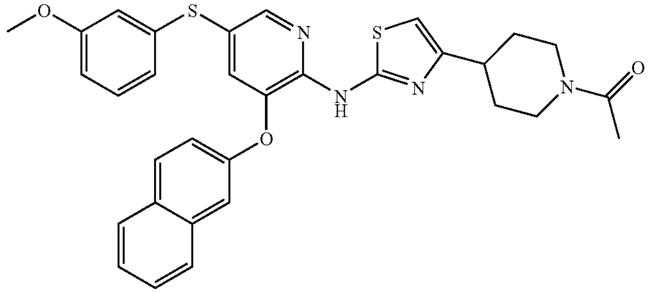 [SMILES: COc1cccc(Sc2cnc(Nc3nc(C4CCN(C(C)=O)CC4)cs3)c(Oc3ccc4ccccc4c3)c2)c1] | 1-(4-(2-(5-(3-Methoxyphenylthio)-3-(naphthalen-2-yloxy)pyridin-2-ylamino)thiazol-4-yl)piperidin-1-yl)ethanone | $^1$H NMR (DMSO-d$_6$) δ 1.38-1.47 (m, 1H), 1.51-1.59 (m, 1H), 1.89-1.99 (m, 5H), 2.61 (t, 1H), 2.81 (t, 1H), 3.11 (t, 1H), 3.68 (s, 3H), 3.84 (d, 1H), 4.40 (d, 1H), 6.71-6.78 (m, 4H), 7.22 (t, 1H), 7.37-7.52 (m, 5H), 7.81 (d, 1H), 7.92 (d, 1H), 7.97 (d, 1H), 8.26 (d, 1H), 11.13 (s, 1H). |

| Ex. # | Structure | Name | Data |
|---|---|---|---|
| 137 | 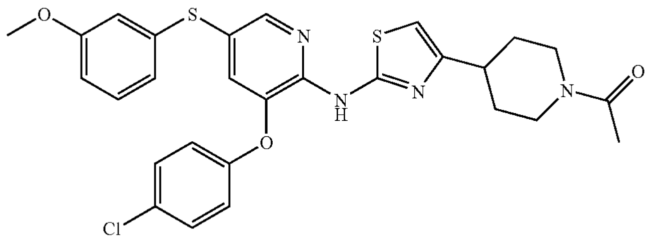 [SMILES: COc1cccc(Sc2cnc(Nc3nc(C4CCN(C(C)=O)CC4)cs3)c(Oc3ccc(Cl)cc3)c2)c1] | 1-(4-(2-(3-(4-Chlorophenoxy)-5-(3-methoxyphenylthio)pyridin-2-ylamino)thiazol-4-yl)piperidin-1-yl)ethanone | $^1$H NMR (DMSO-d$_6$) δ 1.42-1.47 (m, 1H), 1.52-1.60 (m, 1H), 1.89-2.00 (m, 5H), 2.63 (t, 1H), 2.82 (t, 1H), 3.12 (t, 1H), 3.70 (s, 3H), 3.86 (d, 1H), 4.41 (d, 1H), 6.70-6.80 (m, 4H), 7.08 (d, 2H), 7.23 (t, 1H), 7.35 (s, 1H), 7.42 (d, 2H), 8.23 (s, 1H), 11.10 (br s, 1H). |
| 138 | 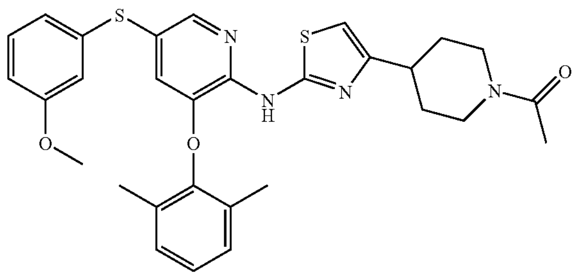 [SMILES: COc1cccc(Sc2cnc(Nc3nc(C4CCN(C(C)=O)CC4)cs3)c(Oc3c(C)cccc3C)c2)c1] | 1-(4-(2-(3-(2,6-Dimethylphenoxy)-5-(3-methoxyphenylthio)pyridin-2-ylamino)thiazol-4-yl)piperidin-1-yl)ethanone | $^1$H NMR (DMSO-d$_6$) δ 1.46-1.53 (m, 1H), 1.56-1.64 (m, 1H), 1.94-2.02 (m, 5H), 2.06 (s, 6H), 2.66 (t, 1H), 2.87 (t, 1H), 3.15 (t, 1H), 3.67 (s, 3H), 3.89 (d, 1H), 4.44 (d, 1H), 6.40 (d, 1H), 6.61-6.63 (m, 2H), 6.74-6.77 (m, 2H), 7.09-7.20 (m, 4H), 8.07 (d, 1H), 11.05 (s, 1H). |
| 139 | 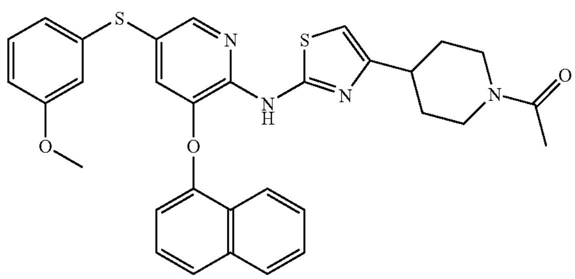 [SMILES: COc1cccc(Sc2cnc(Nc3nc(C4CCN(C(C)=O)CC4)cs3)c(Oc3cccc4ccccc34)c2)c1] | 1-(4-(2-(5-(3-Methoxyphenylthio)-3-(naphthalen-1-yloxy)pyridin-2-ylamino)thiazol-4-yl)piperidin-1-yl)ethanone | $^1$H NMR (DMSO-d$_6$) δ 1.40-1.48 (m, 1H), 1.52-1.61 (m, 1H), 1.90-1.99 (m, 5H), 2.62 (t, 1H), 2.83 (t, 1H), 3.12 (t, 1H), 3.65 (s, 3H), 3.85 (d, 1H), 4.41 (d, 1H), 6.66-6.68 (m, 2H), 6.74 (d, 2H), 7.02 (d, 1H), 7.10 (d, 1H), 7.16 (t, 1H), 7.45 (t, 1H), 7.55-7.62 (m, 2H), 7.75 (d, 1H), 7.98 (d, 1H), 8.15 (d, 1H), 8.22 (d, 1H), 11.29 (s, 1H). |
| 140 | 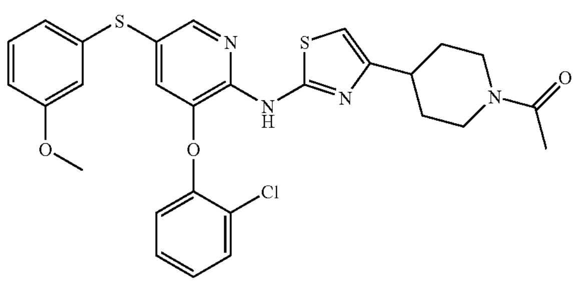 [SMILES: COc1cccc(Sc2cnc(Nc3nc(C4CCN(C(C)=O)CC4)cs3)c(Oc3ccccc3Cl)c2)c1] | 1-(4-(2-(3-(2-Chlorophenoxy)-5-(3-methoxy-phenylthio)pyridin-2-ylamino)thiazol-4-yl) piperidin-1-yl)ethanone | $^1$H NMR (DMSO-d$_6$) δ 1.41-1.49 (m, 1H), 1.54-1.62 (m, 1H), 1.91-2.01 (m, 5H), 2.64 (t, 1H), 2.84 (t, 1H), 3.13 (t, 1H), 3.68 (s, 3H), 3.87 (d, 1H), 4.42 (d, 1H), 6.69-6.71 (m, 3H), 6.76-6.78 (m, 1H), 6.97 (d, 1H), 7.19-7.27 (m, 3H), 7.37 (t, 1H), 7.59 (d, 1H), 8.19 (d, 1H), 11.15 (s, 1H). |
| 141 | 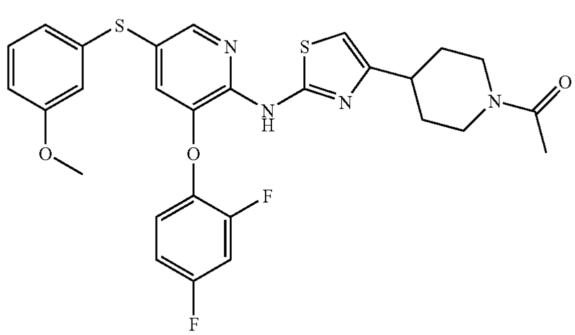 [SMILES: COc1cccc(Sc2cnc(Nc3nc(C4CCN(C(C)=O)CC4)cs3)c(Oc3ccc(F)cc3F)c2)c1] | 1-(4-(2-(3-(2,4-difluorophenoxy)-5-(3-methoxyphenylthio)pyridin-2-ylamino)thiazol-4-yl)piperidin-1-yl)ethanone | $^1$H NMR (DMSO-d$_6$) δ 1.38-1.49 (m, 1H), 1.52-1.61 (m, 1H), 1.93 (t, 2H), 2.00 (s, 3H), 2.62 (t, 1H), 2.82 (t, 1H), 3.12 (t, 1H), 3.70 (s, 3H), 3.86 (d, 1H), 4.01 (d, 1H), 6.70 (s, 1H), 6.75-6.80 (m, 3H), 6.91 (d, 1H), 7.21-7.30 (m, 2H), 7.38 (d, 1H), 7.40-7.47 (m, 1H), 8.22 (d, 1H), 11.09 (s, 1H). |

-continued

| Ex. # | Structure | Name | Data |
|---|---|---|---|
| 142 | 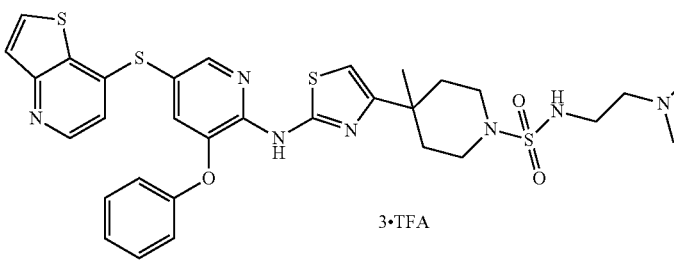 3·TFA | N-(2-(dimethylamino)ethyl)-4-methyl-4-(2-(3-phenoxy-5-(thieno[3,2-b]pyridin-2-ylamino)thiazol-4-yl)piperidine-1-sulfonamide tritrifluoroacetic acid salt | $^1$H NMR (DMSO-d$_6$) δ 8.51 (d, 1H), 8.39 (d, 1H), 8.19 (d, 1H), 7.60 (d, 1H), 7.47 (t, 1H), 7.43-7.37 (m, 3H), 7.15 (m, 3H), 6.94 (d, 1H), 6.86 (s, 1H), 3.22 (m, 4H), 3.13 (m, 2H), 2.98 (m, 2H), 2.79 (d, 6H), 2.24 (m, 2H), 1.67 (m, 2H), 1.23 (s, 3H). |
| 143 | 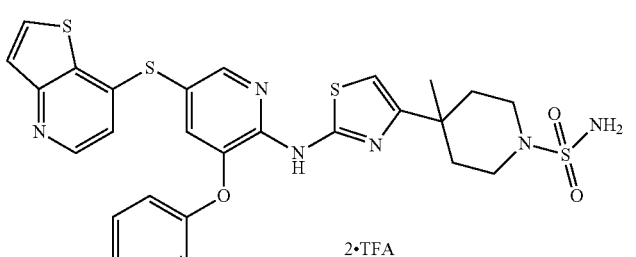 2·TFA | 4-methyl-4-(2-(3-phenoxy-5-(thieno[3,2-b]pyridin-7-ylthio)pyridin-2-ylamino)thiazol-4-yl)piperidine-1-sulfonamide ditrifluoroacetic acid salt | $^1$H NMR (DMSO-d$_6$) δ 8.53 (d, 1H), 8.40 (d, 1H), 8.23 (d, 1H), 7.62 (d, 1H), 7.43 (d, 1H), 7.39 (t, 2H), 7.15 (m, 3H), 6.98 (d, 1H), 6.84 (s, 1H), 6.62 (s, 2H), 3.13 (m, 2H), 2.82 (m, 2H), 2.27 (m, 2H), 1.67 (m, 2H), 1.21 (s, 3H). |
| 144 | 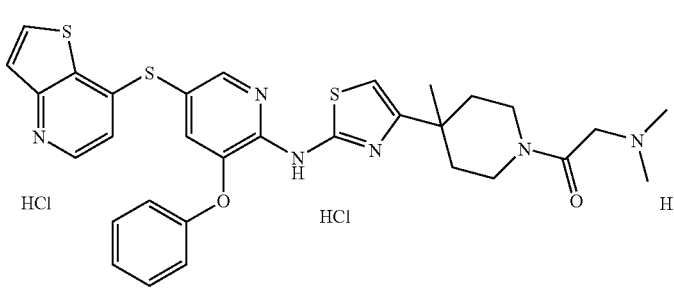 HCl HCl HCl | 2-(dimethylamino)-1-(4-methyl-4-(2-(3-phenoxy-5-(thieno[3,2-b]pyridin-7-ylthio)pyridin-2-ylamino)thiazol-4-yl)piperidin-1-yl)ethanone trihydrochloride | $^1$H NMR (DMSO-d$_6$) δ 11.21 (bs, 1H), 9.52 (bs, 1H), 8.54 (d, 1H), 8.40 (d, 1H), 8.25 (d, 1H), 7.63 (d, 1H), 7.44 (d, 1H), 7.41 (t, 2H), 7.19-7.11 (m, 3H), 6.69 (d, 1H), 6.90 (s, 1H), 4.26 (m, 3H), 3.74 (m, 1H), 3.44-3.18 (m, 2H), 2.80 (dd, 6H), 2.17 (m, 2H), 1.69-1.52 (m, 2H), 1.27 (s, 3H) |
| 145 | 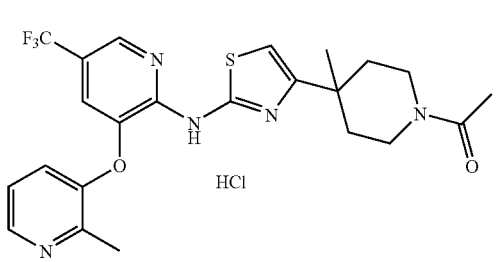 [SMILES: CC(=O)N1CCC(C)(c2csc(Nc3ncc(C(F)(F)F)cc3Oc3cccnc3C)n2)CC1 ; Cl] HCl | 1-(4-methyl-4-(2-(3-(2-methylpyridin-3-yloxy)-5-(trifluoromethyl)pyridin-2-ylamino)thiazol-4-yl)piperidin-1-yl)ethanone hydrochloride | $^1$H NMR (DMSO-d$_6$) δ 11.49 (s, 1H), 8.52 (s, 1H), 8.30 (dd, 1H), 7.50 (s, 1H), 7.32-7.24 (m, 2H), 6.87 (s, 1H), 3.57 (m, 1H), 3.47 (m, 1H), 3.32 (m, 2H), 2.35 (s, 3H), 2.20-2.03 (m, 2H), 1.97 (s, 3H), 1.57 (m, 1H), 1.48 (m, 1H), 1.26 (s, 3H) |
| 146 | 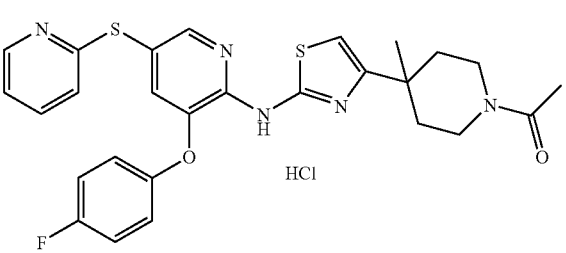 [SMILES: CC(=O)N1CCC(C)(c2csc(Nc3ncc(Sc4ccccn4)cc3Oc3ccc(F)cc3)n2)CC1 ; Cl] HCl | 1-(4-(2-(3-(4-fluorophenoxy)-5-(pyridin-2-ylthio)pyridin-2-ylamino)thiazol-4-yl)-4-methyl-piperidin-1-yl)ethanone hydrochloride | $^1$H NMR (DMSO-d$_6$) δ 11.02 (bs, 1H), 8.37 (dm, 1H), 8.26 (d, 1H), 7.65 (dt, 1H), 7.33 (d, 1H), 7.29-7.12 (m, 5H), 7.07 (d, 1H), 6.81 (s, 1H), 3.59 (m, 1H), 3.48 (m, 1H), 3.33 (m, 2H), 2.19-2.02 (m, 2H), 1.98 (s, 3H), 1.56 (m, 1H), 1.47 (m, 1H), 1.26 (s, 3H). |
| 147 | 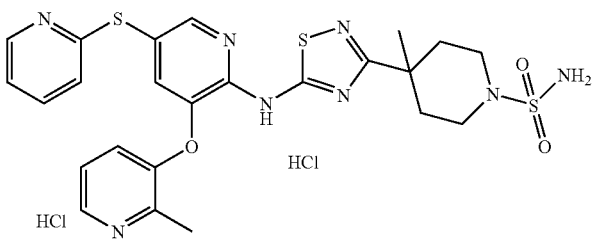 [SMILES: Cc1ncccc1Oc1cc(Sc2ccccn2)cnc1Nc1nc(C2(C)CCN(S(N)(=O)=O)CC2)ns1 ; Cl ; Cl] HCl HCl | 4-methyl-4-(5-(3-(2-methylpyridin-3-yloxy)-5-(pyridin-2-ylthio)pyridin-2-ylamino)-1,2,4-thiadiazol-3-yl)piperidine-1-sulfonamide dihydrochloride | $^1$H NMR (DMSO-d$_6$) δ 12.44 (s, 1H), 8.49 (d, 1H), 8.38 (m, 2H), 7.73 (s, 1H), 7.67 (dt, 1H), 7.60 (m, 1H), 7.49 (m, 1H), 7.16 (m, 2H), 6.57 (s, 2H), 3.25 (m, 2H), 2.65 (m, 5H), 2.46 (m, 2H), 1.68 (m, 2H), 1.24 (s, 3H). |

| Ex. # | Structure | Name | Data |
|---|---|---|---|
| 148 | 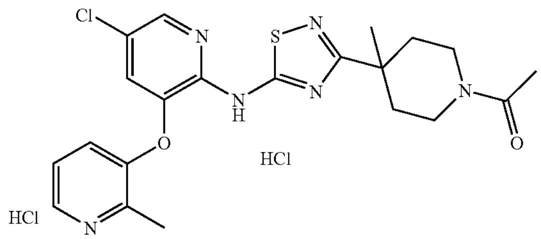 [SMILES: Cl ; CC(=O)N1CCC(C)(c2nsc(Nc3ncc(Cl)cc3Oc3cccnc3C)n2)CC1 ; Cl] | 1-(4-(5-(5-chloro-3-(2-methylpyridin-3-yloxy)pyridin-2-ylamino)-1,2,4-thiadiazol-3-yl)-4-methylpiperidin-1-yl)ethanone dihydrochloride | $^1$H NMR (DMSO-$d_6$) δ 12.28 (s, 1H), 8.50 (d, 1H), 8.46 (d, 1H), 7.87 (d, 1H), 7.81 (d, 1H), 7.67 (m, 1H), 3.89 (m, 1H), 3.59 (m, 1H), 3.17 (m, 1H), 2.90 (m, 1H), 2.75 (s, 3H), 2.36-2.21 (m, 2H), 1.97 (s, 3H), 1.58 (m, 1H), 1.46 (m, 1H), 1.25 (s, 3H). |
| 149 | 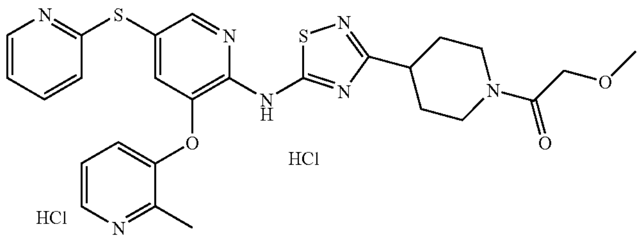 [SMILES: COCC(=O)N1CCC(c2nsc(Nc3ncc(Sc4ccccn4)cc3Oc3cccnc3C)n2)CC1 ; Cl ; Cl] | 2-methoxy-1-(4-(5-(3-(2-methylpyridin-3-yloxy)-5-(pyridin-2-ylthio)pyridin-2-ylamino)1,2,4-thiadiazol-3-yl)piperidin-1-yl)ethanone dihydrochloride | $^1$H NMR (DMSO-$d_6$) δ 12.41 (s, 1H), 8.51 (d, 1H), 8.43 (d, 1H), 8.38 (dd, 1H), 7.80 (s, 1H), 7.73 (d, 1H), 7.68 (dt, 1H), 7.60 (m, 1H), 7.17 (m, 1H), 4.29 (m, 1H), 4.08 (q, 2H), 3.80 (d, 1H), 3.29 (s, 3H), 3.19-3.03 (m, 2H), 2.80 (t, 1H), 2.70 (s, 3H), 2.01 (m, 2H), 1.79-1.54 (m, 2H). |
| 150 | 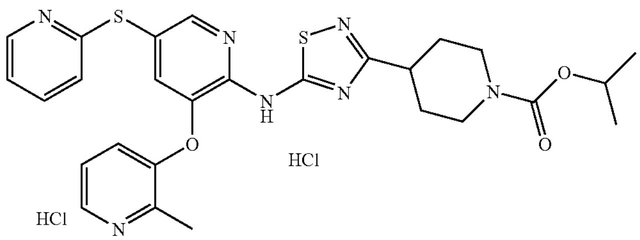 [SMILES: Cc1ncccc1Oc1cc(Sc2ccccn2)cnc1Nc1nc(C2CCN(C(=O)OC(C)C)CC2)ns1 ; Cl ; Cl] | isopropyl 4-(5-(3-(2-methylpyridin-3-yloxy)-5-(pyridin-2-ylthio)pyridin-2-ylamino)-1,2,4-thiadiazol-3-yl)piperidine-1-carboxylate dihydrochloride | $^1$H NMR (DMSO-$d_6$) δ 12.41 (s, 1H), 8.49 (d, 1H), 8.38 (m, 2H), 7.73-7.60 (m, 3H), 7.51 (m, 1H), 7.16 (m, 2H), 4.76 (m, 1H), 3.98 (d, 2H), 2.99 (m, 3H), 2.65 (s, 3H), 1.98 (d, 2H), 1.63 (m, 2H), 1.18 (d, 6H) |
| 151 | 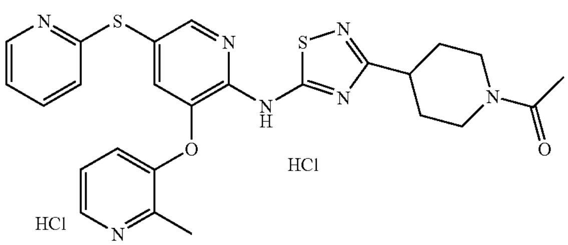 [SMILES: CC(=O)N1CCC(c2nsc(Nc3ncc(Sc4ccccn4)cc3Oc3cccnc3C)n2)CC1 ; Cl ; Cl] | 1-(4-(5-(3-(2-methylpyridin-3-yloxy)-5-(pyridin-2-ylthio)pyridin-2-ylamino)1,2,4-thiadiazol-3-yl)piperidin-1-yl)ethanone dihydrochloride | $^1$H NMR (DMSO-$d_6$) δ 12.42 (s, 1H), 8.47 (d, 1H), 8.37 (m, 2H), 7.68 (m, 2H), 7.56 (m, 1H), 7.45 (m, 1H), 7.16 (m, 2H); 4.32 (d, 1H), 3.83 (d, 1H), 3.19 (t, 1H), 3.05 (m, 1H), 2.76 (t, 1H), 2.62 (s, 3H), 2.06-1.94 (m, 5H), 1.73 (m, 1H), 1.58 (m, 1H) |
| 152 | 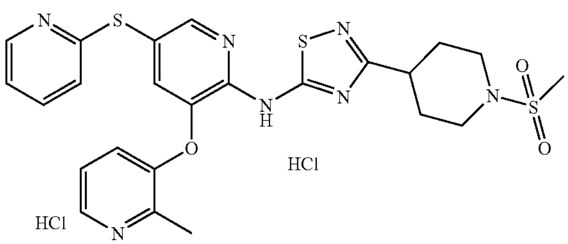 [SMILES: Cc1ncccc1Oc1cc(Sc2ccccn2)cnc1Nc1nc(C2CCN(S(C)(=O)=O)CC2)ns1 ; Cl ; Cl] | N-(3-(2-methylpyridin-3-yloxy(-5-(pyridin-2-ylthio)pyridin-2-yl)-3-(1-(methylsulfonyl)piperidin-4-yl)-1,2,4-thiadiazol-5-amine dihydrochloride | $^1$H NMR (DMSO-$d_6$) δ 12.44 (s, 1H), 8.46 (d, 1H), 8.37 (dm, 1H), 8.33 (d, 1H), 7.67 (dt, 1H), 7.61 (s, 1H), 7.48 (d, 1H), 7.38 (m, 1H), 7.15 (m, 2H), 3.59 (m, 2H), 2.92 (m, 3H), 2.87 (s, 3H), 2.58 (s, 3H), 2.13 (d, 2H), 1.81 (m, 2H). |
| 153 | 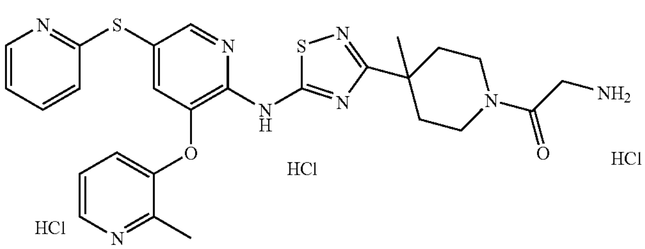 [SMILES: Cc1ncccc1Oc1cc(Sc2ccccn2)cnc1Nc1nc(C2(C)CCN(C(=O)CN)CC2)ns1 ; Cl ; Cl ; Cl] | 2-amino-1-(4-methyl-4-(5-(3-(2-methyl-pyridin-3-yloxy)-5-(pyridin-2-ylthio)pyridin-2-ylamino)-1,2,4-thiadiazol-3-yl)piperidin-1-yl)ethanone trihydrochloride | $^1$H NMR (DMSO-$d_6$) δ 12.45 (s, 1H), 8.56 (s, 1H), 8.48 (m, 1H), 8.40 (m, 1H), 8.15 (m, 2H), 7.95 (m, 1H), 7.85 (m, 1H), 7.71 (m, 2H), 7.20 (s, 2H), 4.00-3.75 (m, 3H), 3.17 (s, 2H), 3.00 (m, 1H), 2.78 (s, 3H), 2.35 (m, 2H), 1.65 (m, 1H), 1.54 (m, 1H), 1.28 (s, 3H). |

| Ex. # | Structure | Name | Data |
| --- | --- | --- | --- |
| 154 | 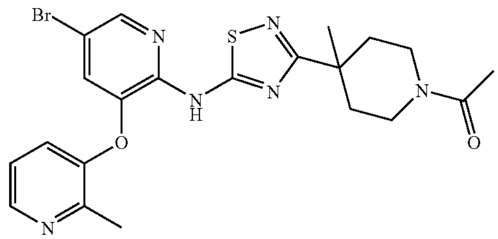 [SMILES: CC(=O)N1CCC(C)(c2nsc(Nc3ncc(Br)cc3Oc3cccnc3C)n2)CC1] | 1-(4-(5-(5-bromo-3-(2-methylpyridin-3-yloxy)pyridin-2-ylamino)-1,2,4-thiadiazol-3-yl)-4-methylpiperidin-1-yl)ethanone | $^1$H NMR (DMSO-d$_6$) δ 12.29 (s, 1H), 8.40 (d, 1H), 8.29 (dd, 1H), 7.59 (d, 1H), 7.31-7.21 (m, 2H), 3.09 (m, 1H), 3.60 (m, 1H), 3.18 (m, 1H), 2.93 (t, 1H), 2.52 (s, 3H), 2.30 (m, 2H), 1.97 (s, 3H), 1.58 (m, 1H), 1.47 (m 1H), 1.26 (s, 3H) |
| 155 | 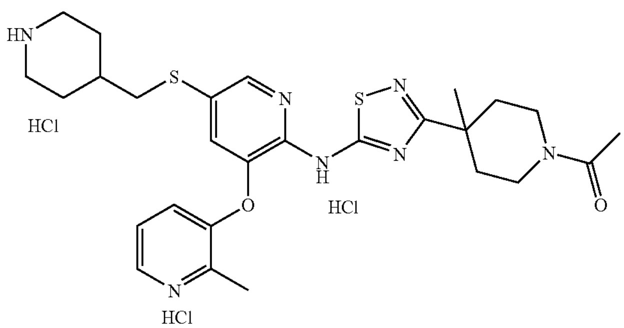 [SMILES: CC(=O)N1CCC(C)(c2nsc(Nc3ncc(SCC4CCNCC4)cc3Oc3cccnc3C)n2)CC1 ; Cl ; Cl ; Cl] | 1-(4-methyl-4-(5-(3-(2-methylpyridin-3-yloxy)-5-(piperidin-4-ylmethylthio)pyridin-2-ylamino)-1,2,4-thiadiazol-3-yl)piperidin-1-yl)ethanone trihydrochloride | $^1$H NMR (DMSO-d$_6$) δ 12.19 (s, 1H), 9.10 (m, 1H), 8.83 (m, 1H), 8.50 (d, 1H), 8.42 (d, 1H), 7.89 (d, 1H), 7.80 (d, 1H), 7.75 (m, 1H), 3.88 (m, 1H), 3.60 (m, 1H), 3.21 (m, 2H), 3.14 (m, 1H), 2.94 (d, 2H), 2.89 (m, 1H), 2.85 (s, 3H), 2.78 (m, 2H), 2.35-221 (m, 2H), 1.97 (s, 3H), 1.89 (d, 2H), 1.72 (m, 1H), 1.57 (m, 1H), 1.42 (m, 3H), 1.25 (s, 3H). |
| 156 | 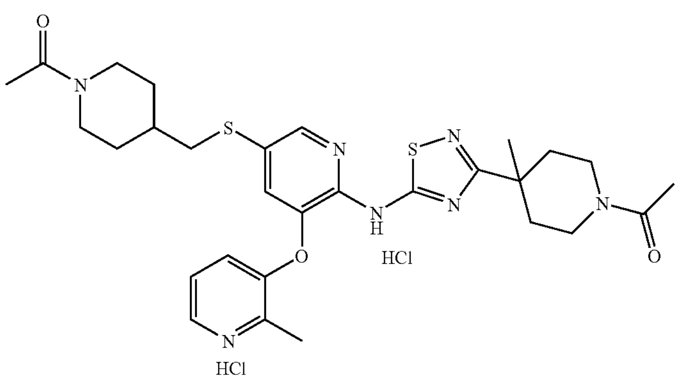 [SMILES: CC(=O)N1CCC(CSc2cnc(Nc3nc(C4(C)CCN(C(C)=O)CC4)ns3)c(Oc3cccnc3C)c2)CC1 ; Cl ; Cl] | 1-(4-((6-(3-(1-acetyl-4-methylpiperidin-4-yl)-1,2,4-thiadiazol-5-ylamino)-5-(2-methyl-pyridin-3-yloxy)pyridin-3-ylthio)methyl)piperidin-1-yl)ethanone dihydrochloride | $^1$H NMR (DMSO-d$_6$) δ 12.18 (s, 1H), 8.39 (m, 1H), 8.34 (d, 1H), 7.61 (s, 1H), 7.48 (m, 2H), 4.31 (d, 1H), 3.89 (d, 1H), 3.77 (d, 1H), 3.60 (m, 1H), 3.17 (m, 1H), 2.98-2.86 (m, 4H), 2.66 (s, 3H), 2.45 (m, 1H), 2.28 (m, 2H), 1.97 (s, 3H), 1.96 (s, 3H), 1.75 (m, 2H), 1.60 (m, 2H), 1.45 (m, 1H), 1.25 (s, 3H), 1.10 (m, 1H), 0.97 (m, 1H). |
| 157 | 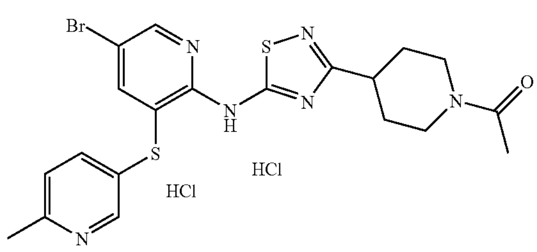 [SMILES: CC(=O)N1CCC(c2nsc(Nc3ncc(Br)cc3Sc3ccc(C)nc3)n2)CC1 ; Cl ; Cl] | 1-(4-(5-(5-bromo-3-(6-methylpyridin-3-ylthio)pyridin-2-ylamino)-1,2,4-thiadiazol)-3-yl)piperidin-1-yl)ethanone dihydrochloride | $^1$H NMR (DMSO-d$_6$) δ 8.74 (d, 1H), 8.65 (s, 1H), 8.17 (bs, 1H), 8.10 (d, 1H), 7.64 (d, 1H), 4.32 (m, 1H), 3.84 (m, 1H), 3.17 (m, 1H), 3.03 (m, 1H), 2.73 (m, 1H), 2.63 (s, 3H), 2.01 (s, 3H), 1.96 (m, 2H), 1.71 (m, 1H), 1.56 (m, 1H). |
| 158 | 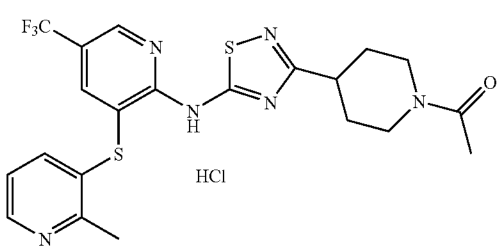 [SMILES: CC(=O)N1CCC(c2nsc(Nc3ncc(C(F)(F)F)cc3Sc3cccnc3C)n2)CC1 ; Cl] | 1-(4-(5-(3-(2-methylpyridin-3-ylthio)-5-(trifluoromethyl)pyridin-2-ylamino)-1,2,4-thiadiazol)-3-yl)piperidin-1-yl)ethanone hydrochloride | $^1$H NMR (DMSO-d$_6$) δ 12.20 (bs, 1H), 8.96 (ds 1H), 8.45 (s, 1H), 8.25 (bs, 1H), 7.45 (bs, 1H), 7.34 (m, 1H), 4.32 (m, 1H), 3.83 (m, 1H), 3.16 (m, 1H), 3.03 (m, 1H), 2.72 (m, 1H), 2.65 (s, 3H), 2.01 (s, 3H), 1.96 (m, 2H), 1.71 (m, 1H), 1.56 (m, 1H). |

-continued

| Ex. # | Structure | Name | Data |
|---|---|---|---|
| 159 | 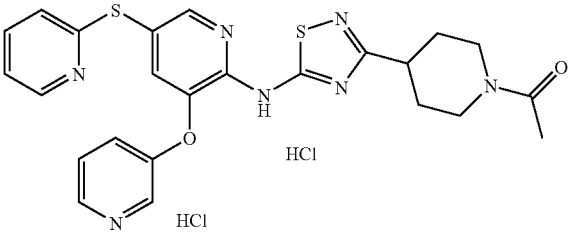 [SMILES: CC(=O)N1CCC(c2nsc(Nc3ncc(Sc4ccccn4)cc3Oc3cccnc3)n2)CC1 ; Cl ; Cl] | 1-(4-(5-(5-(pyridin-2-ylthio)-3-(pyridin-3-yloxy)pyridin-2-ylamino)-1,2,4-thiadiazol-3-yl)piperidin-1-yl)ethanone dihydrochloride | $^1$H NMR (DMSO-d$_6$) δ 8.80 (d, 1H), 8.61 (dd, 1H), 8.55 (d, 1H), 8.43 (ddd, 1H), 8.11 (ddd, 1H), 8.06 (d, 1H), 7.91 (dd, 1H), 7.72 (td, 1H), 7.20 (m, 2H), 4.31 (m, 1H), 3.83 (m, 1H), 3.19 (m, 1H), 3.05 (m, 1H), 2.75 (m, 1H), 2.00 (m, 5H), 1.72 (m, 1H), 1.57 (m, 1H). |
| 160 | 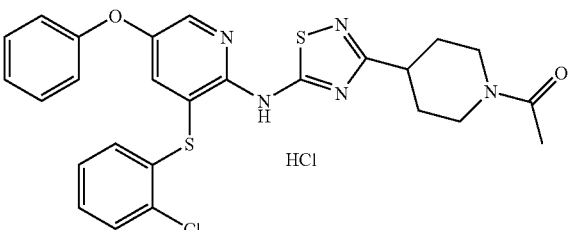 | 1-(4-(5-(3-(2-chlorophenylthio)-5-phenoxypyridin-2-ylamino)-1,2,4-thiadiazol-3-yl)piperidin-1-yl)ethanone hydrochloride | $^1$H NMR (DMSO-d$_6$) δ 8.25 (m, 1H), 7.59 (m, 1H), 7.44 (m, 1H), 7.37 (m, 2H), 7.25-7.15 (m, 3H), 7.02 (m, 3H), 4.57 (d, 1H), 3.85 (d, 1H), 3.11 (m, 1H), 2.75 (m, 1H), 2.12 (m, 4H), 1.86 (m, 2H), 1.55 (m, 2H). |
| 161 | 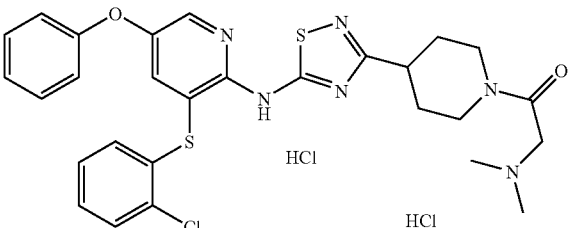 | 1-(4-(5-(3-(2-chlorophenylthio)-5-phenoxypyridin-2-ylamino)-1,2,4-thiadiazol-3-yl)piperidin-1-yl)-2-(dimethylamino)ethanone dihydrochloride | $^1$H NMR (DMSO-d$_6$) δ 11.51 (s, 1H), 9.50 (s, 1H), 8.34 (s, 1H), 7.63 (s, 1H), 7.50 (m, 1H), 7.32 (m, 2H), 7.21 (m, 2H), 7.09 (t, 1H), 7.00 (m, 2H), 6.80 (m, 1H), 4.23 (m, 3H), 3.55 (m, 1H), 3.20-2.84 (m, 2H), 2.75 (d, 6H), 2.65 (m, 1H), 1.99 (m, 2H), 1.76 (m, 1H), 1.55 (m, 1H). |
| 162 | 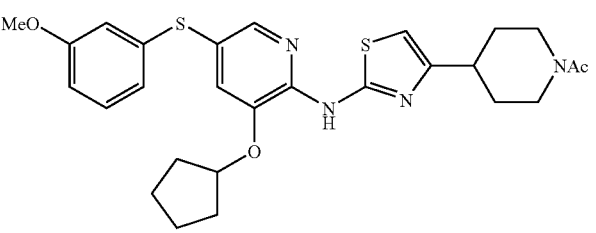 | 1-(4-(2-(3-(cyclopentyloxy)-5-(3-methoxyphenylthio)pyridin-2-ylamino)thiazol-4-yl)piperidin-1-yl)ethanone | $^1$H NMR (CDCl$_3$) δ 1.20-1.44 (m, 4H), 1.56-1.72 (m, 2H), 1.84-2.15 (m, 6H), 2.12 (s, 3H), 2.73 (bs, 1H), 3.02 (t, 1H), 3.20 (bs, 1H), 3.77 (s, 3H), 3.95 (bs, 1H), 4.79 (bs, 1H), 4.84 (bs, 1H), 6.40 (s, 1H), 6.81-6.89 (m, 3H), 7.27 (s, 1H), 7.21-7.31 (m, 2H), 7.92 (s, 1H). |
| 163 | 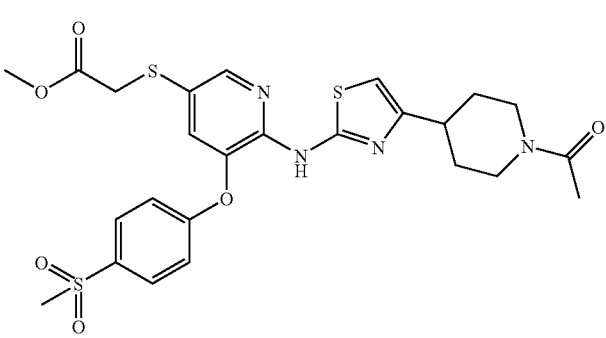 [SMILES: COC(=O)CSc1cnc(Nc2nc(C3CCN(C(C)=O)CC3)cs2)c(Oc2ccc(S(C)(=O)=O)cc2)c1] | methyl 2-(6-(4-(1-acetylpiperidin-4-yl)thiazol-2-ylamino)-5-(4-(methylsulfonyl)phenoxy)pyridin-3-ylthio)acetate | $^1$H NMR (DMSO-d$_6$) δ 11.18 (s, 1H), 8.28 (s, 1H), 7.94 (d, 2H), 7.71 (s, 1H), 7.19 (d, 2H), 6.69 (brs, 1H), 4.42 (d, 1H), 3.84 (s, 3H), 3.59 (s, 3H), 3.21 (m, 3H), 3.11 (t, 1H), 2.80 (m, 1H), 2.62 (t, 1H), 2.00 (s, 3H), 1.92 (t, 2H), 1.61-1.37 (m, 2H). |
| 164 | 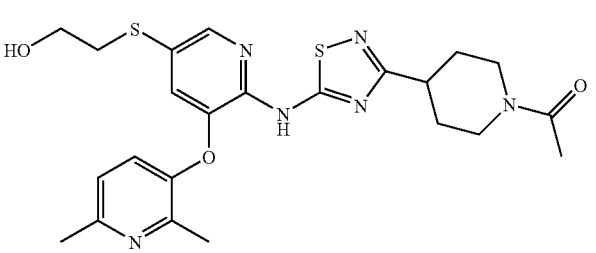 [SMILES: CC(=O)N1CCC(c2nsc(Nc3ncc(SCCO)cc3Oc3ccc(C)nc3C)n2)CC1] | 1-(4-(5-(3-(2,6-dimethylpyridin-3-yloxy)-5-(2-hydroxyethylthio)pyridin-2-ylamino)1,2,4-thiadiazol-3-yl)pyridin-1-yl)ethanone | $^1$H NMR (CDCl$_3$) δ 1.85 (m, 2H), 2.12 (m, 1H), 2.14 (s, 3H), 2.73 (s, 3H), 2.77 (s, 3H), 2.85 (m, 2H), 3.03 (t, 2H), 3.13 (m, 1H), 3.27 (t, 1H), 3.81 (t, 2H), 3.92 (m, 1H), 4.61 (d, 1H), 7.37 (d, 1H), 7.49 (s, 1H), 7.57 (d, 1H), 8.32 (s, 1H). |

Example 165 (Representative Example)

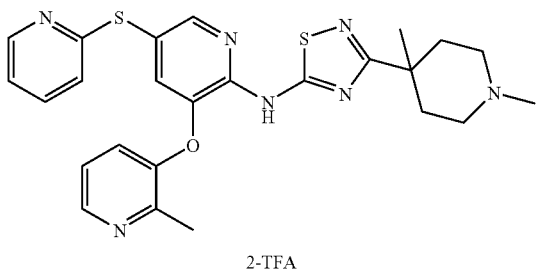 [SMILES: Cc1ncccc1Oc1cc(Sc2ccccn2)cnc1Nc1nc(C2(C)CCN(C)CC2)ns1]

2-TFA 3-(1,4-dimethylpiperidin-4-yl)-N-(3-(2-methylpyridin-3-yloxy)-5-(pyridin-2-ylthio)pyridin-2-yl)-1,2,4-thiadiazol-5-amine bis(2,2,2-trifluoroacetate)

3-(4-Methylpiperidin-4-yl)-N-(3-(2-methylpyridin-3-yloxy)-5-(pyridin-2-ylthio)pyridin-2-yl)-1,2,4-thiadiazol-5-amine (70 mg, 0.142 mmol) was dissolved in dichloroethane (25 mL). Paraformaldehyde (4.28 mg, 0.142 mmol) and NaBH(OAc)$_3$ (60.4 mg, 0.285 mmol) were added and stirred at ambient temperature for 18 hours. Water was added, extracted with methylene chloride, dried, filtered, and concentrated. The residue was purified by reverse phase chromatography (with 0.1% TFA buffer) to afford 3-(1,4-dimethylpiperidin-4-yl)-N-(3-(2-methylpyridin-3-yloxy)-5-(pyridin-2-ylthio) pyridin-2-yl)-1,2,4-thiadiazol-5-amine bis(2,2,2-trifluoroacetate) (62 mg, 0.0845 mmol, 59.3% yield). $^1$H NMR (d$_6$-DMSO) δ 12.49 (bs, 1H), 9.40 (bs, 1H), 8.47 (m, 1H), 8.36 (m, 1H), 8.33 (m, 1H), 7.67 (m, 1H), 7.62 (m, 1H), 7.44 (m, 1H), 7.37 (m, 1H), 7.16 (m, 2H), 3.37 (m, 2H), 2.89-2.56 (m, 9H), 2.25-2.00 (m, 1h), 1.82 (m, 2H), 1.45-1.24 (m, 3H).

The following compounds were also prepared according to the method of Example 165.

| Example | Structure | Name | Data |
|---|---|---|---|
| 166 (Representative example) | 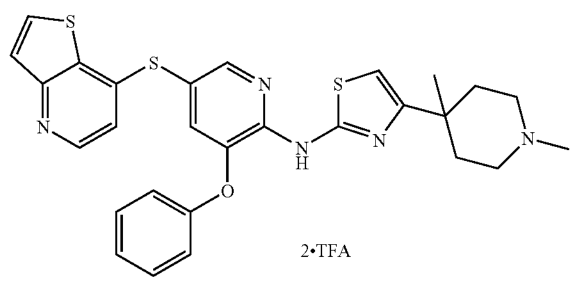 [SMILES: CN1CCC(C)(c2csc(Nc3ncc(Sc4ccnc5ccsc45)cc3Oc3ccccc3)n2)CC1 ; "2·TFA"] | 4-(1,4-dimethylpiperidin-4-yl)-N-(3-phenoxy-5-(thieno[3,2-b]pyridin-7-ylthio)pyridin-2-yl)thiazol-2-amine ditrifluoroacetic acid salt | $^1$H NMR (d$_6$-DMSO) δ 8.52 (d, 1H), 8.39 (d, 1H) 8.20 (d, 1H), 7.61 (d, 1H), 7.41 (m, 3H), 7.15 (m, 3H), 7.20 (s, 0.6H), 6.95 (m, 1H), 6.85 (s, 0.4H), 3.35 (m, 2H), 3.20 (m, 1H), 2.86 (m, 2H), 2.72 (m, 2H), 2.46 (m, 2H), 2.00 (m, 1H), 1.78 (m, 1H), 1.36 (s, 1H), 1.21 (s, 2H) |
| 167 | 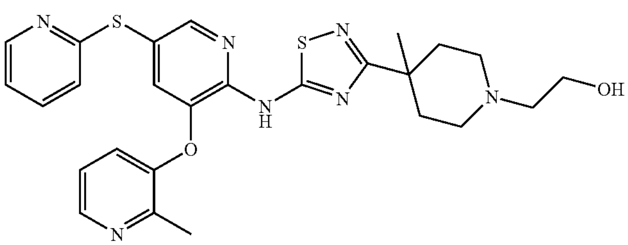 [SMILES: Cc1ncccc1Oc1cc(Sc2ccccn2)cnc1Nc1nc(C2(C)CCN(CCO)CC2)ns1] | 2-(4-methyl-4-(5-(3-(2-methylpyridin-3-yloxy)-5-(pyridin-2-ylthio) pyridin-2-ylamino)-1,2,4-thiadiazol-3-yl)piperidin-1-yl)ethanol | $^1$H NMR (CDCl$_3$) δ 11.27 (bs, 1H), 9.28 (s, 1H), 8.44 (d, 1H), 8.34 (d, 1H), 8.32 (m, 1H), 7.51 (dt, 1H), 7.37 (d, 1H), 7.23 (dd, 1H), 7.11 (d, 1H), 7.04 (m, 2H), 3.98 (m, 2H), 3.59 (m, 2H), 3.04 (m, 2H), 2.88 (m, 2H), 2.64 (m, 2H), 2.52 (s, 3H), 2.46 (m, 2H), 1.40 (s, 3H). |
| 168 (Representative example) | 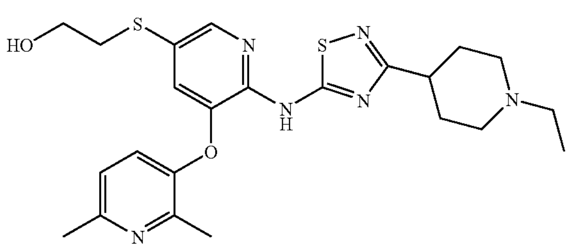 [SMILES: CCN1CCC(c2nsc(Nc3ncc(SCCO)cc3Oc3ccc(C)nc3C)n2)CC1] | 1-(5-(2,6-dimethylpyridin-3-yloxy)-6-(3-(1-ethyl-piperidin-4-yl)-1,2,4-thiadiazol-5-ylamino)pyridin-3-ylthio)ethanol | $^1$H NMR (CDCl$_3$) δ 1.38 (m, 3H), 2.36 (m, 2H), 2.41 (m, 2H), 2.67 (m, 1H), 2.73 (s, 3H), 2.77 (s, 3H), 3.00 (m, 3H), 3.13 (m, 3H), 3.53 (d, 1H), 3.81 (m, 3H), 7.39 (m, 1H), 7.45 (m, 1H), 7.64 (m, 1H), 8.32 (m, 1H). |
| 169 | 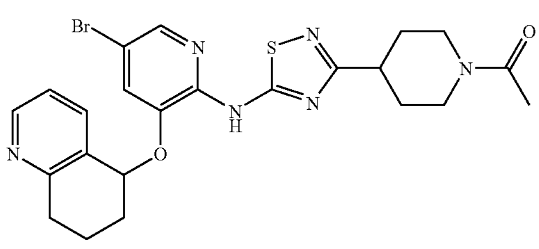 [SMILES: CC(=O)N1CCC(c2nsc(Nc3ncc(Br)cc3OC3CCCc4ncccc43)n2)CC1] | 1-(4-(5-(5-bromo-3-(5,6,7,8-tetrahydroquinolin-5-yloxy)pyridin-2-ylamino)-1,2,4-thiadiazol-3-yl)piperidin-1-yl)ethanone | $^1$H NMR (CDCl$_3$) δ 1.68-1.90 (m, 2H), 1.92-2.16 (m, 5H), 2.08 (s, 3H), 2.17-2.26 (m, 1H), 2.77 (t, 1H), 2.92-3.07 (m, 2H), 3.08-3.22 (m, 2H), 3.86 (d, 1H), 4.54 (d, 1H), 5.52 (t, 1H), 7.19 (dd, 1H), 7.45 (d, 1H), 7.60 (dd, 1H), 8.12 (d, 1H), 8.59 (dd, 1H), 8.91 (bs, 1H). |

Example 170

Ethyl 3-(5-(5-bromo-3-(2-methylpyridin-3-yloxy)pyridin-2-ylamino)-1,2,4-thiadiazol-3-yl)-8-azabicyclo[3.2.1]octane-8-carboxylate

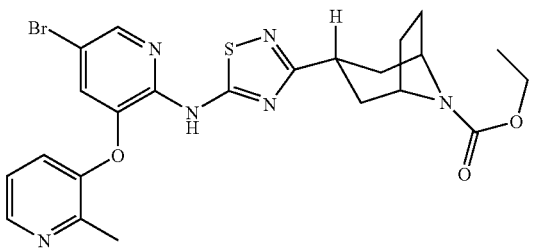 [SMILES: CCOC(=O)N1C2CCC1CC(c1nsc(Nc3ncc(Br)cc3Oc3cccnc3C)n1)C2]

Following the procedures in Example 4 steps A-D and using ethyl 3-formyl-8-azabicyclo[3.2.1]octane-8-carboxylate and 5-bromo-3-(2-methylpyridin-3-yloxy)pyridine-2-amine the title compound was synthesized. Mass spectrum (apci) m/z=545.1, 547.1 (M+H).

Example 171

Ethyl 3-(5-(3-(2-methylpyridin-3-yloxy)-5-(pyridin-2-ylthio)pyridin-2-ylamino)-1,2,4-thiadiazol-3-yl)-8-azabicyclo[3.2.1]octane-8-carboxylate

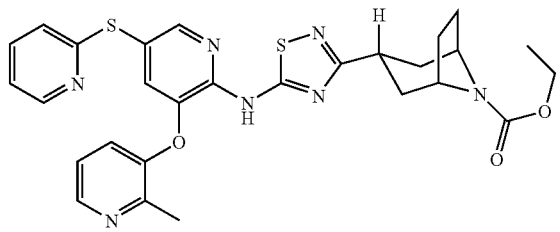 [SMILES: CCOC(=O)N1C2CCC1CC(c1nsc(Nc3ncc(Sc4ccccn4)cc3Oc3cccnc3C)n1)C2]

Ethyl 3-(5-(5-bromo-3-(2-methylpyridin-3-yloxy)pyridin-2-ylamino)-1,2,4-thiadiazol-3-yl)-8-azabicyclo[3.2.1]octane-8-carboxylate (127 mg, 0.233 mmol) was dissolved in THF (3 mL) and cooled to −78° C. Methyllithium (175 μL, 0.279 mmol) was added and the reaction was stirred for 3 minutes Butyllithium (112 μL, 0.279 mmol) was added and stirred for 3 minutes 1,2-di(pyridin-2-yl)disulfane (103 mg, 0.466 mmol) was added and the reaction was stirred for 30 min and quenched with saturated aqueous $NH_4Cl$. The reaction was partitioned between water and EtOAc, dried over sodium sulfate, filtered and concentrated. The residue was purified on silica gel (85% EtOAc in hexanes) to afford ethyl 3-(5-(3-(2-methylpyridin-3-yloxy)-5-(pyridin-2-ylthio)pyridin-2-ylamino)-1,2,4-thiadiazol-3-yl)-8-azabicyclo[3.2.1]octane-8-carboxylate (95.3 mg, 0.166 mmol, 71.1% yield) as a solid. Mass spectrum (apci) m/z=576.2 (M+H).

Example 172

1-(3-(5-(3-(2-methylpyridin-3-yloxy)-5-(trifluoromethyl)pyridin-2-ylamino)-1,2,4-thiadiazol-3-yl)-8-azabicyclo[3.2.1]octan-8-yl)ethanone hydrochloride

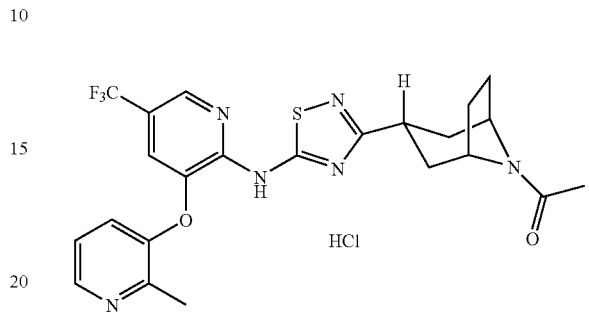

Step A: Following the procedure in Example 4 step D and using ethyl 3-(chloro(methylsulfonyloxyimino)methyl)-8-azabicyclo[3.2.1]octane-8-carboxylate (126 mg, 0.371 mmol) and 3-(2-methylpyridin-3-yloxy)-5-(trifluoromethyl)pyridin-2-amine (50 mg, 0.186 mmol) afforded ethyl 3-(5-(3-(2-methylpyridin-3-yloxy)-5-(trifluoromethyl)pyridin-2-ylamino)-1,2,4-thiadiazol-3-yl)-8-azabicyclo[3.2.1]octane-8-carboxylate (69.5 mg, 0.130 mmol, 70.0% yield).

Step B: Ethyl 3-(5-(3-(2-methylpyridin-3-yloxy)-5-(trifluoromethyl)pyridin-2-ylamino)-1,2,4-thiadiazol-3-yl)-8-azabicyclo[3.2.1]octane-8-carboxylate (69.5 mg, 0.130 mmol) was dissolved in iPrOH (5 mL) and potassium hydroxide (72.9 mg, 1.30 mmol) was added. The reaction was heated to reflux for 3 days. More KOH (72.9 mg, 1.30 mmol) was added and the reaction was heated for another 2 days. Water (~10 drops) was added and the reaction was heated for 1 week. The solution was partitioned between saturated aqueous $NH_4Cl$ and $CH_2Cl_2$. The aqueous layer was extracted 3 times with $CH_2Cl_2$, dried over sodium sulfate, filtered and concentrated to afford crude 3-(8-azabicyclo[3.2.1]octan-3-yl)-N-(3-(2-methylpyridin-3-yloxy)-5-(trifluoromethyl)pyridin-2-yl)-1,2,4-thiadiazol-5-amine (45 mg, 0.0973 mmol, 74.8% yield).

Step C: 3-(8-azabicyclo[3.2.1]octan-3-yl)-N-(3-(2-methylpyridin-3-yloxy)-5-(trifluoromethyl)pyridin-2-yl)-1,2,4-thiadiazol-5-amine (45 mg, 0.0973 mmol) was dissolved in $CH_2Cl_2$ (2 mL) and triethylamine (67.8 μL, 0.486 mmol) and acetic anhydride (13.8 μL, 0.146 mmol) were added. After 10 minutes the reaction was partitioned between saturated aqueous $NaHCO_3$ and $CH_2Cl_2$, dried over sodium sulfate, filtered and concentrated. The residue was purified on silica gel (10% methanol in EtOAc) to afford 1-(3-(5-(3-(2-methylpyridin-3-yloxy)-5-(trifluoromethyl)pyridin-2-ylamino)-1,2,4-thiadiazol-3-yl)-8-azabicyclo[3.2.1]octan-8-yl)ethanone hydrochloride (25 mg, 0.0462 mmol, 47.5% yield) as a solid after HCl salt formation. Mass spectrum (apci) m/z=505.2 (M+H—HCl).

Example 173

1-(3-(5-(3-(2-methylpyridin-3-yloxy)-5-(pyridin-2-ylthio)pyridin-2-ylamino)-1,2,4-thiadiazol-3-yl)-8-azabicyclo[3.2.1]octan-8-yl)ethanone hydrochloride

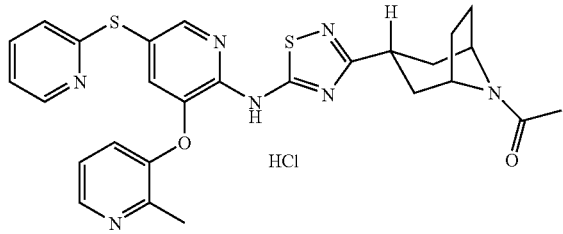 [SMILES: CC(=O)N1C2CCC1CC(c1nsc(Nc3ncc(Sc4ccccn4)cc3Oc3cccnc3C)n1)C2 ; Cl]

Step A: Following the procedure in Example 4, Step D and using tert-butyl 3-(chloro(methylsulfonyloxyimino)methyl)-8-azabicyclo[3.2.1]octane-8-carboxylate (496 mg, 1.35 mmol) and 3-(2-methylpyridin-3-yloxy)-5-(pyridin-2-ylthio)pyridin-2-amine (350 mg, 1.13 mmol) afforded tert-butyl 3-(5-(3-(2-methylpyridin-3-yloxy)-5-(pyridin-2-ylthio)pyridin-2-ylamino)-1,2,4-thiadiazol-3-yl)-8-azabicyclo[3.2.1]octane-8-carboxylate (550 mg, 0.911 mmol, 80.8% yield).

Step B: tert-Butyl 3-(5-(3-(2-methylpyridin-3-yloxy)-5-(pyridin-2-ylthio)pyridin-2-ylamino)-1,2,4-thiadiazol-3-yl)-8-azabicyclo[3.2.1]octane-8-carboxylate (550 mg, 0.911 mmol) was dissolved in $CH_2Cl_2$ (2 mL) and TFA (1 mL) was added and the reaction was stirred for 45 minutes. The reaction was partitioned between saturated aqueous $NaHCO_3$ and $CH_2Cl_2$, dried over sodium sulfate, filtered and concentrated to afford 3-(8-azabicyclo[3.2.1]octan-3-yl)-N-(3-(2-methylpyridin-3-yloxy)-5-(pyridin-2-ylthio)pyridin-2-yl)-1,2,4-thiadiazol-5-amine (438 mg, 0.870 mmol, 95.5% yield).

Step C: 3-(8-azabicyclo[3.2.1]octan-3-yl)-N-(3-(2-methylpyridin-3-yloxy)-5-(pyridin-2-ylthio)pyridin-2-yl)-1,2,4-thiadiazol-5-amine (100 mg, 0.199 mmol) was dissolved in $CH_2Cl_2$ (3 mL) and triethylamine (41.5 µL, 0.298 mmol) and acetic anhydride (22.5 µL, 0.238 mmol) were added and the reaction stirred for 5 minutes. The reaction was partitioned between saturated aqueous $NaHCO_3$ and $CH_2Cl_2$, dried over sodium sulfate, filtered, concentrated and purified on silica gel (10% methanol in EtOAc) to afford 1-(3-(5-(3-(2-methylpyridin-3-yloxy)-5-(pyridin-2-ylthio)pyridin-2-ylamino)-1,2,4-thiadiazol-3-yl)-8-azabicyclo[3.2.1]octan-8-yl)ethanone hydrochloride (95.2 mg, 0.164 mmol, 82.4% yield) as a solid after HCl salt formation. Mass spectrum (apci) m/z=546.0 (M+H—HCl).

Example 174

1-(3-(5-(5-(2-hydroxy-2-methylpropylthio)-3-(2-methylpyridin-3-yloxy)pyridin-2-ylamino)-1,2,4-thiadiazol-3-yl)-8-azabicyclo[3.2.1]octan-8-yl)ethanone

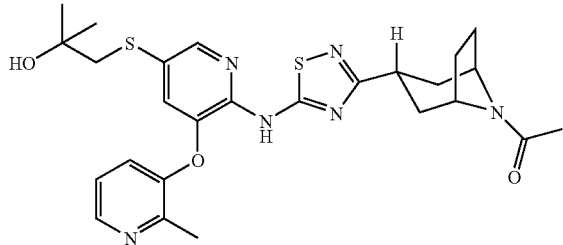 [SMILES: CC(=O)N1C2CCC1CC(c1nsc(Nc3ncc(SCC(C)(C)O)cc3Oc3cccnc3C)n1)C2]

Step A: Following the procedure in Example 4, step D and using tert-butyl 3-(chloro(methylsulfonyloxyimino)methyl)-8-azabicyclo[3.2.1]octane-8-carboxylate (491 mg, 1.34 mmol) and 5-bromo-3-(2-methylpyridin-3-yloxy)pyridin-2-amine (300 mg, 1.07 mmol) afforded tert-butyl 3-(5-(5-bromo-3-(2-methylpyridin-3-yloxy)pyridin-2-ylamino)-1,2,4-thiadiazol-3-yl)-8-azabicyclo[3.2.1]octane-8-carboxylate (526 mg, 0.917 mmol, 85.6% yield).

Step B: Following the procedure in Example 52, tert-butyl 3-(5-(5-bromo-3-(2-methylpyridin-3-yloxy)pyridin-2-ylamino)-1,2,4-thiadiazol-3-yl)-8-azabicyclo[3.2.1]octane-8-carboxylate (526 mg, 0.917 mmol) and methyl 2-mercaptoacetate (92.3 µL, 1.01 mmol) afforded tert-butyl 3-(5-(5-(2-methoxy-2-oxoethylthio)-3-(2-methylpyridin-3-yloxy)pyridin-2-ylamino)-1,2,4-thiadiazol-3-yl)-8-azabicyclo[3.2.1]octane-8-carboxylate (461 mg, 0.770 mmol, 83.9% yield).

Step C: tert-Butyl 3-(5-(5-(2-methoxy-2-oxoethylthio)-3-(2-methylpyridin-3-yloxy)pyridin-2-ylamino)-1,2,4-thiadiazol-3-yl)-8-azabicyclo[3.2.1]octane-8-carboxylate (461 mg, 0.770 mmol) was dissolved in $CH_2Cl_2$ (10 mL) and TFA (5 mL) was added. The reaction was stirred at ambient temperature for 15 minutes. The reaction was partitioned between $CH_2Cl_2$ and saturated aqueous $NaHCO_3$, dried over sodium sulfate, filtered and concentrated to afford methyl 2-(6-(3-(8-azabicyclo[3.2.1]octan-3-yl)-1,2,4-thiadiazol-5-ylamino)-5-(2-methylpyridin-3-yloxy)pyridin-3-ylthio)acetate (402 mg, 0.806 mmol, 105% yield) as a pale yellow foam.

Step D: Methyl 2-(6-(3-(8-azabicyclo[3.2.1]octan-3-yl)-1,2,4-thiadiazol-5-ylamino)-5-(2-methylpyridin-3-yloxy)pyridin-3-ylthio)acetate (384 mg, 0.770 mmol) was dissolved in $CH_2Cl_2$ (7 mL), and triethylamine (16 µL, 1.16 mmol) and acetic anhydride (87.4 µL, 0.924 mmol) were added. The reaction was stirred at ambient temperature for 5 minutes. The reaction was partitioned between $CH_2Cl_2$ and saturated aqueous $NaHCO_3$, dried over sodium sulfate, filtered and concentrated to afford methyl 2-(6-(3-(8-acetyl-8-azabicyclo[3.2.1]octan-3-yl)-1,2,4-thiadiazol-5-ylamino)-5-(2-methylpyridin-3-yloxy)pyridin-3-ylthio)acetate (397 mg, 0.734 mmol, 95.3% yield).

Step E: Methyl 2-(6-(3-(8-acetyl-8-azabicyclo[3.2.1]octan-3-yl)-1,2,4-thiadiazol-5-ylamino)-5-(2-methylpyridin-3-yloxy)pyridin-3-ylthio)acetate (188 mg, 0.348 mmol) was dissolved in THF (4 mL), cooled to 0° C. and 3M methylmagnesium chloride (580 µL, 1.74 mmol) was added. After 30 minutes the reaction was partitioned between saturated aqueous $NH_4Cl$ and $CH_2Cl_2$, dried over sodium sulfate, filtered and concentrated. The residue was purified on silica gel (10% methanol in EtOAc) afforded 1-(3-(5-(5-(2-hydroxy-2-methylpropylthio)-3-(2-methylpyridin-3-yloxy)pyridin-2-ylamino)-1,2,4-thiadiazol-3-yl)-8-azabicyclo[3.2.1]octan-8-yl)ethanone (142 mg, 0.263 mmol, 75.5% yield) as a solid. Mass spectrum (apci) m/z=541.2 (M+H).

Example 175

1-(3-(5-(5-(2-hydroxyethylthio)-3-(2-methylpyridin-3-yloxy)pyridin-2-ylamino)-1,2,4-thiadiazol-3-yl)-8-azabicyclo[3.2.1]octan-8-yl)ethanone

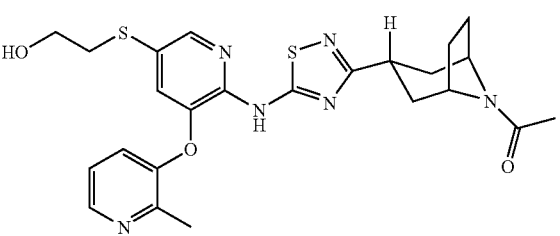 [SMILES: CC(=O)N1C2CCC1CC(c1nsc(Nc3ncc(SCCO)cc3Oc3cccnc3C)n1)C2]

Methyl 2-(6-(3-(8-acetyl-8-azabicyclo[3.2.1]octan-3-yl)-1,2,4-thiadiazol-5-ylamino)-5-(2-methylpyridin-3-yloxy)pyridin-3-ylthio)acetate (Prepared in Example 174, step d; 210 mg, 0.388 mmol) was dissolved in THF (4 mL) and LiBH$_4$ (194 µL, 0.194 mmol) was added and stirred at ambient temperature for 30 minutes The reaction was cooled to 0° C. and LiAlH$_4$ (194 µL, 0.194 mmol) was added and stirred for 20 minutes. The reaction was quenched with water and sodium sulfate, stirred for 10 minutes, filtered and concentrated. The residue was purified on silica gel (10% methanol in EtOAc) followed by reverse phase chromatography (5 to 95% ACN in water with 0.1% TFA) to afford 1-(3-(5-(5-(2-hydroxyethylthio)-3-(2-methylpyridin-3-yloxy)pyridin-2-ylamino)-1,2,4-thiadiazol-3-yl)-8-azabicyclo[3.2.1]octan-8-yl)ethanone (52.5 mg, 0.102 mmol, 26.4% yield) as a solid after converting the salt to the free base. Mass spectrum (apci) m/z=513.2 (M+H).

Example 176

2-hydroxy-1-(3-(5-(3-(2-methylpyridin-3-yloxy)-5-(pyridin-2-ylthio)pyridin-2-ylamino)-1,2,4-thiadiazol-3-yl)-8-azabicyclo[3.2.1]octan-8-yl)ethanone hydrochloride

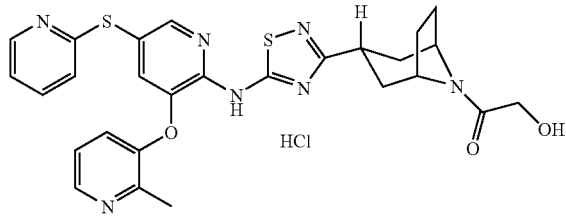 [SMILES: Cc1ncccc1Oc1cc(Sc2ccccn2)cnc1Nc1nc(C2CC3CCC(C2)N3C(=O)CO)ns1 ; Cl]

Step A: 3-(8-Azabicyclo[3.2.1]octan-3-yl)-N-(3-(2-methylpyridin-3-yloxy)-5-(pyridin-2-ylthio)pyridin-2-yl)-1,2,4-thiadiazol-5-amine (80 mg, 0.159 mmol; prepared in Example 174, step C) was dissolved in CH$_2$Cl$_2$, and triethylamine (88.6 µL, 0.635 mmol) and 2-chloro-2-oxoethyl acetate (25.6 µL, 0.238 mmol) were added. The reaction was stirred at ambient temperature for 5 minutes. The reaction was partitioned between CH$_2$Cl$_2$ and saturated aqueous NaHCO$_3$, dried over sodium sulfate, filtered and concentrated to afford 2-(3-(5-(3-(2-methylpyridin-3-yloxy)-5-(pyridin-2-ylthio)pyridin-2-ylamino)-1,2,4-thiadiazol-3-yl)-8-azabicyclo[3.2.1]octan-8-yl)-2-oxoethyl acetate (95.9 mg, 0.159 mmol, 100% yield) as a crude foam.

Step B: 2-(3-(5-(3-(2-Methylpyridin-3-yloxy)-5-(pyridin-2-ylthio)pyridin-2-ylamino)-1,2,4-thiadiazol-3-yl)-8-azabicyclo[3.2.1]octan-8-yl)-2-oxoethyl acetate (95 mg, 0.157 mmol) was dissolved in EtOH (3 mL) and K$_2$CO$_3$ (excess) was added and heated to 50° C. for 1.5 hr. The reaction was partitioned between CH$_2$Cl$_2$ and saturated aqueous NH$_4$Cl, dried over sodium sulfate, filtered and concentrated. The residue was purified on silica gel (15% methanol in EtOAc) to afford 2-hydroxy-1-(3-(5-(3-(2-methylpyridin-3-yloxy)-5-(pyridin-2-ylthio)pyridin-2-ylamino)-1,2,4-thiadiazol-3-yl)-8-azabicyclo[3.2.1]octan-8-yl)ethanone hydrochloride (78.2 mg, 0.131 mmol, 83.1% yield) as a solid after HCl salt formation. Mass spectrum (apci) m/z=562.2 (M+H—HCl).

Example 177

1-(3-(5-(5-(2-methoxyethylthio)-3-(2-methylpyridin-3-yloxy)pyridin-2-ylamino)-1,2,4-thiadiazol-3-yl)-8-azabicyclo[3.2.1]octan-8-yl)ethanone hydrochloride

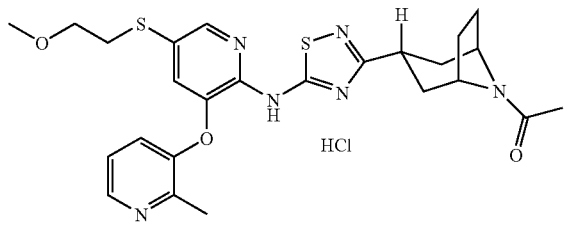 [SMILES: COCCSc1cnc(Nc2nc(C3CC4CCC(C3)N4C(C)=O)ns2)c(Oc2cccnc2C)c1 ; Cl]

Step A: Following the procedure in Example 52 and using, tert-butyl 3-(5-(5-bromo-3-(2-methylpyridin-3-yloxy)pyridin-2-ylamino)-1,2,4-thiadiazol-3-yl)-8-azabicyclo[3.2.1]octane-8-carboxylate (386 mg, 0.673 mmol) and methyl 3-mercaptopropanoate (89.9 µL, 0.808 mmol) afforded tert-butyl 3-(5-(5-(3-methoxy-3-oxopropylthio)-3-(2-methylpyridin-3-yloxy)pyridin-2-ylamino)-1,2,4-thiadiazol-3-yl)-8-azabicyclo[3.2.1]octane-8-carboxylate (347 mg, 0.566 mmol, 84.1% yield).

Step B: tert-Butyl 3-(5-(5-(3-methoxy-3-oxopropylthio)-3-(2-methylpyridin-3-yloxy)pyridin-2-ylamino)-1,2,4-thiadiazol-3-yl)-8-azabicyclo[3.2.1]octane-8-carboxylate (347 mg, 0.566 mmol) was dissolved in THF (5 mL) and potassium 2-methylpropan-2-olate (1699 µL, 1.70 mmol) was added. The reaction was stirred for 5 minutes. 1-Bromo-2-methoxyethane (53.2 µL, 0.566 mmol) was added and the reaction was stirred at ambient temperature for 1 hour. The reaction was partitioned between saturated aqueous NH$_4$Cl and CH$_2$Cl$_2$, dried over sodium sulfate, filtered and concentrated. The residue was purified on silica gel (100% EtOAc) to afford tert-butyl 3-(5-(5-(2-methoxyethylthio)-3-(2-methylpyridin-3-yloxy)pyridin-2-ylamino)-1,2,4-thiadiazol-3-yl)-8-azabicyclo[3.2.1]octane-8-carboxylate (256 mg, 0.438 mmol, 77.3% yield) as a white solid.

Step C: tert-Butyl 3-(5-(5-(2-methoxyethylthio)-3-(2-methylpyridin-3-yloxy)pyridin-2-ylamino)-1,2,4-thiadiazol-3-yl)-8-azabicyclo[3.2.1]octane-8-carboxylate (256 mg, 0.438 mmol) was dissolved in CH$_2$Cl$_2$ (4 mL) and TFA (2 mL) was added. The reaction was stirred at ambient temperature for 15 minutes. The reaction was concentrated and redissolved in CH$_2$Cl$_2$ and washed with saturated aqueous. NaHCO$_3$, dried over sodium sulfate, filtered and concentrated to afford 3-(8-azabicyclo[3.2.1]octan-3-yl)-N-(5-(2-methoxyethylthio)-3-(2-methylpyridin-3-yloxy)pyridin-2-yl)-1,2,4-thiadiazol-5-amine (193 mg, 0.398 mmol, 91.0% yield) as a crude yellow solid.

Step D: 3-(8-Azabicyclo[3.2.1]octan-3-yl)-N-(5-(2-methoxyethylthio)-3-(2-methylpyridin-3-yloxy)pyridin-2-yl)-1,2,4-thiadiazol-5-amine (96 mg, 0.198 mmol) was dissolved in THF (4 mL) and triethylamine (55.2 µL, 0.396 mmol) and acetic anhydride (22.5 µL, 0.238 mmol) were added. The reaction was stirred at ambient temperature for 5 minutes. The reaction was partitioned between saturated aqueous NaHCO$_3$ and CH$_2$Cl$_2$, dried over sodium sulfate, filtered and concentrated. The residue was purified on silica gel (20% methanol in EtOAc) to afford 1-(3-(5-(5-(2-methoxyethylthio)-3-(2-methylpyridin-3-yloxy)pyridin-2-ylamino)-1,2,4-thiadiazol-3-yl)-8-azabicyclo[3.2.1]octan-8-yl)ethanone hydrochloride (91.6 mg, 0.163 mmol, 82.1% yield) as a solid after HCl salt formation. Mass spectrum (apci) m/z=527.2 (M+H—HCl).

Example 178

1-(4-(5-(3-(2-(hydroxymethyl)pyridin-3-yloxy)-5-(pyridin-2-ylthio)pyridin-2-ylamino)-1,2,4-thiadiazol-3-yl)piperidin-1-yl)ethanone hydrochloride

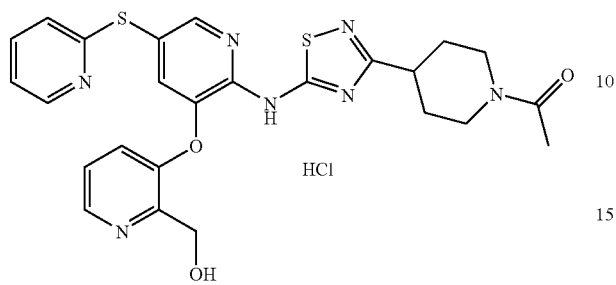

Steps A and B: Following the procedure in Example 45 steps A and B and using 2-((tert-butyldimethylsilyloxy)methyl)pyridin-3-ol and pyridine-2-thiol afforded 3-(2-((tert-butyldimethylsilyloxy)methyl)pyridin-3-yloxy)-5-(pyridin-2-ylthio)picolinonitrile.

Step C: Following the procedure in Example 51, step E, and using 3-(2-((tert-butyldimethylsilyloxy)methyl)pyridin-3-yloxy)-5-(pyridin-2-ylthio)picolinonitrile afforded 3-(2-(hydroxymethyl)pyridin-3-yloxy)-5-(pyridin-2-ylthio)picolinamide.

Step D: 3-(2-(Hydroxymethyl)pyridin-3-yloxy)-5-(pyridin-2-ylthio)picolinamide (575 mg, 1.62 mmol) was dissolved in $CH_2Cl_2$ (20 mL) and 1H-imidazole (166 mg, 2.43 mmol) and tert-butylchlorodimethylsilane (293 mg, 1.95 mmol) were added. The reaction was stirred at ambient temperature for 2 hours. The solids were filtered and the filtrate was concentrated. The residue was purified on silica gel (5% methanol in EtOAc) to afford 3-(2-((tert-butyldimethylsilyloxy)methyl)pyridin-3-yloxy)-5-(pyridin-2-ylthio)picolinamide (391 mg, 0.834 mmol, 51.4% yield).

Steps E and F: Following the procedure in Example 51, steps F and G, using 3-(2-((tert-butyldimethylsilyloxy)methyl)pyridin-3-yloxy)-5-(pyridin-2-ylthio)picolinamide and 1-acetyl-N-(methylsulfonyloxy)piperidine-4-carbimidoyl chloride afforded 1-(4-(5-(3-(2-(hydroxymethyl)pyridin-3-yloxy)-5-(pyridin-2-ylthio)pyridin-2-ylamino)-1,2,4-thiadiazol-3-yl)piperidin-1-yl)ethanone hydrochloride as solid after HCl salt formation. Mass spectrum (apci) m/z=536.2 (M+H—HCl).

Example 179

1-(4-(5-(3-([1,2,4]triazolo[1,5-a]pyridin-8-yloxy)-5-bromopyridin-2-ylamino)-1,2,4-thiadiazol-3-yl)piperidin-1-yl)ethanone hydrochloride

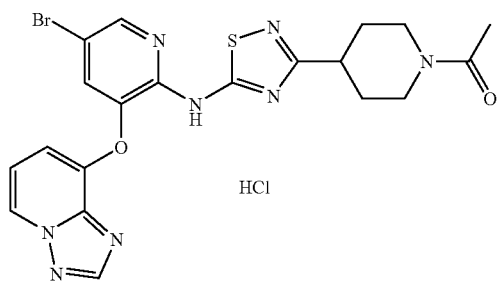 [SMILES: CC(=O)N1CCC(c2nsc(Nc3ncc(Br)cc3Oc3cccn4ncnc34)n2)CC1 ; Cl]

Following the procedures in Example 51, and using [1,2,4]triazolo[1,5-a]pyridin-8-ol in place of 2-methylpyridin-3-ol in step D afforded 1-(4-(5-(3-([1,2,4]triazolo[1,5-a]pyridin-8-yloxy)-5-bromopyridin-2-ylamino)-1,2,4-thiadiazol-3-yl)piperidin-1-yl)ethanone hydrochloride as a solid. Mass spectrum (apci) m/z=515.2, 517.2 (M+H—HCl).

Example 180

1-(4-(5-(3-([1,2,4]triazolo[1,5-a]pyridin-8-yloxy)-5-(2-hydroxy-2-methylpropylthio)pyridin-2-ylamino)-1,2,4-thiadiazol-3-yl)piperidin-1-yl)ethanone hydrochloride

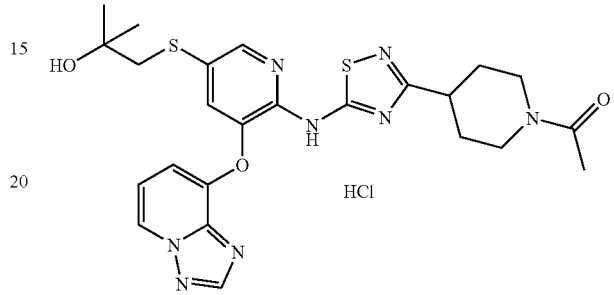

Step A: Following the procedure in Example 52 and using 1-(4-(5-(3-([1,2,4]triazolo[1,5-a]pyridin-8-yloxy)-5-bromopyridin-2-ylamino)-1,2,4-thiadiazol-3-yl)piperidin-1-yl)ethanone and methyl 2-mercapto acetate afforded methyl 2-(5-([1,2,4]triazolo[1,5-a]pyridin-8-yloxy)-6-(3-(1-acetylpiperidin-4-yl)-1,2,4-thiadiazol-5-ylamino)pyridin-3-ylthio)acetate.

Step B: Methyl 2-(5-([1,2,4]triazolo[1,5-a]pyridin-8-yloxy)-6-(3-(1-acetylpiperidin-4-yl)-1,2,4-thiadiazol-5-ylamino)pyridin-3-ylthio)acetate (195 mg, 0.361 mmol) was dissolved in THF and cooled to 0° C. Methylmagnesium chloride (48 µL, 1.44 mmol) was added and the reaction was stirred at 0° C. The reaction was allowed to warm to ambient temperature and quenched by addition of saturated aqueous $NH_4Cl$. The reaction was extracted with EtOAc, dried over sodium sulfate, filtered and concentrated. The residue was purified on silica gel (15% methanol in EtOAc) to afford 1-(4-(5-(3-([1,2,4]triazolo[1,5-a]pyridin-8-yloxy)-5-(2-hydroxy-2-methylpropylthio)pyridin-2-ylamino)-1,2,4-thiadiazol-3-yl)piperidin-1-yl)ethanone hydrochloride (110 mg, 0.191 mmol, 52.8% yield) as a solid after HCl salt formation. Mass spectrum (apci) m/z=541.2 (M+H—HCl).

Example 181

1-(4-(2-(5-bromo-3-(2-methylpyridin-3-yloxy)pyridin-2-ylamino)thiazol-4-yl)azepan-1-yl)ethanone dihydrochloride

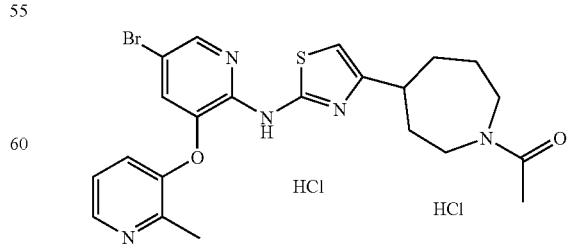

Following the procedure in Example 1, steps F and G, and using 1-(5-bromo-3-(2-methylpyridin-3-yloxy)pyridin-2-yl)

thiourea and tert-butyl 4-(2-chloroacetyl)azepane-1-carboxylate (WO 2003/062234) afforded 1-(4-(2-(5-bromo-3-(2-methylpyridin-3-yloxy)pyridin-2-ylamino)thiazol-4-yl)azepan-1-yl)ethanone dihydrochloride as a solid after HCl salt formation. Mass spectrum (apci) m/z=502.2, 504.2 (M+H-2HCl).

Following the procedure in Example 181, the following compounds were also synthesized:

mixture was warmed to ambient temperature and water was added. When the mixture became clear, it was extracted with $CH_2Cl_2$, the solvent evaporated to afford crude tert-butyl 4-formylazepane-1-carboxylate (2.78 g, 100%).

Steps C-G: Following the procedures in Example 4, steps A-E, and using tert-butyl 4-formylazepane-1-carboxylate and 3-(2-methylpyridin-3-yloxy)-5-(trifluoromethyl)pyridin-2-amine affords 1-(4-(5-(3-(2-methylpyridin-3-yloxy)-

| Ex. | Structure | Name | Mass Spectrum |
|---|---|---|---|
| 182 | 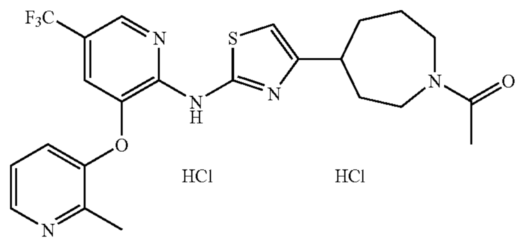 [SMILES: CC(=O)N1CCCC(c2csc(Nc3ncc(C(F)(F)F)cc3Oc3cccnc3C)n2)CC1 ; Cl ; Cl] | 1-(4-(2-(3-(2-methylpyridin-3-yloxy)-5-(trifluoromethyl)pyridin-2-ylamino)thiazol-4-yl)azepan-1-yl)ethanone dihydrochloride | Mass spectrum (apci) m/z = 492.5 (M + H – 2HCl) |
| 183 | 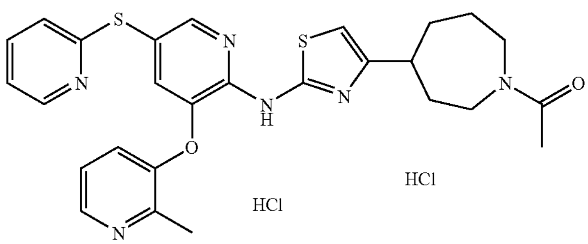 [SMILES: CC(=O)N1CCCC(c2csc(Nc3ncc(Sc4ccccn4)cc3Oc3cccnc3C)n2)CC1 ; Cl ; Cl] | 1-(4-(2-(3-(2-methylpyridin-3-yloxy)-5-(pyridin-2-ylthio)pyridin-2-ylamino)thiazol-4-yl)azepan-1-yl)ethanone dihydrochloride | Mass spectrum (apci) m/z = 533.4 (M + H – 2HCl) |

Example 184

1-(4-(5-(3-(2-methylpyridin-3-yloxy)-5-(trifluoromethyl)pyridin-2-ylamino)-1,2,4-thiadiazol-3-yl)azepan-1-yl)ethanone hydrochloride

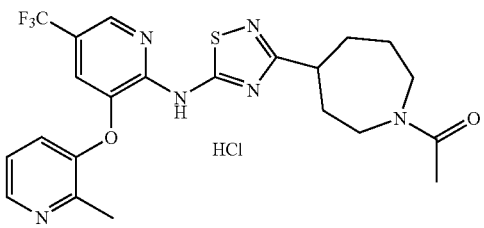 [SMILES: CC(=O)N1CCCC(c2nsc(Nc3ncc(C(F)(F)F)cc3Oc3cccnc3C)n2)CC1 ; Cl]

Step A: 1-tert-Butyl 4-ethyl azepane-1,4-dicarboxylate (3.3 g, 12 mmol, US Publication No. 2006/229289) was dissolved in THF (100 mL) and cooled in an ice bath. LiAlH₄ (12 mL, 12 mmol) was added slowly and stirred for 30 minutes. Water (~3 mL) was added slowly, followed by $Na_2SO_4$. The reaction was filtered and concentrated to afford crude tert-butyl 4-(hydroxymethyl)azepane-1-carboxylate (2.8 g, 100%).

Step B: At –60° C., a solution of DMSO (1.73 ml, 24.4 mmol) in $CH_2Cl_2$ (20 mL) was added dropwise to a 2M solution of oxalyl chloride (1.28 mL, 14.7 mmol) in $CH_2Cl_2$ (7 mL). The mixture was stirred for 20 minutes and then a solution of tert-butyl 4-(hydroxymethyl)azepane-1-carboxylate (2.8 g, 12.2 mmol) in $CH_2Cl_2$ (7 mL) was added dropwise. The mixture was stirred for 10 minutes and triethylamine (8.51 ml, 61.1 mmol) was slowly added. The reaction 5-(trifluoromethyl)pyridin-2-ylamino)-1,2,4-thiadiazol-3-yl)azepan-1-yl)ethanone hydrochloride as a solid after HCl salt formation. Mass spectrum (apci) m/z=492.9 (M+H—HCl).

Example 185

1-(4-(5-(3-(2-methylpyridin-3-yloxy)-5-(pyridin-2-ylthio)pyridin-2-ylamino)-1,2,4-thiadiazol-3-yl)azepan-1-yl)ethanone dihydrochloride

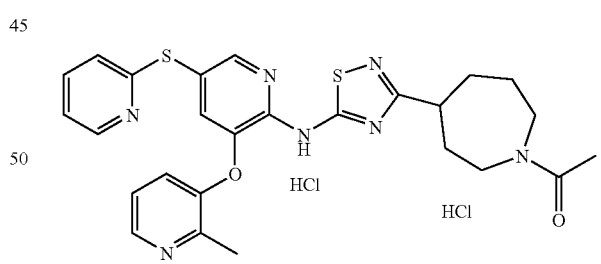

Step A: Following the procedure in Example 4, step D, and using tert-butyl 4-(chloro(methylsulfonyloxyimino)methyl)azepane-1-carboxylate and 5-bromo-3-(2-methylpyridin-3-yloxy)pyridin-2-amine afforded tert-butyl 4-(5-(5-bromo-3-(2-methylpyridin-3-yloxy)pyridin-2-ylamino)-1,2,4-thiadiazol-3-yl)azepane-1-carboxylate as a solid.

Step B: Following the procedure in Example 171, and using tert-butyl 4-(5-(5-bromo-3-(2-methylpyridin-3-yloxy)pyridin-2-ylamino)-1,2,4-thiadiazol-3-yl)azepane-1-carboxylate afforded tert-butyl 4-(5-(3-(2-methylpyridin-3-yloxy)-5-(pyridin-2-ylthio)pyridin-2-ylamino)-1,2,4-thiadiazol-3-yl)azepane-1-carboxylate.

Step C: tert-Butyl 4-(5-(3-(2-methylpyridin-3-yloxy)-5-(pyridin-2-ylthio)pyridin-2-ylamino)-1,2,4-thiadiazol-3-yl)azepane-1-carboxylate (70.4 mg, 0.119 mmol) was dissolved in CH$_2$Cl$_2$ (2 mL) and TFA (2 mL) was added. After 10 minutes the reaction was concentrated and placed on high vacuum pump to remove excess TFA. The residue was dissolved in CH$_2$Cl$_2$ (2 mL) and triethylamine (82.3 µL, 0.591 mmol) and acetic anhydride (16.7 µL, 0.177 mmol) were added. After 10 minutes the reaction was partitioned between saturated aqueous NaHCO$_3$ and EtOAc, dried over sodium sulfate, filtered and concentrated. The residue was purified over silica gel (10% methanol in EtOAc) to afford 1-(4-(5-(3-(2-methylpyridin-3-yloxy)-5-(pyridin-2-ylthio)pyridin-2-ylamino)-1,2,4-thiadiazol-3-yl)azepan-1-yl)ethanone dihydrochloride (68.2 mg, 0.112 mmol, 95.2% yield) as a solid after HCl salt formation. Mass spectrum (apci) m/z=534.2 (M+H-2HCl).

Example 186

1-(4-(5-(5-bromo-3-(1,5-dimethyl-1H-pyrazol-4-yloxy)pyridine-2-ylamino)-1,2,4-thiadiazol-3-yl)-piperidin-1-yl)ethanone hydrochloride

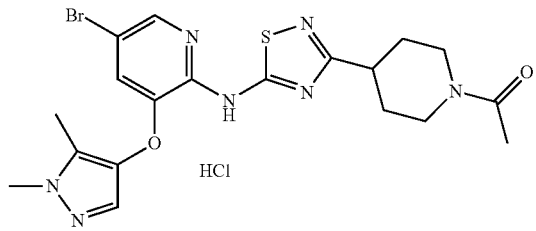 [SMILES: CC(=O)N1CCC(c2nsc(Nc3ncc(Br)cc3Oc3cnn(C)c3C)n2)CC1 ; Cl]

Step A: To a 0° C. solution of methylhydrazine (5.8 g, 126 mmol) in n-butyl acetate (50 mL) was added sodium sulfate (16 g) and a 37% solution of formaldehyde (9.3 mL, 126 mmol)). This mixture was stirred at 0° C. for 10 minutes and at ambient temperature for 1 hour. The solution was decanted from the solid. The solid was washed with n-butyl acetate and the organics were combined to give the hydrazone intermediate. 2-oxopropanal (40% in water) (34 g, 189 mmol) was stirred with sodium sulfate (40 g) in n-Bu acetate (100 mL) for 15 minutes The solution was filtered and MgSO$_4$ (40 g) was added. This mixture was stirred for 15 minutes and the solution was filtered. MgSO$_4$ (10 g) and acetic acid (10 mL) were added and the mixture was cooled to 0° C. The hydrazone intermediate was added and the mixture stirred at ambient temperature for 10 minutes and then at 110° C. for 1 hour. The reaction mixture was filtered while hot and the solid was washed with n-butyl acetate (50 mL). The solvent was removed from the filtrate under reduced pressure. The residue was dissolved in 1N NaOH (100 mL), washed with DCM (100 mL) and the aqueous layer was evaporated to dryness under reduced pressure. The product was purified by chromatography to afford 1,5-dimethyl-1H-pyrazol-4-ol (3.5 g, 31 mmol, 25%).

Steps B-E: Following the procedures in Example 51, steps D-G, and using 1,5-dimethyl-1H-pyrazol-4-ol afforded 1-(4-(5-(5-bromo-3-(1,5-dimethyl-1H-pyrazol-4-yloxy)pyridine-2-ylamino)-1,2,4-thiadiazol-3-yl)-piperidin-1-yl)ethanone. Mass spectrum (apci) m/z=492.2, 494.2 (M+H—HCl).

Example 187

1-(4-(5-(3-([1,2,4]triazolo[4,3-a]pyridin-5-yloxy)-5-bromopyridin-2-ylamino)-1,2,4-thiadiazol-3-yl)piperidin-1-yl)ethanone

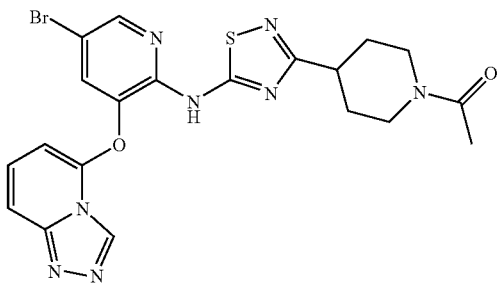 [SMILES: CC(=O)N1CCC(c2nsc(Nc3ncc(Br)cc3Oc3cccc4nncn34)n2)CC1]

Steps A-C: Preparation of 1-acetyl-N-(methylsulfonyloxy)piperidine-4-carbimidoyl chloride: Prepared according to Example 4, steps A-C, using 1-acetylpiperidine-4-carbaldehyde.

Step D: Preparation of 5-chloro-[1,2,4]triazolo[4,3-a]pyridine: Charge a 125 mL round-bottomed flask with 2-chloro-6-hydrazinylpyridine (3.0 g, 20.9 mmol), triethoxymethane (20 mL, 120.2 mmol). The mixture was heated at reflux for 4 hours and allowed to cool to ambient temperature overnight. The mixture was concentrated to dryness and 50 ml POCl$_3$ was added. The mixture was refluxed overnight. The reaction was quenched over ice and washed with CH$_2$Cl$_2$. The aqueous layer was adjusted to pH 6 with 1N NaOH and extracted with CH$_2$Cl$_2$ and the organics concentrated and purified on Si gel eluting with 100% EtOAc (500 ml) followed by 5% MeOH/CH$_2$Cl$_2$ to give 5-chloro-[1,2,4]triazolo[4,3-a]pyridine (1.73 g, 11.25 mmol, 53% yield) as a solid.

Step E: Preparation of 2-amino-5-bromopyridin-3-ol: Prepared according to WO2007/06741.

Step F: Preparation of 3-([1,2,4]triazolo[4,3-a]pyridin-5-yloxy)-5-bromopyridin-2-amine: Prepared according to Example 1, step A, using 2-amino-5-bromopyridin-3-ol and 5-chloro-[1,2,4]triazolo[4,3-a]pyridine.

Step G: Preparation of 1-(4-(5-(3-([1,2,4]triazolo[4,3-a]pyridin-5-yloxy)-5-bromopyridin-2-ylamino)-1,2,4-thiadiazol-3-yl)piperidin-1-yl)ethanone: Prepared according to Example 51, step G, using 1-acetyl-N-(methylsulfonyloxy)piperidine-4-carbimidoyl chloride and 3-([1,2,4]triazolo[4,3-a]pyridin-5-yloxy)-5-bromopyridin-2-amine. Mass spectrum (apci) m/z=515.2, 517.2 (M+H).

Example 188

1-(4-(2-(3-(2-methylpyridin-3-yloxy)-5-(pyridin-2-ylthio)pyridin-2-ylamino)thiazol-4-yl)piperidin-1-yl)ethanone

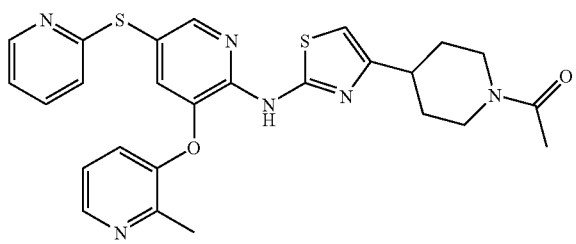 [SMILES: CC(=O)N1CCC(c2csc(Nc3ncc(Sc4ccccn4)cc3Oc3cccnc3C)n2)CC1]

Following the procedure in Example 1, steps D-F, and using 3-(2-methylpyridin-3-yloxy)-5-(pyridin-2-ylthio)pyridin-2-amine and 1-(1-acetylpiperidin-4-yl)-2-bromoethanone afforded 1-(4-(2-(3-(2-methylpyridin-3-yloxy)-5-(pyridin-2-ylthio)pyridin-2-ylamino)thiazol-4-yl)piperidin-1-yl)ethanone as a solid. Mass spectrum (apci) m/z=519.2 (M+H).

Example 189

1-(4-(5-(3-([1,2,4]triazolo[4,3-a]pyridin-8-yloxy)-5-bromopyridin-2-ylamino)-1,2,4-thiadiazol-3-yl)piperidin-1-yl)ethanone

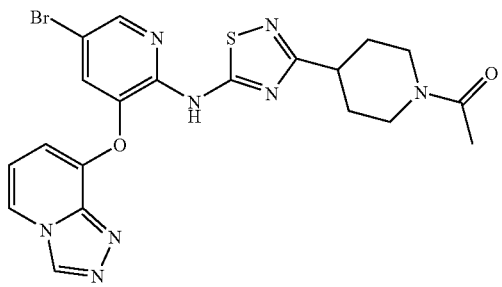 [SMILES: CC(=O)N1CCC(c2nsc(Nc3ncc(Br)cc3Oc3cccn4cnnc34)n2)CC1]

Steps A-C: Preparation of 1-acetyl-N-(methylsulfonyloxy)piperidine-4-carbimidoyl chloride: Prepared according to Example 4, steps A-C, using 1-acetylpiperidine-4-carbaldehyde.

Step D: To a solution of 2-chloropyridin-3-ol (16.3 g, 125 mmol) and K$_2$CO$_3$ (24.3 g, 176 mmol) in acetone (150 ml) was added dropwise (bromomethyl)benzene (17.9 ml, 151 mmol). The mixture was stirred overnight at 50° C. and then concentrated to dryness. Water (100 ml) was added and the mixture extracted with CH$_2$Cl$_2$. The organics were dried over Na$_2$SO$_4$, and concentrated to a crude residue that was dissolved in 20 ml CH$_2$Cl$_2$. Et$_2$O (250 ml) was added and then the solvent was decanted from the residue. The residue was then purified on a silica gel plug by eluting with 25% EtOAc/Hexanes to give 3-(benzyloxy)-2-chloropyridine (22.3 g, 80% yield) as a solid.

Step E: 3-(Benzyloxy)-2-chloropyridine (22.3 g, 101 mmol) was dissolved in EtOH (300 ml) and hydrazine monohydrate (10.2 ml, 203 mmol) added. The reaction was heated to reflux at 90° C. for 90 minutes. Hydrazine monohydrate (50 ml) was added and the reaction was heated at reflux overnight. K$_2$CO$_3$ (10 g) was added and the mixture was heated at refluxed for 4 hours. The mixture was concentrated to a residue and dissolved in n-BuOH (120 ml) and hydrazine monohydrate (40 ml) was added. The mixture was heated at reflux for 6 days. The reaction was cooled, diluted with water and extracted with EtOAc. The organics were concentrated to an oil that was dissolved in CH$_2$Cl$_2$ and decanted away from the solids. The organics were concentrated and dried on high vacuum overnight. The residue solidified on high vacuum. The crude product (24.47 g) was triturated in water and the solids filtered to give 3-(benzyloxy)-2-hydrazinylpyridine (14.9 g, 68% yield) as a solid.

Step F: A flask was charged with 3-(benzyloxy)-2-hydrazinylpyridine (10.0 g, 46.5 mmol) and triethoxymethane (77.3 ml, 465 mmol). The mixture was heated at reflux for 1 hour and then stirred overnight at ambient temperature. The solids were filtered and rinsed with EtOH and dried on high vacuum to afford 8-(benzyloxy)-[1,2,4]triazolo[4,3-a]pyridine (8.05 g, 35.7 mmol, 76% yield).

Step G: To a 8-(benzyloxy)-[1,2,4]triazolo[4,3-a]pyridine (8.05 g, 35.7 mmol) dissolved in EtOH 100 ml was added 300 mg 10% Pd/C (Degussa). The reaction vessel was inerted with nitrogen and then purged with hydrogen 3 times, and the reaction was stirred under double balloon pressure of hydrogen overnight. The catalyst was removed by filtration and the filtrate concentrated to give a residue of [1,2,4]triazolo[4,3-a]pyridin-8-ol (4.23 g, 87% yield) that was used in the next step without further purification.

Steps H-K: 1-(4-(5-(3-([1,2,4]Triazolo[4,3-a]pyridin-8-yloxy)-5-bromopyridin-2-ylamino)-1,2,4-thiadiazol-3-yl)piperidin-1-yl)ethanone was prepared according to Example 51, steps D-G, using 1-acetylpiperidine-4-carbaldehyde and [1,2,4]triazolo[4,3-a]pyridin-8-ol. Mass spectrum (apci) m/z=515.2, 517.2 (M+H).

Example 190

1-(4-(5-(5-bromo-3-(1-(2-hydroxyethyl)-1H-pyrazol-4-yloxy)pyridin-2-ylamino)-1,2,4-thiadiazol-3-yl)piperidin-1-yl)ethanone

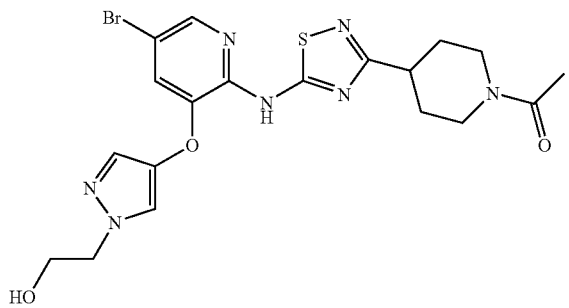 [SMILES: CC(=O)N1CCC(c2nsc(Nc3ncc(Br)cc3Oc3cnn(CCO)c3)n2)CC1]

Step A: POCl$_3$ (12.9 ml, 141.2 mmol) was added to DMF (10.9 ml, 141.2 mmol) at 0° C. The reaction was immediately warmed to ambient temperature and was stirred for 30 minutes. ((2,2-Diethoxyethoxy)methyl)benzene (10.6 g, 47.1 mmol) was added as a solution in 80 mL of chloroform. The solution was stirred at 75° C. for 3.5 hours. The solution was cooled, poured over ice water, and neutralized with Na$_2$CO$_3$. The residue was extracted with chloroform and the organic layer was dried with Na$_2$SO$_4$ and concentrated. The residue was re-dissolved in MeOH (450 mL). NaOMe (25% in MeOH, 58 ml, 253 mmol) was added followed by 2-hydrazinylethanol (10.6 g, 139 mmol). The reaction was stirred overnight at ambient temperature. The material was concentrated in vacuo followed by dilution with saturated NH$_4$Cl solution. The material was extracted with EtOAc, dried (MgSO$_4$), and concentrated. Flash chromatography of the crude material gave 2-(4-(benzyloxy)-1H-pyrazol-1-yl)ethanol (1.81 g, 13%).

Step B: 2-(4-(Benzyloxy)-1H-pyrazol-1-yl)ethanol (1.81 g, 8.3 mmol) was dissolved in THF (15 mL) under nitrogen. Pd/C (0.22 g, 0.21 mmol) was added and the solution was placed under vacuum and then charged with a hydrogen balloon. The mixture stirred at ambient temperature overnight under hydrogen. The solution was filtered through GF/F paper and concentrated to give the crude 1-(2-hydroxyethyl)-1H-pyrazol-4-ol (1.8 g, 100%).

Steps C-I: Following the procedure in Example 51, steps A-G, using 1-(2-hydroxyethyl)-1H-pyrazol-4-ol in step D, afforded 1-(4-(5-(5-bromo-3-(1-(2-hydroxyethyl)-1H-pyrazol-4-yloxy)pyridin-2-ylamino)-1,2,4-thiadiazol-3-yl)piperidin-1-yl)ethanone as a solid. Mass spectrum (apci) m/z=508.1, 510.1 (M+H).

Example 191

1-(4-(5-(3-(1-methyl-1H-pyrazol-4-yloxy)-5-(pyridin-2-ylthio)pyridin-2-ylamino)-1,2,4-thiadiazol-3-yl)piperidin-1-yl)ethanone

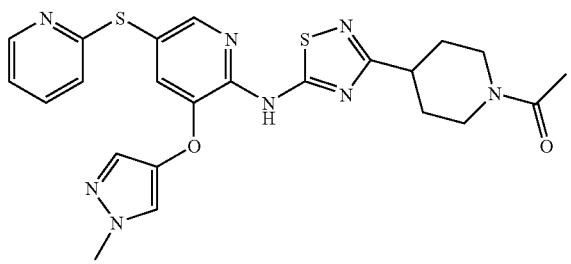 [SMILES: CC(=O)N1CCC(c2nsc(Nc3ncc(Sc4ccccn4)cc3Oc3cnn(C)c3)n2)CC1]

Steps A-B: Following the procedures in Example 190, steps A and B, and using methyl hydrazine, 1-methyl-1H-pyrazol-4-ol was synthesized.

Step C: Following the procedure in Example 51, step D, using 1-methyl-1H-pyrazol-4-ol, 5-bromo-3-(1-methyl-1H-pyrazol-4-yloxy)picolinonitrile was synthesized.

Step D: Following the procedure in Example 45, step B, 3-(1-methyl-1H-pyrazol-4-yloxy)-5-(pyridin-2-ylthio)picolinonitrile was synthesized.

Steps E-G: Following the procedures in Example 51, steps E-G and using 3-(1-methyl-1H-pyrazol-4-yloxy)-5-(pyridin-2-ylthio)picolinonitrile afforded 1-(4-(5-(3-(1-methyl-1H-pyrazol-4-yloxy)-5-(pyridin-2-ylthio)pyridin-2-ylamino)-1,2,4-thiadiazol-3-yl)piperidin-1-yl)ethanone as a solid. Mass spectrum (apci) m/z=509.2 (M+H).

Example 192

1-(4-(5-(5-bromo-3-(6,7-dihydro-5H-cyclopenta[b]pyridin-5-yloxy)pyridin-2-ylamino)-1,2,4-thiadiazol-3-yl)piperidin-1-yl)ethanone

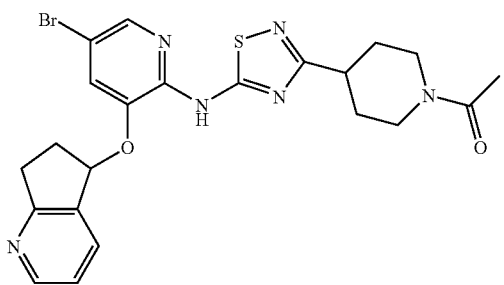 [SMILES: CC(=O)N1CCC(c2nsc(Nc3ncc(Br)cc3OC3CCc4ncccc43)n2)CC1]

Step A: 2-Aminopyridin-3-ol (5.0 g, 45.4 mmol) and 4,6-dichloro-3-methylpyridazine (7.4 g, 45.4 mmol, prepared according to WO 2003/041712) were dissolved in DMSO (100 mL). Cs$_2$CO$_3$ (16.3 g, 49.9 mmol) was added and the reaction stirred at ambient temperature for one hour. The reaction was diluted with water and the material was extracted with CH$_2$Cl$_2$, dried (Na$_2$SO$_4$), filtered and concentrated. Flash chromatography followed by trituration of the concentrated solid with EtOH gave 3-(6-chloro-3-methylpyridazin-4-yloxy)pyridin-2-amine (5.98 g, 25.3 mmol, 55%) as a solid.

Step B: 3-(6-Chloro-3-methylpyridazin-4-yloxy)pyridin-2-amine (3.0 g, 12.7 mmol) was charged with MeOH (150 mL). Pd/C (0.67 g, 0.63 mmol) was added followed by ammonium formate (2.23 g, 35.5 mmol). The mixture was heated at 65° C. overnight. The solution was cooled and filtered through GF/F paper. The filtrate was concentrated and the residue was dissolved in dichloromethane and saturated NaHCO$_3$. The organic layer was separated and the aqueous layer was extracted twice with dichloromethane. The combined organics were dried and concentrated to give 3-(3-methylpyridazin-4-yloxy)pyridin-2-amine (1.85 g, 72%) as a solid.

Step C: 3-(3-Methylpyridazin-4-yloxy)pyridin-2-amine (0.50 g, 2.5 mmol) was dissolved in DMF (7 mL). N-Bromosuccinimide (0.46 g, 2.6 mmol) was added and the solution stirred at ambient temperature for 5 minutes. The solution was diluted with water and filtered through celite (rinsing with chloroform). The solution was extracted with chloroform, dried (Na$_2$SO$_4$), filtered and concentrated. Flash chromatography gave 5-bromo-3-(3-methylpyridazin-4-yloxy)pyridin-2-amine (0.66 g, 95%).

Step D: 1-Acetyl-N-(methylsulfonyloxy)piperidine-4-carbimidoyl chloride (0.15 g, 0.53 mmol), pyridine (0.13 ml, 1.6 mmol), and sodium thiocyanate (0.043 g, 0.53 mmol) were dissolved in acetonitrile (5 mL). The solution was heated to 40° C. for 40 minutes. 5-Bromo-3-(3-methylpyridazin-4-yloxy)pyridin-2-amine (0.10 g, 0.35 mmol) was added and the reaction was heated at 60° C. overnight. The solution was cooled and charged with water. The solid was filtered and dried to give 1-(4-(5-(5-bromo-3-hydroxypyridin-2-ylamino)-1,2,4-thiadiazol-3-yl)piperidin-1-yl)ethanone (0.072 g, 51%).

Step E: 1-(4-(5-(5-Bromo-3-hydroxypyridin-2-ylamino)-1,2,4-thiadiazol-3-yl)piperidin-1-yl)ethanone (0.083 g, 0.21 mmol), 6,7-dihydro-5H-cyclopenta[b]pyridin-5-ol (0.028 g, 0.21 mmol) and triphenylphosphine (0.057 g, 0.22 mmol) were combined in THF (1 mL) under nitrogen. Diisopropyl azodicarboxylate (0.043 ml, 0.22 mmol) was added in one portion. The reaction stirred at ambient temperature overnight. The solution was diluted with water, extracted with CH$_2$Cl$_2$, dried (Na$_2$SO$_4$), filtered and concentrated. Flash chromatography gave 1-(4-(5-(5-bromo-3-(6,7-dihydro-5H-cyclopenta[b]pyridin-5-yloxy)pyridin-2-ylamino)-1,2,4-thiadiazol-3-yl)piperidin-1-yl)ethanone (0.022 g, 21%); Mass spectrum (apci) m/z=515.0, 517.0 (M+H).

Example 193

1-(4-(5-(3-(2-methylpyridin-3-yloxy)-5-(pyridin-2-ylthio)pyridin-2-ylamino)-1,2,4-thiadiazol-3-yl)piperidin-1-yl)ethanone hydrochloride

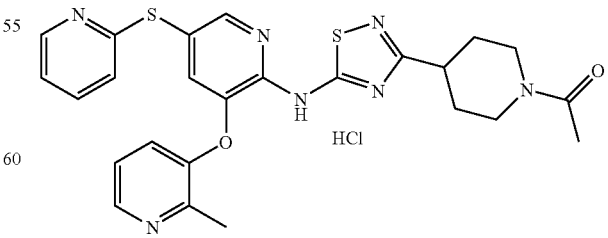

Step A: Following the procedure in Example 51, Step D, and using 2-methylpyridin-3-ol (25.0 g, 229 mmol), sodium hydride (6.37 g, 252 mmol) 5-bromo-3-nitropicolinonitrile (52.2 g, 229 mmol) provided 5-bromo-3-(2-methylpyridin-3-yloxy)picolinonitrile (56.9 g, 196 mmol, 85.6% yield) as a solid.

Step B: 5-Bromo-3-(2-methylpyridin-3-yloxy)picolinonitrile (56.9 g, 196 mmol) and pyridine-2(1H)-thione (22.9 g, 206 mmol) were dissolved in DMF (400 mL) and cooled to 0° C. NaH (4.94 g, 206 mmol) was added portionwise and warmed to ambient temperature. The reaction was stirred for 18 hours and then poured into 2.5 L of water and stirred for 30 minutes The solids were filtered to provide 3-(2-methylpyridin-3-yloxy)-5-(pyridin-2-ylthio)picolinonitrile (60.8 g, 190 mmol, 96.8% yield).

Step C: Following the procedure in Example 51, Step E, and using 3-(2-methylpyridin-3-yloxy)-5-(pyridin-2-ylthio)picolinonitrile (60.8 g, 190 mmol) and sulfuric acid (350 mL) provided 3-(2-methylpyridin-3-yloxy)-5-(pyridin-2-ylthio)picolinamide (61.4 g, 181 mmol, 95.6% yield).

Step D: To a 2M solution of sodium hydroxide (185 ml, 370 mmol) cooled to 0° C. was added bromine (5.6 ml, 111 mmol) and the reaction was stirred at 0° C. for 30 minutes. To this mixture was added 3-(2-methylpyridin-3-yloxy)-5-(pyridin-2-ylthio)picolinamide (25.0 g, 73.9 mmol) in dioxane (300 mL), and the reaction was stirred at ambient temperature for 1 hour followed by heating to 80° C. for 3 hours. The reaction was cooled and acidified to pH 1 using concentrated HCl. The reaction was neutralized using saturated sodium bicarbonate. The reaction mixture was allowed to stir for 45 minutes, then filtered to give 3-(2-methylpyridin-3-yloxy)-5-(pyridin-2-ylthio)pyridin-2-amine (17.36 g, 55.9 mmol, 75.7% yield).

Step E: Following the procedure in Example 51, Step G and using tert-butyl 4-(chloro(methylsulfonyloxyimino)methyl) piperidine-1-carboxylate (34.3 g, 101 mmol), sodium thiocyanate (9.40 g, 116 mmol), pyridine (28.1 ml, 348 mmol), and 3-(2-methylpyridin-3-yloxy)-5-(pyridin-2-ylthio)pyridin-2-amine (24.0 g, 77.3 mmol) provided tert-butyl 4-(5-(3-(2-methylpyridin-3-yloxy)-5-(pyridin-2-ylthio)pyridin-2-ylamino)-1,2,4-thiadiazol-3-yl)piperidine-1-carboxylate (38.1 g, 65.9 mmol, 85.3% yield).

Step F: tert-Butyl 4-(5-(3-(2-methylpyridin-3-yloxy)-5-(pyridin-2-ylthio)pyridin-2-ylamino)-1,2,4-thiadiazol-3-yl) piperidine-1-carboxylate (38.10 g, 65.95 mmol) was dissolved in CH$_2$Cl$_2$ (500 mL) and cooled to 0° C. TFA (25.40 ml, 329.7 mmol) was added over 5 minutes, keeping the internal temperature below 12° C. The reaction was then warmed to ambient temperature and stirred for 1 hour. More TFA (75 mL, 990 mmol) was added and the reaction was stirred for 2 hours. The reaction was concentrated and redissolved in 10% methanol in dichloromethane (450 mL) and saturated sodium bicarbonate was slowly added. The mixture was stirred for 1 hour and filtered. The solids were washed with water and dried in a vacuum oven to give N-(3-(2-methylpyridin-3-yloxy)-5-(pyridin-2-ylthio)pyridin-2-yl)-3-(piperidin-4-yl)-1,2,4-thiadiazol-5-amine (29.7 g, 62.19 mmol, 94.29% yield).

Step G: N-(3-(2-methylpyridin-3-yloxy)-5-(pyridin-2-ylthio)pyridin-2-yl)-3-(piperidin-4-yl)-1,2,4-thiadiazol-5-amine (29.52 g, 61.81 mmol) and triethylamine (21.54 ml, 154.5 mmol) were dissolved in THF (300 mL). Acetic anhydride (6.310 g, 61.81 mmol) was added and the reaction was stirred for 90 minutes. Saturated sodium bicarbonate (200 mL) and water (400 mL) were added and the reaction mixture was extracted with dichloromethane and 10% methanol in dichloromethane. The combined organic layers were dried over sodium sulfate, filtered and concentrated. The residue was dissolved in MeOH (~75 mL) and let stand. The resultant solids were filtered and washed with cold methanol to give a first crop (22.3 g). The filtrate was concentrated and solids were redissolved in methanol (30 mL) and allowed to stand. The precipitated solids were filtered and washed to afford a second crop (4.3 g). The 2 crops were combined to afford 1-(4-(5-(3-(2-methylpyridin-3-yloxy)-5-(pyridin-2-ylthio) pyridin-2-ylamino)-1,2,4-thiadiazol-3-yl)piperidin-1-yl) ethanone (26.7 g, 51.38 mmol, 83.13% yield).

Step H: 1-(4-(5-(3-(2-Methylpyridin-3-yloxy)-5-(pyridin-2-ylthio)pyridin-2-ylamino)-1,2,4-thiadiazol-3-yl)piperidin-1-yl)ethanone (33.76 g, 64.968 mmol) was dissolved in 10% methanol in dichloromethane (300 mL) and 2M hydrogen chloride in ether (32.48 ml, 64.96 mmol) was slowly added. The solution was concentrated and redissolved in refluxing ethanol (75 mL) and cooled. The solids were filtered and washed with cold (0° C.) ethanol to give 27.57 g. The recrystalization procedure was repeated two additional times to give crop 2 (4.22 g) and crop 3 (3.45 g). The solids were combined to afford 1-(4-(5-(3-(2-methylpyridin-3-yloxy)-5-(pyridin-2-ylthio)pyridin-2-ylamino)-1,2,4-thiadiazol-3-yl)piperidin-1-yl)ethanone hydrochloride (34.66 g, 62.32 mmol, 95.93% yield). Mass spectrum (apci) m/z=520.2 (M+H—HCl).

Example 194

1-(4-(5-(5-(3-methylpyridin-2-ylthio)-3-(2-methylpyridin-3-yloxy)pyridin-2-ylamino)-1,2,4-thiadiazol-3-yl)piperidin-1-yl)ethanone hydrochloride

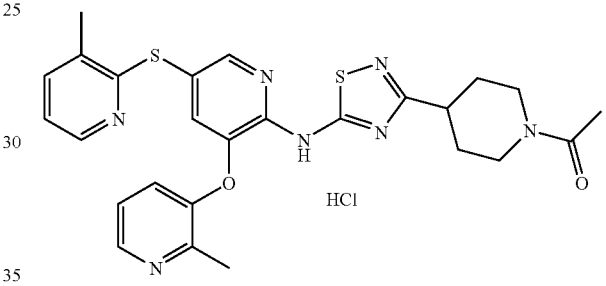

Following the procedures in Example 193 and using 3-methylpyridine-2-thiol affords 1-(4-(5-(5-(3-methylpyridin-2-ylthio)-3-(2-methylpyridin-3-yloxy)pyridin-2-ylamino)-1,2,4-thiadiazol-3-yl)piperidin-1-yl)ethanone hydrochloride as a pale yellow solid. Mass spectrum (apci) m/z=534.2 (M+H—HCl).

Example 195

N,N-dimethyl-4-(5-(3-(2-methylpyridin-3-yloxy)-5-(pyridin-2-ylthio)pyridin-2-ylamino)-1,2,4-thiadiazol-3-yl)piperidine-1-sulfonamide hydrochloride

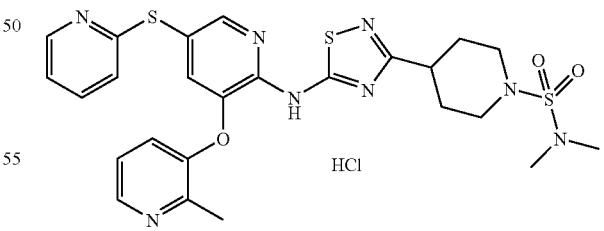

Following the procedure in Example 1, Step G, and using N-(3-(2-methylpyridin-3-yloxy)-5-(pyridin-2-ylthio)pyridin-2-yl)-3-(piperidin-4-yl)-1,2,4-thiadiazol-5-amine (150 mg, 0.314 mmol) and dimethylsulfamoyl chloride (45.1 mg, 0.314 mmol) provided N,N-dimethyl-4-(5-(3-(2-methylpyridin-3-yloxy)-5-(pyridin-2-ylthio)pyridin-2-ylamino)-1,2,4-thiadiazol-3-yl)piperidine-1-sulfonamide hydrochloride (118 mg, 0.190 mmol, 60.5% yield). Mass spectrum (apci) m/z=585.1 (M+H—HCl).

Example 196

2-methyl-1-(4-(5-(3-(2-methylpyridin-3-yloxy)-5-(pyridin-2-ylthio)pyridin-2-ylamino)-1,2,4-thiadiazol-3-yl)piperidin-1-yl)propan-1-one hydrochloride

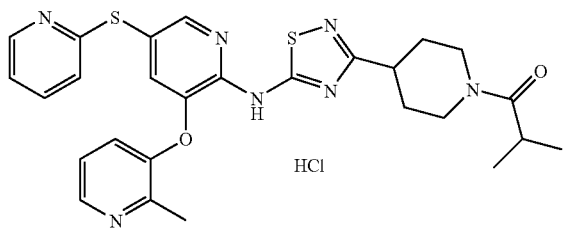 [SMILES: Cc1ncccc1Oc1cc(Sc2ccccn2)cnc1Nc1nc(C2CCN(C(=O)C(C)C)CC2)ns1 ; Cl]

Following the procedure in Example 1, Step G, and using N-(3-(2-methylpyridin-3-yloxy)-5-(pyridin-2-ylthio)pyridin-2-yl)-3-(piperidin-4-yl)-1,2,4-thiadiazol-5-amine (150 mg, 0.314 mmol) and isobutyryl chloride (33.5 mg, 0.314 mmol) provided 2-methyl-1-(4-(5-(3-(2-methylpyridin-3-yloxy)-5-(piperidi-2-ylthio)piperidi-2-ylamino)-1,2,4-thiadiazol-3-yl)piperidine-1-yl)propan-1-one hydrochloride (35 mg, 0.0599 mmol, 19.1% yield). Mass spectrum (apci) m/z=548.2 (M+H—HCl).

Example 197

N,N-dimethyl-4-(5-(3-(2-methylpyridin-3-yloxy)-5-(pyridin-2-ylthio)pyridin-2-ylamino)-1,2,4-thiadiazol-3-yl)piperidine-1-carboxamide hydrochloride

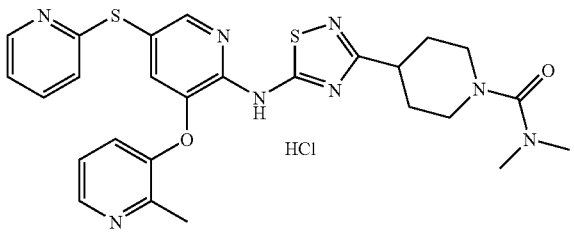 [SMILES: Cc1ncccc1Oc1cc(Sc2ccccn2)cnc1Nc1nc(C2CCN(C(=O)N(C)C)CC2)ns1 ; Cl]

Following the procedure in Example 1, Step G, and using N-(3-(2-methylpyridin-3-yloxy)-5-(pyridin-2-ylthio)pyridin-2-yl)-3-(piperidin-4-yl)-1,2,4-thiadiazol-5-amine (150 mg, 0.3141 mmol) and dimethylcarbamic chloride (33.77 mg, 0.3141 mmol) provided N,N-dimethyl-4-(5-(3-(2-methylpyridin-3-yloxy)-5-(pyridin-2-ylthio)pyridin-2-ylamino)-1,2,4-thiadiazol-3-yl)piperidine-1-carboxamide hydrochloride (145.2 mg, 0.2481 mmol, 79.01% yield). Mass spectrum (apci) m/z=549.1 (M+H—HCl).

Example 198

4-(5-(3-(2-methylpyridin-3-yloxy)-5-(pyridin-2-ylthio)pyridin-2-ylamino)-1,2,4-thiadiazol-3-yl)piperidine-1-sulfonamide hydrochloride

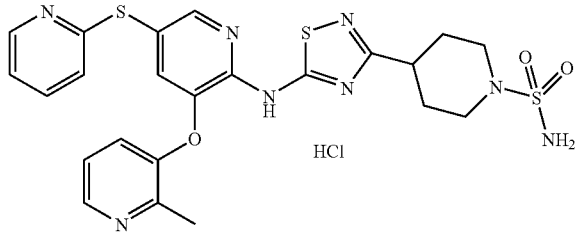 [SMILES: Cc1ncccc1Oc1cc(Sc2ccccn2)cnc1Nc1nc(C2CCN(S(N)(=O)=O)CC2)ns1 ; Cl]

Following the procedure in Example 58, Steps B and C, and using N-(3-(2-methylpyridin-3-yloxy)-5-(pyridin-2-ylthio)pyridin-2-yl)-3-(piperidin-4-yl)-1,2,4-thiadiazol-5-amine (150 mg, 0.314 mmol) and N-(tert-butoxycarbonyl)-N-[4-(dimethylazaniumylidene)-1,4-dihydropyridin-1-ylsulfonyl]azanide (94.6 mg, 0.314 mmol) provided. 4-(5-(3-(2-methylpyridin-3-yloxy)-5-(pyridin-2-ylthio)pyridin-2-ylamino)-1,2,4-thiadiazol-3-yl)piperidine-1-sulfonamide hydrochloride (98 mg, 0.176 mmol, 56.1% yield). Mass spectrum (apci) m/z=557.1 (M+H—HCl).

Example 199

2-hydroxy-1-(4-(5-(3-(2-methylpyridin-3-yloxy)-5-(pyridin-2-ylthio)pyridin-2-ylamino)-1,2,4-thiadiazol-3-yl)piperidin-1-yl)ethanone trifluoroacetate

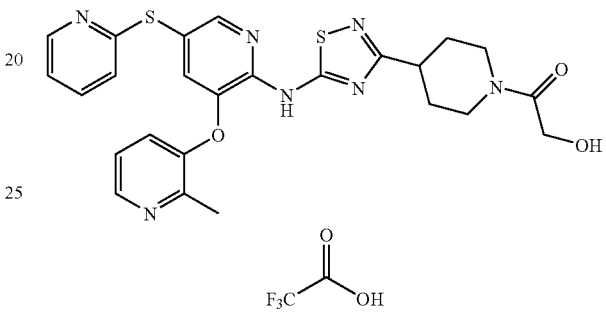

Step A: Following the procedure in Example 1, Step G, and using N-(3-(2-methylpyridin-3-yloxy)-5-(pyridin-2-ylthio)pyridin-2-yl)-3-(piperidin-4-yl)-1,2,4-thiadiazol-5-amine (Example 193, step F; 150 mg, 0.314 mmol) and 2-chloro-2-oxoethyl acetate (42.9 mg, 0.314 mmol) provided 2-(4-(5-(3-(2-methylpyridin-3-yloxy)-5-(pyridin-2-ylthio)pyridin-2-ylamino)-1,2,4-thiadiazol-3-yl)piperidin-1-yl)-2-oxoethyl acetate (175 mg, 0.303 mmol, 96.5% yield).

Step B: 2-(4-(5-(3-(2-Methylpyridin-3-yloxy)-5-(pyridin-2-ylthio)pyridin-2-ylamino)-1,2,4-thiadiazol-3-yl)piperidin-1-yl)-2-oxoethyl acetate (175 mg, 0.303 mmol) was dissolved in ethanol (25 mL) and potassium carbonate (419 mg, 3.03 mmol) was added and stirred for 18 hours. The reaction was filtered, concentrated and purified by reverse phase to give 2-hydroxy-1-(4-(5-(3-(2-methylpyridin-3-yloxy)-5-(pyridin-2-ylthio)pyridin-2-ylamino)-1,2,4-thiadiazol-3-yl)piperidin-1-yl)ethanone 2,2,2-trifluoroacetate (85 mg, 0.131 mmol, 43.2% yield). Mass spectrum (apci) m/z=536.2 (M+H-TFA).

Example 200

1-(4-(5-(5-(2-methoxyethylthio)-3-(2-methylpyridin-3-yloxy)pyridin-2-ylamino)-1,2,4-thiadiazol-3-yl)piperidin-1-yl)ethanone hydrochloride

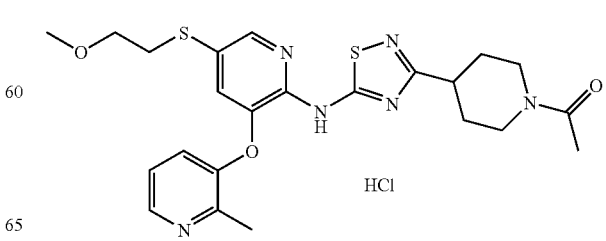

Step A: Following the procedure in Example 4, Step D, and using tert-butyl 4-(chloro(methylsulfonyloxyimino)methyl)piperidine-1-carboxylate (10.2 g, 30.0 mmol), and 5-bromo-3-(2-methylpyridin-3-yloxy)pyridin-2-amine (6.0 g, 21.4 mmol) provided tert-butyl 4-(5-(5-bromo-3-(2-methylpyridin-3-yloxy)pyridin-2-ylamino)-1,2,4-thiadiazol-3-yl)piperidine-1-carboxylate (9.95 g, 18.2 mmol, 84.8% yield).

Steps B and C: Following the procedure in Example 5, Steps A and B, and using tert-butyl 4-(5-(5-bromo-3-(2-methylpyridin-3-yloxy)pyridin-2-ylamino)-1,2,4-thiadiazol-3-yl)piperidine-1-carboxylate and 1-bromo-2-methoxyethane (142 mg, 1.02 mmol) afforded tent-butyl 4-(5-(5-(2-methoxyethylthio)-3-(2-methylpyridin-3-yloxy)pyridin-2-ylamino)-1,2,4-thiadiazol-3-yl)piperidine-1-carboxylate.

Step D: A flask was charged with tert-butyl 4-(5-(5-(2-methoxyethylthio)-3-(2-methylpyridin-3-yloxy)pyridin-2-ylamino)-1,2,4-thiadiazol-3-yl)piperidine-1-carboxylate (376 mg, 0.673 mmol) in TFA (5 mL), and the reaction was stirred for 15 minutes. The reaction mixture was concentrated and redissolved in 10% methanol in dichloromethane. Saturated sodium bicarbonate was added. The mixture was filtered, and the organic layer was separated, dried, filtered to provide N-(5-(2-methoxyethylthio)-3-(2-methylpyridin-3-yloxy)pyridin-2-yl)-3-(piperidin-4-yl)-1,2,4-thiadiazol-5-amine (298 mg, 0.650 mmol, 96.6% yield).

Step E: Following the procedure in Example 1, Step G, and using N-(5-(2-methoxyethylthio)-3-(2-methylpyridin-3-yloxy)pyridin-2-yl)-3-(piperidin-4-yl)-1,2,4-thiadiazol-5-amine (70 mg, 0.15 mmol) and acetic anhydride (16 mg, 0.15 mmol) provided 1-(4-(5-(5-(2-methoxyethylthio)-3-(2-methylpyridin-3-yloxy)pyridin-2-ylamino)-1,2,4-thiadiazol-3-yl)piperidin-1-yl)ethanone hydrochloride (51 mg, 0.095 mmol, 62% yield). Mass spectrum (apci) m/z=501.2 (M+H—HCl).

Example 201

4-(5-(5-(2-methoxyethylthio)-3-(2-methylpyridin-3-yloxy)pyridin-2-ylamino)-1,2,4-thiadiazol-3-yl)piperidine-1-sulfonamide hydrochloride

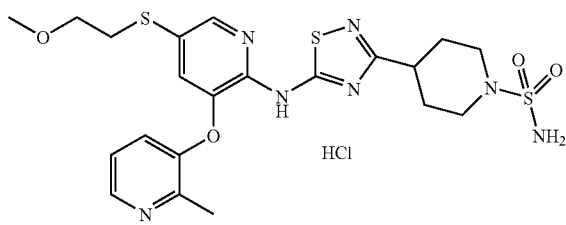 [SMILES: COCCSc1cnc(Nc2nc(C3CCN(S(N)(=O)=O)CC3)ns2)c(Oc2cccnc2C)c1 ; Cl]

Following the procedure in Example 58, Step B, and using N-(5-(2-methoxyethylthio)-3-(2-methylpyridin-3-yloxy)pyridin-2-yl)-3-(piperidin-4-yl)-1,2,4-thiadiazol-5-amine (100 mg, 0.218 mmol) afforded 4-(5-(5-(2-methoxyethylthio)-3-(2-methylpyridin-3-yloxy)pyridin-2-ylamino)-1,2,4-thiadiazol-3-yl)piperidine-1-sulfonamide hydrochloride (54 mg, 0.100 mmol, 46.1% yield). Mass spectrum (apci) m/z=538.1 (M+H—HCl).

Example 202

1-(3-(5-(3-(2-Ethylpyridin-3-yloxy)-5-(2-methoxyethylthio)pyridin-2-ylamino)-1,2,4-thiadiazol-3-yl)-8-azabicyclo[3.2.1]octan-8-yl)ethanone hydrochloride

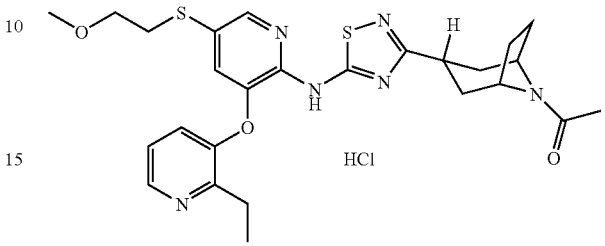

Steps A-D: Following the procedures in Example 51, steps D-G, and using 2-ethylpyridin-3-ol in step A and using tert-butyl 3-(chloro(methylsulfonyloxyimino)methyl)-8-azabicyclo[3.2.1]octane-8-carboxylate in step D afforded tert-butyl 3-(5-(5-bromo-3-(2-ethylpyridin-3-yloxy)pyridin-2-ylamino)-1,2,4-thiadiazol-3-yl)-8-azabicyclo[3.2.1]octane-8-carboxylate.

Step E: Following the procedure in Example 52, tert-butyl 3-(5-(5-bromo-3-(2-ethylpyridin-3-yloxy)pyridin-2-ylamino)-1,2,4-thiadiazol-3-yl)-8-azabicyclo[3.2.1]octane-8-carboxylate (120 mg, 0.2042 mmol) and methyl 3-mercaptopropanoate (24.34 µL, 0.2247 mmol) afforded tert-butyl 3-(5-(3-(2-ethylpyridin-3-yloxy)-5-(3-methoxy-3-oxopropylthio)pyridin-2-ylamino)-1,2,4-thiadiazol-3-yl)-8-azabicyclo[3.2.1]octane-8-carboxylate (115 mg, 0.183 mmol, 89.8% yield).

Step F: tert-Butyl 3-(5-(3-(2-ethylpyridin-3-yloxy)-5-(3-methoxy-3-oxopropylthio)pyridin-2-ylamino)-1,2,4-thiadiazol-3-yl)-8-azabicyclo[3.2.1]octane-8-carboxylate (115 mg, 0.183 mmol) was dissolved in THF (4 mL) and nitrogen was bubbled through the solution for 3 minutes. Potassium 2-methylpropan-2-olate (51.5 mg, 0.459 mmol) was added and the reaction was stirred at ambient temperature for 30 seconds. 1-Bromo-2-methoxyethane (19.0 µL, 0.202 mmol) was added and the reaction was stirred at ambient temperature for 30 minutes. The reaction was partitioned between EtOAc and aqueous NH$_4$Cl. The organic layer was dried over sodium sulfate, filtered, concentrated and purified on silica gel (80% EtOAc in hexanes) to afford tert-butyl 3-(5-(3-(2-ethylpyridin-3-yloxy)-5-(2-methoxyethylthio)pyridin-2-ylamino)-1,2,4-thiadiazol-3-yl)-8-azabicyclo[3.2.1]octane-8-carboxylate (101 mg, 0.169 mmol, 91.9% yield).

Steps G and H: tert-Butyl 3-(5-(3-(2-ethylpyridin-3-yloxy)-5-(2-methoxyethylthio)pyridin-2-ylamino)-1,2,4-thiadiazol-3-yl)-8-azabicyclo[3.2.1]octane-8-carboxylate (101 mg, 0.169 mmol) was treated according to the procedures in Example 174, steps C and D, to afford 1-(3-(5-(3-(2-ethylpyridin-3-yloxy)-5-(2-methoxyethylthio)pyridin-2-ylamino)-1,2,4-thiadiazol-3-yl)-8-azabicyclo[3.2.1]octan-8-yl)ethanone hydrochloride (79.8 mg, 0.138 mmol, 82.1% yield) as a solid after HCl salt formation. Mass spectrum (apci) m/z=541.2 (M+H—HCl).

Example A

In Vitro Glucokinase Assays

The in vitro efficacy of glucokinase activators of the present invention was assessed in two separate assays: an EC$_{50}$ assay to evaluate the potency of each compound at a fixed, physiologically relevant concentration of glucose, and a glucose S$_{0.5}$ assay at a fixed, near saturating (if possible) concentration of compound to evaluate its effect on the Vm and S$_{0.5}$ for glucose. For each of these assays, glucokinase activity was estimated by monitoring the increase in absorbance at 340 nm in a coupled assay system containing NAD+ and glucose 6-phosphate dehydrogenase. Assays were conducted at 30° C. using a thermostatically controlled absorbance plate reader (Spectramax 340PC, Molecular Devices Corp.) and clear, 96-well, flat bottom, polystyrene plates (Costar 3695, Corning). Each 50-μL assay mixture contained 10 mM K+MOPS, pH 7.2, 2 mM MgCl$_2$, 50 mM KCl, 0.01% Triton X-100, 2% DMSO, 1 mM DTT, 1 mM ATP, 1 mM NAD+, 5 U/mL glucose 6-phosphate dehydrogenase, approximately 5 nM human glucokinase and (depending on the assay) varying concentrations of glucose and test compound. The absorbance at 340 nm was monitored kinetically over a period of 5 minutes (10 s/cycle), and rates were estimated from the slopes of linear fits to the raw data.

Glucokinase EC$_{50}$ Assay:

For this assay, the glucose concentration was fixed at 5 mM, while the control or test compound was varied over a 10-point, 3-fold dilution series and typically ranged from a high dose of 50 μM to a low dose of approximately 2.5 nM. A standard, four-parameter logistic model (Equation 1) was fit to the raw data (rate versus concentration of compound):

$$y = A + \frac{B - A}{1 + \left[\frac{C}{x}\right]^D} \quad (1)$$

where x is the concentration of compound, y is the estimated rate, A and B are the lower and upper asymptotes, respectively, C is the EC$_{50}$ and D is the Hill slope. The EC$_{50}$ is defined as the midpoint or inflection point between the upper and lower asymptotes.

The compounds exemplified herein have been found to have an EC$_{50}$ in the range of 6 and 50,000 nM in the above described assay. Certain compounds of the invention have been found to have an EC$_{50}$ in the range of 2 and 5000 nM.

Glucose S$_{0.5}$ Assay:

For this assay, the concentration of control or test compound was fixed at or near a saturating concentration, if possible, typically 50 μM, while the glucose concentration was varied over a 10-point, 2-fold dilution series ranging from 80 to approximately 0.16 mM. The same four-parameter logistic model used for the EC$_{50}$ assay (Equation 1) was employed to estimate the relevant kinetic parameters. In this assay, the definitions for the variables and parameters are similar except that x represents the concentration of glucose, B is the rate at saturating glucose (V$_m$), C is the S$_{0.5}$ for glucose (the concentration of glucose at V$_m$/2) and D is the Hill Coefficient.

Certain compounds exemplified herein have been found to have an S$_{0.5}$ of between 0.3 and 5 mM in the above described assay.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of general Formula I

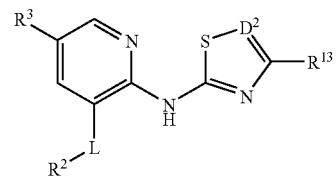

or a salt thereof, wherein:

R$^{13}$ is

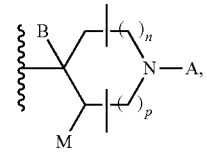

n and p are 1

B is H;

M is H;

A is C(=O)R$^a$, C(=O)OR$^b$, C(=O)NR$^c$R$^d$, SO$_3$H, SO$_2$NR$^e$R$^f$, SO$_2$(1-6C alkyl), (1-6C)fluoroalkyl, or (1-6C alkyl)OH;

R$^a$ is H, CF$_3$, (3-6C cycloalkyl), (1-6C alkyl), -(1-6C alkyl) OH, -(1-6C alkyl)-O-(1-6C alkyl), -(1-6C alkyl)NH$_2$, -(1-6C alkyl)NH(1-6C alkyl), or -(1-6C alkyl)N(1-6C alkyl)$_2$;

R$^b$ is (1-6C alkyl);

R$^c$ is H or (1-6C alkyl);

R$^d$ is H, (1-6C alkyl), or (1-6C alkyl)OH;

R$^e$ is H or (1-6C alkyl);

R$^f$ is H, (1-6C alkyl) or (1-6C alkyl)-N-(1-6C alkyl)$_2$;

L is O or S;

D$^2$ is N or CH;

R$^2$ is Ar$^1$, hetAr$^1$, hetAr$^c$, hetAr$^3$, N-alkyl-pyridinone-5-yl, or cyclopentyl optionally substituted with OH;

Ar$^1$ is aryl optionally substituted with one or more groups independently selected from C$_1$-C$_6$ alkyl, F, Br, Cl, CF$_3$, CN, SO$_2$Me, C(=O)NH(1-3C alkyl)N(alkyl)$_2$, C(=O) NH(1-3C alkyl)hetCyc$^1$, OR$^8$ and C(=O)OR$^8$;

hetAr$^1$ is a 5-6 membered heteroaryl group having 1-3 ring nitrogen atoms and optionally substituted with one or more groups independently selected from (1-6C alkyl), (1-6C alkyl)OH, Cl, and CF$_3$;

hetAr$^c$ is a partially unsaturated 5,5, 5, 6 or 6,6 bicyclic ring system having 1-2 ring nitrogen atoms and optionally having a ring oxygen atom;

hetAr$^3$ is a 9-10 membered bicyclic heteroaryl ring having 1-3 ring nitrogen atoms;

R$^3$ is SR$^6$; and

R$^6$ is pyridyl.

2. A compound of claim 1 or a salt thereof, wherein:

Ar$^1$ is phenyl or naphthyl optionally substituted with one or more groups independently selected from C$_1$-C$_6$ alkyl, OH, F, Br, CF$_3$, CN, SO$_2$Me, C(=O)NH(1-3C alkyl)N(alkyl)$_2$, and C(=O)NH(1-3C alkyl)hetCyc$^1$.

3. A compound of claim 1 or a salt thereof, wherein:
A is C(=O)(C$_1$-C$_6$ alkyl), C(=O)NH$_2$, (CO)NH(C$_1$-C$_6$ alkyl), C(=O)N(C$_1$-C$_6$ alkyl)$_2$, C(=O)CH(C$_1$-C$_6$ alkyl)N(C$_1$-C$_6$ alkyl)$_2$, SO$_2$(C$_1$-C$_6$ alkyl), SO$_2$NH$_2$, SO$_2$NH(C$_1$-C$_6$ alkyl), S(C$_1$-C$_6$ alkyl)$_2$ or C(O)CH(CH$_3$)OH;
L is O;
D$^2$ is N or CH;
R$^2$ is aryl optionally substituted with one or more groups independently selected from C$_1$-C$_6$ alkyl, F, Br, and CF$_3$;
hetAr$^a$ is a 5-6 membered heteroaryl ring having 1-4 nitrogen atoms; and
hetAr$^b$ is a 9-10 membered bicyclic heteroaromatic ring having 2-6 atoms independently selected from N, S and O (provided the ring does not contain an O—O bond).

4. A compound according to claim 1 or a salt thereof, wherein A is selected from C(=O)H, C(=O)CF$_3$, C(=O)CH$_3$, C(=O)CH(CH$_3$)$_2$, C(=O)-cyclopropyl, C(=O)CH$_2$OH, C(=O)CH(CH$_3$)OH, C(=O)CH$_2$OCH$_3$, C(=O)CH$_2$NH$_2$, C(=O)CH$_2$NMe$_2$, CO$_2$C(CH$_3$)$_3$, CO$_2$CH(CH$_3$)$_2$, C(=O)CH$_2$CH$_3$, C(=O)NH$_2$, C(=O)NMe$_2$, C(=O)NHCH$_2$CH$_2$OH, SO$_3$H, SO$_2$NH$_2$, SO$_2$NMe$_2$, SO$_2$NH(CH$_2$)$_2$N(CH$_3$)$_2$, SO$_2$NHCH$_2$CH$_3$, SO$_2$Me, (CH$_2$)$_2$OH, methyl or ethyl.

5. A compound according to claim 1 or a salt thereof, wherein A is C(=O)(C$_1$-C$_6$ alkyl).

6. A compound according to claim 1 or a salt thereof, wherein A is C(=O)NH$_2$.

7. A compound according to claim 1 or a salt thereof, wherein A is C(=O)NMe$_2$.

8. A compound according to claim 1 or a salt thereof, wherein A is C(=O)CH$_2$NMe$_2$.

9. A compound according to claim 1 or a salt thereof, wherein A is SO$_2$Me.

10. A compound according to claim 1 or a salt thereof, wherein A is SO$_2$NH$_2$.

11. A compound according to claim 1 or a salt thereof, wherein R$^2$ is aryl optionally substituted with one or more groups independently selected from C$_1$-C$_6$ alkyl, Br, Cl, CF$_3$, CN, OR$^8$, C(=O)OR$^8$, F, SO$_2$Me and C(=O)NH(1-3C alkyl)N(alkyl)$_2$.

12. A compound according to claim 1 or a salt thereof wherein R$^2$ is selected from the structures:

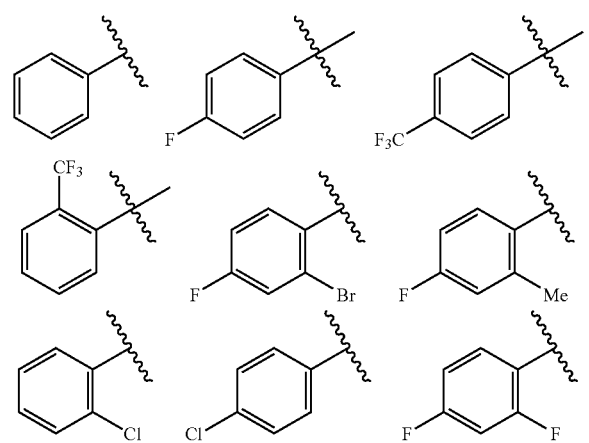

-continued

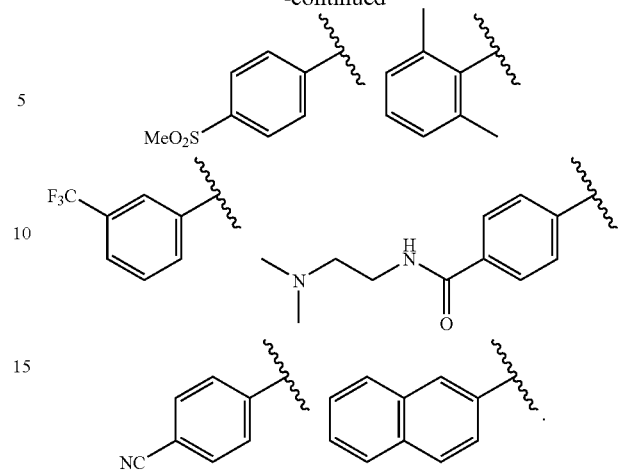

13. A compound according to claim 1 or a salt thereof, wherein R$^2$ is a 6-membered heteroaryl group having 1-2 ring nitrogen atoms or a 5-membered heteroaryl group having 1-2 ring nitrogen atoms, wherein R$^2$ is optionally substituted with one or more groups independently selected from (1-6C alkyl), (1-6C alkyl)OH, Cl, and CF$_3$.

14. A compound according to claim 1 or a salt thereof, wherein R$^2$ is cyclopentyl.

15. A compound according to claim 1 or a salt thereof, wherein R$^2$ is a partially unsaturated 5,5, 5, 6 or 6,6 bicyclic ring system having 1-2 ring nitrogen atoms and optionally having a ring oxygen atom.

16. A compound according to claim 1 or a salt thereof, wherein L is O.

17. A compound according to claim 1 or a salt thereof, wherein L is S.

18. A compound according to claim 1 or a salt thereof, wherein D$^2$ is CH.

19. A compound according to claim 1 or a salt thereof, wherein D$^2$ is N.

20. A compound according to claim 1 or a salt thereof having the formula:

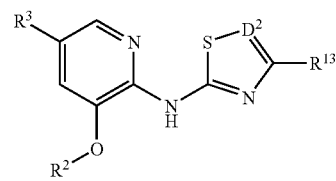

wherein:
R$^{13}$ is

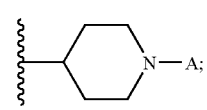

A is C(=O)(C$_1$-C$_6$ alkyl), C(=O)NH$_2$, C(=O)NMe$_2$, C(=O)CH$_2$NMe$_2$, SO$_2$Me, or SO$_2$NH$_2$;
D$^2$ is N or CH;
R$^2$ is phenyl optionally substituted with F; and $R^3$ is

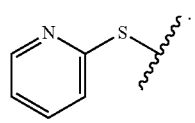 [SMILES: *Sc1ccccn1]

21. A pharmaceutical composition, which comprises a compound of formula (I) as defined in claim 1, or a pharmaceutically acceptable salt thereof, and a pharmaceutically acceptable diluent or carrier.

22. A method of treating non-insulin-dependent diabetes, comprising administering to said mammal a therapeutically effective amount of a compound of formula (I) as defined in claim 1, or a pharmaceutically acceptable salt thereof.

23. A method for preparing a compound of claim 1 or a salt thereof, comprising:

(a) reacting a corresponding compound of the formula (II)

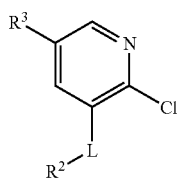
(II)

with a compound of the formula (III)

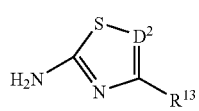
(III)

in the presence of a base catalyst or metal catalyst; or (b) reacting a corresponding compound of the formula (IV)

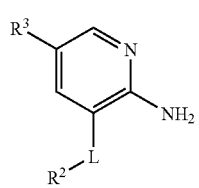
(IV)

with a compound of the formula (V)

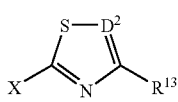
(V)

wherein X is a leaving atom or group in the presence of a base catalyst or metal catalyst; or (c) for a compound of Formula I wherein $D^2$ is CH, reacting a corresponding compound of the formula (VI)

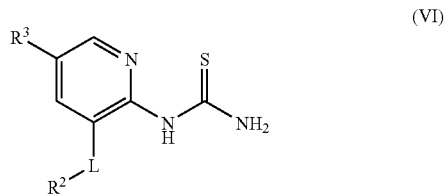
(VI)

with a compound of the formula $R^{13}COCH_2X$, wherein X is a leaving group or atom in the presence of a base; or (d) for a compound of Formula I wherein $D^2$ is N, reacting a corresponding compound of the formula (VII)

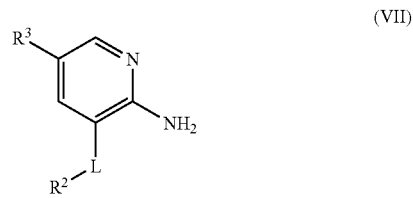
(VII)

with a compound having the formula (VIII)

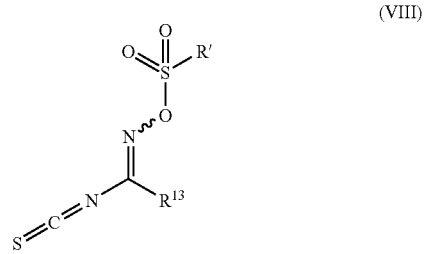
(VIII)

where R' is C1-C6 alkyl or aryl optionally substituted with C1-C6 alkyl, in the presence of a base; or (e) for a compound of Formula I wherein $R^3$ is $SR^6$, reacting a corresponding compound having the formula (IX)

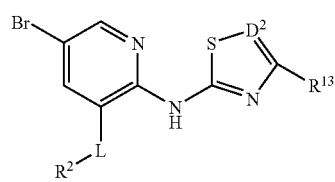
(IX)

with a compound having the formula $R^6SH$ in the presence of a suitable base; or (f) for a compound of Formula I wherein $R^3$ is $SR^6$, reacting a corresponding compound

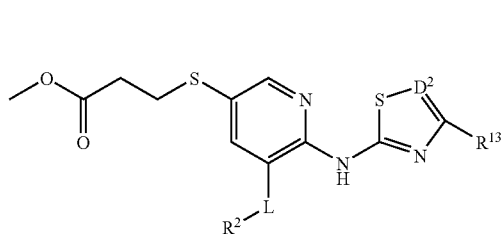

(X)

with a compound having the formula $R^6X$ wherein X is a leaving atom or group in the presence of a suitable base; or (g) reacting a corresponding compound having the formula (XI)

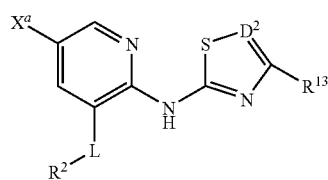

(XI)

wherein $X^a$ is a leaving atom or group, with a compound having the formula $R^3$—$X^b$ wherein $X^b$ is a leaving atom or a leaving group, in the presence of a suitable base; or (h) reacting a corresponding compound having the formula (XII)

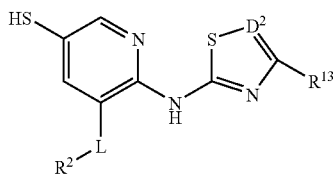

(XII)

with a compound having the formula $R^6$—$X^c$ wherein $X^c$ is a leaving atom or group in the presence of a suitable base; or (i) for a compound of Formula I where L is O, reacting a corresponding compound having the formula (XIII)

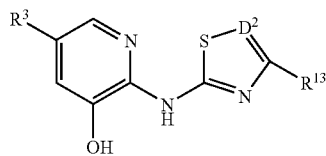

(XIII)

with a compound having the formula $R^2$—$X^d$, wherein $X^d$ is a leaving atom or group in the presence of a base or in the presence of a copper or palladium catalyst; or (j) reacting a corresponding compound having the formula (XIV)

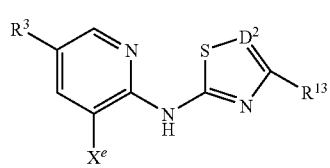

(XIV)

wherein $X^e$ is a leaving group or atom, with a compound having the formula $R^2LH$ wherein L is O or S, in the presence of a palladium catalyst and a suitable base; or (k) for a compound of Formula I wherein A is —C(=O) ($C_1$-$C_6$ alkyl), reacting a corresponding compound having the formula (XV):

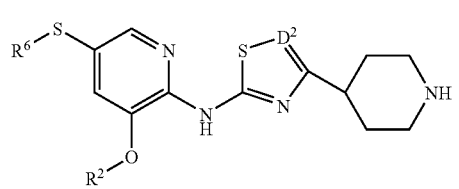

(XV)

with a $C_1$-$C_6$ alkyl anhydride in the presence of a base; or (l) for a compound of Formula I wherein A is C(=O)$NH_2$, reacting a corresponding compound having Formula (XV) with potassium cyanate in the presence of a tertiary amine base; or (m) for a compound of Formula I wherein A is C(=O)$NMe_2$, reacting a corresponding compound having formula (XV) with dimethylcarbamic chloride in the presence of a tertiary amine base; or (n) for a compound of formula I wherein A is C(=O)$CH_2NMe_2$, reacting a compound having formula (XV) with 2-(dimethylamino)acetyl chloride hydrochloride in the presence of a tertiary amine base; or (o) for a compound of formula I wherein A is $SO_2Me$, reacting a compound having formula (XV) with methanesulfonyl chloride in the presence of a tertiary amine base; or (p) for a compound of formula I wherein A is $SO_2NH_2$, reacting a compound having formula (XV) with dimethylsulfamoyl chloride in the presence of a tertiary amine base;

(q) for a compound of Formula I wherein A is —C(=O) ($C_1$-$C_6$ alkyl), reacting a corresponding compound having the formula (XVa)

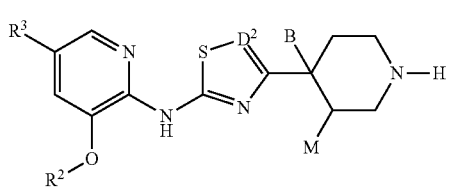

(XVa)

with a $C_1$-$C_6$ alkyl anhydride in the presence of a base; or (r) for a compound of Formula I wherein A is C(=O)$NH_2$, reacting a corresponding compound having Formula (XVa) with potassium cyanate in the presence of a tertiary amine base; or (s) for a compound of Formula I wherein A is C(=O)NMe₂, reacting a corresponding compound having formula (XVa) with dimethylcarbamic chloride in the presence of a tertiary amine base; or (t) for a compound of formula I wherein A is C(=O)CH₂NMe₂, reacting a compound having formula (XVa) with 2-(dimethylamino)acetyl chloride hydrochloride in the presence of a tertiary amine base; or (u) for a compound of formula I wherein A is SO₂Me, reacting a compound having formula (XVa) with methanesulfonyl chloride in the presence of a tertiary amine base; or (v) for a compound of Formula I wherein A is SO₂NH₂, reacting a compound having formula (XVa) with dimethylsulfamoyl chloride in the presence of a tertiary amine base;

(w) for a compound having the Formula I wherein A is C(=O)CH₂OH, hydrolyzing a corresponding compound wherein A is C(=O)CH₂OC(=O)alkyl; or (x) for a compound having the Formula I wherein L is O, reacting a corresponding compound having the formula (XIII)

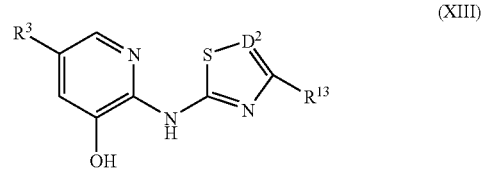

with a compound having the formula HO—R² wherein R² is as defined for Formula I, in the presence of a coupling reagent; and removing any protecting group or groups and, if desired, forming a salt.

* * * * *

UNITED STATES PATENT AND TRADEMARK OFFICE
CERTIFICATE OF CORRECTION

PATENT NO. : 8,362,037 B2
APPLICATION NO. : 12/532374
DATED : January 29, 2013
INVENTOR(S) : Aicher et al.

Page 1 of 1

It is certified that error appears in the above-identified patent and that said Letters Patent is hereby corrected as shown below:

In the Claims:

In column 150, Claim 1, Line 22:

Please delete the figure:

" 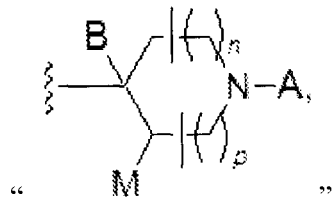 "

and insert:

-- 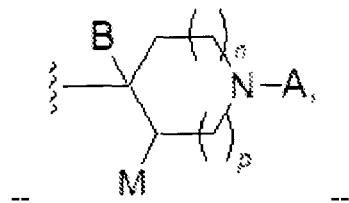 --

In column 155, Claim 23, Lines 1-7

Please delete "reacting a corresponding compound (X)"
and replace with -- reacting a corresponding compound having the formula (X) --

Signed and Sealed this
First Day of October, 2013

Teresa Stanek Rea
*Deputy Director of the United States Patent and Trademark Office*